United States Patent
Sorek et al.

(10) Patent No.: US 12,419,902 B2
(45) Date of Patent: Sep. 23, 2025

(54) ANTI-VIRAL AND ANTI-TUMORAL COMPOUNDS

(71) Applicant: YEDA RESEARCH AND DEVELOPMENT CO. LTD., Rehovot (IL)

(72) Inventors: Rotem Sorek, Rehovot (IL); Aude Bernheim, Rehovot (IL); Adl Jenny Millman Dayan, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 965 days.

(21) Appl. No.: 17/442,198

(22) PCT Filed: Mar. 29, 2020

(86) PCT No.: PCT/IL2020/050377
§ 371 (c)(1),
(2) Date: Sep. 23, 2021

(87) PCT Pub. No.: WO2020/202142
PCT Pub. Date: Oct. 8, 2020

(65) Prior Publication Data
US 2022/0175807 A1    Jun. 9, 2022

Related U.S. Application Data

(60) Provisional application No. 62/967,600, filed on Jan. 30, 2020, provisional application No. 62/827,089, filed on Mar. 31, 2019.

(51) Int. Cl.
| A61K 31/708 | (2006.01) |
| A61K 31/7068 | (2006.01) |
| A61K 31/7072 | (2006.01) |
| A61P 31/12 | (2006.01) |
| C07K 14/195 | (2006.01) |

(52) U.S. Cl.
CPC ........ *A61K 31/708* (2013.01); *A61K 31/7068* (2013.01); *A61K 31/7072* (2013.01); *A61P 31/12* (2018.01); *C07K 14/195* (2013.01)

(58) Field of Classification Search
CPC .......... A61P 31/12; A61P 31/14; A61P 31/20; A61P 31/18; A61P 35/02; A61P 35/00; A61P 1/16; A61P 11/00; C07K 7/645; C12Y 301/13001
USPC ....................................................... 435/69.1
See application file for complete search history.

(56) References Cited

U.S. PATENT DOCUMENTS

| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubinstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,551,433 A | 11/1985 | Deboer |
| 4,666,828 A | 5/1987 | Gusella |
| 4,683,202 A | 7/1987 | Mullis |
| 4,689,406 A | 8/1987 | Banks et al. |
| 4,738,921 A | 4/1988 | Belagaje et al. |
| 4,801,531 A | 1/1989 | Frossard |
| 4,879,219 A | 11/1989 | Wands et al. |
| 5,011,771 A | 4/1991 | Bellet et al. |
| 5,028,530 A | 7/1991 | Lai et al. |
| 5,192,659 A | 3/1993 | Simons |
| 5,272,057 A | 12/1993 | Smulson et al. |
| 5,281,521 A | 1/1994 | Trojanowski et al. |
| 5,464,764 A | 11/1995 | Capecchi et al. |
| 5,487,992 A | 1/1996 | Capecchi et al. |
| 6,242,194 B1 | 6/2001 | Kullen et al. |

(Continued)

FOREIGN PATENT DOCUMENTS

| CN | 108640959 A | 10/2018 |
| EP | 0121775 A1 | 10/1984 |

(Continued)

OTHER PUBLICATIONS

Balzarini et al. "Conversion of 2', 3'-dideoxyadenosine (ddA) and 2', 3'-didehydro-2', 3'-dideoxyadenosine (d4A) to their corresponding aryloxyphosphoramidate derivatives markedlpotentiates their activity against human immunodeficiency virus and hepatitis B virus" FEBS letters. Jun. 30, 1997;410(2-3):324-8.

(Continued)

*Primary Examiner* — Robert B Mondesi
*Assistant Examiner* — Mohammad Y Meah
(74) *Attorney, Agent, or Firm* — Mark S. Cohen; PEARL COHEN ZEDEK LATZER BARATZ LLP

(57) ABSTRACT

Disclosed herein are prokaryotic homologs of viperin (pVips), and nucleotide and nucleoside analogs produced from pVips. These nucleotide and nucleoside analogs stop nucleotide chain synthesis and provide host cells with resistance to viral infections by targeting actively replicating viral genome. Further, these nucleotide and nucleoside analogs decrease DNA replication in malignant cells. Further disclosed are methods of identifying pVips, and nucleotide and nucleoside analogs produced thereof.

4 Claims, 56 Drawing Sheets
(41 of 56 Drawing Sheet(s) Filed in Color)
Specification includes a Sequence Listing.

(56) References Cited

U.S. PATENT DOCUMENTS

| | | |
|---|---|---|
| 8,324,179 B2 | 12/2012 | Chen et al. |
| 8,877,733 B2 | 11/2014 | Cho et al. |
| 2019/0315785 A1 | 10/2019 | Boojamra et al. |

FOREIGN PATENT DOCUMENTS

| | | |
|---|---|---|
| EP | 0036776 B1 | 5/1988 |
| EP | 0267851 B1 | 1/1994 |
| WO | WO 2012/087596 A1 | 6/2012 |
| WO | WO 2018/220616 A2 | 12/2018 |
| WO | WO 2019/040418 A1 | 2/2019 |
| WO | WO 2019/053696 A1 | 3/2019 |
| WO | WO 2020/202142 A2 | 10/2020 |

OTHER PUBLICATIONS

Gao et al. "Efficacies of β-L-D4A against hepatitis B virus in 2.2.15 cells" World Journal of Gastroenterology: WJG. Feb. 2, 2008;14(8):1263.

PUBCHEM 3',4'-Didehydro-3'-deoxyadenosine. SID 274859250. Pubchem Entry (online). National Center for Biotechnology Information. Nov. 21, 2016 [retrieved on Nov. 4, 2021], Retrieved from die Internet: [URL: https://pubchem.ncbi.ntm.nih.gov/substance/274859250].

Amann et al. "Vectors bearing a hybrid trp-lac promoter useful for regulated expression of cloned genes in *Escherichia coli*" Gene. Nov. 1, 1983;25(2-3):167-78.

Balbás P. "Understanding the art of producing protein and nonprotein molecules in *Escherichia coli*" Molecular biotechnology. Dec. 2001;19(3):251-67.

Beadle et al. "Synthesis and antiviral evaluation of octadecyloxyethyl benzyl 9-[(2-Phosphonomethoxy) ethyl] guanine (ODE-Bn-PMEG), a potent inhibitor of transient HPV DNA amplification" Journal of medicinal chemistry. Dec. 8, 2016;59(23):10470-8.

Broderick et al. "Radical S-adenosylmethionine enzymes" Chemical reviews. Apr. 23, 2014;114(8):4229-317.

Brosius et al. "Spacing of the -10 and -35 regions in the tac promoter. Effect on its in vivo activity" Journal of biological chemistry. Mar. 25, 1985;260(6):3539-41.

Chemaly et al. "In vitro comparison of currently available and investigational antiviral agents against pathogenic human double-stranded DNA viruses: A systematic literature review" Antiviral research. Mar. 1, 2019;163:50-8.

Cho et al. "Synthesis and antiviral activity of a series of 1'-substituted 4-aza-7, 9-dideazaadenosine C-nucleosides" Bioorganic & medicinal chemistry letters. Apr. 15, 2012;22(8):2705-7.

Database UniProt [online] Nov. 13, 2019 "SubName: Full= molybdenum cofactor biosynthesis enzyme {ECO:0000313 | EMBL:AA007825.2};", XP055719251, retrieved from EBI accession No. UNIPROT:A0A3Q0KZ59, Database accession No. A0A3Q0KZ59.

Database UniProt [online] Jun. 15, 2010 "SubName: Full=Radical SAM domain protein {ECO:0000313 | EMBL:EMBL:ADE54200.1};", XP055719253, retrieved from EBI accession No. UNIPROT:D5EID4, Database accession No. D5EID4.

Database UniProt [online] Jan. 20, 2016 "SubName: Full=FeS reductase {ECO:0000313 | EMBL:KPQ31663.1};", XP055719254, retrieved from EBI accession No. UNIPROT:A0AOP7Z657, Database accession No. A0A0P7Z657.

Database UniProt [online] Jul. 18, 2018 "SubName: Full=Radical SAM protein {ECO:0000313 | EMBL:PSW18885.1};", XP055719255, retrieved from EBI accession No. UNIPROT:A0A2T3NRM3, Database accession No. A0A2T3NRM3.

Database UniProt [online] Apr. 13, 2016 "SubName: Full= Molybdenum Cofactor Biosynthesis Protein mOAa1 {ECO: 0000313 | EMBL:AMH94978.1};", XP055719256, retrieved from EBI accession No. UNIPROT:A0A110A2W7, Database accession No. A0A110A2W7.

Database UniProt [online] Oct. 7, 2020 "SubName: Full=Radical S-adenosyl methionine domain-containing protein 2 {ECO: 0000313 | EMBL:SHL73076.1};", XP055719257, retrieved from EBI accession No. UNIPROT:A0A1M7DOR2, Database accession No. A0A1M7DOR2.

Database UniProt [online] Oct. 25, 2017 "rECNAME: Full=Radical_SAMdomain-containing Protein {ECO:0000259 | Pfam:PF04055};", XP055719258, retrieved from EBI accession No. UNIPROT:A0A244CMPO, Database accession No. A0A244CMPO.

Database UniProt [Online] Apr. 12, 2017 (Apr. 12, 2017), retrieved from EBI accession No. UNIPROT:A0A1HONKS3 Database accession No. A0A1HONKS3 the whole document.

Davies et al. "Plasmid-determined resistance to antimicrobial agents" Annual Reviews in Microbiology. Oct. 1978;32(1):469-508.

De Boer et al. "The tac promoter: a functional hybrid derived from the trp and lac promoters" Proceedings of the National Academy of Sciences. Jan. 1, 1983;80(1):21-5.

De Clercq et al. "Antiviral prodrugs—the development of successful prodrug strategies for antiviral chemotherapy" British journal of pharmacology. Jan. 2006;147(1):1-1.

Doron et al. "Systematic discovery of antiphage defense systems in the microbial pangenome" Science. Mar. 2, 2018:359(6379).

Dousson CB. "Current and future use of nucleo (s) tide prodrugs in the treatment of hepatitis C virus infection" Antiviral Chemistry and Chemotherapy. Feb. 2018;26:2040206618756430.

Drosu et al. "Tenofovir prodrugs potently inhibit Epstein-Barr virus lytic DNA replication by targeting the viral DNA polymerase" Proceedings of the National Academy of Sciences. Jun. 2, 2020;117(22):12368-74.

Fenwick et al. "Structural studies of viperin, an antiviral radical SAM enzyme" Proceedings of the National Academy of Sciences. Jun. 27, 2017;114(26):6806-11.

Fenwick "Structural basis of the substrate selectivity of viperin" Biochemistry. Jan. 9, 2020:59(5):652-62.

Fortier et al. "Phage production and maintenance of stocks, including expected stock lifetimes" In Bacteriophages 2009 (pp. 203-219). Humana Press.

Ghosh et al. "Viperin: An ancient radical SAM enzyme finds its place in modern cellular metabolism and innate immunity" Journal of Biological Chemistry. Aug. 14, 2020;295(33):11513-28.

Gilboa et al. "Transfer and expression of cloned genes using retroviral vectors" BioTechniques. 1986;4(6):504-12.

Gill et al. "Conserved retinoblastoma protein-binding motif in human cytomegalovirus UL97 kinase minimally impacts viral replication but affects susceptibility to maribavir" Virology Journal. Dec. 2009;6(1):1-5.

Gizzi et al. "A naturally occurring antiviral ribonucleotide encoded by the human genome" Nature. Jun. 2018;558(7711):610-4.

Goeddel et al. "Synthesis of human fibroblast interferon by *E. coli*" Nucleic Acids Research. Sep. 25, 1980;8(18):4057-74.

Goldfarb et al. "BREX is a novel phage resistance system widespread in microbial genomes" The EMBO journal. Jan. 14, 2015;34(2):169-83.

Hartline et al. "A standardized approach to the evaluation of antivirals against DNA viruses: Orthopox-, adeno-, and herpesviruses" Antiviral research. Nov. 1, 2018;159:104-12.

Honarmand et al. "Mechanism of diol dehydration by a promiscuous radical-SAM enzyme homologue of the antiviral enzyme viperin (RSAD2)" ChemBioChem. Jun. 2, 2020;21(11):1605-12.

International Search for PCT Application No. PCT/IL2020/050377 dated Oct. 2, 2020.

Jordheim et al. "Advances in the development of nucleoside and nucleotide analogues for cancer and viral diseases" Nature reviews Drug discovery. Jun. 2013;12(6):447-64.

Keith et al. "A standardized approach to the evaluation of antivirals against DNA viruses: Polyomaviruses and lymphotropic herpesviruses" Antiviral research. Nov. 1, 2018:159:122-9.

Kropinski et al. "Enumeration of bacteriophages by double agar overlay plaque assay" In Bacteriophages 2009 (pp. 69-76). Humana Press.

(56) References Cited

OTHER PUBLICATIONS

Leung et al. "Quantification of polyoma BK viruria in hemorrhagic cystitis complicating bone marrow transplantation" Blood, The Journal of the American Society of Hematology. Sep. 15, 2001;98(6):1971-8.
Li et al. "A survey of sequence alignment algorithms for next-generation sequencing" Briefings in bioinformatics. Sep. 1, 2010;11(5):473-83.
Makarova et al. "Defense islands in bacterial and archaeal genomes and prediction of novel defense systems" Journal of bacteriology. Nov. 1, 2011;193(21):6039-56.
NCBI Accession No. NP_542388.2 Version 2, Mar. 15, 2015.
NCBI Accession No. AF442151.1 Version 1, Mar. 11, 2011.
NCBI Accession No. NP_620236.1 Version 1, Jul. 3, 2021.
NCBI Accession No. NP_067359.2 Version 2, Jun. 22, 2021.
NCBI Accession No. NP_001020727.1 Version 1, Aug. 8, 2021.
Ofir et al. "DISARM is a widespread bacterial defence system with broad anti-phage activities" Nature microbiology. Jan. 2018;3(1):90-8.
Prichard et al. "Activity and mechanism of action of N-methanocarbathymidine against herpesvirus and orthopoxvirus infections" Antimicrobial agents and chemotherapy. Apr. 2006;50(4):1336-41.
Prichard et al. Benzimidazole analogs inhibit human herpesvirus 6 Antimicrobial agents and chemotherapy. May 2011;55(5):2442-5.
Raibaud et al. "Positive control of transcription initiation in bacteria" Annual review of genetics. Dec. 1984;18(1):173-230.
Ray et al. "Tenofovir alafenamide: a novel prodrug of tenofovir for the treatment of human immunodeficiency virus" Antiviral research. Jan. 1, 2016;125:63-70.
Santamaria-Araujo et al. "The tetrahydropyranopterin structure of the sulfur-free and metal-free molybdenum cofactor precursor" Journal of Biological Chemistry. Apr. 16, 2004;279(16):15994-9.
Seley-Radtke et al. "The evolution of nucleoside analogue antivirals: A review for chemists and non-chemists. Part 1: Early structural modifications to the nucleoside scaffold" Antiviral research. Jun. 1, 2018;154:66-86.
Seo et al. "Viperin: a multifunctional, interferon-inducible protein that regulates virus replication" Cell host & microbe. Dec. 15, 2011;10(6):534-9.
Shimatake et al. "Purified λ regulatory protein c II positively activates promoters for lysogenic development" Nature. Jul. 1981;292(5819):128-32.
Shomar Monges H. "*Producing high-value chemicals in Escherichia coli through synthetic biology and metabolic Engineering*" (Doctoral dissertation, Delft University of Technology), published Mar. 28, 2019.
Studier et al. "Use of bacteriophage T7 RNA polymerase to direct selective high-level expression of cloned genes" Journal of molecular biology. May 5, 1986;189(1):113-30.
Swarts et al. "DNA-guided DNA interference by a prokaryotic Argonaute" Nature. Mar. 2014;507(7491):258-61.
Tabor et al. "A bacteriophage T7 RNA polymerase/promoter system for controlled exclusive expression of specific genes" Proc. Natl. Acad. Sci. USA. 1985;82:1074-8.
Thiem et al. "Preparative-enzymatic formation of cytidine 5'-monophosphosialate by integrated cytidine 5'-triphosphate regeneration" Liebigs Annalen der Chemie. Nov. 12, 1990;1990(11):1101-5.
Thomson et al. "Nucleoside analogues as antibacterial agents" Frontiers in microbiology. May 22, 2019;10:952.
Yelverton et al. "Bacterial synthesis of a novel human leukocyte interferon" Nucleic acids research. Feb. 11, 1981;9(3):731-41.
Zabala et al. "Optimization of the Tet-on system to regulate interleukin 12 expression in the liver for the treatment of hepatic tumors" Cancer research. Apr. 15, 2004;64(8):2799-804.
Zhang et al. "Design and synthesis of dipeptidyl glutaminyl fluoromethyl ketones as potent severe acute respiratory syndrome coronavirus (SARS-CoV) inhibitors" Journal of medicinal chemistry. Feb. 9, 2006;49(3):1198-201.
Zheng et al. "Assembly of iron-sulfur clusters: identification of an iscSUA-hscBA-fdx gene cluster from Azotobacter vinelandii" Journal of Biological Chemistry. May 22, 1998;273(21):13264-72.
Bernheim, A., et al. (2021). Prokaryotic viperins produce diverse antiviral molecules. *Nature*, 589(7840), 120-124.

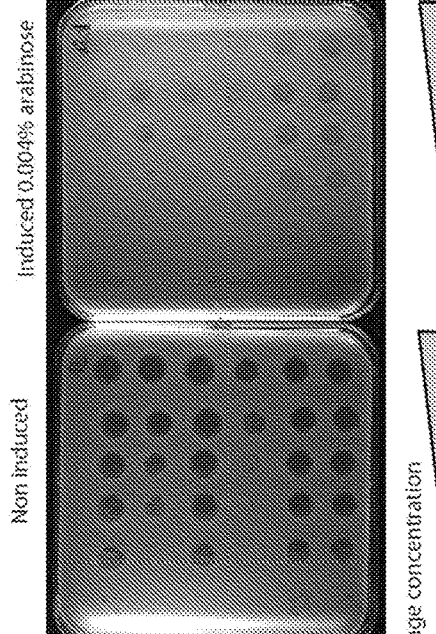
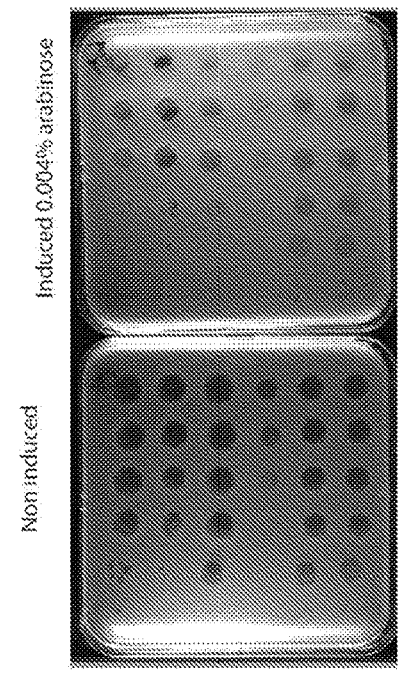
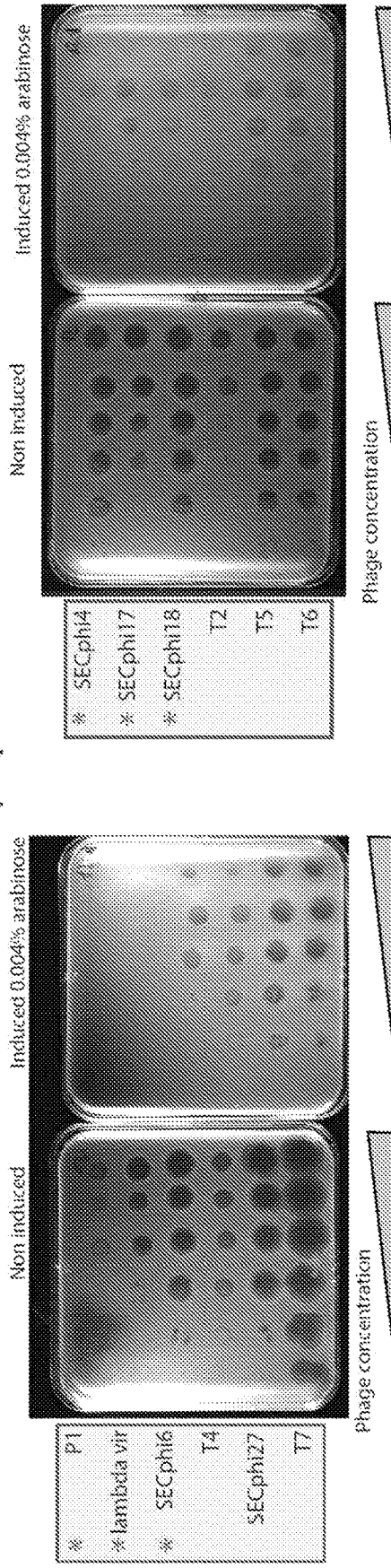
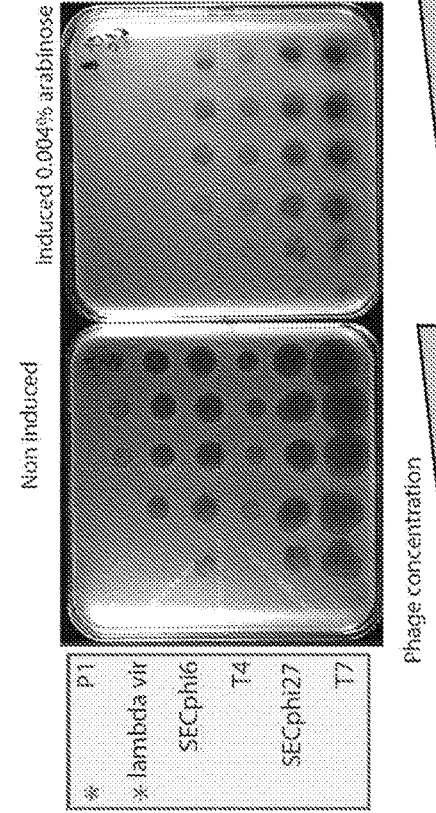
Figure 6C
Figure 6D

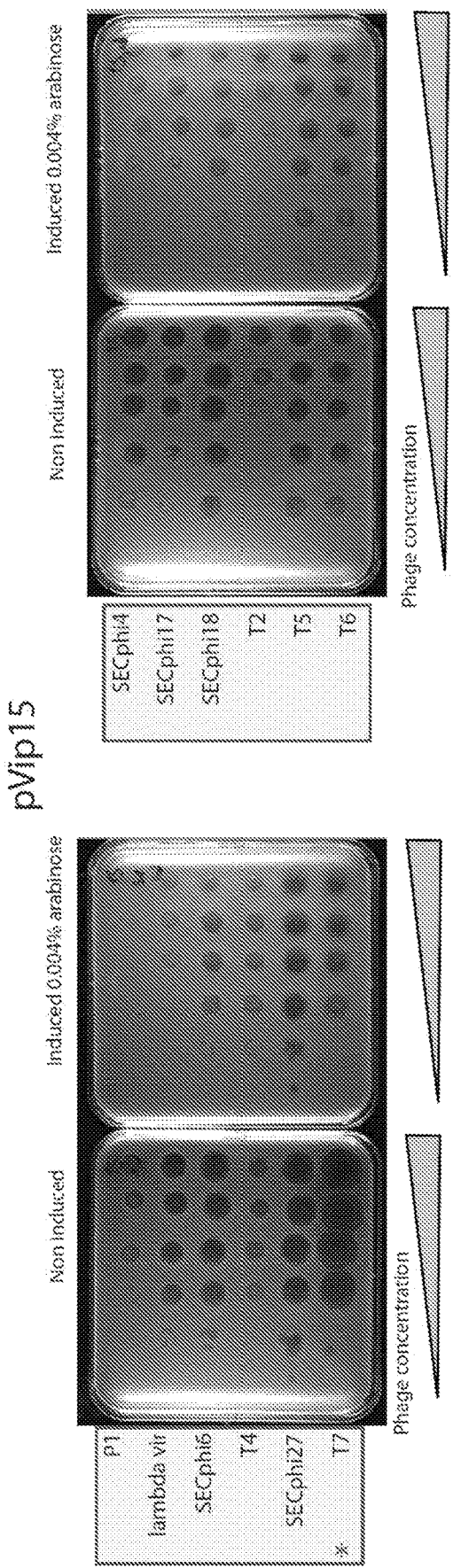
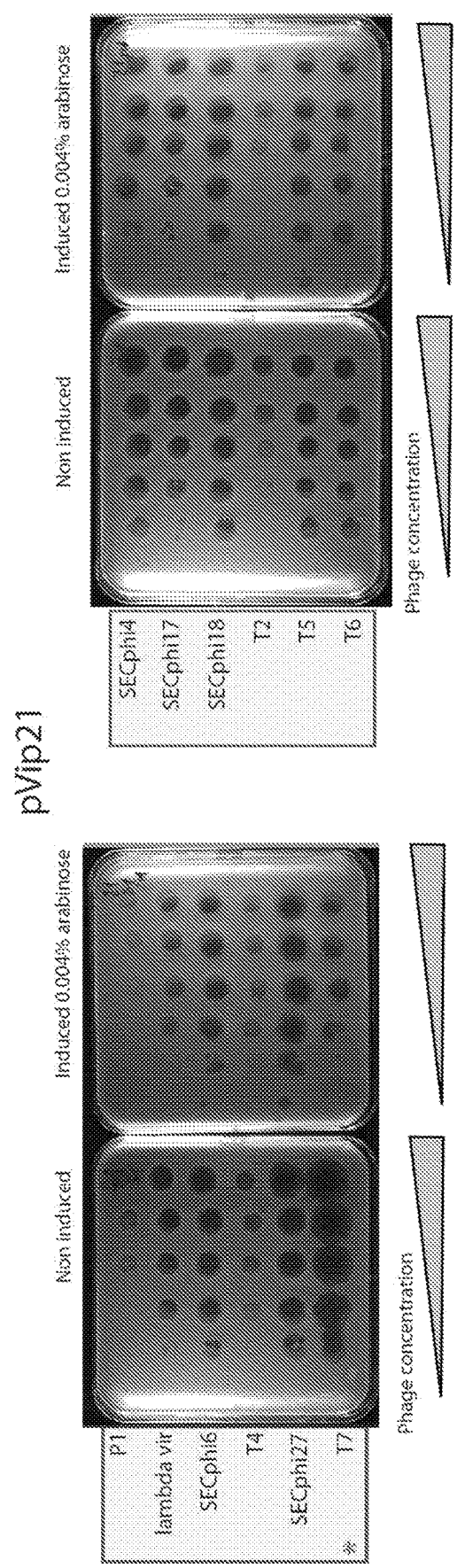
Figure 6I
Figure 6J

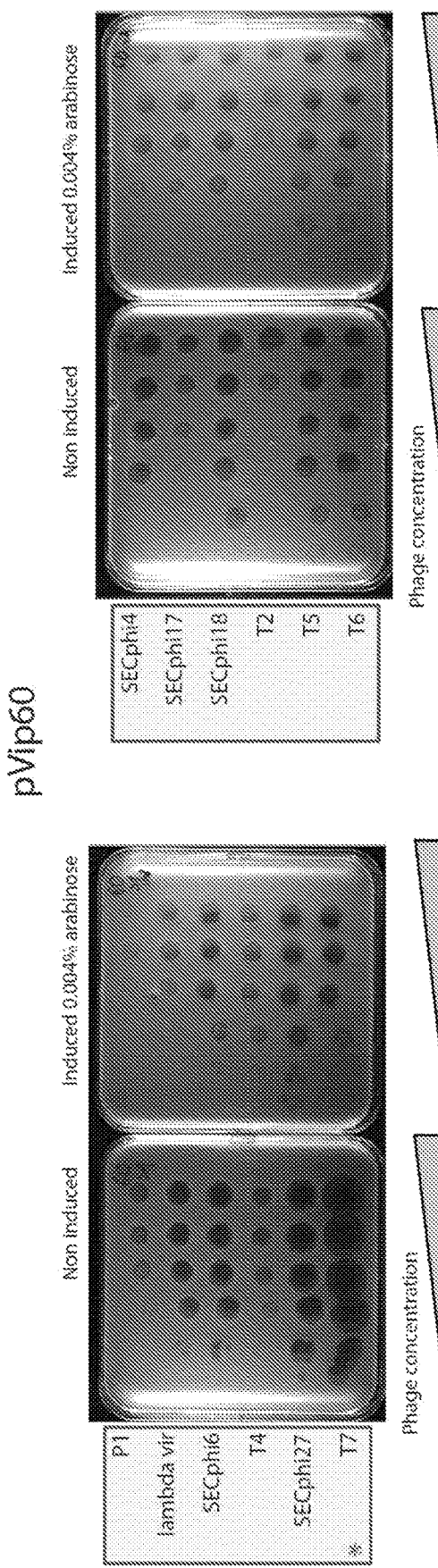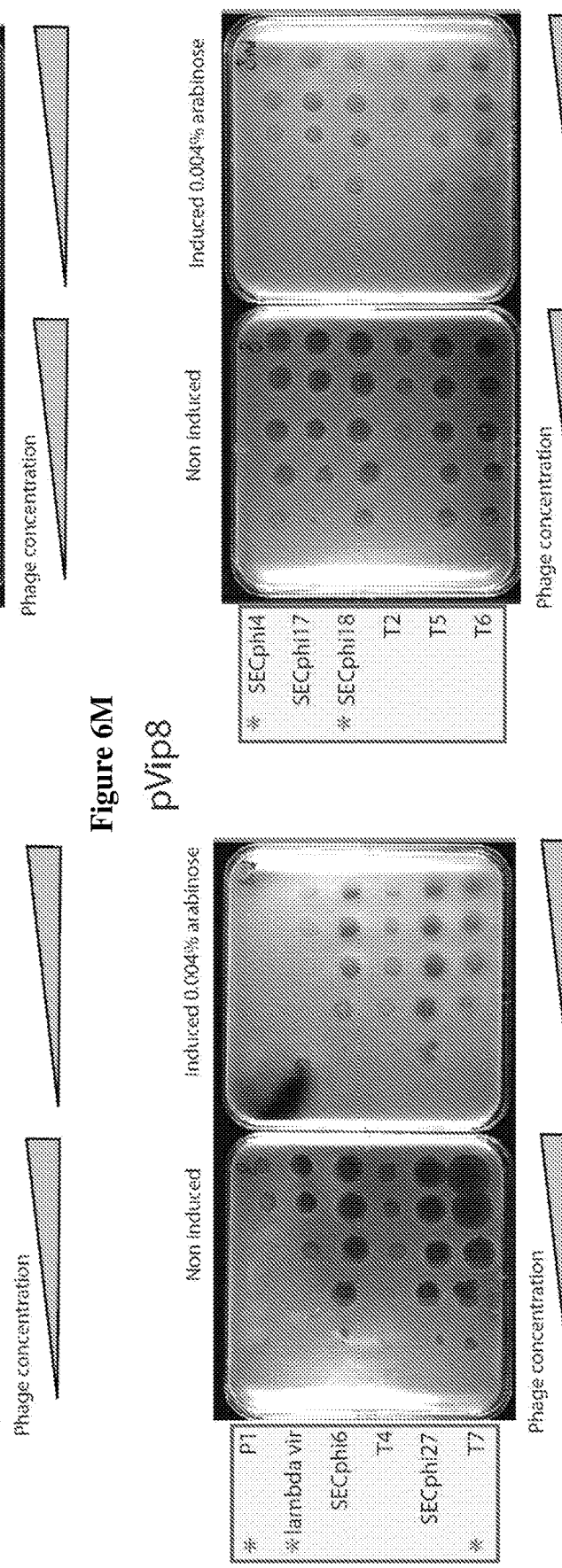
Figure 6M
Figure 6N

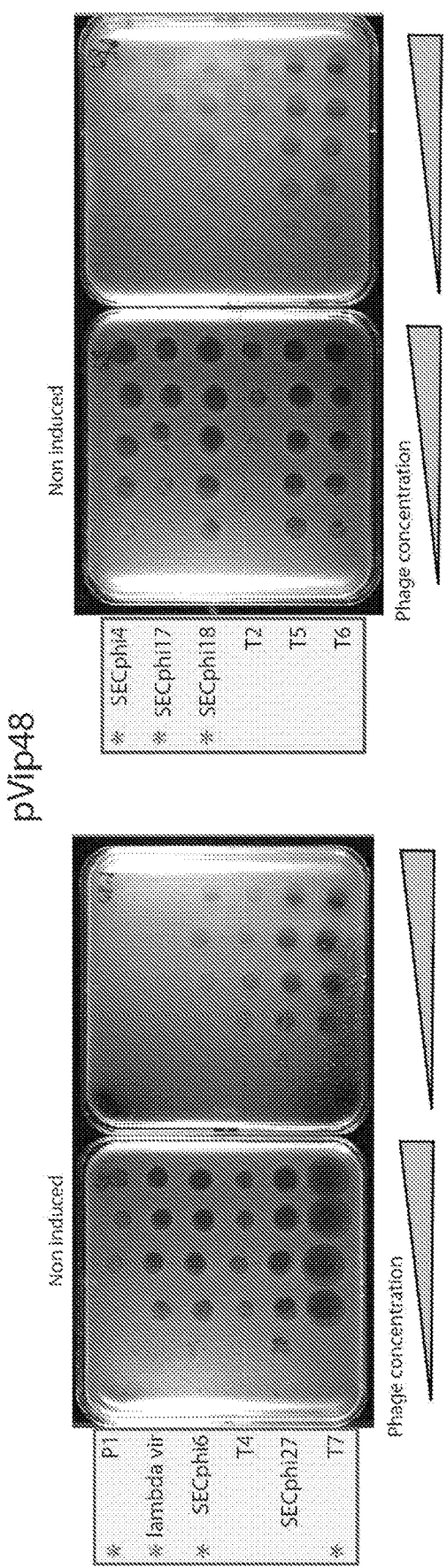
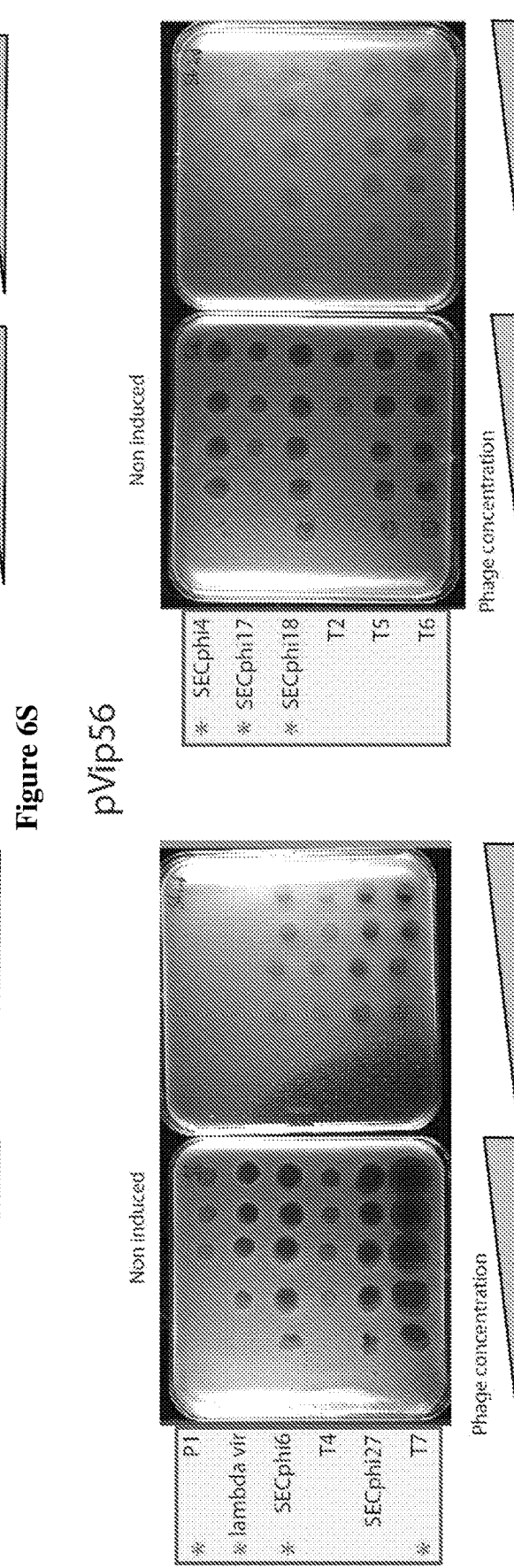
Figure 6S
Figure 6T

ANTI-VIRAL AND ANTI-TUMORAL COMPOUNDS

CROSS-REFERENCE TO RELATED APPLICATIONS

This application is a National Phase Application of PCT International Application No. PCT/IL2020/050377, International Filing Date Mar. 29, 2020, claiming the benefit of U.S. Patent Application Ser. No. 62/967,600, filed Jan. 30, 2020, and U.S. Patent Application Ser. No. 62/827,089, filed Mar. 31, 2019. The entire contents and disclosures of the preceding applications are incorporated in their entirety by reference into this application.

SEQUENCE LISTING

The instant application contains a Sequence Listing which has been submitted electronically in ASCII format and is hereby incorporated by reference in its entirety. Said ASCII copy, created on Mar. 27, 2019, is named P-583071-PC-SQL-27MAR19.txt and is 1,589,259 bytes in size.

FIELD OF DISCLOSURE

Disclosed herein are prokaryotic homologs of viperin (pVips), and nucleotide and nucleoside analogs produced from pVips. These nucleotide and nucleoside analogs stop nucleotide chain synthesis, provide treated cells with resistance to viral infections by targeting actively replicating viral genomes. Further, these nucleotide and nucleoside analogs decrease DNA replication in malignant cells. Further disclosed are methods of identifying pVips, and nucleotide and nucleoside analogs produced thereof.

BACKGROUND

Molecules that irreversibly stop the polymerization of DNA and RNA inside a cell are termed chain terminators. Chain termination is defined as a chemical reaction in which a chain carrier is converted irreversibly into a non-propagating species, without the formation of a new chain carrier. DNA and RNA base chain terminators such as nucleoside or nucleotide analogs have been used as drugs in several contexts such as antiviral agents or in chemotherapies as anti-tumoral molecules. The main mechanism of nucleoside and nucleotide analogs is competition with the natural substrate for the DNA or RNA polymerization reaction. Upon incorporation of this "suicide" nucleotide, a chain cannot polymerize further. There are several types of base chain terminators such as acyclic ones that have, for example, no 3'-hydroxyl function at the riboside part of the molecule (e.g., acyclovir) or cyclic ones such as molecules with 3'-hydroxyl group replaced by an azide group (N3) (AZT).

3'-deoxy-3',4'-didehydro-CTP (ddhCTP) is an RNA nucleotide analog which lacks 4' hydrogen and the 3' hydroxyl group compared to CTP. ddhCTP was discovered as the product of *Rattus norvegicus* Viperin. Viperin is an interferon-induced enzyme, which provides broad anti-viral properties against DNA and RNA viruses such as West Nile virus, hepatitis C and HIV. In eukaryotes, Viperin catalyzes the conversion of CTP to ddhCTP via a SAM-dependent radical mechanism. ddhCTP acts as an RNA chain terminator for viral RNA dependent polymerases. In vertebrate genomes, the kinase cytidylate monophosphate kinase 2 (CMPK2) is adjacent to the viperin gene. This kinase phosphorylates CMP to become CTP thus generating the substrate of vertebrate Viperin enzyme. When tested as an anti-viral agent, the nucleoside ddhC (namely 3'-deoxy-3', 4'-didehydro-C, without the 3 phosphates) was applied to cells, where it was then phosphorylated by endogenous proteins producing ddhCTP, and was shown to directly inhibit replication of Zika virus in vivo.

A broad array of food products, commodity chemicals, and biotechnology products are manufactured industrially by large-scale bacterial fermentation of various substrates. Enormous amounts of bacteria are being cultivated each day in large fermentation vats. Foreign nucleic acid contamination, for example phage contamination, can rapidly bring fermentations to a halt and cause economic setbacks, and is therefore considered a serious threat in these industries. The dairy fermentation industry has openly acknowledged the problem of phages and has been working with academia and starter culture companies to develop defense strategies and systems to curtail the propagation and evolution of phages for decades. There remains a need to provide bacteria with a defense against sources of foreign nucleic acids, such as viral infections.

Further, there remains a need to provide new nucleotide chain terminators that can inhibit the replication of viruses and/or their transcription, as well as DNA replication of malignant cells.

SUMMARY OF THE DISCLOSURE

In one aspect, disclosed herein is a method for treating a disease in a subject in need thereof, the method comprising administering to the subject a nucleoside analog for example but not limited to ddhA, ddhG, ddhU, ddh-deoxy-A, ddh-deoxy-G, and ddh-deoxy-T or a combination thereof, or a nucleoside analog derived from a nucleotide analog produced by a pVip, wherein the amino acid sequence of the pVip is set forth in any one of SEQ ID NOs: 409-789 or a homologue thereof comprising at least 80% homology to the amino acid sequence set forth in any one of SEQ ID NOs: 409-789, or wherein the pVip is encoded by a pVip gene comprising the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408. In a related aspect, disclosed herein is a method for treating a disease in a subject in need thereof, the method comprising administering to the subject a combination of nucleoside analogs. In a further related aspect, nucleoside analogs for example but not limited to ddhA, ddhG, ddhU, ddh-deoxy-A, ddh-deoxy-G, and ddh-deoxy-T or a combination thereof, may be used in a method of treating a disease when in combination with nucleoside analogs ddhC or ddh-deoxy-C or a combination thereof.

In a related aspect, the disease comprises a virus-induced disease, a cancer or a tumor, an autoimmune disease, or an immune disorder, or a combination thereof. A number of diseases and cancer are known to be caused by viruses. In one embodiment, examples of disease-causing viruses include, but are not limited to, norovirus; rotavirus; hepatitis virus A, B, C, D, or E; rabies virus, West Nile virus, enterovirus, echovirus, coxsackievirus, herpes simplex virus (HSV), HSV-2, varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enterovirus D68, severe acute respiratory syndrome (SARS) coronavirus, Middle East respiratory syndrome coronavirus, SARS coronavirus 2, Epstein-Barr virus, influenza virus, respiratory syncytical virus, polyoma viruses (such as JC virus, BK virus), Ebola virus, Dengue virus, or any combination thereof. In a related aspect, the cancer or tumor can be a carcinoma, a sarcoma, a lymphoma, leukemia, a germ cell tumor, a blastoma, chondrosarcoma, Ewing's sarcoma, malignant fibrous histiocytoma of bone/osteosarcoma, osteosarcoma, rhabdomyosarcoma, heart cancer, brain cancer, astrocytoma, glioma, medulloblastoma, neuroblastoma, breast cancer, medullary carcinoma, adrenocortical carcinoma, thyroid cancer, Merkel cell carcinoma, eye cancer, gastrointestinal cancer, colon cancer, gallbladder cancer, gastric (stomach) cancer, gastrointestinal carcinoid tumor, hepatocellular cancer, pancreatic cancer, rectal cancer, bladder cancer, cervical cancer, endometrial cancer, ovarian cancer, renal cell carcinoma, prostate cancer, testicular cancer, urethral cancer, uterine sarcoma, vaginal cancer, head cancer, neck cancer, nasopharyngeal carcinoma, hematopoietic cancer, lymphoma, Non-Hodgkin lymphoma, skin cancer, basal-cell carcinoma, melanoma, small cell lung cancer, or non-small cell lung cancer, or any combination thereof.

In a related aspect, the immune disorder can be arthritis, host-versus-graft disease (HvGD), graft-versus-host disease (GvHD), inflammation, immunodeficiency, or an autoimmune disorder. In a related aspect, the auto-immune disease can be achalasia, amyloidosis, ankylosing spondylitis, anti-gbm/anti-tbm nephritis, antiphospholipid syndrome, arthritis, autoimmune angioedema, autoimmune encephalomyelitis, autoimmune hepatitis, autoimmune myocarditis, autoimmune oophoritis, autoimmune orchitis, autoimmune pancreatitis, autoimmune retinopathy, autoimmune urticaria, Behcet's disease, celiac disease, chagas disease, chronic inflammatory demyelinating polyneuropathy (cidp), Cogan's syndrome, congenital heart block, Crohn's disease, dermatitis, dermatomyositis, discoid lupus, Dressler's syndrome, endometriosis, fibromyalgia, fibrosing alveolitis, granulomatosis with polyangiitis, Graves' disease, Guillain-Barre syndrome, herpes gestationis, immune thrombocytopenic purpura, interstitial cystitis (ic), juvenile arthritis, juvenile diabetes (type 1 diabetes), juvenile myositis (jm), Kawasaki disease, Lambert-Eaton syndrome, lichen planus, lupus, Lyme disease chronic, multiple sclerosis, myasthenia gravis, myositis, neonatal lupus, neutropenia, palindromic rheumatism, peripheral neuropathy, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, reactive arthritis, retroperitoneal fibrosis, rheumatic fever, rheumatoid arthritis, sarcoidosis, Schmidt syndrome, scleritis, scleroderma, Sjögren's syndrome, thrombocytopenic purpura, type 1 diabetes, ulcerative colitis, uveitis, vasculitis, or vitiligo, or any combination thereof.

In one aspect, disclosed herein is a method of terminating polynucleotide chain synthesis in a cell, the method comprising introducing into the cell a nucleoside analog for example but not limited to ddhA, ddhG, ddhU, ddh-deoxy-A, ddh-deoxy-G, ddh-deoxy-T, or a nucleoside analog derived from a nucleotide analog produced by a pVip, wherein the amino acid sequence of the pVip is set forth in any one of SEQ ID NOs: 409-789 or a homologue thereof comprising at least 80% homology to the amino acid sequence set forth in any one of SEQ ID NOs: 409-789, or wherein the pVip is encoded by a pVip gene comprising the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408, or any combination of nucleoside analogs thereof. In a related aspect, disclosed herein is a method of terminating polynucleotide chain synthesis in a cell, the method comprising administering to the cell a combination of nucleoside analogs. In a further related aspect, nucleoside analogs for example but not limited to ddhA, ddhG, ddhU, ddh-deoxy-A, ddh-deoxy-G, and ddh-deoxy-T or a combination thereof, may be used in a method of terminating polynucleotide chain synthesis when in combination with nucleoside analogs ddhC or ddh-deoxy-C or a combination thereof.

In a related aspect, terminating polynucleotide chain synthesis increases termination of DNA chain synthesis, or increases termination of RNA chain synthesis, or a combination thereof. In a related aspect, terminating polynucleotide chain synthesis confers viral resistance, resistance to foreign nucleic acid invasion, anti-viral activity, anti-phage activity, anti-plasmid activity, reduced plasmid transformation efficiency, resistance to entry of a conjugation element, increased resistance to horizontal gene transfer, decreased replication of endogenous DNA, decreased replication of foreign DNA, decreased RNA transcription, decreased RNA replication, increased termination of DNA chain synthesis, increased termination of RNA chain synthesis, or decreased cell proliferation, or any combination thereof, to the cell.

In a related aspect, the cell is a eukaryotic cell. In a related aspect, the eukaryotic cell is a tumor cell, or is infected by a virus or a foreign DNA.

In one aspect, disclosed herein is a pharmaceutical composition comprising a nucleoside analog for example but not limited to ddhA, ddhG, ddhU, ddh-deoxy-A, ddh-deoxy-G, ddh-deoxy-T, or a nucleoside analog derived from a nucleotide analog produced by a pVip, wherein the amino acid sequence of the pVip is set forth in any one of SEQ ID NOs: 409-789 or a homologue thereof comprising at least 80% homology to the amino acid sequence set forth in any one of SEQ ID NOs: 409-789, or wherein the pVip is encoded by a pVip gene comprising the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408, or any combination of nucleoside analogs thereof; and a pharmaceutical acceptable carrier. In a related aspect, disclosed herein is a pharmaceutical composition comprising a combination of nucleoside analogs. In a further related aspect, nucleoside analogs for example but not limited to ddhA, ddhG, ddhU, ddh-deoxy-A, ddh-deoxy-G, and ddh-deoxy-T or a combination thereof, may be comprised in a pharmaceutical composition in combination with nucleoside analogs ddhC or ddh-deoxy-C or a combination thereof.

In one aspect, disclosed herein is a method for treating a disease in a subject in need thereof, the method comprising administering to the subject a composition comprising a prokaryotic viperin homolog (pVip), a nucleic acid construct comprising a pVip gene, or a cell expressing a pVip, wherein the amino acid sequence of the pVip is set forth in any one of SEQ ID NOs: 409-789 or a homologue thereof comprising at least 80% homology to the amino acid sequence set forth in any one of SEQ ID NOs: 409-789, or wherein the pVip gene comprises the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408.

In one aspect, disclosed herein is a method of terminating polynucleotide chain synthesis in a cell, the method comprising introducing into the cell a prokaryotic viperin homolog (pVip), or expressing in the cell a pVip gene, wherein the amino acid sequence of the pVip is set forth in any one of SEQ ID NOs: 409-789 or a homologue thereof comprising at least 80% homology to the amino acid sequence set forth in any one of SEQ ID NOs: 409-789, or wherein the pVip gene comprises the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408.

In one aspect, disclosed herein is a method of producing a nucleoside or a nucleotide analog, the method comprising: (a) introducing a pVip, or a nucleic acid construct encoding a pVip into a cell, wherein the pVip produces a nucleoside analog or a nucleotide analog; (b) purifying the nucleoside analog or nucleotide analog from the cell; wherein the pVip is set forth in any one of SEQ ID NOs: 409-789 or a homologue thereof comprising at least 80% homology to the amino acid sequence set forth in any one of SEQ ID NOs: 409-789, or wherein the pVip is encoded by a pVip gene comprising the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408; thus producing a nucleoside analog or a nucleotide analog.

In a related aspect, when the pVip produces a nucleotide analog, the method further comprises: (c) dephosphorylating the nucleotide analog. In a related aspect, examples of the nucleotide analogs or nucleoside analogs include, but are not limited to, ddhUTP, ddhGTP, ddhATP, ddhGDP, ddhUDP, ddhUMP, ddhGMP, ddh-deoxy-GTP, ddh-deoxy-ATP, ddh-deoxy-TTP, ddhU, ddhG, ddhA, ddh-deoxy-G, ddh-deoxy-A, and ddh-deoxy-T. In a further related aspect, examples of the nucleotide analogs or nucleoside analogs include, but are not limited to, ddhUTP, ddhGTP, ddhATP, ddhCTP, ddhGDP, ddhUDP, ddhUMP, ddhCMP, ddhGMP, ddh-deoxy-GTP, ddh-deoxy-ATP, ddh-deoxy-TTP, ddh-deoxy-CTP, ddhU, ddhG, ddhA, ddhC, ddh-deoxy-G, ddh-deoxy-A, ddh-deoxy-T, and ddh-deoxy-C.

In a related aspect, the method further comprises introducing into the cell pVip co-factors, or pVip substrates, or any combination thereof.

In one aspect, disclosed herein is a method of producing a nucleoside analog or a nucleotide analog in vitro, the method comprising: (a) providing an isolated prokaryotic viperin homolog (pVip) in vitro; (b) mixing the isolated pVip with a pVip nucleotide substrate and co-factors; (c) purifying a nucleoside analog or a nucleotide analog produced in step (b); wherein the amino acid sequence of the pVip is set forth in any one of SEQ ID NOs: 409-789 or a homologue thereof comprising at least 80% homology to the amino acid sequence set forth in any one of SEQ ID NOs: 409-789, or wherein the pVip is encoded by a pVip gene comprising the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408; thus producing a nucleoside analog or a nucleotide analog.

In one aspect, disclosed herein is a nucleic acid construct comprising a polynucleotide encoding a prokaryotic viperin homolog (pVip), wherein the amino acid sequence of the pVip is set forth in any one of SEQ ID NOs: 409-789 or a homologue thereof comprising at least 80% homology to the amino acid sequence set forth in any one of SEQ ID NOs: 409-789, or wherein the pVip is encoded by a pVip gene comprising the sequence set forth in SEQ ID Nos: 3-383 or SEQ ID Nos: 384-408 or a homologue thereof comprising at least 80% identity to the nucleotide sequence set forth in any of SEQ ID Nos: 3-383 or SEQ ID Nos: 384-408; and a non-naturally occurring regulatory element operably linked to the polynucleotide.

In a related aspect, the regulatory element comprises a cis-acting regulatory element for directing expression of the polynucleotide, or a transmissible element for directing transfer of the polynucleotide from one cell to another, or a recombination element for integrating the polynucleotide into a genome of a cell transfected with the construct, or an element providing episomal maintenance of the construct within a cell transfected with the construct, or any combination thereof.

In one aspect, disclosed herein is a transmissible genetic element or an expression vector comprising a nucleic acid construct described herein. In one aspect, disclosed herein is an isolated cell expressing a nucleic acid construct, or a transmissible genetic element disclosed herein.

In one aspect, disclosed herein is a method for identifying a compound comprising anti-viral activity, the method comprising steps of: (a) introducing into a cell a prokaryotic viperin homolog (pVip), or expressing in a cell a pVip gene; (b) contacting the cell of step (a) with a virus; (c) measuring viral resistance of the cell of step (b); (d) screening the cell of step (c) that demonstrate viral resistance, for nucleotide or nucleoside compounds not present in control cell to which the pVip was not introduced; (e) analyzing the compound or compounds identified in step (d) for anti-viral activity; thereby identifying a compound comprising anti-viral activity.

In a related aspect, measuring viral resistance of step (c) comprises comparing cell viability, phage lysogeny, phage genomic replication, phage genomic degradation, or a combination thereof, between the cells of step (b) and control cells which do not express an endogenous or exogenous pVip. In a related aspect, the screening of step (d) comprises analyzing the cytosolic fraction of said bacterial cells by liquid chromatography (LC), by mass spectrometry (MS), or by a combination of both.

In one aspect, disclosed herein is a method of identifying a compound comprising anti-viral activity, the method comprising steps of: (a) expressing a prokaryotic viperin homolog (pVip) in a cell; (b) purifying said pVip from the said cell; (c) adding a nucleotide substrate, and/or pVip co-factors to said pVip in vitro; (d) purifying compound(s) that result from step (c); (e) analyzing said purified compound(s) to identify their chemical identity; (f) adding the compounds identified in step (e), or a modified version thereof, to a cell, and (g) measuring viral resistance of said cell of step (f), wherein increased viral resistance is indicative of said compound having anti-viral activity; thus, identifying a compound comprising anti-viral activity.

In one aspect, disclosed herein is a method of identifying a prokaryotic viperin homolog (pVip), the method comprising: (a) searching a prokaryotic protein dataset for proteins comprising at least 25% homology to a eukaryotic viperin; (b) clustering the genes encoding the proteins comprising at least 25% homology from step (a) into gene clusters; (c) calculating a defense score for each gene cluster, wherein a defense score above a predetermined threshold is indicative of the proteins encoded by the genes of said cluster being pVips; thus identifying a pVip.

In a related aspect, the amino acid sequence of the eukaryotic pVip comprises an amino acid sequence set forth in any of SEQ ID NOs: 2, or 826-828. In a related aspect, the predetermined threshold of said defense score comprises a proportion of genes with defensive neighborhood (score 1) of 0.6, an average number of defense genes in the neighborhood (score 2) of 1.6, or a combination thereof.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The subject matter disclosed herein is particularly pointed out and distinctly claimed in the concluding portion of the specification. The prokaryotic viperin homologs (pVips) and method of producing and using thereof, together with objects, features, and advantages thereof, may best be understood by reference to the following detailed description when read with the accompanying drawings in which:

FIG. 3A shows the phylogenetic tree of the pVip genes disclosed herein. Branch colors correspond to major clades. Filled circles represent presence of nucleotide kinases. Purple circles: predicted thymidilate kinases; brown circles: predicted cytidilate kinases; blue circles: predicted adenylate kinases. Stars represent pVip genes that we have experimentally showed to have anti-phage activity. Colors of stars represent different defense phenotypes for different pVips. Red stars: anti T7 and anti P1/lambda activity; green star: anti T7 activity; light blue star: anti P1 and anti lambda activity. FIG. 3B shows the phylogenetic tree of pVip genes including sequences extracted from metagenomes. Branch colors correspond to major clades of FIG. 3A. Black branches are sequences from metagenomes.

FIGS. 5A and 5B show plaque assays of bacteria transformed with pVip9 (FIG. 5A) or pVip10 (FIG. 5B). The left panel shows WT MG1655 colonies. The right panel shows Keio ΔiscR colonies. Bacteria were challenged with phages SECPhi6, SECPhi17, SECPhi18, SECPhi27, SECPhi32, and T7 (dilutions from $10^{-3}$ to $10^{-8}$). A star indicates phages in which pVip anti-viral activity was observed. Shown is an experiment representative of triplicates.

FIG. 6A shows Keio ΔiscR control colonies transfected with MoaA. Three main defense phenotypes were observed for the different pVips: activity against P1 and lambda but not T7 (FIGS. 6B-6H) activity against T7 only (FIGS. 6I-6M), and activity against P1, lambda and T7 (FIGS. 6N-6Z). All experiments were performed at 37° C.

FIG. 7A shows in vivo anti-viral activity of pVip7 in solid plaque assays. The left panel shows colonies in which pVip7 expression was not induced. The right panel shows colonies in which pVip7 expression was induced by 1 mM IPTG. *B. subtilis* colonies were challenged with the following phages: SBSphiC, SPO1, rho14, spbeta, SPR, phi3T (dilution from $10^{-1}$ to $10^{-6}$ of the original stock). A star indicates phages for which pVip7 anti-viral activity was observed. Shown here is an experiment representative of triplicates. FIG. 7B shows in vivo anti-viral activity of pVip7 in a liquid infection assay using phage phi3T (MOI=0.1). Grey=non-infected controls, salmon=phage-infected bacteria in which pVip7 expression was not induced, red=phage-infected bacteria in which pVip7 expression was induced. Shown here is one representative experiment of triplicates.

FIG. 8A shows the experimental design of the assay. A GFP reporter operably linked to a T7 promoter was cloned into a plasmid and transfected to bacterial cells expressing the T7 RNAP. T7 polymerase is activated by a pLac promoter inducible by IPTG. pVips are activated by a pAra promoter inducible by arabinose. A plasmid cloned with MoaA instead of pVips was used as a control. Cells were first provided with arabinose and then IPTG, thus inducing first pVip and then T7 RNAP. The expressed T7 RNAP in turn transcribed GFP. It was reasoned that if T7 RNAP is sensitive to pVip products, the presumed chain terminator will be incorporated generating prematurely terminated transcripts, leading to reduced GFP translation and signal. FIGS. 8B-8G show the experimental results. FIG. 8B shows that activation of the control plasmid, expressing MoaA, did not affect GFP expression. FIGS. 8C-8G show that co-expression of pVip8, pVip9, pVip37, pVip46, and pVip63, respectively, affected GFP expression. Graphs represent GFP divided by optical density (OD) (A.U). Grey curves indicate no GFP induction (no IPTG), green curves indicate GFP induction but no pVip induction (IPTG 0.01 mM, no arabinose), pink curves indicate GFP and pVip induction (IPTG 0.01 mM, arabinose 0.02%).

FIG. 9A shows extracted ion chromatogram for singly charged masses corresponding to ddhC (m/z 226.08223, retention time (RT) of 2.2 minutes), ddhCMP (m/z 306.04856, RT 9.7), ddhCTP (m/z 465.98122, RT 11.1), ddhUMP (m/z 307.03258, RT 8.7), ddhUTP (m/z 466.96524, RT 9.5), ddhGMP (m/z 266.08838, RT 9.8), and ddhGTP (m/z 505.98737, RT 10.6). X-axis depicts RT in minutes. Y axis, normalized ion intensity (arbitrary units). Normalization was performed on all pVips and MoaA samples, with maximal value set to 1.0. Representative of 3 replicates. FIG. 9B shows production of ddh nucleotide derivatives by pVips. Colored boxes depict detected compounds. Lighter color corresponds to compounds detected in a smaller quantity.

FIG. 12 shows quantification of ddh cytidine in lysates of cells expressing pVips. Detection and quantification of ddhC was performed using LC-MS with a synthesized chemical standard. For MoaA, the measurement was under the limit of detection. Bar graph represents average of three replicates, with individual data points overlaid.

DETAILED DESCRIPTION

Figure 1:
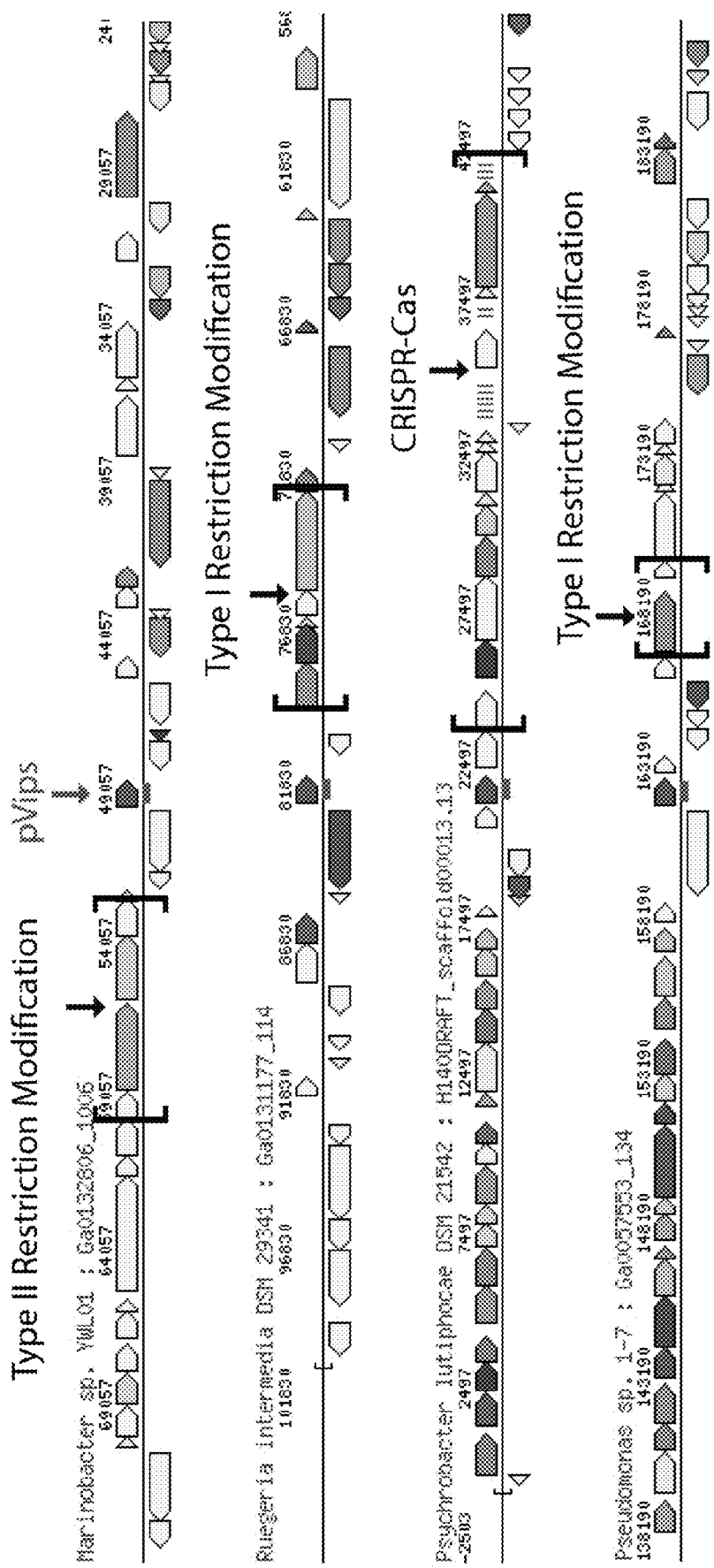
FIG. 1 shows an embodiment of the defensive genomic context of pVip genes. pVip genes are marked as red. Black arrows point to known anti-phage defense systems (bracketed by black brackets).
Figure 1:
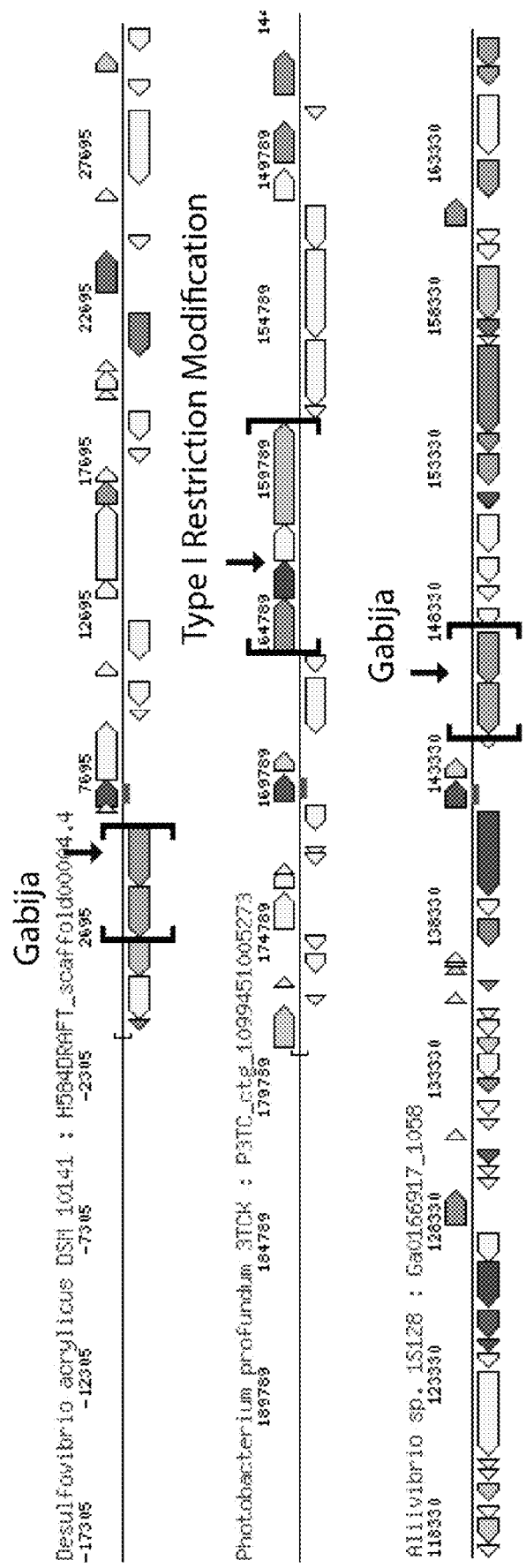

In the following detailed description, numerous specific details and embodiments are set forth in order to provide a thorough understanding of the proteins that produce anti-viral and anti-tumoral chain terminators disclosed herein, including methods for terminating polynucleotide chain synthesis in a cell, comprising introducing into bacteria a prokaryotic viperin homolog (pVip) or a product of said pVip, methods for treating a disease, methods for protecting bacteria, nucleic acid constructs comprising a pVip, cells comprising an ectopic pVip, food and food ingredients comprising a cell comprising a pVip, methods for producing food and food ingredients, and methods of identifying new pVips. In some instances, well-known methods, procedures, and components have not been described in detail so as not to obscure the present disclosure.

Prokaryotic Viperin Homologs (pVips)

In some embodiments, disclosed herein are prokaryotic viperin homologs (pVips). Viperin is a protein found in eukaryotic cells, usually localized in the endoplasmic reticulum where it is anchored via its N-terminal domain, though it is also found in other cell compartments. The presence of viperin in a cell was reported to inhibit replication of many DNA and RNA viruses in the cell, viruses including by not limited to chikungunya, human cytomegalovirus (HCV), hepatitis C virus, dengue, West Nile virus, sindbis virus, influenza, HIV LAI strain, and others. Viperin expression can be induced by the release of inflammatory signals, such as IFN-γ. Viperin was reported to down-regulate the concentration of viral structural proteins essential for viral assembling and maturation.

In eukaryotes, viperin catalyzes the conversion of the nucleotide cytidine triphosphate (CTP) to 3'-deoxy-3',4'-didehydro-CTP (ddhCTP) via a SAM-dependent radical mechanism. This RNA nucleotide analog lacks 4' hydrogen and the 3' hydroxyl group compared to CTP, and acts as a new type of polynucleotide chain terminator for viral RNA dependent polymerases. In vertebrate genomes, the kinase cytidylate monophosphate kinase 2 (CMPK2) is adjacent to the viperin. This kinase phosphorylates cytidine monophosphate (CMP) to CTP thus generating the substrate of vertebrate viperins. When tested as an anti-viral agent, 3'-deoxy-3',4'-didehydro-C (ddhC), was applied to cells, where it was phosphorylated by endogenous proteins producing ddhCTP, and directly inhibited replication of Zika virus in vivo.

The present application discloses prokaryotic enzymes showing sequence similarity to vertebrate viperin, and that produce modified nucleotides that function as anti-viral chain terminators. The present application also discloses methods to identify such prokaryotic enzymes out of other prokaryotic enzymes that show sequence similarity to the vertebrate viperin but do not have anti-viral activities. In some embodiments, bacterial and archeal enzymes showing sequence or functional similarity to eukaryotic viperin, are referred to herein as "prokaryotic viperin homologs" or "pVips".

While prokaryotic homologs of viperins share some sequence similarity with eukaryotic viperins, an initial similarity-based search revealed a very large number of enzymes. Only by using the method disclosed herein, it was possible to predict the defense score of these enzymes, and to reduce considerably the number of proteins to find true viperin homologs. The in vivo verification of the activity of such enzymes required a complex strategy to heterologously express enzymes in model organisms (including the use of a specific strains to increase iron-sulfur cluster production) and test them against a wide array of bacteriophages.

A skilled artisan would recognize that immune genes from eukaryotes, such a viperin gene, are expected to be different from immune genes in prokaryotes. This is corroborated, for example, by the almost absence of immune systems present in both eukaryotes and prokaryotes. Only the pAgo proteins have been described as being involved in both RNA interference in eukaryotes and plasmid restriction in prokaryotes. This stresses the unexpectedness to discover prokaryotic viperin homologs (pVips). The fact that no prokaryotic defense systems similar to the disclosed herein is known, i.e. a defense system comprising enzymes generating chain terminators, further highlights the unexpectedness of the of the present disclosure.

A skilled artisan will recognize that, in some embodiments, prokaryotes or prokaryotic cells comprise unicellular organisms lacking a membrane-restricted nucleus, mitochondria, or other eukaryotic-specific organelle. In some embodiments a prokaryote comprises Euryarchaeota. In some embodiments a prokaryote comprises Proteobacteria. In some embodiments a prokaryote comprises Firmicutes. In some embodiments a prokaryote comprises Bacteriodetes. In some embodiments a prokaryote comprises cyanobacteria.

In some embodiments, a prokaryote comprises a microbial cell such as bacteria, e.g., Gram-positive or Gram-negative bacteria. In some embodiments, a bacteria comprise Gram-negative bacteria or Negativicutes that stain negative in Gram stain. In some embodiments, a bacteria comprises gram-positive bacteria, gram-negative bacteria, or archaea.

In some embodiments, Gram-negative bacteria comprise *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis,*

*Bordetella* spp., *Borrelia burgdorferi, Branhamella catarrhalis, Brucella* spp., *Campylobacter* spp., *Chlamydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis.*

In some embodiments, the bacteria comprise gammaproteobacteria (e.g. *Escherichia coli, pseudomonas, vibrio* and *klebsiella*) or Firmicutes (belonging to class Negativicutes that stain negative in Gram stain).

In some embodiments, Gram-positive bacteria comprise *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *Streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis.*

In some embodiments the bacteria is a species selected from the group consisting of *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Campylobacter, Klebsiella, Frankia, Bartonella, Rickettsia, Shewanella, Serratia, Enterobacter, Proteus, Providencia, Brochothrix*, and *Brevibacterium.*

In some embodiments, a prokaryote comprises archaea. In some embodiments, the archaea is selected from a group comprising: Archaeoglobi, Methanobacteria, Methanococci, Methanomicrobia, Methanopyri, Nanohaloarchaea, Thermococci, Thermoplasmata, Thermoprotei, *Aeropyrum pernix, Cenarchaeum symbiosum, Haladaptatus paucihalophilus, Haloarcula quadrata, Halobacterium salinarum, Halobiforma haloterrestris, Haloferax larsenii, Haloferax volcanii, Haloquadratum walsbyi, Halorubrum salsolis, Metallosphaera sedula, Methanobrevibacter curvatus, Methanobrevibacter cuticularis, Methanobrevibacter filiformis, Methanobrevibacter gottschalkii, Methanobrevibacter oralis, Methanobrevibacter smithii, Methanobrevibacter thaueri, Methanobrevibacter woesei, Methanobrevibacter wolinii, Methanocella paludicola, Methanococcoides methylutens, Methanogenium boonei, Methanogeniumfrigidum, Methanogenium marinum, Methanosarcina acetivorans, Methanosarcina thermophila, Methanosphaera stadtmaniae, Methanothrix soehngenii, Methylosphaera hansonii, Nanoarchaeum equitans, Palaeococcus helgesonii, Picrophilus oshimae, Picrophilus torridus, Pyrococcus abyssi, Pyrococcus furiosus, Pyrococcus horikoshii, Pyrococcus woesei, Pyrodictium abyssi, Pyrolobus fumarii, Saccharolobus shibatae, Salinirubellus salinus, Thermococcus alcaliphilus, Thermococcus barophilus, Thermococcus celer, Thermococcus chitonophagus, Thermococcus gammatolerans, Thermococcus hydrothermalis, Thermococcus kodakarensis, Thermococcus litoralis, Thermococcus profundus*, and *Thermococcus stetteri.*

In some embodiments, a pVip comprises a prokaryotic protein comprising an amino acid sequence homologous to the sequence of a vertebrate viperin, for example but not limited to NCBI accession NP_542388.2 (SEQ ID NO: 2) or SEQ ID NOs 826-828.

A skilled artisan will recognize that there are several methods that can be used to determine sequence homology and/or sequence identity. Such techniques are thoroughly explained in the literature. See, for example, "A survey of sequence alignment algorithms for next-generation sequencing", Li H et al. Brief Bioinform. 2010 September; 11(5): 473-83; or "Sequence Alignment" Altschul S F et al in SourceHandbook of Discrete and Combinatorial Mathematics. 2017 Nov. 20.

In some embodiments, a pVip comprises an amino acid sequence comprising at least 10% sequence identity to eukaryotic viperin. In some embodiments, a pVip comprises an amino acid sequence comprising at least 20% sequence identity to eukaryotic viperin. In some embodiments, a pVip comprises an amino acid sequence comprising at least 25% sequence identity to eukaryotic viperin. In some embodiments, a pVip comprises an amino acid sequence comprising at least 30% sequence identity to eukaryotic viperin. In some embodiments, a pVip comprises an amino acid sequence comprising at least 35% sequence identity to eukaryotic viperin. In some embodiments, a pVip comprises an amino acid sequence comprising at least 40% sequence identity to eukaryotic viperin. In some embodiments, a pVip comprises an amino acid sequence comprising at least 45% sequence identity to eukaryotic viperin. In some embodiments, a pVip comprises an amino acid sequence comprising at least 50% sequence identity to eukaryotic viperin.

In some embodiments, a pVip comprises an amino acid sequence comprising at least 55% sequence identity to eukaryotic viperin. In some embodiments, a pVip comprises an amino acid sequence comprising at least 60% sequence identity to eukaryotic viperin. In some embodiments, a pVip comprises an amino acid sequence comprising at least 65% sequence identity to eukaryotic viperin. In some embodiments, a pVip comprises an amino acid sequence comprising at least 70% sequence identity to eukaryotic viperin. In some embodiments, a pVip comprises an amino acid sequence comprising at least 75% sequence identity to eukaryotic viperin. In some embodiments, a pVip comprises an amino acid sequence comprising at least 80% sequence identity to eukaryotic viperin. In some embodiments, a pVip comprises an amino acid sequence comprising at least 85% sequence identity to eukaryotic viperin. In some embodiments, a pVip comprises an amino acid sequence comprising at least 90% sequence identity to eukaryotic viperin. In some embodiments, a pVip comprises an amino acid sequence comprising at least 95% sequence identity to eukaryotic viperin. A skilled artisan would recognize that, in some embodiments, the terms "sequence identity" and "sequence homology" are used herein interchangeably having all the same elements and qualities.

In some embodiments, a pVip comprises an amino acid sequence comprising between about 15% to about 25% sequence identity to eukaryotic viperin. In some embodiments, a pVip comprises an amino acid sequence comprising between about 25% to about 35% sequence identity to eukaryotic viperin. In some embodiments, a pVip comprises an amino acid sequence comprising between about 35% to about 45% sequence identity to eukaryotic viperin. In some embodiments, a pVip comprises an amino acid sequence comprising between about 45% to about 15% sequence identity to eukaryotic viperin. In some embodiments, a pVip comprises an amino acid sequence comprising between about 55% to about 65% sequence identity to eukaryotic viperin. In some embodiments, a pVip comprises an amino acid sequence comprising between about 65% to about 75% sequence identity to eukaryotic viperin. In some embodiments, a pVip comprises an amino acid sequence comprising between about 75% to about 85% sequence identity to eukaryotic viperin. In some embodiments, a eukaryotic viperin is a human viperin.

In some embodiments, pVips are clustered according to their homology across prokaryotic species into pVip clusters. In some embodiments, a defense score is calculated for a pVip cluster. In some embodiments, pVip clusters have a "defense score" above a pre-determined threshold. In some embodiments, a defense score above a pre-determined threshold is indicative that a cluster of genes comprises pVips. As used herein, "defense score" is a value computed for a cluster of homologous genes, that is useful in predicting whether the genes of said cluster have antiviral functions. The computation of defense scores is detailed in Doron, S. et al. Systematic discovery of antiphage pVips in the microbial pangenome. Science (80). 4120, eaar4120 (2018), and WO 2018/220616 A2, which are incorporated herein by reference. Briefly, the neighborhood of a gene of interest (+/−10 genes) is screened for known defense genes. In some embodiments, enrichment of known defense genes in the vicinity of genes of a cluster is a predictor that said genes of said cluster perform anti-viral functions.

In some embodiments, a defense score is calculated for a cluster of genes comprising homology to a viperin. In some embodiments, a defense score comprises a first score indicating the proportion of genes with defensive neighborhood, termed also "Score 1". In some embodiments a defense score comprises a second score indicating the average number of defense genes in the neighborhood of the genes of said cluster, termed also "Score 2". In some embodiments, a defense score comprises a Score 1 and a Score 2.

In some embodiments, the enrichment of known defense genes in the vicinity to the genes of a cluster predicts that the cluster comprises pVips. In some embodiments, enrichment of known defense genes in the vicinity of genes of the cluster can be calculated as statistically significant enrichment beyond the background expected by chance. In some embodiments, enrichment of known defense genes in the vicinity of genes of the cluster, or a Score 1, can be calculated as a fraction of the total genes in the cluster that are found in the vicinity of known defense genes, wherein this fraction is above the fraction expected by chance.

In some embodiments, a fraction of at least 40% of the genes of a cluster predicts that the cluster comprises pVips. In some embodiments, a fraction of at least 50% of the genes of a cluster predicts that the cluster comprises pVips. In some embodiments, a fraction of at least 75% of the genes of a cluster predicts that the cluster comprises pVips. In some embodiments, a fraction of at least 100% of the genes of a cluster predicts that the cluster comprises pVips.

In some embodiments, the average number of known defense genes in the vicinity of the genes of a cluster, or a Score 2, provides an additional support to the prediction that the cluster comprises pVips. In some embodiments, an average of at least 0.75, 1, 1.5, 2, 3, 4, or 5 known defense genes in the vicinity to the genes of a cluster predicts that the cluster comprises pVips. In some embodiments, an average of between 0.75 and 1 known defense genes in the vicinity to the genes of a cluster predicts that the cluster comprises pVips. In some embodiments, an average of between 1 and 2 known defense genes in the vicinity to the genes of a cluster predicts that the cluster comprises pVips. In some embodiments, an average of between 2 and 5 known defense genes in the vicinity to the genes of a cluster predicts that the cluster comprises pVips.

In some embodiments, a gene encoding a pVip is located in the vicinity of a gene encoding a nucleotide kinase. In some embodiments, proximity to a nucleotide kinase gene predicts that a gene of interest is a pVip. In some embodiments, said nucleotide kinase is selected from a group comprising a Cytidine/Uridine Monophosphate Kinase 2 (CMPK2), a cytidylate kinase, a thymidylate kinase, a guanylate kinase, and an adenylate kinase. In some embodiments, the substrate of the nucleotide kinases is a ribonucleoside or a ribonucleotide. In some embodiments, the substrate of the nucleoside kinases is a deoxy-ribonucleoside or a deoxy-ribonucleotide.

In some embodiments, pVips produce nucleotide analogs. In some embodiments, pVips produce nucleoside analogs. In some embodiment, a pVip produces 3'-deoxy-3',4'-didehydro (ddh) ATP. In some embodiment, a pVip produces ddhGTP. In some embodiment, a pVip produces ddhCTP. In some embodiment, a pVip produces ddhUTP. In some embodiment, a pVip produces ddhGDP. In some embodiment, a pVip produces ddhUDP. In some embodiment, a pVip produces ddhCDP. In some embodiment, a pVip produces ddhGMP. In some embodiment, a pVip produces ddhUMP. In some embodiment, a pVip produces ddhCMP. In some embodiment, a pVip produces ddh-deoxy-ATP. In some embodiment, a pVip produces ddh-deoxy-GTP. In some embodiment, a pVip produces ddh-deoxy-CTP. In some embodiment, a pVip produces ddh-deoxy-TTP. In some embodiment, a pVip produces ddhA. In some embodiment, a pVip produces ddhG. In some embodiment, a pVip produces ddhC. In some embodiment, a pVip produces ddhU.

In some embodiments, pVips produce nucleotide analogs that are different than the above ddhATP, ddhGTP, ddhCTP, ddhUTP, ddh-deoxy-ATP, ddh-deoxy-GTP, ddh-deoxy-CTP, ddh-deoxy-TTP.

In some embodiments, a pVip produces a combinations of nucleoside analogs. In some embodiments, a pVip produces a combination of nucleotide analogs. In some embodiments, a pVip produces a combination of nucleoside and nucleotide analogs. In some embodiments, disclosed herein is a pVip.

In some embodiments a pVip comprises any of the pVips provided in Table 1, Table 2, or Table 3. In some embodiments a pVip comprises an amino acid sequence comprising at least 80% sequence identity to an amino acid sequence selected from the group provided in SEQ ID Nos: 409-789. In some embodiments a pVip comprises any of the amino acid sequences set forth in SEQ ID Nos: 409-789. In some embodiments, a pVip comprises an amino acid sequence with at least 20%, with at least 30%, with at least 40%, at least 50%, or with at least 60% sequence identity to SEQ ID NO: 2. In some embodiments, a pVip comprises an amino acid sequence with at least 20%, with at least 30%, with at least 40%, at least 50%, or with at least 60% sequence identity to a vertebrate viperin.

TABLE 4 shows examples of protein and gene sequences of eukaryotic viperins.

| SEQ ID No | description | NCBI Accession number |
|---|---|---|
| 1 | human viperin gene | AF442151.1 |
| 2 | human viperin protein | NP_542388.2 |
| 826 | rat viperin protein | NP_620236.1 |
| 827 | mouse viperin protein | NP_067359.2 |
| 828 | zebra fish viperin protein | NP_001020727.1 |

In some embodiments the terms "prokaryotic viperin homolog", "pVip", "pVip protein", and "pVip polypeptide" are used herein interchangeably having all the same elements and qualities.

In some embodiments, a pVip comprises an amino acid sequence encoded by a polynucleotide sequence selected from SEQ ID Nos: 3-383. In some embodiments, a pVip comprises an amino acid sequence encoded by a polynucleotide sequence selected from the group provided in SEQ ID Nos: 384-408. In some embodiments, a pVip comprises an amino acid sequence encoded by a polynucleotide sequence comprising at least 80% identity to a polynucleotide sequence selected from SEQ ID Nos: 3-383. In some embodiments, a pVip comprises an amino acid sequence encoded by a polynucleotide sequence comprising at least 80% identity to a polynucleotide sequence selected from SEQ ID Nos: 384-408.

In some embodiments, a pVip comprises an amino acid sequence encoded by an amino acid sequence selected from SEQ ID Nos: 409-789. In some embodiments, a pVip comprises an amino acid sequence encoded by an amino acid sequence comprising at least 80% homology to an amino acid sequence selected from SEQ ID Nos: 409-789.

In some embodiments, a pVip gene comprises a gene encoding a pVip. In some embodiments, a pVip gene comprises a gene encoding a pVip, wherein said pVip amino acid sequence is set forth in any of SEQ ID NO: 409-789. In some embodiments, said pVip gene comprises a sequence with at least 20%, at least 30%, at least 40%, at least 50%, at least 60%, at least 70% to SEQ ID No: 1.

In some embodiments, a pVip comprises a fragment, a functional domain, or a polypeptide comprised in a pVip. In some embodiments, the pVip is selected from SEQ ID Nos: 409-789.

In some embodiments, a pVip provides a host cell with viral resistance. In some embodiments, viral resistance comprises resistance to foreign nucleic acid invasion, or anti-viral activity, or anti-phage activity, or anti-plasmid activity, or reduced plasmid transformation efficiency, or resistance to entry of a conjugation element, or increased resistance to horizontal gene transfer, or decreased DNA replication, or decreased RNA replication (for viruses with RNA genomes), or decreased RNA transcription, increased termination of DNA synthesis, or increased termination of RNA synthesis, or any combination thereof.

pVips and viperins are Radical-SAM enzymes that contain an iron sulfur cluster 4Fe-4S8. For such enzymes, the 4Fe-4S cluster is built by a complex of proteins and then carried into the apoenzyme making it an active holoenzyme. This metabolic step can require some specific interactions between the proteins that build the iron sulfur cluster and the pVip. Heterologous expression of iron-sulfur cluster enzymes such as viperins can thus be devoid of catalytic activity, if the cell in which the viperin is expressed does not express the iron sulfur clusters to high enough levels.

A skilled artisan would recognize that catalytic activity of metaloenzymes in heterologous hosts can be promoted by a number of strategies. For example, synthesis of iron sulfur cluster in the host can be promoted by deleting the regulator iscR in E. coli. Further, heterologous iron sulfur cluster operons can be expressed to promote iron sulfur cluster synthesis, for example by transfection with plasmids as pDB1282, which encodes the isc operon from Azotobacter vinelandii. A further strategy comprises expressing the protein in a more closely related organism from a phylogenetic point of view. Given the sensitivity to oxygen of iron-sulfur cluster proteins, growth in anaerobic conditions, as well as engineering electron transfer pathways into the host cells, are avenues that can also be followed to improve metaloenzymes activities. Further methods can be found, for example, in Shomar H, "Producing high-value chemicals in Escherichia coli through synthetic biology and metabolic engineering", ISBN number 978-90-8593-386-1.

Table 1, which is displayed at the end of this specification, shows 381 pVip genes, each with its correspondent IMG_id number, metagenome genome IMG_id number, genome or metagenome name, nucleic acid sequence, the clade to which it was clustered (see Example 2, and FIGS. 3A and 3B), and whether a kinase was found in its genomic neighborhood, and its SEQ ID NO. "IMG_id" refers to an identification number in the "Integrated Microbial Genomes and Metagenomes" database, https://img.jgi.doe.gov/.

Table 2, which is displayed at the end of this specification, shows 25 pVips experimentally shown to have anti-viral activity, each with its correspondent IMG_id number, metagenome or genome IMG_id number, genome or metagenome name, the codon-optimized sequence used for its expression (see Example 4), the clade to which it was clustered (see Example 2, and FIGS. 3A and 3B), whether a kinase was found in its genomic neighborhood, and its SEQ ID No.

Table 3, which is displayed at the end of this specification, shows 381 pVip proteins, each with its correspondent IMG_id number, metagenome or genome IMG_id number, genome or metagenome name, amino acid sequence, and SEQ ID No.

Nucleic Acid Constructs Encoding pVips

In some embodiments, disclosed herein is a nucleic acid construct encoding a pVip, said construct comprising a pVip gene. In some embodiments, said pVip gene comprises any of the pVip genes provided in Table 1 or Table 2. In some embodiments, said pVip gene comprises any of SEQ ID Nos: 3-383. In some embodiments, said pVip gene comprises any of SEQ ID Nos: 384-408. In some embodiments, said pVip gene comprises a nucleic acid sequence comprising at least 80% identity to a nucleic acid sequence selected from SEQ ID Nos: 3-383. In some embodiments, said pVip gene comprises a nucleic acid sequence comprising at least 80% identity to a nucleic acid sequence selected from SEQ ID Nos: 384-408. In some embodiments, a pVip gene comprises a nucleotide sequence comprised in any of SEQ ID Nos: 3-383 or in SEQ ID Nos: 384-408, or a nucleotide sequence encoding a fragment of any of SEQ ID Nos: 409-789.

In some embodiments, provided herein is a nucleic acid construct encoding a pVip, said nucleic acid construct comprising a pVip gene and a non-naturally occurring regulatory element operably linked. In some embodiments, said regulatory element comprises a cis-acting regulatory element for directing expression of said pVip gene, a transmissible element for directing transfer of said pVip gene from one cell to another, or a recombination element for integrating said pVip gene into a genome of a cell transfected with said construct, or an element providing episomal maintenance of said construct within a cell transfected with said construct, or any combination thereof.

In some embodiments, a nucleic acid construct comprises a regulatory element operably linked to said construct comprising a cis-acting regulatory element for directing expression of said pVip gene. In some embodiment, the nucleic acid sequence of the regulatory element is from the same species of the pVip gene. In some embodiment, the nucleic acid sequence of the regulatory element is not from the same species as the pVip gene. In some embodiment, the nucleic acid sequence of the regulatory element is not from the donor species of the pVip gene. In some embodiment, when a host cell comprises a pVip gene, the nucleic acid sequence of the regulatory element is from the host species.

In some embodiments, cis-acting regulatory elements include those that direct constitutive expression of a nucleic acid sequence. In some embodiments, cis-acting regulatory elements comprise those that direct inducible expression of the nucleic acid sequence only under certain conditions.

Constitutive promoters suitable for use with some embodiments of the nucleic acid constructs disclosed herein are promoter sequences which are active under most environmental conditions and most types of cells such as the cytomegalovirus (CMV) and Rous sarcoma virus (RSV). Inducible promoters suitable for use with some embodiments of PVip constructs disclosed herein, include for example but not limited to the tetracycline-inducible promoter (Zabala M, et al., Cancer Res. 2004, 64(8): 2799-804) or pathogen-inducible promoters. Such promoters include those from pathogenesis-related proteins (PR proteins), which are induced following infection by a pathogen.

According to some embodiments, the promoter is a bacterial nucleic acid (e.g., expression) construct. A skilled artisan would appreciate that bacterial promoter encompasses any DNA sequence capable of binding bacterial RNA polymerase and initiating the downstream (3') transcription of a coding sequence into mRNA. A promoter can have a transcription initiation region, which is usually placed proximal to the 5' end of the coding sequence. This transcription initiation region typically includes an RNA polymerase binding site and a transcription initiation site. A bacterial promoter can also have a second domain called an operator, which can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence.

A non-limiting example of a gene activator protein is the catabolite activator protein (CAP), which helps initiate transcription of the lac operon in *Escherichia coli* (Raibaud et al. (1984) Annu. Rev. Genet. 18:173). Regulated expression can therefore be either positive or negative, thereby either enhancing or reducing transcription. Other examples of positive and negative regulatory elements are well known in the art. Various promoters that can be included in the protein expression system include, but are not limited to, a T7/LacO hybrid promoter, a trp promoter, a T7 promoter, a lac promoter, and a bacteriophage lambda promoter.

Any suitable promoter can be used with the pVips disclosed herein, including the native promoter or a heterologous promoter. In some embodiments, the promoter is a naturally occurring pVip promoter. In some embodiments, the promoter is a non-naturally occurring, or a heterologous pVip promoter. Heterologous promoters can be constitutively active or inducible. A non-limiting example of a heterologous promoter is given in U.S. Pat. No. 6,242,194 to Kullen and Klaenhammer, which is incorporated herein in full. In some embodiments, the promoter comprises a pARA promoter. In some embodiments, the promoter comprises a pHypraspank promoter. In some embodiments, a pARA promoter is induced by arabinose. In some embodiments, a pHypraspank promoter is induced by IPTG.

Sequences encoding metabolic pathway enzymes provide particularly useful promoter sequences. Examples include promoter sequences derived from sugar metabolizing enzymes, such as galactose, lactose (lac) (Chang et al. (1987) Nature 198:1056), and maltose. Additional examples include promoter sequences derived from biosynthetic enzymes such as tryptophan (trp) (Goeddel et al. (1980) Nucleic Acids Res. 8:4057; Yelverton et al. (1981) Nucleic Acids Res. 9:731; U.S. Pat. No. 4,738,921; EPO Publication Nos. 36,776 and 121,775). The beta-lactamase (bla) promoter system (Weissmann, (1981) "The Cloning of Interferon and Other Mistakes," in Interferon 3 (ed. I. Gresser); bacteriophage lambda PL (Shimatake et al. (1981) Nature 292:128); the arabinose-inducible araB promoter (U.S. Pat. No. 5,028,530); and T5 (U.S. Pat. No. 4,689,406) promoter systems also provide useful promoter sequences. See also Balbas (2001) Mol. Biotech. 19:251-267, where *E. coli* expression systems are discussed.

In addition, synthetic promoters that do not occur in nature also function as bacterial promoters. For example, transcription activation sequences of one bacterial or phage promoter can be joined with the operon sequences of another bacterial or phage promoter, creating a synthetic hybrid promoter (U.S. Pat. No. 4,551,433). For example, the tac (Amann et al. (1983) Gene 25:167; de Boer et al. (1983) Proc. Natl. Acad. Sci. 80:21) and trc (Brosius et al. (1985) J. Biol. Chem. 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-β-D-galactoside (IPTG). Furthermore, bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The phage T7 RNA polymerase/ promoter system is an example of a coupled promoter system (Studier et al. (1986) J. Mol. Biol. 189:113; Tabor et al. (1985) Proc. Natl. Acad. Sci. 82:1074). In addition, a hybrid promoter can also be comprised of a phage promoter and an E. coli operator region (EPO Publication No. 267, 851).

The nucleic acid construct can additionally contain a nucleic acid sequence encoding the repressor or the inducer for that promoter. For example, an inducible construct can regulate transcription from the Lac operator (LacO) by expressing the nucleotide sequence encoding the LacI repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., lambda CI857, rendering lambda pL thermo-inducible, or lambda CI+, rendering lambda pL chemo-inducible) can be employed.

In the construction of the construct, in some embodiments, the promoter is positioned approximately the same distance from the heterologous transcription start site as it is from the transcription start site in its natural setting. As is known in the art, however, some variation in this distance can be accommodated without loss of promoter function.

According to some embodiments, the nucleic acid construct includes a promoter sequence for directing transcription of the nucleic acid sequence in the cell in a constitutive or inducible manner. In some embodiments, the expression of the pVip genes disclosed herein can be transient or consistent, episomal or integrated into the chromosome of a host cell. According to some embodiments, the expression is on a transmissible genetic element.

The nucleic acid construct disclosed herein may further include additional sequences which render this construct suitable for replication and integration in prokaryotes, eukaryotes, or both (e.g., shuttle vectors). In some embodiments, the nucleic acid construct comprises a recombination element for integrating the pVip gene into the genome of a cell transfected with the construct. A skilled artisan would appreciate that the term "recombination element" encompasses a nucleic acid sequence that allows the integration of the polynucleotide in the genome of a cell (e.g. bacteria) transfected with the construct.

In some embodiments, the nucleic acid construct comprises an element providing episomal maintenance of said construct within a cell transfected with said construct.

In some embodiments, a construct may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

In some embodiments, the nucleic acid construct provides a host cell with viral resistance. In some embodiments, viral resistance comprises resistance to foreign nucleic acid invasion, or anti-viral activity, or anti-phage activity, or anti-plasmid activity, or reduced plasmid transformation efficiency, or resistance to entry of a conjugation element, or increased resistance to horizontal gene transfer, or decreased DNA replication, or decreased RNA transcription, increased termination of DNA synthesis, or increased termination of RNA synthesis, or any combination thereof.

In some embodiments, the nucleic acid construct further comprises a transmissible element for directing transfer of said nucleic acid sequence from one cell to another. In some embodiments, a pVip gene is on a transmissible genetic element. In some embodiments, a pVip gene selected from a gene provided in Table 1, Table 2, or comprising any of SEQ ID Nos: 3-383, or SEQ ID Nos: 384-408 is on a transmissible genetic element.

A skilled artisan would appreciate that the term "transmissible element" or "transmissible genetic element", which are interchangeably used, encompasses a polynucleotide that allows the transfer of the nucleic acid sequence from one cell to another, e.g. from one bacterium to another.

According to some embodiments, a transmissible genetic element comprises a conjugative genetic element or mobilizable genetic element. In some embodiments, a transmissible genetic element comprises a conjugative genetic element. In some embodiments, a transmissible genetic element comprises a mobilizable genetic element. The skilled artisan would appreciate that a "conjugative plasmid" encompasses a plasmid that is transferred from one cell (e.g. bacteria) to another during conjugation, and the term "mobilizable element" encompasses a transposon, which is a DNA sequence that can change its position within the genome.

In some embodiments, a nucleic acid construct disclosed herein, comprises an expression vector. In some embodiments, an "expression vector" or a "vector", used interchangeably herein, comprises and expresses a pVip gene encoding a pVip disclosed herein. In some embodiments, expression comprises transient expression. In some embodiments, expression comprises constitutive expression. In some embodiments, expression is from an episomal nucleic acid sequence. In some embodiments, expression is from a nucleic acid sequence integrated into the chromosome of the cell. According to specific embodiments, the expression is on a transmissible genetic element.

In some embodiments, provided herein is a transmissible genetic element comprising a nucleic acid construct comprising a pVip gene. In some embodiments, disclosed herein is an expression vector comprising a nucleic acid construct comprising a pVip gene.

According to some embodiments, a construct further comprises a recombination element for integrating the pVip gene into a genome of cell transfected with the construct. A skilled artisan would appreciate that the term "recombination element" encompasses a polynucleotide that allows the integration of the nucleic acid sequence in the genome of a cell (e.g. bacteria) transfected with the construct.

In addition, typical constructs may also, in certain embodiments, contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

According to some embodiment, the nucleic acid construct comprises a plurality of cloning sites for ligating a nucleic acid sequence of a pVip gene, such that it is under transcriptional regulation of the regulatory elements.

Selectable marker genes that ensure maintenance of a construct in a host cell can also be included in the construct. In some embodiments, selectable markers include those which confer resistance to drugs such as ampicillin, chloramphenicol, erythromycin, kanamycin (neomycin), and tetracycline (Davies et al. (1978) Annu. Rev. Microbiol. 32:469). Selectable markers can also allow a cell to grow on minimal medium, or in the presence of toxic metabolite and can include biosynthetic genes, such as those in the histidine, tryptophan, and leucine biosynthetic pathways.

Other than containing the necessary elements for the transcription and translation of the inserted coding sequence, the expression construct of some embodiments can also include sequences engineered to enhance stability, production, purification, yield or toxicity of the expressed polypeptide. Where appropriate, the nucleic acid sequences may be optimized for increased expression in the transformed organism. For example, the nucleic acid sequences can be synthesized using preferred codons for improved expression.

Introduction of pVips into Cells

Various methods known within the art can be used to introduce a pVip into a cell. In some embodiments, introducing a pVip into a cell comprises introducing a pVip polypeptide into a cell. In some embodiments, introducing a pVip into a cell comprises introducing a nucleic acid construct encoding a pVip gene into a cell. Methods for introducing a nucleic acid construct or a polypeptide into a cell are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, natural or induced transformation, lipofection, electroporation and infection with recombinant viral vectors. In addition, see U.S. Pat. Nos. 5,464,764 and 5,487,992 for positive-negative selection methods, which are incorporated herein.

Some methods of introducing a construct or constructs into bacterial cells include for example conventional transformation or transfection techniques, or by phage-mediated infection. A skilled artisan would appreciate that the terms "transformation", "transduction", "conjugation", and "protoplast fusion" are intended to encompass a variety of art-recognized techniques for introducing foreign nucleic acid (e.g., DNA) into a cell, such as calcium chloride co-precipitation. A skilled artisan would appreciate that introduction of a construct or constructs into a bacterial cell, may in certain embodiments, result in expression of a polypeptide or polypeptides encoded by the construct or constructs.

Introduction of nucleic acids by phage infection offers several advantages over other methods such as transformation, since higher transfection efficiency can be obtained due to the infectious nature of phages. These methods are especially useful for rendering bacteria more sensitive to phage attack for antibiotics purposes as further described hereinbelow.

It will be appreciated that a pVip can be introduced directly into the cell (e.g., bacterial cell) and not via recombinant expression to confer viral resistance. Thus, according to some embodiments, disclosed herein are isolated pVips or functional fragments thereof as described herein.

In some embodiments, a pVip can be introduced directly into the cell (e.g., bacterial cell) and not via recombinant expression, for example to confer viral resistance. In some embodiments, said pVip comprises a pVip provided in Table 3, or any of SEQ ID Nos: 409-789. In some embodiments, viral resistance comprises resistance to foreign nucleic acid invasion, to at least to one phage infection, resistance to plasmid transformation, resistance to entry of a conjugative element, or any combination thereof.

In some embodiments, a pVip or a pVip gene is introduced into a cell together with co-factors. In some embodiments, these co-factors are needed for pVip proper functioning. In some embodiments, said co-factors comprise an s-adenosyl methionine. In some embodiments, said co-factors comprise the pVip specific substrate. In some embodiments, said specific substrates are selected from a group comprising: ATP, CTP, GTP, TTP, or UTP, or any combination thereof.

In some embodiments, the cell to which a pVip is introduced is a eukaryotic cell. In some embodiments, the eukaryotic cell is a tumor cell. In some embodiments, the cell to which a pVip is introduced is a prokaryotic cell. In some embodiments, the prokaryotic cell is a bacterium or achaea. In some embodiments said bacteria is a gram-positive bacterium or a gram-negative bacterium.

Isolated Cells Comprising Prokaryotic Viperin Homologs (pVips)

In some embodiments, provided herein are isolated cells comprising an ectopic prokaryotic viperin homolog (pVip). In some embodiments, provided herein are cells genetically modified to express a pVip or a fragment thereof. pVips have been described in detail above. In some embodiments, a pVip comprises a pVip provided in Table 3, or any of SEQ ID Nos: 409-789. In some embodiments, a pVip comprises an amino acid sequence with at least 80% homology to pVip provided in Table 3, or any of SEQ ID Nos: 409-789. In some embodiments, the isolated cell comprises more than one pVip.

In some embodiments, the cell comprises an ectopic pVip gene. In some embodiments, the cell comprises a pVip gene selected from a gene provided in Table 1, Table 2, or comprising any of SEQ ID Nos: 3-383, or SEQ ID Nos: 384-408. In some embodiment the cell comprises more than one ectopic pVip gene. In some embodiments, the cell comprises endogenous pVip co-factors. In some embodiments, pVip co-factors are ectopically provided.

In some embodiments, a cell is genetically modified to express a pVip gene. In some embodiments, a cell is genetically modified to express a combination of more than one pVip gene. In some embodiments, the cell comprises anti-phage, anti-plasmid, or anti-phage and anti-plasmid resistance provided by pVip genes. In some embodiments, multiple pVips are comprised in a single nucleic acid construct. In some embodiments, multiple pVips are comprised in multiple nucleic acid constructs.

In some embodiments, an isolated cell comprising an ectopic pVip or a cell genetically modified to express a pVip comprises viral resistance. In some embodiments, an isolated cell comprising an ectopic pVip or a cell genetically modified to express a pVip comprises resistance to foreign nucleic acid invasion. In some embodiments, an isolated cell comprising an ectopic pVip or a cell genetically modified to express a pVip has an anti-viral activity. In some embodiments, an isolated cell comprising an ectopic pVip or a cell genetically modified to express a pVip has an anti-phage activity. In some embodiments, an isolated cell comprising an ectopic pVip or a cell genetically modified to express a pVip has an anti-plasmid activity, or reduced plasmid transformation efficiency. In some embodiments, an isolated cell comprising an ectopic pVip or a cell genetically modified to express a pVip comprises resistance to entry of a conjugation element. In some embodiments, an isolated cell comprising an ectopic pVip or a cell genetically modified to express a pVip has increased resistance to horizontal gene transfer.

In some embodiments, an isolated cell comprising an ectopic pVip or a cell genetically modified to express a pVip has decreased DNA replication. In some embodiments, an isolated cell comprising an ectopic pVip or a cell genetically modified to express a pVip has decreased RNA transcription. In some embodiments, an isolated cell comprising an ectopic pVip or a cell genetically modified to express a pVip has increased termination of DNA synthesis. In some embodiments, an isolated cell comprising an ectopic pVip or a cell genetically modified to express a pVip has increased termination of RNA synthesis. In some embodiments, an isolated cell comprising an ectopic pVip or a cell genetically modified to express a pVip has decreased proliferation. In some embodiments, an isolated cell comprising an ectopic pVip or a cell genetically modified to express a pVip has anti-tumor activity.

In some embodiments, the cell expressing a pVip (e.g., bacterial cell) is resistant to infection by at least one phage. In some embodiments the cell is resistant to at least one lytic phage. In some embodiments, the cell is resistant to at least one temperate (also referred as lysogenic) phage. In some embodiments, the cell is resistant to phage lysogeny. In some embodiments, the cell is resistant to phage DNA replication. In some embodiments, the cell is resistant to plasmid transformation. In some embodiments, the cell is resistant to infection by at least one phage and is resistant to plasmid transformation.

In some embodiments, a cell (e.g., a bacterial cell) does not express an endogenous pVip. In some embodiments, the cell expresses an endogenous pVip which is different than the ectopically expressed pVip. In some embodiments, the cell expresses an endogenous pVip similar to the ectopically expressed pVip. In some embodiments, when an endogenous pVip is similar to the ectopically expressed pVip, expression of the ectopic pVip increases the concentration of said pVip in the cell.

In some embodiments, a cell comprises a microbial cell such as bacteria. In some embodiments, a bacterium comprise Gram-negative bacteria or Negativicutes. In some embodiments, a bacterium comprises Gram-positive bacteria. In some embodiments, the cell comprises archaea.

Expression of the pVip genes or pVip enzymes would lead to production of nucleotide analogs or nucleoside analogs that can be used as DNA or RNA terminators. Examples of these analogs include, but are not limited to, ddhGTP, ddhATP, ddhUTP, ddh-deoxy-GTP, ddh-deoxy-ATP, and ddh-deoxy-TTP, ddhG, ddhA, ddhU, ddhGDP, ddhUDP, ddhUMP, ddhGMP, ddh-deoxy-G, ddh-deoxy-A, and ddh-deoxy-T, or combinations thereof, as well as modified versions of these analogs. In some embodiments, combinations of analogs that include, but are not limited to, ddhGTP, ddhATP, ddhUTP, ddh-deoxy-GTP, ddh-deoxy-ATP, and ddh-deoxy-TTP, ddhG, ddhA, ddhU, ddhGDP, ddhUDP, ddhUMP, ddhGMP, ddh-deoxy-G, ddh-deoxy-A, and ddh-deoxy-T, or combinations thereof, as well as modified versions of these analogs, additionally include ddhC, ddhCTP, ddhCMP, ddhCDP, ddh-deoxy-CTP, or ddh-deoxy-C, or a combination thereof.

These nucleotide or nucleoside analogs, or combinations thereof, can be applied in the various methods of uses as described herein. In one embodiment, a pVip may produce one nucleotide or nucleoside analog. In another embodiment, a pVip may produce multiple nucleotide or nucleoside analogs or a combination thereof. For example, a pVip may produce two kinds of nucleotide or nucleoside analogs or a combination thereof, or a pVip may produce three kinds of nucleotide or nucleoside analogs or a combination thereof, etc. In another embodiment, the DNA or RNA chain terminators, or anti-viral substances, produced by a pVip may not be any nucleotide or nucleoside analogs described herein.

Uses of a Prokaryotic Viperin Homolog (pVip)

Structural elements, such as amino acid sequences of prokaryotic viperin homologs (pVips) have been described in detail above, as well as the genes that encode these pVips. Uses of pVips is presented herein and exemplified in the Examples section below. In some embodiments, methods of use a pVip disclosed herein comprises use of a pVip, or a pVip gene. In some embodiments, said pVip comprises a pVip provided in Table 3, or any of SEQ ID Nos: 409-789. In some embodiments, said pVip comprises an amino acid comprising at least 80% homology to a pVip provided in Table 3, or to any of SEQ ID Nos: 409-789. In some embodiments, methods of use of a pVip comprise use of a combination of pVips. In some embodiments, said pVips is encoded by a polynucleotide having at least 80% identity to a gene provided in Table 1, Table 2, or to any of SEQ ID Nos: 3-383, or SEQ ID Nos: 384-408.

The methods of use of a nucleoside analog or pVip described herein include but are not limited to, methods of protecting a eukaryotic cell from viral infection, methods for decreasing viral replication in a eukaryotic cell, methods of decreasing RNA transcription, for example for viruses with RNA genomes. Further disclosed herein are methods of increasing termination of DNA synthesis, methods of increasing termination of RNA synthesis, methods of decreasing proliferation in a cell, methods of conferring tumor resistance to a cell. In some embodiment, said eukaryotic cell is selected from a human cell, a non-human animal cell, and a plant cell.

The methods of use of a pVip described herein include but are not limited to, methods of protecting bacteria from viral infection, methods of protecting bacteria from phage infection, methods of protecting bacteria from plasmid transformation, methods of protecting bacteria from conjugative elements, methods of protecting bacteria from any combination of phage infection, conjugative elements, and plasmid transformation, methods of producing bacteria resistant to phage infection, methods of protecting bacteria from horizontal gene transfer, methods of decreasing DNA replication, methods of decreasing RNA transcription, for example for viruses with RNA genomes.

Methods of use of a pVip described herein include but are not limited to methods of producing modified nucleosides and modified nucleotides, methods for the discovery of nucleotide chain terminator molecules, methods to produce nucleotide analogs, methods to produce nucleoside analogs, and methods to produce anti-viral compounds. In some embodiments, methods of use of pVips described herein produce nucleotide analogs and nucleoside analogs including for example but not limited to, methods to produce 3'-deoxy-3',4'-didehydro (ddh) ATP, ddhUTP, ddhGTP, ddhCTP, ddhGDP, ddh-CDP, ddhUDP, ddhUMP, ddhCMP, ddhGMP, ddh-deoxy-GTP, ddh-deoxy-ATP, ddh-deoxy-TTP, ddh-deoxy-CTP, ddhU, ddhG, ddhA, ddhC, ddh-deoxy-G, ddh-deoxy-A, ddh-deoxy-T, or ddh-deoxy-C, or combinations thereof. In some embodiments, methods of use of pVips described herein produce nucleotide analogs and nucleoside analogs including for example but not limited to, methods to produce 3'-deoxy-3',4'-didehydro (ddh) ATP, ddhUTP, ddhGTP, ddhGDP, ddhUDP, ddhUMP, ddhGMP, ddh-deoxy-GTP, ddh-deoxy-ATP, ddh-deoxy-TTP, ddhU, ddhG, ddhA, ddh-deoxy-G, ddh-deoxy-A, or ddh-deoxy-T, or combinations thereof.

In some embodiments, the nucleotide analogs and nucleoside analogs used in a method described herein comprise for example but are not limited to, 3'-deoxy-3',4'-didehydro (ddh) ATP, ddhUTP, ddhGTP, ddhCTP, ddhGDP, ddh-CDP, ddhUDP, ddhUMP, ddhCMP, ddhGMP, ddh-deoxy-GTP, ddh-deoxy-ATP, ddh-deoxy-TTP, ddh-deoxy-CTP, ddhU, ddhG, ddhA, ddhC, ddh-deoxy-G, ddh-deoxy-A, ddh-deoxy-T, or ddh-deoxy-C, or a combination thereof. In some embodiments, the nucleotide analogs and nucleoside analogs used in a method described herein comprise for example but are not limited to, 3'-deoxy-3',4'-didehydro (ddh) ATP, ddhUTP, ddhGTP, ddhGDP, ddhUDP, ddhUMP, ddhGMP, ddh-deoxy-GTP, ddh-deoxy-ATP, ddh-deoxy-TTP, ddhU, ddhG, ddhA, ddh-deoxy-G, ddh-deoxy-A, or ddh-deoxy-T, or a combination thereof. In some embodiments a method of use of a nucleotide analog or a nucleoside analog, or combinations thereof, comprises use of for example but not limited to any of 3'-deoxy-3',4'-didehydro (ddh) ATP, ddhUTP, ddhGTP, ddhGDP, ddhUDP, ddhUMP, ddhGMP, ddh-deoxy-GTP, ddh-deoxy-ATP, ddh-deoxy-TTP, ddhU, ddhG, ddhA, ddh-deoxy-G, ddh-deoxy-A, or ddh-deoxy-T, or a combination thereof. In some embodiments a method of use of a nucleotide analog or a nucleoside analog, or combinations thereof, comprises use of for example but not limited to any of 3'-deoxy-3',4'-didehydro (ddh) ATP, ddhUTP, ddhGTP, ddhGDP, ddhUDP, ddhUMP, ddhGMP, ddh-deoxy-GTP, ddh-deoxy-ATP, ddh-deoxy-TTP, ddhU, ddhG, ddhA, ddh-deoxy-G, ddh-deoxy-A, or ddh-deoxy-T, or a combination thereof, in combination with ddhC, ddh-deoxy-C, ddhCMP, ddh-CDP, ddh-CTP, or ddh-deoxy-CTP or a combination thereof.

In some embodiments, a nucleoside analog or nucleotide analog described herein is produced synthetically. In some embodiment, a synthetic nucleoside analog is used in methods described herein. In some embodiment, a synthetic nucleotide analog is used in methods described herein. In some embodiment, combinations of synthetic nucleoside analogs are used in methods described herein. In some embodiment, combinations of synthetic nucleotide analogs are used in methods described herein. In some embodiments, a combination comprises 2 or more nucleoside analogs. In some embodiments, a combination comprises 2 or more nucleotide analogs. In some embodiments, a combination comprises 3 or more nucleoside analogs. In some embodiments, a combination comprises 3 or more nucleotide analogs. In some embodiments, a nucleotide or nucleoside analog comprising ddhA, ddhG, ddhC, ddhU, ddh-deoxy-A, ddh-deoxy-G, ddh-deoxy-C, ddh-deoxy-O, ddhATP, ddhGTP, ddhCTP, ddhUTP, ddhGDP, ddhUMP, ddhCMP, ddh-deoxy-ATP, ddh-deoxy-GTP, ddh-deoxy-CTP, and/or ddh-deoxy-TTP, is produced synthetically. In some embodiments, a nucleotide or nucleoside analog comprising ddhA, ddhG, ddhU, ddh-deoxy-A, ddh-deoxy-G, ddh-deoxy-T, ddhATP, ddhGTP, ddhUTP, ddhGDP, ddhUMP, ddh-deoxy-ATP, ddh-deoxy-GTP, and/or ddh-deoxy-TTP, is produced synthetically.

Expression of the pVip genes or pVip enzymes would lead to production of nucleotide analogs or nucleoside analogs that can be used as DNA or RNA chain terminators. Examples of these analogs include, but are not limited to, ddhUTP, ddhGTP, ddhATP, ddhCTP, ddhGDP, ddh-CDP, ddhUDP, ddhUMP, ddhCMP, ddhGMP, ddh-deoxy-GTP, ddh-deoxy-ATP, ddh-deoxy-TTP, ddh-deoxy-CTP, ddhU, ddhG, ddhA, ddhC, ddh-deoxy-G, ddh-deoxy-A, ddh-deoxy-T, and ddh-deoxy-C, as well as modified versions of these analogs. In certain embodiments, analogs include, but are not limited to, ddhUTP, ddhGTP, ddhATP, ddhGDP, ddhUDP, ddhUMP, ddhGMP, ddh-deoxy-GTP, ddh-deoxy-ATP, ddh-deoxy-TTP, ddhU, ddhG, ddhA, ddh-deoxy-G, ddh-deoxy-A, or ddh-deoxy-T, as well as modified versions of these analogs. These nucleotide or nucleoside analogs can be applied in the various methods of uses as described herein. In one embodiment, a pVip may produce one kind of nucleotide or nucleoside analogs. In another embodiment, a pVip may produce multiple kinds of nucleotide or nucleoside analogs. For example, a pVip may produce two kinds of nucleotide or nucleoside analogs, or a pVip may produce three kinds of nucleotide or nucleoside analogs, etc. In another embodiment, the DNA or RNA chain terminators, or anti-viral substances, produced by a pVip may not include any nucleotide or nucleoside analogs described herein.

In one embodiment, the various methods of uses of pVip described herein may include the uses of a combination of (i) nucleotide or nucleoside analogs produced by one or more pVips, and (ii) the anti-viral substances (which do not include any nucleotide or nucleoside analogs) produced by one or more pVips.

Methods for Terminating Polynucleotide Chain Synthesis

In some embodiments, disclosed herein are methods for terminating polynucleotide chain synthesis in a cell, said methods comprising introducing into said cell a pVip or a fragment thereof. In some embodiments, disclosed herein are methods for terminating synthesis of polynucleotide (RNA or DNA) chains in a cell, said methods comprising expressing in a cell a pVip gene or a fragment thereof. In some embodiments, disclosed herein are methods for terminating polynucleotide chain synthesis in a cell, said methods comprising introducing into said cell a pVip gene selected from a gene provided in Table 1, Table 2, or comprising any of SEQ ID Nos: 3-383, or SEQ ID Nos: 384-408. In some embodiments, disclosed herein are methods for terminating polynucleotide chain synthesis in a cell, said methods comprising introducing more than one pVip to a cell.

As described herein, a pVip may produce one or more kinds of nucleotide or nucleoside analogs. In one embodiment, a pVip may produce one kind of nucleotide or nucleoside analogs. In another embodiment, a pVip may produce multiple kinds of nucleotide or nucleoside analogs. In another embodiment, the DNA or RNA chain terminators, or anti-viral substances, produced by a pVip may not include any nucleotide or nucleoside analogs described herein. In another embodiment, two or more pVips may be expressed together, wherein expression of one pVip leads to production of nucleotide or nucleoside analogs as polynucleotide chain terminators, and expression of another pVip leads to production of polynucleotide chain terminators which are not nucleotide or nucleoside analogs.

In some embodiments, a method for terminating synthesis of polynucleotide (RNA or DNA) chains comprises increasing the concentration of a chain terminator in a cell. In some embodiments, said chain terminator comprises a nucleoside or a nucleotide analog. In some embodiments, a pVip increases the concentration of a nucleoside or a nucleotide analog inside a cell. In some embodiments, examples of nucleoside or nucleotide analogs include, but are not limited to 3'-deoxy-3',4'-didehydro (ddh) ddhUTP, ddhGTP, ddhATP, ddhCTP, ddhGDP, ddh-CDP, ddhUDP, ddhUMP, ddhCMP, ddhGMP, ddh-deoxy-GTP, ddh-deoxy-ATP, ddh-deoxy-TTP, ddh-deoxy-CTP, ddhU, ddhG, ddhA, ddhC, ddh-deoxy-G, ddh-deoxy-A, ddh-deoxy-T, and ddh-deoxy-C, as well as modified versions of these analogs. In some embodiments, examples of nucleoside or nucleotide analogs include, but are not limited to 3'-deoxy-3',4'-didehydro (ddh) ddhUTP, ddhGTP, ddhATP, ddhGDP, ddhUDP, ddhUMP, ddhGMP, ddh-deoxy-GTP, ddh-deoxy-ATP, ddh-deoxy-TTP, ddhU, ddhG, ddhA, ddhC, ddh-deoxy-G, ddh-deoxy-A, and ddh-deoxy-T, as well as modified versions of these analogs.

In some embodiments, a method for terminating synthesis of polynucleotide (RNA or DNA) chains comprises increasing the concentration of a chain terminator in a cell by adding the chain terminator molecule externally. In some embodiments, said chain terminator comprises a nucleoside or a nucleotide analog. In some embodiments, the 3 phosphate groups of a nucleotide produced by a pVip are removed from the chain terminator so that it could enter cells. In some embodiments, a nucleoside analog comprises a nucleotide analog produced by a pVip without the phosphate residues. In some embodiments, a nucleoside analog derived from a nucleotide analog produced by a pVip comprises said nucleotide without the phosphate residues.

In some embodiments, disclosed herein are methods for preventing a viral infection with a pVip. In some embodiments, said phosphate-less nucleoside or nucleotide analog gets phosphorylated by endogenous kinases or by viral kinases after entering the cell. In some embodiments, examples of phosphate-less nucleosides or nucleotide analogs include, but are not limited to, 3'-deoxy-3',4'-didehydro (ddh) A, ddhG, ddhC, ddhU, ddh-deoxy-A, ddh-deoxy-G, ddh-deoxy-C, ddh-deoxy-T.

In some embodiments the pVip is expressed in the cell in which termination of polynucleotide chain synthesis is desired. In some embodiments, pVip is expressed in a heterologous expression system, purified, and supplied to the cell. In some embodiments, a pVip is supplied together with co-factors. In some embodiments, said co-factors comprise s-adenosyl methionine. In some embodiments, said co-factors comprise the pVip specific substrate. In some embodiments, said specific substrates are selected from a group comprising: ATP, CTP, GTP, UTP, or any combination thereof.

In some embodiments, the cell in which termination of polynucleotide chain synthesis is desired is a eukaryotic cell. In some embodiments, the eukaryotic cell is a tumor cell. In some embodiments, the cell in which termination of polynucleotide chain synthesis is desired is a prokaryotic cell. In some embodiments, the prokaryotic cell is a bacterium. In some embodiments said bacteria is a gram-positive bacterium or a gram-negative bacterium.

In some embodiments, termination of polynucleotide chain synthesis confers viral resistance to a cell. In some embodiments, termination of polynucleotide chain synthesis confers phage resistance to a cell. In some embodiments, termination of polynucleotide chain synthesis confers plasmid resistance to a cell. In some embodiments, termination of polynucleotide chain synthesis confers resistance to horizontal gene transfer to a cell. In some embodiments, termination of polynucleotide chain synthesis decreases DNA replication in a cell. In some embodiments, termination of polynucleotide chain synthesis decreases RNA transcription in a cell.

In some embodiments, termination of polynucleotide chain synthesis comprises increased termination of DNA chain synthesis. In some embodiments, termination of polynucleotide chain synthesis comprises increased termination of RNA chain synthesis. In some embodiments, termination of polynucleotide chain synthesis decreases proliferation of a cell. In some embodiments, termination of polynucleotide chain synthesis comprises an anti-tumor activity.

In some embodiments, terminating polynucleotide chain synthesis in a cell comprises reducing polynucleotide chain synthesis in a cell by at least 1%, by at least 2%, by at least 3%, by at least 4%, by at least 5%, by at least 6%, by at least 7%, by at least 8%, by at least 9%, by at least 10%, by at least 20%, by at least 30%, by at least 40%, by at least 50%, by at least 60%, by at least 70%, by at least 80%, by at least 90%, or by a 100%.

In some embodiments, terminating polynucleotide chain synthesis in a cell comprises reducing viral DNA replication. In some embodiments, terminating polynucleotide chain synthesis in a cell comprises reducing viral RNA chain synthesis. In some embodiments, terminating polynucleotide chain synthesis in a cell comprises reducing viral DNA or RNA chain synthesis without modifying DNA replication of the host cell.

In some embodiments, terminating polynucleotide chain synthesis in a cell comprises reducing eukaryotic DNA replication. In some embodiments, said eukaryotic cell is a tumor cell.

In some embodiments, terminating polynucleotide chain synthesis in a cell comprises reducing polynucleotide chain synthesis in a cell by between about 0% and about 10%. In some embodiments, terminating polynucleotide chain synthesis in a cell comprises reducing polynucleotide chain synthesis in a cell by between about 10% and about 20%. In some embodiments, terminating polynucleotide chain synthesis in a cell comprises reducing polynucleotide chain synthesis in a cell by between about 20% and about 30%. In some embodiments, terminating polynucleotide chain synthesis in a cell comprises reducing polynucleotide chain synthesis in a cell by between about 30% and about 40%. In some embodiments, terminating polynucleotide chain synthesis in a cell comprises reducing polynucleotide chain synthesis in a cell by between about 40% and about 50%.

In some embodiments, terminating polynucleotide chain synthesis in a cell comprises reducing polynucleotide chain synthesis in a cell by between about 50% and about 60%. In some embodiments, terminating polynucleotide chain synthesis in a cell comprises reducing polynucleotide chain synthesis in a cell by between about 60% and about 70%. In some embodiments, terminating polynucleotide chain synthesis in a cell comprises reducing polynucleotide chain synthesis in a cell by between about 70% and about 80%. In some embodiments, terminating polynucleotide chain synthesis in a cell comprises reducing polynucleotide chain synthesis in a cell by between about 80% and about 90%. In some embodiments, terminating polynucleotide chain synthesis in a cell comprises reducing polynucleotide chain synthesis in a cell by between about 90% and about 100%.

Methods for Treating a Disease

In some embodiments, disclosed herein is a method for treating a disease in a subject in need thereof, the method comprising administering to said subject a composition comprising a prokaryotic viperin homolog (pVip). In some embodiments, disclosed herein is a method for treating a disease in a subject in need thereof, the method comprising administering to said subject a composition comprising a nucleic acid construct comprising pVip gene. In some embodiments, disclosed herein is a method for treating a disease in a subject in need thereof, the method comprising administering to said subject a composition comprising a cell comprising a pVip gene. In some embodiments, disclosed herein is a method for treating a disease in a subject in need thereof, the method comprising administering to said subject a composition comprising a nucleoside or a nucleotide analog produced by a pVip. In some embodiments, disclosed herein is a method for treating a disease in a subject in need thereof, the method comprising administering to said subject a composition comprising a nucleoside comprising a nucleotide analog produced by a pVip without the phosphate residues.

In some embodiments, a nucleoside analog or nucleotide analog described herein is produced synthetically. In some embodiment, a synthetic nucleoside analog is used in the methods described herein. In some embodiment, a synthetic nucleotide analog is used in methods described herein.

In some embodiments, disclosed herein is a method for treating a disease in a subject in need thereof, the method comprising administering to said subject a composition comprising a nucleoside or a nucleotide analog produced by a pVip. In some embodiments, disclosed herein is a method for treating a disease in a subject in need thereof, the method comprising administering to said subject a composition comprising a nucleoside comprising a nucleotide analog produced by a pVip without the phosphate residues.

In some embodiments, said nucleoside or nucleotide analog comprises a DNA analog. In some embodiments, said nucleoside or nucleotide analog comprises an RNA analog. In some embodiments, said nucleotide analog comprises 3'-deoxy-3',4'-didehydro (ddh) ATP. In some embodiment, said nucleotide analog comprises ddhGTP. In some embodiment, said nucleotide analog comprises ddhCTP. In some embodiment, said nucleotide analog comprises ddhUTP. In some embodiment, said nucleotide analog comprises ddhUMP. In some embodiment, said nucleotide analog comprises ddhGMP. In some embodiment, said nucleotide analog comprises ddhCMP. In some embodiment, said nucleotide analog comprises ddhGDP. In some embodiment, said nucleotide analog comprises ddhCDP. In some embodiment, said nucleotide analog comprises ddhUDP. In some embodiment, said nucleotide analog comprises ddh-deoxy-ATP. In some embodiment, said nucleotide analog comprises ddh-deoxy-GTP. In some embodiment, said nucleotide analog comprises ddh-deoxy-CTP. In some embodiment, said nucleotide analog comprises ddh-deoxy-TTP. In some embodiments, said nucleoside analog comprises 3'-deoxy-3',4'-didehydro (ddh) Adenine (ddhA). In some embodiment, said nucleoside analog comprises ddhG (Guanine). In some embodiment, said nucleoside analog comprises ddhC (Cytosine). In some embodiment, said nucleoside analog comprises ddhU (Uracil). In some embodiment, said nucleoside analog comprises ddh-deoxy-A. In some embodiment, said nucleoside analog comprises ddh-deoxy-G. In some embodiment, said nucleoside analog comprises ddh-deoxy-C. In some embodiment, said nucleoside analog comprises ddh-deoxy-T. In some embodiments, said nucleoside or nucleotide analogs is produced by a pVip and is not one of the above-mentioned molecules.

In some embodiments, disclosed herein are methods for treating a viral infection with a pVip. In some embodiments, disclosed herein are methods for treating a viral infection with a nucleoside or nucleotide analog produced by a pVip. In some embodiments, disclosed herein are methods for treating a viral infection with a nucleoside comprising a nucleotide analog produced by a pVip without the phosphate residues. In some embodiments, disclosed herein are methods for preventing a viral infection with a pVip. In some embodiments, disclosed herein are methods for preventing a viral infection with a nucleoside analog produced by a pVip. In some embodiments, disclosed herein are methods for preventing a viral infection with a nucleoside comprising a nucleotide analog produced by a pVip without the phosphate residues. In some embodiments, disclosed herein are methods for preventing a viral infection with a pVip. In some embodiments, disclosed herein are methods for treating a virus-induced disease with a pVip. In some embodiments, disclosed herein are methods for treating a virus-induced disease with a nucleoside analog produced by a pVip.

In some embodiments, said viral infection comprises a respiratory viral infection (e.g. common cold, seasonal influenze). In some embodiments, said viral infection comprises a gastrointestinal viral infection. In some embodiments, said viral infection comprises a liver viral infection. In some embodiments, said viral infection comprises a nervous system viral infection. In some embodiments, said viral infection comprises a skin viral infection. In some embodiments, said viral infection comprises a sexually transmitted viral infection. In some embodiments, said viral infection comprises a placental viral infection. In some embodiments, said viral infection comprises a fetal viral infection. In some embodiments, examples of said viral infection include but are not limited to gastroenteritis, keratoconjunctivitis, pharyngitis, croup, pharyngoconjunctival fever, pneumonia, cystitis (Adenovirus); Hand, foot and mouth disease, pleurodynia, aseptic meningitis, pericarditis, myocarditis (Coxsackievirus); infectious mononucleosis, Burkitt's lymphoma, Hodgkin's lymphoma, nasopharyngeal carcinoma (Epstein-Barr virus); acute hepatitis (Hepatitis A virus); acute hepatitis, chronic hepatitis, hepatic cirrhosis, hepatocellular carcinoma (Hepatitis B virus); acute hepatitis, chronic hepatitis, hepatic cirrhosis, hepatocellular carcinoma (Hepatitis C virus); herpes labialis, cold sores—can recur by latency, gingivostomatitis in children, tonsillitis & pharyngitis in adults, keratoconjunctivitis (Herpes simplex virus, type 1); skin vesicles, mucosal ulcers, oral and/or genital ulcers, Aseptic meningitis (Herpes simplex virus, type 2); infectious mononucleosis, Cytomegalic inclusion disease, Premature birth, liver, lung and spleen diseases in the newborn, congenital seizures in the newborn (Cytomegalovirus); Kaposi sarcoma, multicentric Castleman disease, primary effusion lymphoma (Human herpesvirus, type 8); AIDS (HIV); influenza, Reye syndrome (Influenza virus); measles, postinfectious encephalomyelitis (Measles virus); mumps (mumps virus); hyperplastic epithelial lesions (common, flat, plantar and anogenital warts, laryngeal papillomas, epidermodysplasia verruciformis), cervical carcinoma, squamous cell carcinomas) (Human papillomavirus); croup, pneumonia, bronchiolitis, common cold (Parainfluenza virus); poliomyelitis (Poliovirus); rabies (fatal encephalitis) (rabies virus); bronchiolitis, pneumonia, influenza-like syndrome, severe bronchiolitis with pneumonia (Respiratory syncytial virus); congenital rubella, German measles (Rubella virus); and chickenpox, herpes zoster, Congenital varicella syndrome (Varicella-zoster virus).

In some embodiments, the viral infection is caused by viruses of human or non-human origin. In some embodiments, the viral infection is caused by modified or unmodified viruses that originate from animals or any foreign organism, for example, infection caused by SARS coronavirus, SARS coronavirus 2 etc.

A number of diseases and cancer are known to be caused by viruses. The International Committee on Taxonomy of Viruses (ICTV) has developed a classification system for viruses. As of 2019, 5560 species of viruses have been defined by ICTV. Viruses can also be classified into seven groups by the Baltimore classification, i.e. Group I: double-stranded DNA viruses (e.g. Adenoviruses, Herpesviruses, Poxviruses); Group II: single-stranded (or "sense") DNA viruses (e.g. Parvoviruses); Group III: double-stranded RNA viruses (e.g. Reoviruses); Group IV: single-stranded (sense) RNA viruses (e.g. Picornaviruses, Togaviruses, Coronavirus); Group V: single-stranded (antisense) RNA viruses (e.g.

Orthomyxoviruses, Rhabdoviruses); Group VI: single-stranded (sense) RNA viruses with DNA intermediate in life-cycle (e.g. Retroviruses); and Group VII: double-stranded DNA viruses with RNA intermediate in life-cycle (e.g. Hepadnaviruses). In some embodiments, viral infections can be produced by viruses such as, but are not limited to, norovirus; rotavirus; hepatitis virus A, B, C, D, or E; rabies virus, West Nile virus, enterovirus, echovirus, coxsackievirus, herpes simplex virus (HSV), HSV-2, varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enteovirus D68, severe acute respiratory syndrome (SARS) coronavirus, Middle East respiratory syndrome coronavirus, SARS coronavirus 2, Epstein-Barr virus, influenza virus, respiratory syncytical virus, polyoma viruses (such as JC virus, BK virus), Ebola virus, Dengue virus or any combination thereof.

In some embodiments, the viral infection is caused by viruses in the Baltimore classification Group I group of viruses: double-stranded DNA viruses (e.g. Adenoviruses, Herpesviruses, Poxviruses). In some embodiments, the viral infection is caused by viruses in the Baltimore classification Group II group of viruses: single-stranded (or "sense") DNA viruses (e.g. Parvoviruses). In some embodiments, the viral infection is caused by viruses in the Baltimore classification Group III group of viruses: double-stranded RNA viruses (e.g. Reoviruses). In some embodiments, the viral infection is caused by viruses in the Baltimore classification Group IV group of viruses: single-stranded (sense) RNA viruses (e.g. Picornaviruses, Togaviruses, Coronavirus). In some embodiments, the viral infection is caused by viruses in the Baltimore classification Group V of viruses: single-stranded (antisense) RNA viruses (e.g. Orthomyxoviruses, Rhabdoviruses). In some embodiments, the viral infection is caused by viruses in the Baltimore classification Group VI group of viruses: single-stranded (sense) RNA viruses with DNA intermediate in life-cycle (e.g. Retroviruses). In some embodiments, the viral infection is caused by viruses in the Baltimore classification Group VII group of viruses: double-stranded DNA viruses with RNA intermediate in life-cycle (e.g. Hepadnaviruses).

In some embodiments, treating a viral infection comprises protecting an organism from foreign nucleic acid invasion. In some embodiments, treating a viral infection comprises decreasing viral nucleic acid replication. In some embodiments, treating a viral infection comprises any of the viral infections disclosed herein.

A skilled artisan would appreciate that cancer cells divide relentlessly, and that for said division to occur the cell is intensely replicating its DNA. Therefore, nucleoside or nucleotide analogs decreasing DNA synthesis can inhibit DNA replication and cell division. In some embodiments, nucleoside or nucleotide analogs would also decrease RNA synthesis, thus inhibiting RNA replication/transcription and cell division. In some embodiments, disclosed herein are methods for treating cancer with a pVip. In some embodiments, disclosed herein are methods for treating cancer with a nucleoside or nucleotide analog produced by a pVip. In some embodiments, disclosed herein are methods for treating cancer with a nucleoside comprising a nucleotide analog produced by a pVip without the phosphate residues. In some embodiments, disclosed herein are methods for preventing a viral infection with a pVip.

In some embodiments, said cancer is selected from the group comprising a carcinoma, a sarcoma, a lymphoma, leukemia, a germ cell tumor, a blastoma, chondrosarcoma, Ewing's sarcoma, malignant fibrous histiocytoma of bone/osteosarcoma, osteosarcoma, rhabdomyosarcoma, heart cancer, brain cancer, astrocytoma, glioma, medulloblastoma, neuroblastoma, breast cancer, medullary carcinoma, adrenocortical carcinoma, thyroid cancer, Merkel cell carcinoma, eye cancer, gastrointestinal cancer, colon cancer, gallbladder cancer, gastric (stomach) cancer, gastrointestinal carcinoid tumor, hepatocellular cancer, pancreatic cancer, rectal cancer, bladder cancer, cervical cancer, endometrial cancer, ovarian cancer, renal cell carcinoma, prostate cancer, testicular cancer, urethral cancer, uterine sarcoma, vaginal cancer, head cancer, neck cancer, nasopharyngeal carcinoma, hematopoetic cancer, lymphoma, Non-hodgkin lymphoma, skin cancer, basal-cell carcinoma, melanoma, small cell lung cancer, non-small cell lung cancer, or any combination thereof.

In some embodiments, disclosed herein are methods for treating an autoimmune disease with a pVip. In some embodiments, disclosed herein are methods for treating an autoimmune disease with a nucleoside or nucleotide analog produced by a pVip. In some embodiments, disclosed herein are methods for treating an autoimmune disease with a nucleoside comprising a nucleotide analog produced by a pVip without the phosphate residues. In some embodiments, disclosed herein are methods for preventing a viral infection with a pVip.

In some embodiments, said autoimmune disease is selected from the group comprising achalasia, amyloidosis, ankylosing spondylitis, anti-gbm/anti-tbm nephritis, antiphospholipid syndrome, arthritis, autoimmune angioedema, autoimmune encephalomyelitis, autoimmune hepatitis, autoimmune myocarditis, autoimmune oophoritis, autoimmune orchitis, autoimmune pancreatitis, autoimmune retinopathy, autoimmune urticaria, Behcet's disease, celiac disease, chagas disease, chronic inflammatory demyelinating polyneuropathy (cidp), Cogan's syndrome, congenital heart block, Crohn's disease, dermatitis, dermatomyositis, discoid lupus, Dressler's syndrome, endometriosis, fibromyalgia, fibrosing alveolitis, granulomatosis with polyangiitis, Graves' disease, Guillain-Barre syndrome, herpes gestationis, immune thrombocytopenic purpura, interstitial cystitis (ic), juvenile arthritis, juvenile diabetes (type 1 diabetes), juvenile myositis (jm), Kawasaki disease, Lambert-Eaton syndrome, lichen planus, lupus, Lyme disease chronic, multiple sclerosis, myasthenia gravis, myositis, neonatal lupus, neutropenia, palindromic rheumatism, peripheral neuropathy, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, reactive arthritis, retroperitoneal fibrosis, rheumatic fever, rheumatoid arthritis, sarcoidosis, Schmidt syndrome, scleritis, scleroderma, Sjögren's syndrome, thrombocytopenic purpura, type 1 diabetes, ulcerative colitis, uveitis, vasculitis, and vitiligo.

In some embodiments, disclosed herein are methods for treating an immune disorder with a pVip. In some embodiments, disclosed herein are methods for treating an immune disorder with a nucleoside or nucleotide analog produced by a pVip. In some embodiments, disclosed herein are methods for treating an immune disorder with a nucleoside comprising a nucleotide analog produced by a pVip without the phosphate residues. In some embodiments, disclosed herein are methods for preventing a viral infection with a pVip. In some embodiments, said immune disorder is selected from a group comprising arthritis, host-versus-graft disease (HvGD), graft-versus-host disease (GvHD), inflammation, immunodeficiency, and autoimmune disorders.

It will be appreciated that the pVips, the pVip polynucleotides, the pVip nucleic acid constructs, the nucleoside or nucleotide analogs produced by pVips, or other agents can be provided to the individual with additional active agents to achieve an improved therapeutic effect as compared to treatment with each agent by itself. In some embodiments, additional active agents include anti-viral agents or anti-cancer drugs.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

A skilled artisan would appreciate that a "pharmaceutical composition" or a "pharmaceutical formulation" may encompass a preparation comprising a pVip, a nucleic acid construct comprising a pVip gene, a cell comprising nucleic acid construct comprising a pVip gene, or a nucleoside or a nucleotide produced by a pVip as described herein, or nucleoside comprising a nucleotide analog produced by a pVip without the phosphate residues. In some embodiments, disclosed herein are methods for preventing a viral infection with a pVip, with other chemical components such as physiologically suitable carriers and excipients. The purpose of a pharmaceutical composition or a pharmaceutical formulation is to facilitate administration of a compound to an organism.

In some embodiments, disclosed herein is a pharmaceutical composition comprising a nucleoside described above, for example but not limited to ddhA, ddhG, ddhU, ddh-deoxy-A, ddh-deoxy-G, ddh-deoxy-T, or a combination thereof, and an excipient. In some embodiments, disclosed herein is a pharmaceutical composition comprising a nucleoside described above, for example but not limited to ddhA, ddhG, ddhU, ddh-deoxy-A, ddh-deoxy-G, ddh-deoxy-T, or a combination thereof, further in combination with ddhC or ddh-deoxy-C or a combination thereof, and an excipient. In some embodiments, disclosed herein is a pharmaceutical composition comprising a nucleoside analog derived from a nucleotide analog produced by a pVip, and an excipient.

Pharmaceutical compositions may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the disclosure herein, may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added.

All formulations for oral administration should be in dosages suitable for the chosen route of administration.

For buccal administration, the compositions may take the form of tablets or lozenges formulated in conventional manner.

For administration by nasal inhalation, the active ingredients for use according to the disclosure herein are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water-based solution, before use.

The preparation may also be formulated in rectal compositions such as suppositories or retention enemas, using, e.g., conventional suppository bases such as cocoa butter or other glycerides.

The preparation may also be formulated as a topical composition, such as a spray, a cream, a mouthwash, a wipe, a foam, a soap, an oil, a solution, a lotion, an ointment, a paste, a gel and a patch.

Pharmaceutical compositions suitable for use in context include compositions wherein the active ingredients are contained in an amount effective to achieve the intended purpose. More specifically, a therapeutically effective amount means an amount of active ingredients effective to prevent, alleviate or ameliorate symptoms of disease (e.g., bacterial infection) or prolong the survival of the subject being treated.

Determination of a therapeutically effective amount is well within the capability of those skilled in the art.

For any preparation used in the methods disclosed herein, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on e.g. the subject being treated, the severity of the affliction, the manner of administration, the judgment of the prescribing physician, etc.

Compositions of some embodiments, may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation formulated in a compatible pharmaceutical carrier may also be prepared, placed in an appropriate container, and labeled for treatment of an indicated condition, as is further detailed above.

In some embodiments, bacteria are isolated bacteria. In some embodiments, a cell comprises isolated microbial cells. In some embodiments, the cell is a microbial cell such as bacteria, e.g., Gram-positive or Gram-negative bacteria. In some embodiments, the bacteria comprise Gram-negative bacteria or Negativicutes that stain negative in Gram stain. In some embodiments, a host cell comprises gram-positive bacteria, gram-negative bacteria, or archaea.

In some embodiments, Gram-negative bacteria comprise *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chlamydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pal-*

*lidum endemicum, Treponema pertenue, Veillonella* spp., *Vibrio cholerae, Vibrio vulnificus, Yersinia enterocolitica, Yersinia pestis.*

In some embodiments, the bacteria comprise gammaproteobacteria (e.g. *Escherichia coli, pseudomonas, vibrio* and *klebsiella*) or Firmicutes (belonging to class Negativicutes that stain negative in Gram stain).

In some embodiments, Gram-positive bacteria comprise *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *Streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis.*

In some embodiments the bacteria is a species selected from the group consisting of *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Campylobacter, Klebsiella, Frankia, Bartonella, Rickettsia, Shewanella, Serratia, Enterobacter, Proteus, Providencia, Brochothrix,* and *Brevibacterium.*

Methods of Protecting from Viral Infection

In some embodiments, disclosed herein is a method of protecting a cell from viral infection, said method comprising a step of introducing into said cell a prokaryotic viperin homolog (pVip), a pVip gene, or a nucleoside or nucleotide analog produced thereof. In some embodiments, a nucleoside derivative comprises a nucleotide produced by a pVip without the phosphate residues. In some embodiments, a method of protecting a cell from viral infection comprises a step of introducing into said cell a pVip gene selected from a gene provided in Table 1, Table 2, or comprising any of SEQ ID Nos: 3-383, or SEQ ID Nos: 384-408. In some embodiments, a method of protecting a cell from viral infection comprises a step of introducing into said cell a pVip gene encoding for a protein with an amino acid sequence selected from a those provided in Table 3, or comprising any of SEQ ID Nos: 409-789. In some embodiments, a method of protecting a cell from viral infection comprises a step of introducing into said cell a pVip gene encoding for a protein with an amino acid sequence with at least 80% homology to a protein selected from a those provided in Table 3, or any of SEQ ID Nos: 409-789.

In some embodiments, a method of protecting a cell from viral infection comprises a step of introducing into said cell a nucleotide analog as described above. For example, in some embodiments, a method of protecting a cell from viral infection comprises a step of introducing into said cell 3'-deoxy-3',4'-didehydro (ddh) ATP. In some embodiments, a method of protecting a cell from viral infection comprises a step of introducing into said cell ddhGTP. In some embodiments, a method of protecting a cell from viral infection comprises a step of introducing into said cell ddhUTP. In some embodiments, a method of protecting a cell from viral infection comprises a step of introducing into said cell ddhCTP in combination with at least a non-cytosine-based nucleoside or nucleotide. In some embodiments, a method of protecting a cell from viral infection comprises a step of introducing into said cell ddh-deoxy-ATP. In some embodiments, a method of protecting a cell from viral infection comprises a step of introducing into said cell ddh-deoxy-GTP. In some embodiments, a method of protecting a cell from viral infection comprises a step of introducing into said cell ddh-deoxy-TTP. In some embodiments, a method of protecting a cell from viral infection comprises a step of introducing into said cell ddh-deoxy-CTP in combination with at least a non-cytosine based nucleoside or nucleotide.

In some embodiments, a method of protecting a cell from viral infection comprises a step of introducing into said cell a combination of nucleotide analogs for example but not limited to combinations of ddh-ATP, ddh-GTP, ddh-UTP, ddh-deoxy-ATP, ddh-deoxy-GTP, and ddh-deoxy-TTP. In some embodiments, a method of protecting a cell from viral infection comprises a step of introducing into said cell a combination of nucleotide analogs for example but not limited to combinations of ddh-ATP, ddh-GTP, ddh-UTP, ddh-CTP, ddh-deoxy-ATP, ddh-deoxy-GTP, ddh-deoxy-CTP, and ddh-deoxy-TTP. In some embodiments, a method of protecting a cell from viral infection comprises a step of introducing into said cell nucleotide analogs for example but not limited to any of ddh-ATP, ddh-GTP, ddh-UTP, ddh-deoxy-ATP, ddh-deoxy-GTP, and ddh-deoxy-TTP, or a combination thereof, further in combination with ddh-C or ddh-deoxy-CTP or a combination thereof.

In some embodiments, a method of protecting a cell from viral infection comprises a step of introducing into said cell a nucleoside analog as described above. For example, a method of protecting a cell from viral infection comprises a step of introducing into said cell 3'-deoxy-3',4'-didehydro (ddh) A. In some embodiments, a method of protecting a cell from viral infection comprises a step of introducing into said cell ddhG. In some embodiments, a method of protecting a cell from viral infection comprises a step of introducing into said cell ddhU. In some embodiments, a method of protecting a cell from viral infection comprises a step of introducing into said cell ddhC in combination with at least a non-cytosine-based nucleoside or nucleotide. In some embodiments, a method of protecting a cell from viral infection comprises a step of introducing into said cell ddh-deoxy-A. In some embodiments, a method of protecting a cell from viral infection comprises a step of introducing into said cell ddh-deoxy-G. In some embodiments, a method of protecting a cell from viral infection comprises a step of introducing into said cell ddh-deoxy-T. In some embodiments, a method of protecting a cell from viral infection comprises a step of introducing into said cell ddh-deoxy-C in combination with at least a non-cytosine based nucleoside or nucleotide.

In some embodiments, the viral infection comprises infection with a phage. In some embodiments, the viral infection comprises infection with a virus. In some embodiments, the virus is selected from the group comprising: a norovirus; a rotavirus; a hepatitis virus A, B, C, D, or E; a rabies virus, a West Nile virus, an enterovirus, a echovirus, a coxsackievirus, herpes simplex virus (HSV), a HSV-2, a varicella-zoster virus, mosquito-borne viruses, an arbovirus, a St. Louis encephalitis virus, a California encephalitis virus, a lymphocytic choriomeningitis virus, a human immunodeficiency virus (HIV), a poliovirus, a zika virus, a rubella virus, a cytomegalovirus, an echovirus, a human papillomavirus (HPV), and an enteovirus D68.

In some embodiments, a method of protecting a cell from viral infection comprises a method of protecting a host cell from foreign nucleic acid invasion. In some embodiments, a method of protecting a host cell from viral infection comprises introducing into the host cells a pVip, a pVip gene, or a nucleoside analog or a nucleotide analog produced by a pVip described herein. In some embodiments, a method of protecting a host cell from viral infection comprises introducing into the host cells a combination of a pVip, a pVip gene, or a nucleoside analog or a nucleotide analog produced by a pVip described herein. In some embodiments, a method of protecting a host cell from viral infection comprises introducing into the host cells at least 1, 2, 3, 4, 5, 6, 7, 8, 9, or 10 pVips described herein. In some embodiments, a nucleoside comprises a nucleotide analog produced by a pVip without the phosphate residues.

In some embodiments, a method of protecting a host cell from viral infection comprises introducing into the host cells at least one functional pVip described herein. In some embodiments, a method of protecting a host cell from viral infection comprises introducing into the host cells a combination of functional pVips described herein. In some embodiments, a method of protecting a host cell from viral infection comprises introducing into the host cells at least 1, 2, 3, 4, 5, 6, 7, 8, 9, or 10 functional pVip described herein.

As described herein, a pVip may produce one or more kinds of nucleotide or nucleoside analogs. In one embodiment, a pVip may produce one kind of nucleotide or nucleoside analogs. In another embodiment, a pVip may produce multiple kinds of nucleotide or nucleoside analogs. In another embodiment, the DNA or RNA chain terminators, or anti-viral substances, produced by a pVip may not include any nucleotide or nucleoside analogs described herein.

In one embodiment, the various methods of uses of pVip described herein may include the uses of a combination of (i) nucleotide or nucleoside analogs produced by one or more pVips, and (ii) the anti-viral substances (which do not include any nucleotide or nucleoside analogs) produced by one or more pVips.

In some embodiments, a method of protecting a bacterial cell from viral infection comprises introducing into the bacterial cells a pVip, a pVip gene, or a nucleoside analog or a nucleotide analog produced by a pVip described herein. In some embodiments, a method of protecting a bacterial cell from viral infection comprises introducing into the bacterial cells a combination of a pVip, a pVip gene, or a nucleoside analog or a nucleotide analog produced by a pVip described herein. In some embodiments, a method of protecting a bacterial cell from viral infection comprises introducing into the bacterial cells at least 1, 2, 3, 4, 5, 6, 7, 8, 9, or 10 pVips described herein.

In some embodiments, a method of protecting a bacterial cell from viral infection comprises introducing into the bacterial cells at least one functional pVip described herein. In some embodiments, a method of protecting a bacterial cell from viral infection comprises introducing into the bacterial cells a combination of functional pVips described herein. In some embodiments, a method of protecting a bacterial cell from viral infection comprises introducing into the bacterial cells at least 1, 2, 3, 4, 5, 6, 7, 8, 9, or 10 pVips described herein.

In some embodiments, a method of protecting a host cell from viral infection comprises protecting said host cell from phage infection. In some embodiments, a method of protecting a host cell from viral infection comprises protecting said host cell from at least one phage infection. In some embodiments, a method of protecting a host cell from viral infection comprises protecting said host cell from more than one phage infection. In some embodiments, a method of protecting a host cell from viral infection comprises protecting said host cell from plasmid transformation. In some embodiments, a method of protecting a host cell from viral infection comprises protecting said host cell from at least one plasmid transformation. In some embodiments, a method of protecting a host cell from viral infection comprises protecting said host cell from more than one plasmid transformation. In some embodiments, a method of protecting a host cell from viral infection comprises protecting said host cell from entry of conjugative elements. In some embodiments, a method of protecting a host cell from viral infection comprises protecting said host cell from entry of at least one conjugative element. In some embodiments, a method of protecting a host cell from viral infection comprises protecting said host cell from entry of more than one conjugative element. In some embodiments, a method of protecting a host cell from viral infection comprises conferring resistance to horizontal gene transfer. In some embodiments, a method of protecting a host cell from viral infection comprises decreasing DNA replication. In some embodiments, a method of protecting a host cell from viral infection comprises decreasing RNA transcription. In some embodiments, a method of protecting a host cell from viral infection comprises increasing DNA synthesis termination. In some embodiments, a method of protecting a host cell from viral infection comprises increasing RNA synthesis termination.

In some embodiments, a method of protecting a bacterial cell from viral infection comprises protecting said bacterial cell from phage infection. In some embodiments, a method of protecting a bacterial cell from viral infection comprises protecting said bacterial cell from at least one phage infection. In some embodiments, a method of protecting a bacterial cell from viral infection comprises protecting said bacterial cell from more than one phage infection. In some embodiments, a method of protecting a bacterial cell from viral infection comprises protecting said bacterial cell from plasmid transformation. In some embodiments, a method of protecting a bacterial cell from viral infection comprises protecting said bacterial cell from at least one plasmid transformation. In some embodiments, a method of protecting a bacterial cell from viral infection comprises protecting said bacterial cell from more than one plasmid transformation. In some embodiments, a method of protecting a bacterial cell from viral infection comprises protecting said bacterial cell from entry of conjugative elements. In some embodiments, a method of protecting a bacterial cell from viral infection comprises protecting said bacterial cell from entry of at least one conjugative element. In some embodiments, a method of protecting a bacterial cell from viral infection comprises protecting said bacterial cell from entry of more than one conjugative element. In some embodiments, a method of protecting a bacterial cell from viral infection comprises conferring resistance to horizontal gene transfer. In some embodiments, a method of protecting a bacterial cell from viral infection comprises decreasing DNA replication. In some embodiments, a method of protecting a bacterial cell from viral infection comprises decreasing RNA transcription. In some embodiments, a method of protecting a bacterial cell from viral infection comprises increasing DNA synthesis termination. In some embodiments, a method of protecting a bacterial cell from viral infection comprises increasing RNA synthesis termination.

In some embodiments, a method disclosed herein comprises the use of a pVip described herein for protecting bacteria from phage infection. In some embodiments, a method disclosed herein comprises a method of protecting bacteria from plasmid transformation. In some embodiments, a method disclosed herein comprises a method of protecting bacteria from conjugative elements. In some embodiments, a method disclosed herein comprises a method of protecting bacteria from phage infection, and/or conjugative elements, and/or plasmid transformation. In some embodiments, a method disclosed herein comprises a method of producing bacteria resistant to phage infection. In some embodiments, a method disclosed herein comprises a method of producing bacteria resistant to plasmids. In some embodiments, a method disclosed herein comprises a method of producing bacteria resistant to conjugative elements. In some embodiments, a method disclosed herein comprises a method of producing bacteria resistant to phage infection, and/o conjugative elements, and/or plasmids.

In some embodiments, a method disclosed herein comprises the use of a pVip described herein for controlling phages in microbiomes. In some embodiments, a method disclosed herein comprises the use of a nucleoside analog or a nucleotide analog produced by a pVip described herein for controlling phages in microbiomes. Phages have recently been reported to play an important role in microbiomes. Nucleoside or nucleotide analogs could be used to regulate phages for different applications. The phageome content has been correlated to different diseases. In some embodiments, the nucleoside or nucleotide analog produced by a pVip can be used to act on phage control. In some embodiments, disclosed herein is a method of phage inactivation. In some embodiments, a method of phage inactivation comprising administering the pVips or the nucleoside or nucleotide analogs produced by the pVips to phages, thereby inactivating them. In some embodiments, a phage therapy comprises a step of inactivating phages by a method comprising administering the pVips or the nucleoside or nucleotide analogs produced by the pVips to phages.

In some embodiments, a method of protecting a first bacterial cell from viral infection comprises contacting a first bacterial cell with a second bacterial cell comprising a pVip, or a nucleic acid construct comprising a pVip gene. In some embodiments a method of protecting a first bacterial cell from viral infection comprises contacting bacterial conjugation of said first bacterial cell with a second bacterial cell comprising a pVip, or a nucleic acid construct comprising a pVip gene.

A skilled artisan would appreciate that the phrase "bacterial conjugation" encompasses a direct transfer of genetic material between bacterial cells by cell-to-cell contact or by bridge-like connection between the cells. During conjugation the donor bacterium provides a transmissible genetic element, typically a plasmid or a transposon. The transfer of the transmissible genetic element takes advantage of the complementary nature of double stranded DNA. Thus, one strand of the transmissible genetic element is transferred, and the other remains in the original bacteria. Both strands have the complementary stranded added so that each bacterium ends up with a complete transmissible element.

According to some embodiments, contacting a first bacteria with second bacteria comprise the step of incubating the bacterial cell (e.g., first bacteria) with a substance or cell (e.g., second bacteria) such that the substance or a substance contained in the cell affects the bacterial cell resistance to phage infection, or to plasmid transformation, or to phage infection and plasmid transformation.

In some embodiments, the first bacteria and the second bacteria are non-identical. In some embodiments, the first bacteria do not express an endogenous pVip. In some embodiments, the first bacteria do not express any pVip gene provided in Table 1, Table 2, or comprising any of SEQ ID Nos: 3-383, or SEQ ID Nos: 384-408.

In some embodiments, the first bacteria comprise a commercially valuable bacteria such as those used for fermentation as described above. Thus, following the above teachings, in some embodiments, there is provided isolated bacteria comprising a nucleic acid sequence encoding a pVip comprising a pVip provided in Table 3, or any of SEQ ID Nos: 409-789, said pVip having anti-phage activity, said bacteria comprising a transmissible genetic element expressing a pVip gene selected from a gene provided in Table 1, Table 2, or comprising any of SEQ ID Nos: 3-383, or SEQ ID Nos: 384-408.

A skilled artisan would appreciate that the terms "anti-phage activity" or "resistant to infection by at least one phage" or "resistance to at least one phage" or "anti-phage defense" encompasses an activity provided by a pVip, a nucleic acid construct comprising a pVip gene, or a nucleoside or nucleotide analog produced by a pVip to a host cell, for example but not limited to bacterial cell expressing a functional pVip or provided with nucleoside or nucleotide analog produced by a pVip disclosed herein, wherein said bacterial cell then comprises an increased resistance to infection by at least one phage in comparison to bacteria of the same species under the same developmental stage (e.g. culture state) which does not express an endogenous functional pVip or a nucleoside or nucleotide analog produced by a pVip. Resistance to infection, may be determined by for example but not limited to bacterial viability, phage lysogeny, phage genomic replication, or phage genomic degradation. The phage can be a lytic phage or a temperate (lysogenic) phage described herein. In some embodiments, the increase in resistance is at least 1.5 fold, at least 2 fold, at least 3 fold, at least 5 fold, at least 10 fold, or at least 20 fold as compared to same bacterial host in the absence of the pVip.

In some embodiments, the increase in resistance is by at least 5%, by at least a 10%, at least 20%, at least 30%, at least 40%, at least 50%, at least 60%, at least 70%, at least 80%, at least 90% or more than 100% as compared to same host bacteria in the absence of the pVip.

Assays for testing phage resistance are well known in the art and are further described hereinbelow.

A skilled artisan would appreciate that the terms "anti-plasmid activity" or "defense against plasmid transformation" or "reduced transformation by a plasmid" or "anti-plasmid defense" or "plasmid resistance" encompasses an activity provided by a pVip, a nucleic acid construct comprising a pVip gene, or a nucleoside or nucleotide analog produced by a pVip to a host cell, for example but not limited to bacterial cell expressing a functional pVip or provided with a nucleoside or nucleotide analog produced by a pVip disclosed herein, wherein the bacterial cell then comprises a decreased efficiency of transformation by at least one plasmid in comparison to bacteria of the same species under the same developmental stage (e.g. culture state) which does not express a functional pVip or comprises a nucleoside or nucleotide analog produced by a pVip. Decreased efficiency of plasmid transformation, may be determined by for example but not limited to a transformation efficiency assay comparing bacteria comprising pVip with those not comprising the pVip. The plasmid may be an episomal plasmid. In some embodiments, the decreased transformation efficiency is at least 1.5 fold, at least 2 fold, at least 3 fold, at least 5 fold, at least 10 fold, or at least 20 fold as compared to same bacterial host in the absence of the pVip.

In some embodiments, the decreased transformation efficiency is by at least 5%, by at least a 10%, at least 20%, at least 30%, at least 40%, at least 50%, at least 60%, at least 70%, at least 80%, at least 90% or more than 100% as compared to same host bacteria in the absence of the pVip.

A skilled artisan would appreciate that the term "donor species" may in certain embodiments, encompass the bacterial or archaeal species in which a pVip was identified and sequenced. The skilled artisan would also appreciate that the term "host cell" may in certain embodiments, encompass bacterial or archaeal or eukaryotic cell in which a pVip, a nucleic acid construct comprising a pVip gene, or a nucleoside or nucleotide analog produced by a pVip has been introduced. In some embodiments, the host cell does not endogenously comprise the pVip or the nucleoside or nucleotide analog produced by a pVip introduced. In some embodiments, the host cell does not endogenously comprise a functional version of the pVip introduced. In some embodiments, the host cell comprises the pVIP introduced but it is not functional in the host cell. In some embodiments, the host cell does not endogenously express the Pvip introduced. In some embodiments, the host cell does not endogenously express a functional version of the pVip introduced.

In some embodiments, disclosed herein is a method of protecting a plant from viral infection, said method comprising a step of introducing into a cell of said plant a prokaryotic viperin homolog (pVip), a pVip gene, or a nucleoside or nucleotide analog produced thereof. In some embodiments, a nucleoside comprises a nucleotide analog produced by a pVip without the phosphate residues In some embodiments, a method of protecting a plant from viral infection comprises a step of introducing into a cell of said plant a pVip gene selected from a gene provided in Table 1, Table 2, or comprising at least 80% identity to any of SEQ ID Nos: 3-383, or SEQ ID Nos: 384-408. In some embodiments, a method of protecting a plant from viral infection comprises a step of introducing into a cell of said plant a pVip gene encoding for a protein with an amino acid sequence comprising at least 80% homology to any of SEQ ID Nos: 409-789.

Products Comprising pVips and Methods of Producing Thereof

Bacterial fermentation, such as the one done in the dairy industry, suffers from bacterial population collapses due to phage infections. Preventing phage infections is thus of economic interest. Given the wide anti-viral activity of pVip products, the small size of its genes, and the absence of growth defect for most pVips strains, pVips can be introduced into fermentation strains such as *lactobacillus lactis* and *lactobacillus cremoris*, to protect them from phage infections.

In some embodiments, disclosed herein is food comprising a cell comprising an ectopic pVip, a nucleic acid construct comprising a pVip gene, a pVip product, or a combination thereof. In some embodiments, disclosed herein is food additive comprising a cell comprising an ectopic pVip, a nucleic acid construct comprising a pVip gene, a pVip product, or a combination thereof. In some embodiments, disclosed herein is feed comprising a cell comprising an ectopic pVip, a nucleic acid construct comprising a pVip gene, a pVip product, or a combination thereof. In some embodiments, disclosed herein is a nutritional supplement comprising a cell comprising an ectopic pVip, a nucleic acid construct comprising a pVip gene, a pVip product, or a combination thereof. In some embodiments, disclosed herein is a probiotic supplement comprising a cell comprising an ectopic pVip, a nucleic acid construct comprising a pVip gene, a pVip product, or a combination thereof. In some embodiments, disclosed herein is a personal care product comprising a cell comprising an ectopic pVip, a nucleic acid construct comprising a pVip gene, a pVip product, or a combination thereof. In some embodiments, disclosed herein is a health care product comprising a cell comprising an ectopic pVip, a nucleic acid construct comprising a pVip gene, a pVip product, or a combination thereof. In some embodiments, disclosed herein is a veterinary product comprising a cell comprising an ectopic pVip, a nucleic acid construct comprising a pVip gene, a pVip product, or a combination thereof.

In some embodiments, disclosed herein is food comprising a nucleoside or nucleotide analog produced by a pVip. In some embodiments, disclosed herein is food additive comprising a nucleoside or nucleotide analog produced by a pVip. In some embodiments, disclosed herein is feed comprising a nucleoside or nucleotide analog produced by a pVip. In some embodiments, disclosed herein is a nutritional supplement comprising a nucleoside or nucleotide analog produced by a pVip. In some embodiments, disclosed herein is a probiotic supplement comprising a nucleoside or nucleotide analog produced by a pVip. In some embodiments, disclosed herein is a personal care product comprising a nucleoside or nucleotide analog produced by a pVip. In some embodiments, disclosed herein is a health care product comprising a nucleoside or nucleotide analog produced by a pVip. In some embodiments, disclosed herein is a veterinary product comprising a nucleoside or nucleotide analog produced by a pVip.

In some embodiments, a pVip comprises a pVip provided in Table 3, or any of SEQ ID Nos: 409-789, or a combination thereof. In some embodiments, a nucleotide produced by a pVip comprises 3'-deoxy-3',4'-didehydro (ddh) ATP, ddhGTP, ddhGDP, ddhCTP, ddhUTP, ddhUMP, ddh-deoxy-ATP, ddh-deoxy-GTP, ddh-deoxy-CTP, ddh-deoxy-TTP. In some embodiments, a nucleoside produced by a pVip comprises 3'-deoxy-3',4'-didehydro (ddh) Adenine (ddhA), ddhG, ddhC, ddhU, ddh-deoxy-A, ddh-deoxy-G, ddh-deoxy-C, ddh-deoxy-T, or a combination thereof.

Phage contamination is now considered to be a main cause of slow fermentation or complete starter failure. The lack of bacteria which survive adequately can result in milk products which do not have a desirable taste. Thus, a goal of scientists working to produce better milk products lies in providing bacteria which have all the characteristics associated with production of a good flavor and which are able to resist infection by phages.

In some embodiments, the cells comprising an ectopic pVip, a nucleic acid construct comprising a pVip gene, or a pVip product is a prokaryotic cell, bacterium or archaeon.

In some embodiments, the bacteria may be useful in the manufacture of dairy and fermentation processing such as, but not limited to, milk-derived products, such as cheeses, yogurt, fermented milk products, sour milks, and buttermilk. In some embodiments, the bacteria are useful as a part of the starter culture in the manufacture of dairy and fermentation processing. In some embodiments, the starter culture is a food grade starter culture. In some embodiments, the bacteria may be useful in the manufacture of molecules by metabolic engineering.

A bacterium traditionally used in the production of milk products is *S. thermophilus*. It is particularly employed in the production of yogurt, mozzarella and Swiss type cheeses. One problem with *S. thermophilus* is that it is extremely sensitive to phage infection.

In some embodiments, the bacteria are lactic acid bacteria. A skilled artisan would appreciate that the term "lactic acid bacteria" encompasses Gram positive, microaerophillic or anaerobic bacteria which ferment sugar with the production of acids including lactic acid as the predominantly produced acid, acetic acid, formic acid and propionic acid.

In some embodiments, bacteria used in methods disclosed herein, are selected from a species selected from the group of the industrially most useful lactic acid bacteria comprising *Lactococcus* species, *Streptococcus* species, *Lactobacillus* species, *Leuconostoc* species, *Oenococcus* species, *Pediococcus* species, *Bifidobacterium* species, and *Propionibacterium* species. In some embodiments, bacteria protected in a method of protecting bacteria from phage infection comprises bacteria selected from a *Lactococcus* species, a *Streptococcus* species, a *Lactobacillus* species, a *Leuconostoc* species, a *Oenococcus* species, a *Pediococcus* species, a *Bifidobacterium*, and a *Propionibacterium* species. In some embodiments a method of protecting bacteria from phage infection comprises protecting a *Lactococcus* species of bacteria. In some embodiments a method of protecting bacteria from phage infection comprises protecting a *Streptococcus* species of bacteria. In some embodiments a method of protecting bacteria from phage infection comprises protecting a *Lactobacillus* species of bacteria. In some embodiments a method of protecting bacteria from phage infection comprises protecting a *Leuconostoc* species of bacteria. In some embodiments a method of protecting bacteria from phage infection comprises protecting a *Oenococcus* species of bacteria. In some embodiments a method of protecting bacteria from phage infection comprises protecting a *Pediococcus* species of bacteria. In some embodiments a method of protecting bacteria from phage infection comprises protecting a *Bifidobacterium* of bacteria. In some embodiments a method of protecting bacteria from phage infection comprises protecting a *Propionibacterium* species of bacteria.

In some embodiments, bacteria protected in a method of protecting bacteria from plasmid transformation comprises bacteria selected from a *Lactococcus* species, a *Streptococcus* species, a *Lactobacillus* species, a *Leuconostoc* species, a *Oenococcus* species, a *Pediococcus* species, a *Bifidobacterium* species, and a *Propionibacterium* species. In some embodiments, bacteria protected in a method of protecting bacteria from plasmid transformation comprises bacteria selected from a *Lactococcus* species, a *Streptococcus* species, a *Lactobacillus* species, a *Leuconostoc* species, a *Oenococcus* species, a *Pediococcus* species, a *Bifidobacterium*, and a *Propionibacterium* species. In some embodiments a method of protecting bacteria from plasmid transformation comprises protecting a *Lactococcus* species of bacteria. In some embodiments a method of protecting bacteria from plasmid transformation comprises protecting a *Streptococcus* species of bacteria. In some embodiments a method of protecting bacteria from plasmid transformation comprises protecting a *Lactobacillus* species of bacteria. In some embodiments a method of protecting bacteria from plasmid transformation comprises protecting a *Leuconostoc* species of bacteria. In some embodiments a method of protecting bacteria from plasmid transformation comprises protecting a *Oenococcus* species of bacteria. In some embodiments a method of protecting bacteria from plasmid transformation comprises protecting a *Pediococcus* species of bacteria. In some embodiments a method of protecting bacteria from plasmid transformation comprises protecting a *Bifidobacterium* of bacteria. In some embodiments a method of protecting bacteria from plasmid transformation comprises protecting a *Propionibacterium* species of bacteria.

In some embodiments, bacteria protected in a method of protecting bacteria from phage infection and plasmid transformation comprises bacteria selected from a *Lactococcus* species, a *Streptococcus* species, a *Lactobacillus* species, a *Leuconostoc* species, a *Oenococcus* species, a *Pediococcus* species, a *Bifidobacterium* species, and a *Propionibacterium* species. In some embodiments, bacteria protected in a method of protecting bacteria from phage infection and plasmid transformation comprises bacteria selected from a *Lactococcus* species, a *Streptococcus* species, a *Lactobacillus* species, a *Leuconostoc* species, a *Oenococcus* species, a *Pediococcus* species, a *Bifidobacterium*, and a *Propionibacterium* species. In some embodiments a method of protecting bacteria from phage infection and plasmid transformation comprises protecting a *Lactococcus* species of bacteria. In some embodiments a method of protecting bacteria from phage infection and plasmid transformation comprises protecting a *Streptococcus* species of bacteria. In some embodiments a method of protecting bacteria from phage infection and plasmid transformation comprises protecting a *Lactobacillus* species of bacteria. In some embodiments a method of protecting bacteria from phage infection and plasmid transformation comprises protecting a *Leuconostoc* species of bacteria. In some embodiments a method of protecting bacteria from phage infection and plasmid transformation comprises protecting a *Oenococcus* species of bacteria. In some embodiments a method of protecting bacteria from phage infection and plasmid transformation comprises protecting a *Pediococcus* species of bacteria. In some embodiments a method of protecting bacteria from phage infection and plasmid transformation comprises protecting a *Bifidobacterium* of bacteria. In some embodiments a method of protecting bacteria from phage infection and plasmid transformation comprises protecting a *Propionibacterium* species of bacteria.

In some embodiments, a cell used in the manufacturing of a food, a food additive, feed, a nutritional supplement, a probiotic supplement, a personal care product, a health care product, or a veterinary product comprises a cell ectopically expressing a pVip. In some embodiments, said pVip comprises a pVip provided in Table 3, or any of SEQ ID Nos: 409-789. In some embodiments, bacteria used in the manufacturing of a food, a food additive, feed, a nutritional supplement, a probiotic supplement, a personal care product, a health care product, or a veterinary product comprises an ectopically expressed pVip. In some embodiments, said pVip comprises a pVip provided in Table 3, or any of SEQ ID Nos: 409-789.

In some embodiments, a cell used in the manufacturing of a food, a food additive, feed, a nutritional supplement, a probiotic supplement, a personal care product, a health care product, or a veterinary product comprises a nucleoside or nucleotide analog produced by an pVip as described above. In some embodiments, bacteria used in the manufacturing of a food, a food additive, feed, a nutritional supplement, a probiotic supplement, a personal care product, a health care product, or a veterinary product comprises a nucleoside or nucleotide analog produced by an pVip as described above. In some embodiments, said nucleotide analog comprises, e.g., ddhATP, ddhGTP, ddhUTP, ddh-deoxy-ATP, ddh-deoxy-GTP, ddh-deoxy-TTP, or a combination thereof. In some embodiments, said nucleoside analog comprises, e.g., ddhA, ddhG, ddhU, ddh-deoxy-A, ddh-deoxy-G, ddh-deoxy-T, or a combination thereof. In some embodiments, said nucleotide analog comprises, e.g., ddhATP, ddhGTP, ddhCTP, ddhUTP, ddh-deoxy-ATP, ddh-deoxy-GTP, ddh-deoxy-CTP, ddh-deoxy-TTP, or a combination thereof. In some embodiments, said nucleoside analog comprises, e.g., ddhA, ddhG, ddhU, ddhC, ddh-deoxy-A, ddh-deoxy-G, ddh-deoxy-T, or ddh-deoxy-C, or a combination thereof.

In some embodiments, a cell used in the manufacturing of a food, a food additive, feed, a nutritional supplement, a probiotic supplement, a personal care product, a health care product, or a veterinary product comprises a transmissible genetic element comprising an ectopic pVip. In some embodiments, bacteria used in the manufacturing of a food, a food additive, feed, a nutritional supplement, a probiotic supplement, a personal care product, a health care product, or a veterinary product comprise a transmissible genetic element comprising an ectopic pVip.

In some embodiments, a cell used in the manufacturing of a food, a food additive, feed, a nutritional supplement, a probiotic supplement, a personal care product, a health care product, or a veterinary product comprises an expression vector comprising a pVip gene selected from a gene provided in Table 1, Table 2, or comprising any of SEQ ID Nos: 3-383, or SEQ ID Nos: 384-408. In some embodiments, bacteria used in the manufacturing of a food, a food additive, feed, a nutritional supplement, a probiotic supplement, a personal care product, a health care product, or a veterinary product comprises an expression vector comprising a pVip gene selected from a gene provided in Table 1, Table 2, or comprising any of SEQ ID Nos: 3-383, or SEQ ID Nos: 384-408.

In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to at least one phage. In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to plasmid transformation. In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to at least one phage and is resistant to plasmid transformation.

In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to plasmid transformation. In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to at least one phage and is resistant to plasmid transformation.

In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to at least one phage. In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to plasmid transformation. In some embodiments, a cell used in the manufacturing of a food, a food additive, feed, a nutritional supplement, a probiotic supplement, a personal care product, a health care product, or a veterinary product comprising an ectopic pVip, as disclosed herein, is resistant to at least one phage and is resistant to plasmid transformation.

In some embodiments, a cell used in the manufacturing of a food, a food additive, feed, a nutritional supplement, a probiotic supplement, a personal care product, a health care product, or a veterinary product comprising an ectopic pVip, as disclosed herein, comprises resistance to horizontal gene transfer. In some embodiments, a cell used in the manufacturing of a food, a food additive, feed, a nutritional supplement, a probiotic supplement, a personal care product, a health care product, or a veterinary product comprising an ectopic pVip, as disclosed herein, comprises decreased DNA replication. In some embodiments, a cell used in the manufacturing of a food, a food additive, feed, a nutritional supplement, a probiotic supplement, a personal care product, a health care product, or a veterinary product comprising an ectopic pVip, as disclosed herein, comprises decreased RNA replication. In some embodiments, a cell used in the manufacturing of a food, a food additive, feed, a nutritional supplement, a probiotic supplement, a personal care product, a health care product, or a veterinary product comprising an ectopic pVip, as disclosed herein, comprises increased termination of DNA synthesis. In some embodiments, a cell used in the manufacturing of a food, a food additive, feed, a nutritional supplement, a probiotic supplement, a personal care product, a health care product, or a veterinary product comprising an ectopic pVip, as disclosed herein, comprises increased termination of RNA synthesis.

Cultures, and starter cultures, in particular are used extensively in the food industry in the manufacture of fermented products including milk products (e.g., yogurt, buttermilk, and cheese), meat products, bakery products, wine, and vegetable products. The preparation of cultures is labor intensive, occupying much space and equipment, and there is a considerable risk of contamination with spoilage bacteria and/or phages during the propagation steps. The failure of bacterial cultures due to phage infection and multiplication is a major problem with the industrial use of bacterial cultures. There are many different types of phages and new strains continue to emerge. Indeed, despite advances in culture development, there is a continuing need to improve cultures for use in industry.

In some embodiments, a method disclosed herein comprises a method of making a food. In some embodiments, a method disclosed herein comprises a method of making a food additive. In some embodiments, a method disclosed herein comprises a method of making a feed. In some embodiments, a method disclosed herein comprises a method of making a nutritional supplement. In some embodiments, a method disclosed herein comprises a method of making a probiotic supplement. In some embodiments, a method disclosed herein comprises a method of making a personal care product. In some embodiments, a method disclosed herein comprises a method of making a health care product. In some embodiments, a method disclosed herein comprises a method of making an antibiotic. In some embodiments, a method disclosed herein comprises a method of making a veterinary product.

In some embodiments, there is provided a method of preparing a food, the method comprising adding to the food a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the food. In some embodiments, there is provided a method of preparing a food, the method comprising adding to the food a nucleoside or nucleotide analog produced by pVip thereby preparing the food.

In some embodiments, a food comprises an alcoholic beverage. In some embodiments, there is provided a method of preparing an alcoholic beverage, the method comprising adding to the beverage a cell comprising an ectopic pVip, or a nucleic acid construct comprising a pVip gene, or a pVip product, wherein said pVip gene is selected from a gene provided in Table 1, Table 2, or comprises any of SEQ ID Nos: 3-383, or SEQ ID Nos: 384-408, or a combination thereof, thereby preparing the alcoholic beverage. In some embodiments, there is provided a method of preparing an alcoholic beverage, the method comprising adding to the alcoholic beverage a nucleoside or nucleotide analog produced by pVip thereby preparing the alcoholic beverage. In some embodiments, the alcoholic beverage comprises a wine or a sake.

In some embodiments, a food comprises a dairy product. In some embodiments, a dairy product comprises a milk product, a sour milk, a buttermilk, a milk, a cheese, a yogurt, viili, yakult, or casein. In some embodiments, a food comprises natto.

In some embodiments, there is provided a method of preparing a dairy product, the method comprising adding to the dairy product a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the dairy product. In some embodiments, there is provided a method of preparing a dairy product, the method comprising adding to the dairy product a nucleoside or nucleotide analog produced by pVip thereby preparing the dairy product.

In some embodiments, there is provided a method of preparing a milk product, the method comprising adding to the milk product a cell comprising an ectopic pVip, or a nucleic acid construct comprising a pVip gene, or a pVip product, wherein said pVip comprises a pVip provided in Table 3, or any of SEQ ID Nos: 409-789, or pVip gene is selected from a gene provided in Table 1, Table 2, or comprises any of SEQ ID Nos: 3-383, or SEQ ID Nos: 384-408, thereby preparing the milk product. In some embodiments, there is provided a method of preparing a milk product, the method comprising adding to the milk product a nucleoside or nucleotide analog produced by a pVip thereby preparing the milk product.

In some embodiments, provided herein is a method of preparing a sour milk, a butter milk, a cheese, a yogurt, viili, yakult, casein, or a natto, the method comprising adding a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing a sour milk, butter milk, cheese, yogurt, viili, yakult, casein, or the natto. In some embodiments, there is provided a method of preparing a sour milk, a butter milk, a cheese, a yogurt, viili, yakult, casein, or a natto, the method comprising adding to the sour milk, a butter milk, a cheese, a yogurt, viili, yakult, casein, or natto a nucleoside or nucleotide analog produced by pVip thereby preparing the sour milk, butter milk, cheese, yogurt, viili, yakult, casein, or natto.

In some embodiments, there is provided a method of preparing a food additive, the method comprising adding to the food additive a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the food additive. In some embodiments, there is provided a method of preparing a food additive, the method comprising adding to the food additive a nucleoside or nucleotide analog produced by pVip, thereby preparing the food additive.

In some embodiments, there is provided a method of preparing a feed, the method comprising adding to the feed a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the feed. In some embodiments, there is provided a method of preparing a feed, the method comprising adding to the feed a nucleoside or nucleotide analog produced by pVip, thereby preparing the feed.

In some embodiments, there is provided a method of preparing a nutritional supplement, the method comprising adding to the nutritional supplement a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the nutritional supplement. In some embodiments, there is provided a method of preparing a nutritional supplement, the method comprising adding to the nutritional supplement a nucleoside or nucleotide analog produced by pVip, thereby preparing the nutritional supplement.

In some embodiments, there is provided a method of preparing a probiotic supplement, the method comprising adding to the probiotic supplement a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the probiotic supplement. In some embodiments, there is provided a method of preparing a probiotic supplement, the method comprising adding to the probiotic supplement a nucleoside or nucleotide analog produced by pVip, thereby preparing the probiotic supplement.

In some embodiments, there is provided a method of preparing a health care product, the method comprising adding to the health care product a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the health care product. In some embodiments, there is provided a method of preparing a health care product, the method comprising adding to the health care product a nucleoside or nucleotide analog produced by pVip, thereby preparing the health care product. In some embodiments, a health care product comprises an antibiotic.

In some embodiments, there is provided a method of preparing an antibiotic, the method comprising adding to the antibiotic a cell comprising an ectopic pVip, or a nucleic acid construct comprising a pVip gene, or a pVip product, wherein said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the antibiotic. In some embodiments, there is provided a method of preparing an antibiotic, the method comprising adding to the antibiotic a nucleoside or nucleotide analog produced by pVip, thereby preparing the antibiotic. In some embodiments, an antibiotic comprises a polymyxin, a colistin, or a bacitracin.

In some embodiments, there is provided a method of preparing a food, the method comprising adding to the food an isolated cell comprising an ectopic pVip, or a nucleic acid construct comprising a pVip gene, said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408.

In some embodiments, there is provided a method of preparing a feed, the method comprising adding to the feed an isolated cell comprising an ectopic pVip, or a nucleic acid construct comprising a pVip gene, said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408.

In some embodiments, there is provided a method of preparing a nutritional supplement, the method comprising adding to the nutritional supplement an isolated cell comprising an ectopic pVip, or a nucleic acid construct comprising a pVip gene, said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the nutritional supplement.

In some embodiments, there is provided a method of preparing a probiotic supplement, the method comprising adding to the probiotic supplement an isolated cell comprising an ectopic pVip, or a nucleic acid construct comprising a pVip gene, said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the probiotic supplement.

In some embodiments, there is provided a method of preparing a personal care product, the method comprising adding to the personal care product an isolated cell comprising an ectopic pVip, or a nucleic acid construct comprising a pVip gene, said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the personal care product.

In some embodiments, there is provided a method of preparing a health care product, the method comprising adding to the health care product an isolated cell comprising an ectopic pVip, or a nucleic acid construct comprising a pVip gene, said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the health care product.

In some embodiments, there is provided a method of preparing a veterinary product, the method comprising adding to the veterinary product an isolated cell comprising an ectopic pVip, or a nucleic acid construct comprising a pVip gene, said pVip comprises a pVip provided in Table 3, or any of SEQ ID Nos: 409-789, or said pVip gene is selected from a gene provided in Table 1, Table 2, or comprises any of SEQ ID Nos: 3-383, or SEQ ID Nos: 384-408, thereby preparing the veterinary product.

Compositions and Articles of Manufacture

In some embodiments, there is provided a composition comprising a prokaryotic homolog of viperin (pVip), a nucleic acid construct comprising a pVip gene, or a nucleoside or nucleotide analog produced by a pVip disclosed herein. In some embodiments, there is provided a composition comprising a cell comprising a pVip, a nucleic acid construct comprising a pVip gene, or a nucleoside or nucleotide analog produced by a pVip disclosed herein. In some embodiments, the composition is for use producing bacteria resistant to at least one phage, wherein the bacteria do not naturally comprise the pVip, the pVip gene, or the nucleoside or nucleotide analog produced by a pVip. In some embodiments, the composition is for use producing bacteria resistant to plasmid transformation. In some embodiments, the composition is for use producing bacteria resistant to at least one phage and resistant to plasmid transformation.

In some embodiments, the composition comprises a number of different pVips, a nucleic acid construct comprising a number of different pVip genes, or nucleoside or nucleotide produced by a number of different pVips. In some embodiments, the composition comprises 2 different pVips, a nucleic acid construct comprising 2 different pVip genes, or nucleosides or nucleotides produced by 2 different pVips. In some embodiments, the composition comprises 3 different pVips, a nucleic acid construct comprising 3 different pVip genes, or nucleosides or nucleotides produced by 3 different pVips. In some embodiments, the composition comprises more than 3 different pVips, a nucleic acid construct comprising more than 3 different pVip genes, or nucleosides or nucleotides produced by more than 3 different pVips. In some embodiments, the pVip comprises a pVip provided in Table 3, or any of SEQ ID Nos: 409-789, or a combination thereof.

As described herein, a pVip may produce one or more kinds of nucleotide or nucleoside analogs. Thus, in one embodiment, the above composition may include one kind of nucleotide or nucleoside analogs produced by one pVip.

In another embodiment, the above composition may include more than one kind of nucleotide or nucleoside analogs produced by one pVip. In another embodiment, the above composition of pVip may include DNA or RNA chain terminators, or anti-viral substances, that do not include any nucleotide or nucleoside analogs described herein.

Methods for Producing Nucleoside or Nucleotide Analogs

Disclosed herein are methods of producing a nucleoside or a nucleotide analog in a cell comprising introducing into a cell a prokaryotic viperin homolog (pVip), or introducing and expressing a nucleic acid construct comprising a pVip gene, wherein said pVip synthesizes a nucleotide or a nucleoside analog, and purifying said nucleoside or nucleotide analog from said cell, or introducing and expressing a nucleic acid construct comprising and expressing a pVip gene, then purifying the expressed pVip protein, then using the purified pVip protein to produce a nucleotide or a nucleoside analog in vitro. In some embodiments, when the pVip synthesizes a nucleoside analog, said nucleoside analog is phosphorylated into a nucleotide analog. In some embodiments, when the pVip synthesizes a nucleotide analog, said nucleotide analog is de-phosphorylated into a nucleoside analog.

As described herein, a pVip may produce one or more kinds of nucleotide or nucleoside analogs. In one embodiment, a pVip may produce one kind of nucleotide or nucleoside analogs. In another embodiment, a pVip may produce multiple kinds of nucleotide or nucleoside analogs. In another embodiment, the DNA or RNA chain terminators, or anti-viral substances, produced by a pVip may not include any nucleotide or nucleoside analogs described herein.

A skilled artisan would recognize that catalytic activity of metaloenzymes in heterologous hosts can be promoted by a number of strategies. For example, synthesis of iron sulfur cluster in the host can be promoted by deleting the regulator iscR in *E. coli*. Further, heterologous iron sulfur cluster operons can be expressed to promote iron sulfur cluster synthesis, for example by transfection with plasmids as pDB1282, which encodes the iscR operon from *Azotobacter vinelandii*. A further strategy comprises expressing the protein in a more closely related organism from a phylogenetic point of view. Given the sensitivity to oxygen of these proteins, anaerobic growth, engineering electron transfer pathways are avenues that can also be followed to improve metaloenzymes activities. Further methods can be found, for example, in Shomar H, "Producing high-value chemicals in *Escherichia coli* through synthetic biology and metabolic engineering", ISBN number 978-90-8593-386-1. In some embodiments, said pVip comprises a pVip provided in Table 3, or any of SEQ ID Nos: 409-789.

In some embodiments, an analog molecule comprises a molecule having a structure similar to that of another molecule, but differing from it in respect to a certain component. In some embodiments, the terms "analog", "structural analog" and "chemical analog" are used herein interchangeably, having all the same elements and qualities.

In some embodiments, a nucleoside analog comprises a variant of the nucleoside lacking a 4' hydrogen and a 3' hydroxyl group. In some embodiments, a nucleoside analog comprises a dehydrated form of said nucleoside. In some embodiments, the dehydration positions are the 3' and 4' of the sugar molecule. In some embodiments, a nucleotide analog comprises a variant of the nucleotide lacking a 4' hydrogen and a 3' hydroxyl group. In some embodiments, a nucleotide analog comprises a dehydrated form of said nucleotide. In some embodiments, the dehydration positions are the 3' and 4' of the sugar molecule. In some embodiments, said sugar is a ribose. In some embodiments said sugar is a deoxyribose.

Various examples of nucleotide analogs have been described above. In some embodiments, said nucleotide analog comprises 3'-deoxy-3',4'-didehydro (ddh) ATP. In some embodiments, said nucleotide analog comprises ddhGTP. In some embodiments, said nucleotide analog comprises ddhUTP. In some embodiments, said nucleotide analog comprises ddhCTP. In some embodiments, said nucleotide analog comprises ddh-deoxy-ATP. In some embodiments, said nucleotide analog comprises ddh-deoxy-GTP. In some embodiments, said nucleotide analog comprises ddh-deoxy-TTP. In some embodiments, said nucleotide analog comprises ddh-deoxy-GTP. In some embodiments, said nucleotide analog comprises an unknown nucleotide analog. In some embodiments, said nucleotide analog comprises a derivative, or a chemical modification of ddhATP, ddhGTP, or ddhUTP, or of their deoxy versions. In some embodiments, said nucleotide analog comprises a derivative, or a chemical modification of ddhATP, ddhGTP, ddhUTP, or ddhCTP, or of their deoxy versions.

In some embodiments, said nucleoside analog comprises 3'-deoxy-3',4'-didehydro (ddh) A. In some embodiments, said nucleoside analog comprises ddhG. In some embodiments, said nucleotide analog comprises ddhU. In some embodiments, said nucleoside analog comprises ddh-deoxy-A. In some embodiments, said nucleotide analog comprises ddh-deoxy-G. In some embodiments, said nucleoside analog comprises ddh-deoxy-T. In some embodiments, said nucleoside analog comprises an unknown nucleoside analog. In some embodiments, said nucleoside analog comprises a derivative, or a chemical modification of ddhA, ddhG, ddhC, ddhU, or of their deoxy versions.

In some embodiments, introduction of the pVip comprises transformation, transduction, conjugation, protoplast fusion, or phage-mediated infection. In some embodiments, a pVip co-factor is administered to the cell. In some embodiments, a pVip substrate is administered to the cell. In some embodiments, said cell comprises a eukaryotic cell. In some embodiments, said cell comprises a bacterium. In some embodiments, said bacteria is selected from a group comprising *E. coli* and *B. subtilis*.

In some embodiments, said cell comprises a ΔiscR bacterial cell. The bacterial strain ΔiscR is disclosed in Akhtar M K et al. Deletion of iscR stimulates recombinant clostridial Fe—Fe hydrogenase activity and H2-accumulation in *Escherichia coli* BL21(DE3). Appl. Microbiol. Biotechnol. 78, 853-862 (2008), which is incorporated herein by reference. In some embodiments, said cell further comprises or is administered a pDB1282 plasmid. The pDB1282 encodes the iscR operon from *Azotobacter vinelandii*. The pDB1282 plasmid is disclosed in Zheng L et al. Assembly of Iron-Sulfur Clusters. identification of an iscSUA-hscBA-fdx gene cluster from *Azotobacter vinelandii*. J. Biol. Chem. 273, 13264-13272 (1998), which is incorporated herein by reference.

Methods for Identifying Anti-Viral Compounds

Disclosed herein are methods for identifying compounds comprising anti-viral activity. In some embodiments, a method for identifying a compound comprising anti-viral activity comprises:

(a) introducing into bacteria a pVip, or expressing in bacteria a pVip gene;
(b) contacting the bacteria of step (a) with a virus;
(c) measuring viral resistance of the bacteria of step (b);

(d) screening the bacteria of step (c) that demonstrate viral resistance for nucleotide or nucleoside compounds not present in control bacteria to which the pVip was not introduced;

(e) analyzing the compound or compounds identified in step (d), for anti-viral activity; thereby identifying the compound comprising anti-viral activity.

In some embodiments, the screening of step (d) comprises analyzing the cytosolic fraction of said bacterial cells by liquid chromatography (LC), by mass spectrometry (MS), or by a combination of both.

In some embodiments, a method for identifying compounds comprising anti-viral activity comprises:
(a) Purifying pVips within a bacterial strain deleted for iscR and/or with transfected with the pDB1282 plasmid.
(b) Screening for pVips nucleotide substrates through a biochemical assay based on 5'-dA production.
(c) Identification of pVip products. Products can first be separated using liquid chromatography and their spectrum analyzed. Using described protocols, Identification of negative-ion mass to charge ratio (−m/z) through LC-MS can allow product identification.
(d) NMR analysis to confirm identity of the product.

A biochemical assay based on 5'-dA production can be used for screening for pVips nucleotide substrates. Radical SAM enzymes produce 5'-dA radical species after the reductive SAM cleavage. Thus, the production of 5'-dA is used as an indicator of substrate activation. pVips can be subjected to a panel of nucleotides in in vitro reactions with co-factors. 5'-dA detection is performed using electrospray ionization in positive mode (ESI+) with multiple reaction monitoring (MRM). The correct substrate will generate enhanced 5'-dA levels.

pVip products can be identified by first separating them using liquid chromatography and analyzing the spectrum. Identification of negative-ion mass to charge ratio (−m/z) through LC-MS can allow product identification.

In some embodiments, pVip purification is conducted in strict anaerobic conditions, following known protocols.

Methods to identify pVip products also include isolating active anti-viral fractions (through cell lysates for example), isolating pVips products through HPLC, identifying pVip products through NMR analysis, or any combination thereof. In some embodiments, a pVip comprises a pVip provided in Table 3, or any of SEQ ID Nos: 409-789. In some embodiments, a pVip comprises a protein with at least 80% sequence homology to a pVip provided in Table 3, or any of SEQ ID Nos: 409-789.

In some embodiments, introducing a pVip into bacteria comprises introducing a pVip fragment into bacteria. In some embodiments, introducing a pVip into bacteria comprises introducing a functional pVip fragment into bacteria. In some embodiments, introducing a pVip into bacteria comprises introducing a nucleic acid construct comprising a pVip gene. In some embodiments, the method further comprises introducing into bacteria a pVip co-factor. In some embodiments, the method further comprises introducing into bacteria a pVip substrate.

In some embodiments, said pVip gene is selected from a gene provided in Table 1, Table 2, or comprises any of SEQ ID Nos: 3-383, or SEQ ID Nos: 384-408.

A skilled artisan would appreciate that there are several methods in the art for measuring viral resistance of a cell. Any of them can be applied to the methods disclosed herein. In some embodiments, measuring viral resistance comprises comparing cell viability, phage lysogeny, phage genomic replication, and/or phage genomic degradation, between the cells to which a pVip, or a pVip gene was introduced and control cells which do not express an endogenous or exogenous pVip.

In some embodiments, measuring viral resistance of a cell comprises plaque assays. Plaque assays are disclosed in Kropinski, A. M., Mazzocco, A., Waddell, T. E., Lingohr, E. & Johnson, R. P. Enumeration of Bacteriophages by Double Agar Overlay Plaque Assay. in Bacteriophages: Methods and Protocols, Volume 1: Isolation, Characterization, and Interactions (eds. Clokie, M. R. J. & Kropinski, A. M.) 69-76 (Humana Press, 2009). doi:10.1007/978-1-60327-164-6_7. In some embodiments, bacteria are mixed with an appropriate solid agar and serial dilutions of phage lysate are dropped on top of them. Plates are then incubated at the appropriate conditions, and plaque formation is measured and compared to plaque formation of control bacteria. In some embodiments, measuring viral resistance of a cell comprises liquid infection assays. In some embodiments, bacteria are grown in a liquid medium and infected with phages. Optical density (OD) is monitored using a plate reader, thus assessing the number of bacteria in the medium.

In some embodiments, screening infected bacteria for nucleoside or nucleotide analog compounds comprises analyzing the cytosolic fraction of said bacterial cells by liquid chromatography (LC). In some embodiments, screening infected bacteria for nucleotide or nucleoside compounds comprises analyzing the cytosolic fraction of said bacterial cells by mass spectrometry (MS). In some embodiments, screening infected bacteria for nucleotide or nucleoside compounds comprises analyzing the cytosolic fraction of said bacterial cells by a combination of LC and MS.

In some embodiments, analyzing for anti-viral activity of a compound comprises:
(a) providing cells sensitive to viral activity;
(b) contacting the cells with said compound;
(c) infecting said cells of step (b) with a virus; and
(d) measuring whether said cells of step (c) have increased survival compared to control cells wherein the said compound was not introduced;
wherein increased survival in cells indicates that said compound provide viral resistance to the cell.

In some embodiments, a pVip is identified by a method comprising:
(a) providing a prokaryotic protein;
(b) determining whether the sequence of said prokaryotic protein comprises identity to the amino acid sequence of a viperin protein above a predetermined threshold; and
(c) determining whether there are defense genes located in the vicinity of the genomic location of the prokaryotic gene encoding said prokaryotic protein;
wherein identity to a viperin protein above a predetermined percentage, the presence of defense genes above a predetermined number in the vicinity, or a combination thereof indicate that said prokaryotic protein is a pVip.

In some embodiments, a method of identifying a prokaryotic viperin homolog (pVip) comprises:
(a) searching a prokaryotic protein dataset for proteins comprising at least 25% homology to a eukaryotic viperin;
(b) clustering the genes encoding the proteins comprising at least 25% homology from step (a) into gene clusters;

(c) calculating a defense score for each gene cluster, wherein a defense score above a predetermined threshold is indicative of the proteins encoded by the genes of said cluster being pVips.

In some embodiments, a eukaryotic pVip comprises an amino acid sequence set forth in any of SEQ ID NOs: 2, or 826-828. In some embodiments, a defense score comprises a first score indicating the proportion of genes with defensive neighborhood, and a second score indicating the average number of defense genes in the neighborhood of the genes of said cluster. In some embodiments said first score is above 0.3, 0.4, 0.5, 0.6, 0.7, or 0.8. In some embodiments, said second score is above 1, 1.2, 1.4, 1.6, 1.8, or 2.

In some embodiments, determining whether the sequence of a prokaryotic protein comprises identity to the amino acid sequence of a viperin above a predetermined percentage, comprises determining whether the sequence of said prokaryotic protein comprises at least 20%, 30%, 40%, or 50% sequence identity to a viperin protein. In some embodiments, determining whether the sequence of a prokaryotic protein comprises identity to the amino acid sequence of a viperin protein above a predetermined percentage, comprises determining whether the sequence of said prokaryotic protein comprises at least 25% sequence identity to a viperin protein. There are several methods that can be used to determine sequence homology and/or sequence identity. Such techniques are thoroughly explained in the literature and can be applied for measuring the similarity between a prokaryotic protein a viperin protein.

In some embodiments, a defense gene comprises a gene belonging to a defense system. Defense systems are disclosed in scientific papers and databases known to the skilled in the art (see e.g. Makarova et al. J Bacteriol. 2011 November; 193(21): 6039-6056; Swarts et al. Nature (2014) 507, 258-261; Goldfarb et al. EMBO J. (2015) 34, 169-83; Doron et al. Science (2018) Vol. 359, Issue 6379, eaar4120; Ofir et al. Nature Microbiology (2018) 3, 90-98. Non-limiting examples of annotated defense systems that can be used with some embodiments of the methods for identifying pVips include, but are not limited to surface modifications to prevent adsorption of phages, restriction-modification (R/M) systems, infection (Abi) mechanisms, the CRISPR/Cas adaptive defense system, the prokaryotic argonaute, the BREX system, the DISARM system, the Gabija system, the Hachiman system, the Wadjet system, the Kiwa system, the Lamassu system, the Shedu system, the Spetu system, the Druantia system, and the Zorya system.

In some embodiments, the defense system is selected from the group consisting of a restriction-modification (R/M) system, an infection (Abi) system, a CRISPR/Cas adaptive defense system, a prokaryotic argonaute and a BREX system.

In some embodiments, the vicinity of a gene comprises 30 genes upstream (5') in a genome. In some embodiments, the vicinity of a gene comprises 20 genes upstream (5'). In some embodiments, the vicinity of a gene comprises 10 genes upstream (5'). In some embodiments, the vicinity of a gene comprises 5 genes upstream (5'). In some embodiments, the vicinity of a gene comprises 30 genes downstream (3'). In some embodiments, the vicinity of a gene comprises 20 genes downstream (3'). In some embodiments, the vicinity of a gene comprises 10 genes downstream (3'). In some embodiments, the vicinity of a gene comprises 5 genes downstream (3').

In some embodiments, the vicinity of known defense genes to the genes of a cluster predicts that the cluster comprises pVips. In some embodiments, the vicinity of known defense genes to at least 40%, 50%, 60, 70%, or 100% of the genes of a cluster, predicts that the cluster comprises pVips. In some embodiments, the average number of known defense genes in the neighborhood to the genes of a cluster predicts that the cluster comprises pVips. In some embodiments, an average of at least 0.5, 0.75, 1, 1.5, 2, 3, 4, or more known defense genes in the neighborhood to the genes of a cluster predicts that the cluster comprises pVips.

In some embodiments, the presence of a nucleoside kinase or a nucleotide kinase in the vicinity of a gene is indicative of the gene being a pVip. In some embodiments, proximity to a nucleoside kinase or a nucleotide kinase gene predicts that a gene of interest is a pViP.

In some embodiments, disclosed herein is a method for protecting a cell from viral infection, the method comprising contacting said cell with a compound comprising anti-viral activity identified by the method disclosed herein, wherein the compound is not naturally present in said cell.

As used herein the term "about" refers to +10%. As used herein, the singular form "a", "an" and "the" include plural references unless the context clearly dictates otherwise. For example, the term "a compound" or "at least one compound" may include a plurality of compounds, including mixtures thereof.

Throughout this application, various embodiments are disclosed that may be presented in a range format. It should be understood that the description in range format is merely for convenience and brevity and should not be construed as an inflexible limitation on the scope. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

In one embodiment, the present disclosure provides a method for treating a disease in a subject in need thereof, the method comprising administering to the subject a nucleoside analog derived from a nucleotide analog produced by a prokaryotic homologs of viperin (pVip) or any combination of nucleoside analogs thereof. In one embodiment, the amino acid sequence of the pVip is set forth in any one of SEQ ID NOs:409-789 or a homologue thereof comprising at least 80% homology to any one of SEQ ID NOs:409-789. In another embodiment, the pVip is encoded by a pVip gene comprising one of the sequence set forth in SEQ ID NOs: 3-408 or a homologue thereof comprising at least 80% identity to any one of SEQ ID NOs:3-408. In one embodiment, the disease can be a virus-induced disease, a cancer or a tumor, an autoimmune disease, an immune disorder, or a combination thereof. Examples of virus-induced diseases include, but are not limited to, diseases induced by norovirus, rotavirus, hepatitis virus A, B, C, D, or E, rabies virus, West Nile virus, enterovirus, echovirus, coxsackievirus, herpes simplex virus (HSV), HSV-2, varicella-zoster virus, mosquito-borne viruses, arbovirus, St. Louis encephalitis virus, California encephalitis virus, lymphocytic choriomeningitis virus, human immunodeficiency virus (HIV), poliovirus, zika virus, rubella virus, cytomegalovirus, human papillomavirus (HPV), enteovirus D68, severe acute respiratory syndrome (SARS) coronavirus, Middle East respiratory syndrome coronavirus, SARS coronavirus 2, Epstein-Barr virus, influenza virus, respiratory syncytical virus, polyoma viruses (such as JC virus, BK virus), Ebola virus, Dengue virus, or any combination thereof. Examples of cancer or tumor include, but are not limited to, carcinoma, sarcoma, lymphoma, leukemia, germ cell tumor, blastoma, chondrosarcoma, Ewing's sarcoma, malignant fibrous histiocytoma of bone/osteosarcoma, osteosarcoma, rhabdomyosarcoma, heart cancer, brain cancer, astrocytoma, glioma, medulloblastoma, neuroblastoma, breast cancer, medullary carcinoma, adrenocortical carcinoma, thyroid cancer, Merkel cell carcinoma, eye cancer, gastrointestinal cancer, colon cancer, gallbladder cancer, gastric (stomach) cancer, gastrointestinal carcinoid tumor, hepatocellular cancer, pancreatic cancer, rectal cancer, bladder cancer, cervical cancer, endometrial cancer, ovarian cancer, renal cell carcinoma, prostate cancer, testicular cancer, urethral cancer, uterine sarcoma, vaginal cancer, head cancer, neck cancer, nasopharyngeal carcinoma, hematopoietic cancer, lymphoma, Non-Hodgkin lymphoma, skin cancer, basal-cell carcinoma, melanoma, small cell lung cancer, non-small cell lung cancer, or any combination thereof. Examples of immune disorder include, but are not limited to, arthritis, host-versus-graft disease (HvGD), graft-versus-host disease (GvHD), inflammation, immunodeficiency, or an autoimmune disorder. Examples of auto-immune disease include, but are not limited to, achalasia, amyloidosis, ankylosing spondylitis, anti-gbm/anti-tbm nephritis, antiphospholipid syndrome, arthritis, autoimmune angioedema, autoimmune encephalomyelitis, autoimmune hepatitis, autoimmune myocarditis, autoimmune oophoritis, autoimmune orchitis, autoimmune pancreatitis, autoimmune retinopathy, autoimmune urticaria, Behcet's disease, celiac disease, chagas disease, chronic inflammatory demyelinating polyneuropathy (cidp), Cogan's syndrome, congenital heart block, Crohn's disease, dermatitis, dermatomyositis, discoid lupus, Dressler's syndrome, endometriosis, fibromyalgia, fibrosing alveolitis, granulomatosis with polyangiitis, Graves' disease, Guillain-Barre syndrome, herpes gestationis, immune thrombocytopenic purpura, interstitial cystitis (ic), juvenile arthritis, juvenile diabetes (type 1 diabetes), juvenile myositis (jm), Kawasaki disease, Lambert-Eaton syndrome, lichen planus, lupus, Lyme disease chronic, multiple sclerosis, myasthenia gravis, myositis, neonatal lupus, neutropenia, palindromic rheumatism, peripheral neuropathy, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, reactive arthritis, retroperitoneal fibrosis, rheumatic fever, rheumatoid arthritis, sarcoidosis, Schmidt syndrome, scleritis, scleroderma, Sjögren's syndrome, thrombocytopenic purpura, type 1 diabetes, ulcerative colitis, uveitis, vasculitis, vitiligo, or any combination thereof.

In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a respiratory viral infection (e.g. common cold, seasonal influenze). In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a gastrointestinal viral infection. In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a liver viral infection. In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a nervous system viral infection. In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a skin viral infection. In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a sexually transmitted viral infection. In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a placental viral infection. In some embodiments, methods for treating a disease in a subject in need thereof comprises administering to the subject a nucleoside analog derived from a nucleotide analog produced by a prokaryotic homolog of viperin (pVip) or any combination of nucleoside analogs thereof, wherein said viral-induced disease comprises a disease induced by a fetal viral infection.

In one embodiment, the present disclosure provides a method for treating a disease in a subject in need thereof, the method comprising administering to the subject a nucleoside analog derived from a nucleotide analog produced by a prokaryotic homologs of viperin (pVip) or any combination of nucleoside analogs thereof, wherein said disease comprises a viral-induced disease. In some embodiments, examples of said viral induced disease include but are not limited to gastroenteritis, keratoconjunctivitis, pharyngitis, croup, pharyngoconjunctival fever, pneumonia, cystitis (Adenovirus); Hand, foot and mouth disease, pleurodynia, aseptic meningitis, pericarditis, myocarditis (Coxsackievirus); infectious mononucleosis, Burkitt's lymphoma, Hodgkin's lymphoma, nasopharyngeal carcinoma (Epstein-Barr virus); acute hepatitis (Hepatitis A virus); acute hepatitis, chronic hepatitis, hepatic cirrhosis, hepatocellular carcinoma (Hepatitis B virus); acute hepatitis, chronic hepatitis, hepatic cirrhosis, hepatocellular carcinoma (Hepatitis C virus); herpes labialis, cold sores—can recur by latency, gingivostomatitis in children, tonsillitis & pharyngitis in adults, keratoconjunctivitis (Herpes simplex virus, type 1); skin vesicles, mucosal ulcers, oral and/or genital ulcers, Aseptic meningitis (Herpes simplex virus, type 2); infectious mononucleosis, Cytomegalic inclusion disease, Premature birth, liver, lung and spleen diseases in the newborn, congenital seizures in the newborn (Cytomegalovirus); Kaposi sarcoma, multicentric Castleman disease, primary effusion lymphoma (Human herpesvirus, type 8); AIDS (HIV); influenza, Reye syndrome (Influenza virus); measles, postinfectious encephalomyelitis (Measles virus); mumps (mumps virus); hyperplastic epithelial lesions (common, flat, plantar and anogenital warts, laryngeal papillomas, epidermodysplasia verruciformis), cervical carcinoma, squamous cell carcinomas) (Human papillomavirus); croup, pneumonia, bronchiolitis, common cold (Parainfluenza virus); poliomyelitis (Poliovirus); rabies (fatal encephalitis) (rabies virus); bronchiolitis, pneumonia, influenza-like syndrome, severe bronchiolitis with pneumonia (Respiratory syncytial virus); congenital rubella, German measles (Rubella virus); and chickenpox, herpes zoster, Congenital varicella syndrome (Varicella-zoster virus).

In some embodiments, said viral induced disease is caused by viruses of human or non-human origin. In some embodiments, said viral induced disease is caused by modified or unmodified viruses that originate from animals or any foreign organism, for example, infection caused by SARS coronavirus, SARS coronavirus 2 etc.

In some embodiments, said viral induced disease is caused by viruses in the Baltimore classification Group I group of viruses: double-stranded DNA viruses (e.g. Adenoviruses, Herpesviruses, Poxviruses). In some embodiments, said viral induced disease is caused by viruses in the Baltimore classification Group II group of viruses: single-stranded (or "sense") DNA viruses (e.g. Parvoviruses). In some embodiments, said viral induced disease is caused by viruses in the Baltimore classification Group III group of viruses: double-stranded RNA viruses (e.g. Reoviruses). In some embodiments, said viral induced disease is caused by viruses in the Baltimore classification Group IV group of viruses: single-stranded (sense) RNA viruses (e.g. Picornaviruses, Togaviruses, Coronavirus). In some embodiments, said viral induced disease is caused by viruses in the Baltimore classification Group V of viruses: single-stranded (antisense) RNA viruses (e.g. Orthomyxoviruses, Rhabdoviruses). In some embodiments, said viral induced disease is caused by viruses in the Baltimore classification Group VI group of viruses: single-stranded (sense) RNA viruses with DNA intermediate in life-cycle (e.g. Retroviruses). In some embodiments, said viral induced disease is caused by viruses in the Baltimore classification Group VII group of viruses: double-stranded DNA viruses with RNA intermediate in life-cycle (e.g. Hepadnaviruses).

In some embodiments, treating a viral infection comprises treating any of the viral-induced diseases disclosed herein.

In one embodiment, the nucleotide analog or nucleoside analog used in the above method can be ddhUTP, ddhGTP, ddhATP, ddhGDP, ddhUDP, ddhUMP, ddh-deoxy-GTP, ddh-deoxy-ATP, ddh-deoxy-TTP, ddhG, ddhA, ddhU, ddh-deoxy-G, ddh-deoxy-A, ddh-deoxy-T, or any combination thereof. In another embodiment, the nucleotide analog or nucleoside analog can further include ddhCTP, ddhCDP, ddhCMP, ddh-deoxy-CTP, ddhC, ddh-deoxy-C, or a combination thereof.

In one embodiment, the present disclosure provides a nucleoside analog derived from a nucleotide analog produced by a prokaryotic homologs of viperin (pVip), or any combination of nucleoside analogs thereof, for use in the treatment of a disease in a subject in need thereof. In one embodiment, the pVip has the amino acid sequence of one of SEQ ID NOs:409-789 or a homologue thereof comprising at least 80% homology to one of SEQ ID NOs:409-789. In another embodiment, the pVip is encoded by a pVip gene comprising the sequence of one of SEQ ID Nos:3-408 or a homologue thereof comprising at least 80% identity to one of SEQ ID Nos:3-408. In one embodiment, the disease can be a virus-induced disease, a cancer or a tumor, an autoimmune disease, an immune disorder, or a combination thereof. Examples of virus-induced diseases, cancer or tumor, autoimmune diseases, or immune disorders have been listed above. In one embodiment, the nucleotide analog or nucleoside analog employed in the above use can be ddhUTP, ddhGTP, ddhATP, ddhGDP, ddhUDP, ddhUMP, ddh-deoxy-GTP, ddh-deoxy-ATP, ddh-deoxy-TTP, ddhG, ddhA, ddhU, ddh-deoxy-G, ddh-deoxy-A, ddh-deoxy-T, or any combination thereof. In another embodiment, the nucleotide analog or nucleoside analog can further include ddhCTP, ddhCDP, ddhCMP, ddh-deoxy-CTP, ddhC, ddh-deoxy-C, or a combination thereof.

In one embodiment, the present disclosure provides a method of terminating polynucleotide chain synthesis in a cell, the method comprising introducing into the cell a nucleoside analog derived from a nucleotide analog produced by a pVip or any combination of nucleoside analogs thereof. In one embodiment, the amino acid sequence of the pVip is set forth in any one of SEQ ID NOs:409-789 or a homologue thereof comprising at least 80% homology to any one of SEQ ID NOs:409-789. In another embodiment, the pVip is encoded by a pVip gene comprising the sequence set forth in one of SEQ ID NOs:3-408 or a homologue thereof comprising at least 80% identity to any one of SEQ ID NOs:3-408. In one embodiment, terminating polynucleotide chain synthesis increases termination of DNA chain synthesis, or increases termination of RNA chain synthesis, or a combination thereof. In another embodiment, terminating polynucleotide chain synthesis confers to the cell viral resistance, resistance to foreign nucleic acid invasion, antiviral activity, anti-phage activity, anti-plasmid activity, reduced plasmid transformation efficiency, resistance to entry of a conjugation element, increased resistance to horizontal gene transfer, decreased replication of endogenous DNA, decreased replication of foreign DNA, decreased RNA transcription, decreased RNA replication, increased termination of DNA chain synthesis, increased termination of RNA chain synthesis, decreased cell proliferation, or any combination thereof. In one embodiment, the cell is a eukaryotic cell; for example, the eukaryotic cell is a tumor cell, or a cell infected by a virus or a foreign DNA. In one embodiment, the nucleotide analog or nucleoside analog used in the method can be ddhGTP, ddhATP, ddhGDP, ddhUTP, ddhUMP, ddh-deoxy-GTP, ddh-deoxy-ATP, ddh-deoxy-TTP, ddhG, ddhA, ddhU, ddh-deoxy-G, ddh-deoxy-A, ddh-deoxy-T, or any combination thereof. In another embodiment, the nucleotide analog or nucleoside analog or combination thereof can further include ddhCTP, ddhCDP, ddhCMP, ddh-deoxy-CTP, ddhC, ddh-deoxy-C, or a combination thereof.

In another embodiment, the present disclosure provides a pharmaceutical composition comprising a pharmaceutical acceptable carrier and a nucleoside analog derived from a nucleotide analog produced by a pVip or any combination of nucleoside analogs thereof. In one embodiment, the amino acid sequence of the pVip is set forth in any one of SEQ ID NOs:409-789 or a homologue thereof comprising at least 80% homology to any one of SEQ ID NOs:409-789. In another embodiment, the pVip is encoded by a pVip gene comprising any one of SEQ ID Nos:3-408 or a homologue thereof comprising at least 80% identity to any one of SEQ ID Nos:3-408. In one embodiment, the nucleotide analog or nucleoside analog can be ddhGTP, ddhATP, ddhGDP, ddhUTP, ddhUMP, ddh-deoxy-GTP, ddh-deoxy-ATP, ddh-deoxy-TTP, ddhG, ddhA, ddhU, ddh-deoxy-G, ddh-deoxy-A, ddh-deoxy-T, or any combination thereof. In another embodiment, the nucleotide analog or nucleoside analog or combination thereof can further include ddhCTP, ddhCDP, ddhCMP, ddh-deoxy-CTP, ddhC, ddh-deoxy-C, or a combination thereof.

In another embodiment, the present disclosure provides a method for treating a disease in a subject in need thereof, the method comprising administering to the subject a composition comprising a prokaryotic viperin homolog (pVip), a nucleic acid construct comprising a pVip gene, or a cell expressing a pVip. In one embodiment, the amino acid sequence of the pVip is set forth in any one of SEQ ID NOs:409-789 or a homologue thereof comprising at least 80% homology to any one of SEQ ID NOs:409-789. In one embodiment, the pVip gene comprises the sequence set forth in one of SEQ ID Nos:3-408 or a homologue thereof comprising at least 80% identity to any one of SEQ ID Nos:3-408.

In another embodiment, the present disclosure provides a method of terminating polynucleotide chain synthesis in a cell, the method comprising introducing into the cell a prokaryotic viperin homolog (pVip), or expressing in the cell a pVip gene. In one embodiment, the amino acid sequence of the pVip is set forth in any one of SEQ ID NOs:409-789 or a homologue thereof comprising at least 80% homology to any one of SEQ ID NOs:409-789. In one embodiment, the pVip gene comprises the sequence set forth in one of SEQ ID Nos:3-408 or a homologue thereof comprising at least 80% identity to any one of SEQ ID Nos:3-408.

In another embodiment, the present disclosure provides a method of producing a nucleoside or a nucleotide analog, the method comprising: (a) introducing a pVip, or a nucleic acid construct encoding a pVip into a cell, wherein the pVip produces a nucleoside analog or a nucleotide analog; and (b) purifying the nucleoside analog or nucleotide analog from the cell, thereby producing a nucleoside analog or a nucleotide analog. In one embodiment, the pVip has the sequence of any one of SEQ ID NOs:409-789 or a homologue thereof comprising at least 80% homology to the amino acid sequence set forth in any one of SEQ ID NOs:409-789. In another embodiment, the pVip is encoded by a pVip gene comprising one of the sequence of SEQ ID Nos:3-408 or a homologue thereof comprising at least 80% identity to any one of SEQ ID Nos:3-408. In one embodiment, when the pVip in the above method produces a nucleotide analog, the method further comprises dephosphorylating the nucleotide analog. In one embodiment, the nucleotide analog or nucleoside analog in the above method can be ddhUTP, ddhGTP, ddhATP, ddhGDP, ddhUTP, ddhUMP, ddh-deoxy-GTP, ddh-deoxy-ATP, ddh-deoxy-TTP, ddhT, ddhG, ddhA, ddhU, ddh-deoxy-G, ddh-deoxy-A, ddh-deoxy-T, or any combination thereof. In another embodiment, the above nucleotide analog or nucleoside analog or combination thereof can further include ddhCTP, ddhCDP, ddhCMP, ddh-deoxy-CTP, ddhC, ddh-deoxy-C, or a combination thereof. In one embodiment, the above method further comprises introducing into the cell pVip co-factors, or pVip substrates, or any combination thereof.

In another embodiment, the present disclosure provides a method of producing a nucleoside analog or a nucleotide analog in vitro, the method comprising: (a) providing an isolated prokaryotic viperin homolog (pVip) in vitro; (b) mixing the isolated pVip with a pVip nucleotide substrate and co-factors; (c) purifying a nucleoside analog or a nucleotide analog produced in step (b), thereby producing a nucleoside analog or a nucleotide analog, or a combination thereof. In one embodiment, the amino acid sequence of the pVip is set forth in any one of SEQ ID NOs:409-789 or a homologue thereof comprising at least 80% homology to any one of SEQ ID NOs:409-789. In anther embodiment, the pVip is encoded by a pVip gene comprising the sequence of one of SEQ ID Nos:3-408 or a homologue thereof comprising at least 80% identity to any one of SEQ ID Nos:3-408.

In another embodiment, the present disclosure provides a nucleic acid construct comprising a polynucleotide encoding a prokaryotic viperin homolog (pVip), and a non-naturally occurring regulatory element operably linked to the polynucleotide. In one embodiment, the amino acid sequence of the pVip is set forth in any one of SEQ ID NOs:409-789 or a homologue thereof comprising at least 80% homology to any one of SEQ ID NOs:409-789. In another embodiment, the pVip is encoded by a pVip gene comprising the sequence of one of SEQ ID Nos:3-408 or a homologue thereof comprising at least 80% identity to any one of SEQ ID Nos:3-408. In one embodiment, the regulatory element comprises a cis-acting regulatory element for directing expression of the polynucleotide, or a transmissible element for directing transfer of the polynucleotide from one cell to another, or a recombination element for integrating the polynucleotide into a genome of a cell transfected with the construct, or an element providing episomal maintenance of the construct within a cell transfected with the construct, or any combination thereof.

In another embodiment, the present disclosure provides a transmissible genetic element or an expression vector comprising the above nucleic acid construct.

In another embodiment, the present disclosure provides an isolated cell expressing the above nucleic acid construct, or the above transmissible genetic element.

In another embodiment, the present disclosure provides a method for identifying a compound comprising anti-viral activity, the method comprising: (a) introducing into a cell a prokaryotic viperin homolog (pVip) or a combination thereof, or expressing in a cell a pVip gene; (b) contacting the cell of step (a) with a virus; (c) measuring viral resistance of the cell of step (b); (d) screening the cell of step (c) that demonstrated viral resistance for nucleotide or nucleoside compounds not present in control cell to which the pVip was not introduced; and (e) analyzing the compound or compounds identified in step (d) for anti-viral activity; thereby identifying a compound comprising anti-viral activity. In one embodiment, measuring viral resistance of step (c) comprises comparing cell viability, phage lysogeny, phage genomic replication, phage genomic degradation, or a combination thereof, between the cells of step (b) and control cells which do not express an endogenous or exogenous pVip. In another embodiment, the screening of step (d) comprises analyzing the cytosolic fraction of the cells by liquid chromatography (LC), by mass spectrometry (MS), or by a combination of both.

In another embodiment, the present disclosure provides a method of identifying a compound comprising anti-viral activity, the method comprising steps of: (a) expressing a prokaryotic viperin homolog (pVip) in a cell; (b) purifying the pVip from the cell; (c) adding a nucleotide substrate, and/or pVip co-factors to the pVip in vitro; (d) purifying compound(s) that result from step (c); (e) analyzing the purified compound(s) to identify their chemical identity; (f) adding the compounds identified in step (e), or a modified version thereof, to a cell, and (g) measuring viral resistance of the cell of step (f), wherein increased viral resistance is indicative of the compound having anti-viral activity.

In another embodiment, the present disclosure provides a method of identifying a prokaryotic viperin homolog (pVip), the method comprising: (a) searching a prokaryotic protein dataset for proteins comprising at least 25% homology to a eukaryotic viperin; (b) clustering the genes encoding the proteins comprising at least 25% homology from step (a) into gene clusters; (c) calculating a defense score for each gene cluster, wherein a defense score above a predetermined threshold is indicative of the proteins encoded by the genes of the cluster being pVips. In one embodiment, the amino acid sequence of the eukaryotic pVip in the above method comprises any one of SEQ ID NOs:2, or 826-828. In another embodiment, the predetermined threshold of the defense score comprises a proportion of genes with defensive neighborhood (score 1) above 0.6, an average number of defense genes in the neighborhood (score 2) above 1.6, or a combination thereof.

EXAMPLES

Reference is now made to the following examples, which together with the above descriptions illustrate some embodiments in a non-limiting fashion.

Generally, the nomenclature used herein, and the laboratory procedures utilized, include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are well known in the art and are provided for the convenience of the reader. All the information contained therein is incorporated herein by reference.

Example 1—Materials and Methods

Bacterial Strains and Growth Conditions

*Escherichia coli* strains (MG1655, Keio ΔiscR, DH5a) were grown in LB or LB agar at 37° C. unless mentioned otherwise. Whenever applicable, media were supplemented with ampicillin (100 μgml$^{-1}$), kanamycin (50 μgml$^{-1}$) or tetracycline (10 ugmL$^{-1}$) to ensure the maintenance of plasmids. *Bacillus subtilis* strain BEST7003 and its derivatives were grown in LB or LB agar at 37° C. Whenever applicable, media were supplemented with spectinomicin (100 μgml$^{-1}$). Expression from pAra and pHypraspank promoters was induced by the addition of respectively arabinose (0.2%) or IPTG (1 mM).

Plasmids and Strain Construction pVip genes were codon optimized and synthetized by Twist Bioscience (pVips 6-10, and 12) or by Genscript (all other pVips). Synthetized pVip are shown in Table 2. Each candidate sequence was cloned in two plasmids: pDR111 and pBad/His A (Thermofisher, Catalog number 43001). For pVips 6-12, PCR fragments were joined using Gibson Assembly®. The primers used in these experiments are shown in Table 5. For other candidates, cloning was performed by Genscript. Candidate pVip plasmids were first cloned and propagated in DH5α. pBad/HisA derivatives were further transformed in relevant strains (MG1655, Keio ΔiscR). pDR111 derivatives were integrated in the amyE locus of the BEST strains. pAGG encodes a GFP under a T7 promoter and a module with T7 lyzozyme to limit the leakiness of RNAP in strain BL21-DE3. The pAGG plasmid was obtained though two consecutives Gibbson assemblies, the first to generate pAG (insert pDR793 primers OG630, OG631, vector pACYc, primers OG629, OG628) and then a second to generate pAGG (insert pLysS primers AB55, AB56, vectorpAG, primers AB53, AB54) (Table 5).

TABLE 5

Primers

| Name | SEQ ID NO: |
|---|---|
| AB_Vip1-gibbson_coli_vector_F | 790 |
| AB_Vip2-gibbson_coli_vector_R | 791 |
| AB_Vip3-gibbson_coli_insert_F | 792 |
| AB_Vip4-gibbson_coli_insert_R | 793 |
| AB_Vip5-res_coli_vector_F | 794 |
| AB_Vip6-res_coli_vector_R | 795 |
| AB_Vip7-gibbson_subtilis_vector_F | 796 |
| AB_Vip8-gibbson_subtilis_vector_R | 797 |
| AB_Vip19-gibbson_subtilis_insert_pVip6_F | 798 |
| AB_Vip20-gibbson_subtilis_insert_pVip6_R | 799 |
| AB_Vip21-gibbson_subtilis_insert_pVip7_F | 800 |
| AB_Vip22-gibbson_subtilis_insert_pVip7_R | 801 |
| AB_Vip23-gibbson_subtilis_insert_pVip8_F | 802 |
| AB_Vip24-gibbson_subtilis_insert_pVip8_R | 803 |
| AB_Vip25-gibbson_subtilis_insert_pVip9_F | 804 |
| AB_Vip26-gibbson_subtilis_insert_pVip9_R | 805 |
| AB_Vip27-gibbson_subtilis_insert_pVip10_F | 806 |
| AB_Vip28-gibbson_subtilis_insert_pVip10_R | 807 |
| AB_Vip31-gibbson_subtilis_insert_pVip12_F | 808 |
| AB_Vip32-gibbson_subtilis_insert_pVip12_R | 809 |
| AB_Vip37-sequencing_primer_coli_1 | 810 |
| AB_Vip38-sequencing_primer_coli_2 | 811 |
| AB_Vip39-sequencing_primer_subtilis_1 | 812 |
| AB_Vip40-sequencing_primer_subtilis_2 | 813 |
| AB_Vip41-pVip_control_coli_vector_F | 814 |
| AB_Vip42-pVip_control_coli_vector_R | 815 |
| AB_Vip43-pVip_control_coli_insert_F | 816 |
| AB_Vip44-pVip_control_coli_insert_R | 817 |
| AB53 | 818 |
| AB54 | 819 |
| AB55 | 820 |
| AB56 | 821 |
| OG628 | 822 |
| OG629 | 823 |
| OG630 | 824 |
| OG631 | 825 |

Phage Propagation

Phages were propagated on either *E. coli* MG1655, *E. coli* MG1655 F+ or *B. subtilis* BEST7003 using the plate lysate method as described in Fortier, L. C. et al. Phage Production and Maintenance of Stocks, Including Expected Stock Lifetimes; in "Bacteriophages: Methods and Protocols, Vol 1: Isolation, Characterization, and Interactions" (eds. Clokie, M. R. J. & Kropinski, A. M.) 203-219 (Humana Press, 2009). Lysate titer was determined using the small drop plaque assay method as described in Kropinski et al. Enumeration of Bacteriophages by Double Agar Overlay Plaque Assay; in "Bacteriophages: Methods and Protocols, Volume 1: Isolation, Characterization, and Interactions" (eds. Clokie, M. R. J. & Kropinski, A. M.) 69-76 (Humana Press, 2009). Phages used in this study are presented in Table 6.

TABLE 6

Phages used in these experiments

| Phage | Host | Taxonomy | Accession number |
|---|---|---|---|
| SBSphi28-4 | *B. subtilis* | Siphoviridae | N/A |
| SP82G | *B. subtilis* | Myoviridae | N/A |
| phi105 | *B. subtilis* | Siphoviridae | HM072038.1 |
| SPP1 | *B. subtilis* | Siphoviridae | NC_004166.2 |
| Phi3T | *B. subtilis* | Siphoviridae | KY030782.1 |
| SPBeta | *B. subtilis* | Siphoviridae | AF020713.1 |
| SPR | *B. subtilis* | Siphoviridae | N/A |
| Rho14 | *B. subtilis* | Siphoviridae | N/A |
| SPO1 | *B. subtilis* | Myoviridae | NC_011421.1 |
| phi29 | *B. subtilis* | Podoviridae | NC_011048.1 |
| SBSphiC | *B. subtilis* | Myoviridae | LT960610.1 |
| SBSphiJ | *B. subtilis* | Myoviridae | LT960608.1 |
| SECphi18 | *E. coli* | Siphoviridae | LT960609.1 |
| SECphi27 | *E. coli* | Siphoviridae | LT961732.1 |
| SEC32-2 | *E. coli* | Siphoviridae | N/A |
| Lambda_VIR | *E. coli* | Siphoviridae | NC_001416.1 |
| SECphi17 | *E. coli* | Microviridae | LT960607.1 |
| SECphi6_1 | *E. coli* | Siphoviridae | N/A |
| P1 | *E. coli* | Myoviridae | AF234172.1 |
| T2 | *E. coli* | Myoviridae | LC348380.1 |
| T4 | *E. coli* | Myoviridae | AF158101.6 |
| T5 | *E. coli* | Siphoviridae | AY543070.1 |
| T6 | *E. coli* | Myoviridae | MH550421.1 |
| T7 | *E. coli* | Podoviridae | NC_001604.1 |

Plaque Assays

Plaque assays were performed as previously described in Kropinski, A M et al. Enumeration of Bacteriophages by Double Agar Overlay Plaque Assay. in Bacteriophages: Methods and Protocols, Volume 1: Isolation, Characterization, and Interactions (eds. Clokie, M. R. J. & Kropinski, A. M.) 69-76 (Humana Press, 2009). doi:10.1007/978-1-60327-164-6_7. Bacteria from overnight cultures were mixed with MMB agar (LB+0.1 mM MnCl2+5 mM MgCl2+5 mM CaCl2)+0.5% agar), and serial dilutions of phage lysate in MMB agar were dropped on top of them. After the drops dried up, plates were incubated overnight at room temperature for *B. subtilis* phages and for *E. coli* phages SECphi6, SECphi17, SECphi18, SECphi27, SECphi32, and T7, or at 37° C. for *E. coli* phages P1, T2, T4, T5, T6, λvir, Qbeta, M13, Fd, and MS2. Efficiency of plating (EOP) was measured by performing small drop plaque assay with the same phage lysate on control and induced bacteria, and comparing the ratio of plaque formation.

Liquid Infection Assays

Bacteria were grown for one hour at 37° C. Inducer (arabinose or IPTG) was added and cells were incubated one hour at room temperature. Cells were infected with phages within 96-well plates. OD was monitored using Tecan Plate reader.

Example 2—Sequence Homology-Based Discovery of Prokaryotic Homologs of Viperins

Search for Viperin Homologs in Prokaryotic Genomes

The human viperin protein sequence (NCBI accession NP_542388.2 (SEQ ID NO: 2)) was used as a seed for a MMseqs search (v6-f5a1c, default parameters, 3 iterations) on the IMG database (https://img.jgi.doe.gov/downloaded October 2017, 38183 genomes). MMseqs (Many-against-Many sequence searching) is a software suite for fast and deep clustering and searching of large datasets. MMseqs is open-source software available at https://github.com/soedinglab/MMseqs. The search yielded 2150 hits, that show between 25%-41% sequence identity to the human viperin. Genes with an e-value higher than $10^{-5}$ were discarded, leaving 1724 genes. This dataset was clustered using MMseqs (v6-f5a1c, default parameter, coverage 60%, sensitivity 7.5) and redundancy was removed resulting in 17 clusters, among which 5 clusters had more than 10 genes (Table 1). For each cluster, defense scores were computed as described in Doron, S. et al. Systematic discovery of antiphage pVips in the microbial pangenome. Science (80). 4120, eaar4120 (2018).

Some of these bacterial and archaeal genes distantly homologous to the human viperin may function in antiphage activities in prokaryotes. However, it was not trivial to predict which of these homologs is indeed an anti-phage gene. In prokaryotes, genes involved in anti-viral function co-localize on the genome forming "defense islands". Enrichment next to known defense genes can be a predictor that this group of genes performs anti-viral functions. Briefly, neighborhood of the selected gene (+/−10 genes) was screened for known defense genes. A first score corresponds to the proportion of genes in the cluster which exhibit at least one defense gene in its neighborhood. A second score corresponds to the average number of defense genes found in the neighborhood of the genes of the cluster. Only one of viperin-homolog clusters obtained showed high propensity for being enriched next to known defense systems (Table 7). Manual examination of the genomic context of genes of this cluster confirmed the presence of many known anti-phage defense genes in its vicinity (FIG. 1). This cluster (of 134 genes) showed high defense scores (0.602 and 1.687 respectively), and was selected for further analysis. Given that the online IMG database is constantly growing (31242 additional genomes since the download on October 2017), additional candidate prokaryotic viperin homologs (pVips) were searched manually using the "top IMG homologs" function in IMG. This added 84 genes to the cluster. Finally, a MMseqs search using genes of this cluster as seeds was performed on a metagenomes database (downloaded from IMG in October 2017, comprising 9769 metagenomes altogether, scaffolds with less than 21 genes were removed). Hits were filtered to cover at least 200 aa and hit at least 20 target genes from the pVip cluster. This added 163 genes, resulting in a total of 381 pVips (Table 1 and Table 3).

Table 7 below shows clusters (sized at least 10 genes) of hits of homologs search. The first column indicates the number of genes in the cluster. Second and third columns show defense scores (proportion of genes in the cluster with known anti-phage defense genes in their vicinity; average number of known defense genes in neighborhood).

TABLE 7

Clusters of genes retrieved in the homology-based search

|  | Number of genes | Proportion of genes with defensive neighborhood (score 1) | Average number of Defense Genes in neighborhood (score 2) |
| --- | --- | --- | --- |
| Cluster 1 | 855 | 0.061 | 0.094 |
| Cluster 2 | 134 | 0.602 | 1.687 |
| Cluster 3 | 54 | 0.2 | 0.32 |
| Cluster 4 | 21 | 0.077 | 0.077 |
| Cluster 5 | 17 | 0.077 | 0.077 |

Example 3—Diversity of pVips

Figure 2:
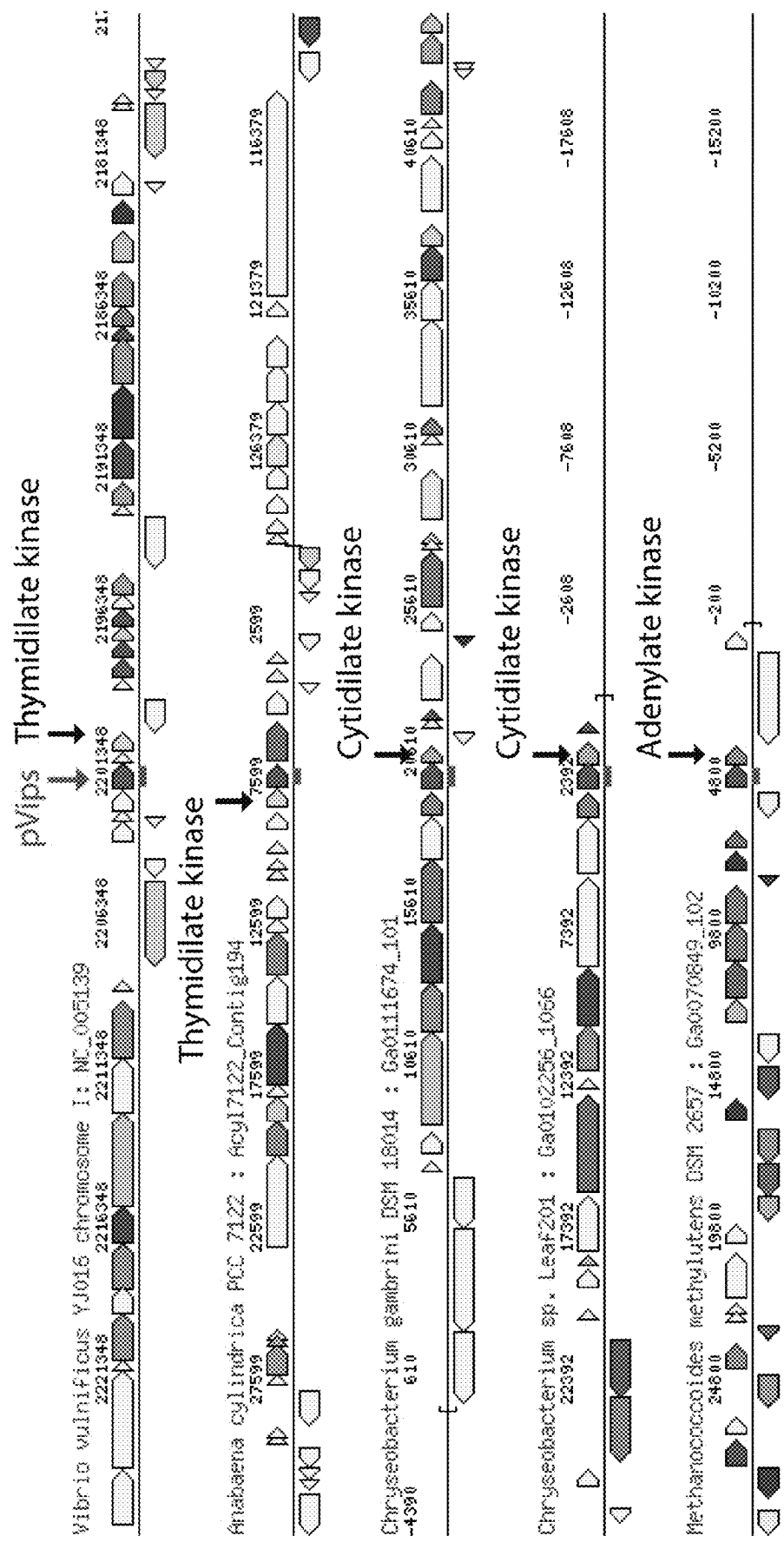
FIG. 2 shows an embodiment of the genomic neighborhood of pVip genes. The presence of diverse kinases, predicted to supply nucleotide substrates to the pVip, is observed in the neighborhood of pVip genes. pVip genes are represented in red. Black arrows point at genes annotated as nucleotide kinases.

Examination of the genomic context of pVips revealed the presence of nucleoside kinases or nucleotide kinases in their vicinity, an observation reminiscent of the organization of the human system, in which viperin is located close to CMPK2 (FIG. 2). In vertebrates, CMPK2 phosphorylates cytidine monophosphate (CMP) to generate cytidine triphosphate (CTP), which is the viperin substrate that is converted by the viperin to ddhCTP. The adjacent kinases might therefore be indicative of the potential substrate of the nearby viperin. In total, 15% of the pVips encode a kinase in their neighborhood. Some pVip-associated kinases are annotated as cytidylate kinase pointing at a potentially identical substrate as CMPK2, namely that the substrate of these pVips is predicted to be CTP. However, many other pVips are found next to nucleoside kinases or nucleotide kinases annotated as thymidylate, guanylate or adenylate kinases (FIG. 2). This suggests that the substrate of some pVips may be nucleotides other than CTP, and that they can thus generate new chain terminators that were not described previously. For example, pVips found next to thymidylate or guanylate kinases may generate ddhUTP or ddhGTP or derivatives thereof. Moreover, some of these kinases are annotated as kinases of deoxy-nucleosides or deoxy-nucleotides, namely the DNA form of the nucleoside or nucleotide rather than the RNA form that is modified by the eukaryotic viperins. In this case, the relevant pVips can generate deoxy form of ddh nucleosides or nucleotides, leading to new DNA chain terminator molecules rather than RNA chain terminator molecules.

Figure 3A:
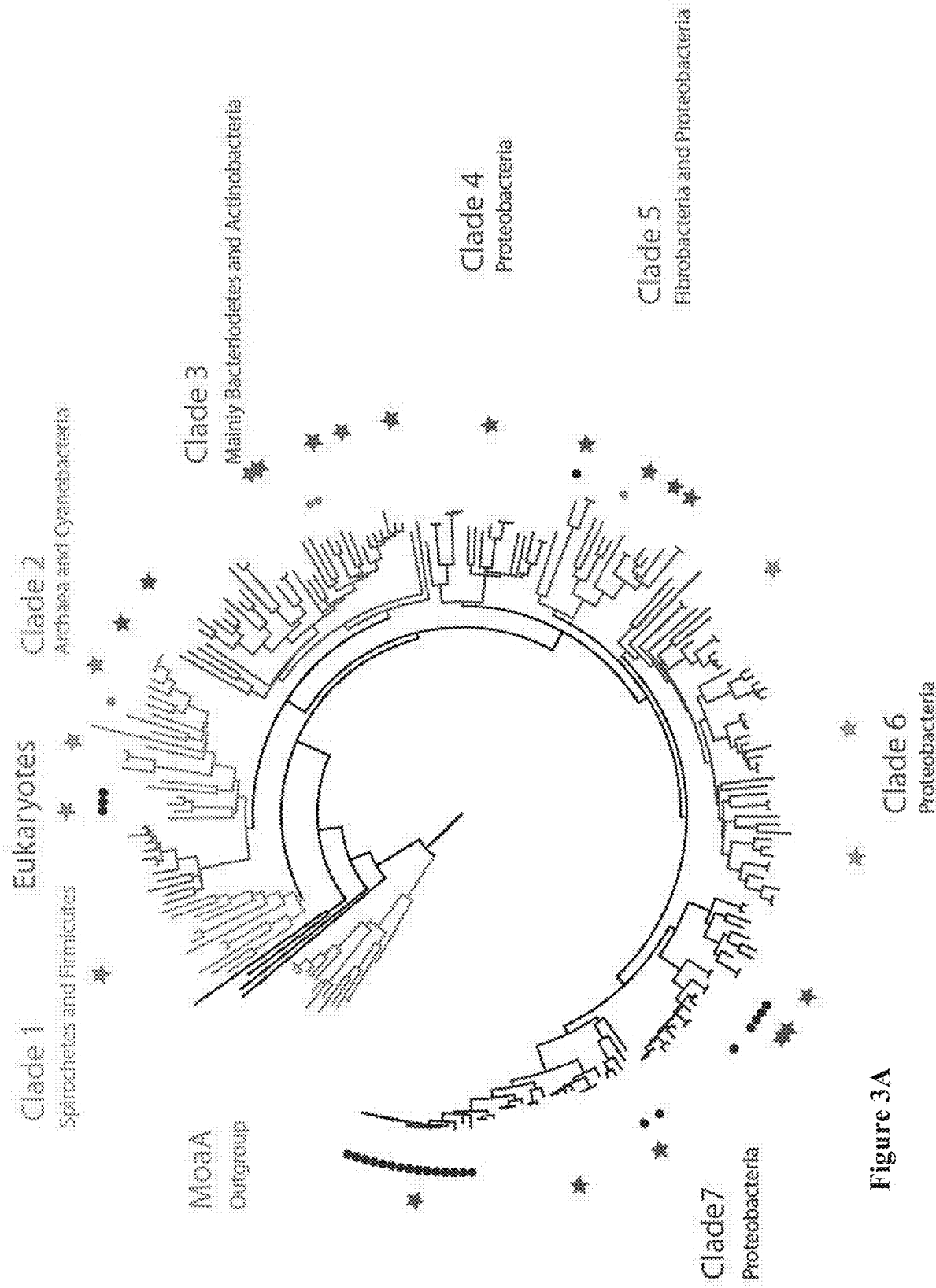
FIGS. 3A-3B show phylogenetic trees of pVip genes.

The sequences of pVips are highly diverse with on average 37% identity at the protein level when compared to one another. pVips were found in 94 genera of diverse phyla including Euryarchaeota, Proteobacteria, Firmicutes, and Bacteriodetes. To better understand this diversity and phylogenetic relationship with eukaryotic viperins, a phylogenetic tree of the protein family was built (FIG. 3A).

The Molybdenum cofactor biosynthesis protein (MoaA) is known to be a structural homolog of Viperin, but MoaA does not participate in defense against viruses and does not generate antiviral chain terminator nucleotide analogs (Santamaria-Araujo J A et al. (2004) J Biol Chem. 279(16): 15994-9; Fenwick M K et al. (2017) Proc Natl Acad Sci USA. 114(26):6806-6811). Hence, the MoaA gene can be used as an outgroup for phylogenetic analyses. Eukaryotic sequences of viperins were chosen to represent a diversity of species for the tree building and are provided in attached files. Prokaryotic viperins, eukaryotic viperins and MoaA sequences were aligned using mafft (v7.402, default parameters). The tree was computed with IQ-TREE multicore v.1.6.5 under model LG+I+G4. This model gave the lowest Bayesian Information Criterion (BIC) among all models available for both trees (option—m TEST in IQ-TREE). 1000 ultra-fast bootstraps were made in order to evaluate node support (options—bb 1000—wbtl in IQ-TREE). Phylogenetic trees figures were designed using ITOL.

It was found that pVips are grouped in 7 major clades (FIG. 3A) that partly correspond to major prokaryotic phyla. For example, clade 2 encompasses many archaea and cyanobacteria versions while clades 5, 6, 7 mainly encode pVips from Proteobacteria. Interestingly, all eukaryotic viperins are found in one clade within the tree, with a closest common ancestor with pVips from clade 2. This specific place of eukaryotic viperins in the pVip tree suggests that the evolutionary origin of all eukaryotic viperins was a pVip from clade 2. This also means that pVips encode higher diversity than eukaryotic viperins, suggesting again that pVips would produce a variety of polynucleotide chain terminators other than ddhCTP. While some clades encode exclusively one type of kinases, like clade 7 (thymidylate kinases) some encode diverse kinases like clade 5 (both thymidylate and adenylate) (FIG. 3A).

Figure 3B:
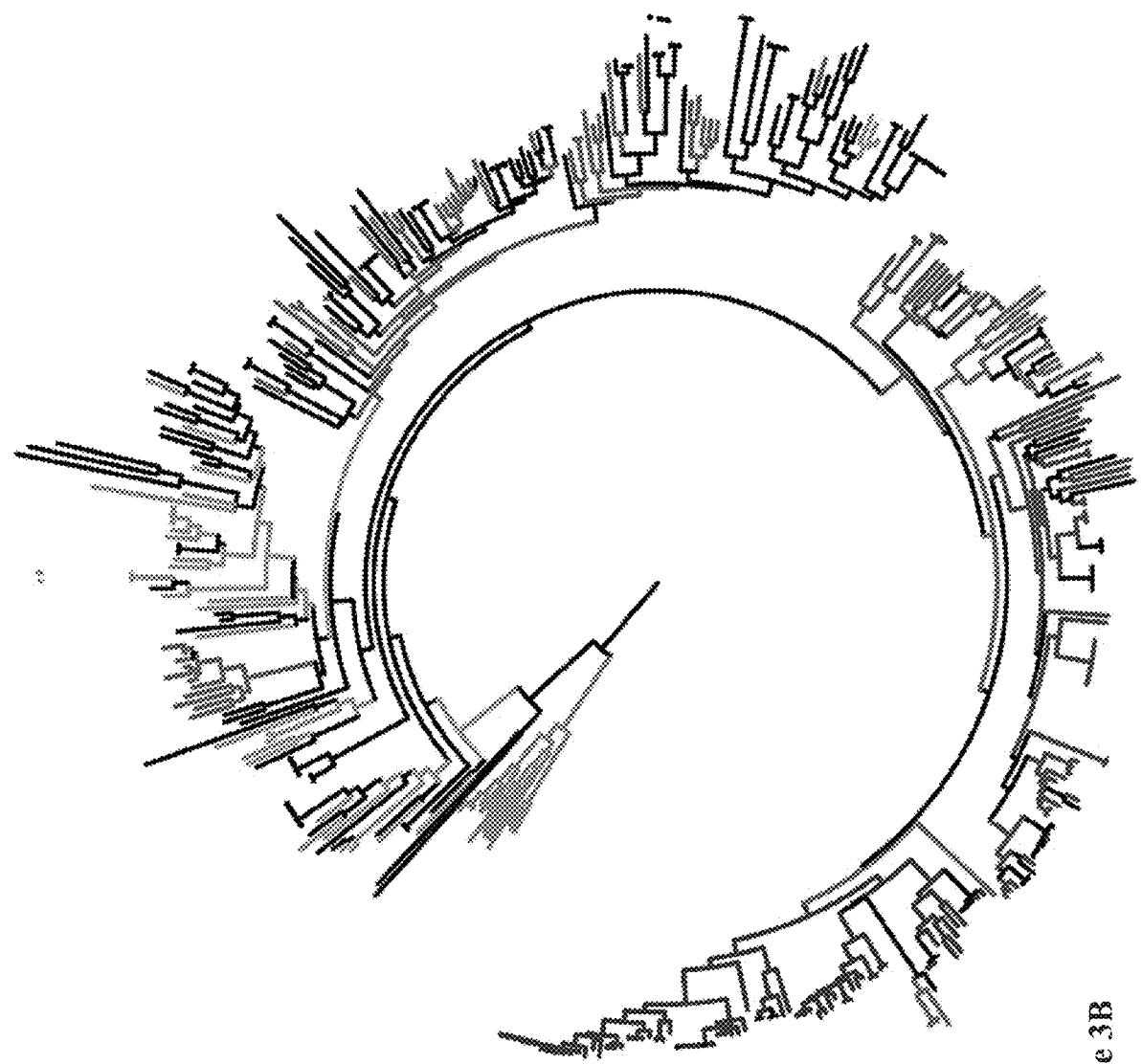

To fully capture the diversity of this protein family, homologs search was extended to metagenomes. Sequences from the initial cluster were used as a seed for a MMseqs search on a database of 9769 metagenomes that were downloaded from IMG in October 2017 as described in Example 2. This search added, after filtering (coverage of at least 200 aa and hit at least 20 target genes from the pVips cluster), 163 sequences to the pVips dataset yielding 381 homologs in total. These additional 163 pVips identified within metagenomes also had a high propensity to be found next to known defense genes (85 of the 163, 52%), suggesting that these set of genes also functions in antiviral defense. A second phylogenetic tree was built that includes the pVips from isolate genomes as well as these 163 additional genes (FIG. 3B). Sequences found in metagenomes do not change the topology of the initial tree, with still seven major clades and eukaryotic viperins being embedded in one of the prokaryotic clades. These observations suggest that the dataset of 381 pVips is representative of the diversity of the protein family.

Altogether, these results indicate the existence of a diverse family of pVips. While quite rare among microbial genomes, they are present in phylogenetically very distant organisms suggesting an ancient evolutionary origin. Their genomic context is indicative of a potential anti-viral activity. Presence of nearby nucleoside kinases or nucleotide kinases with diverse predicted substrates suggest a diversity of substrates and subsequently of products generated by the pVips which are predicted to be other than the known ddhCTP produced by the eukaryotic viperins.

Example 4—pVips Provide Anti-Viral Activity In Vivo

Figure 4:
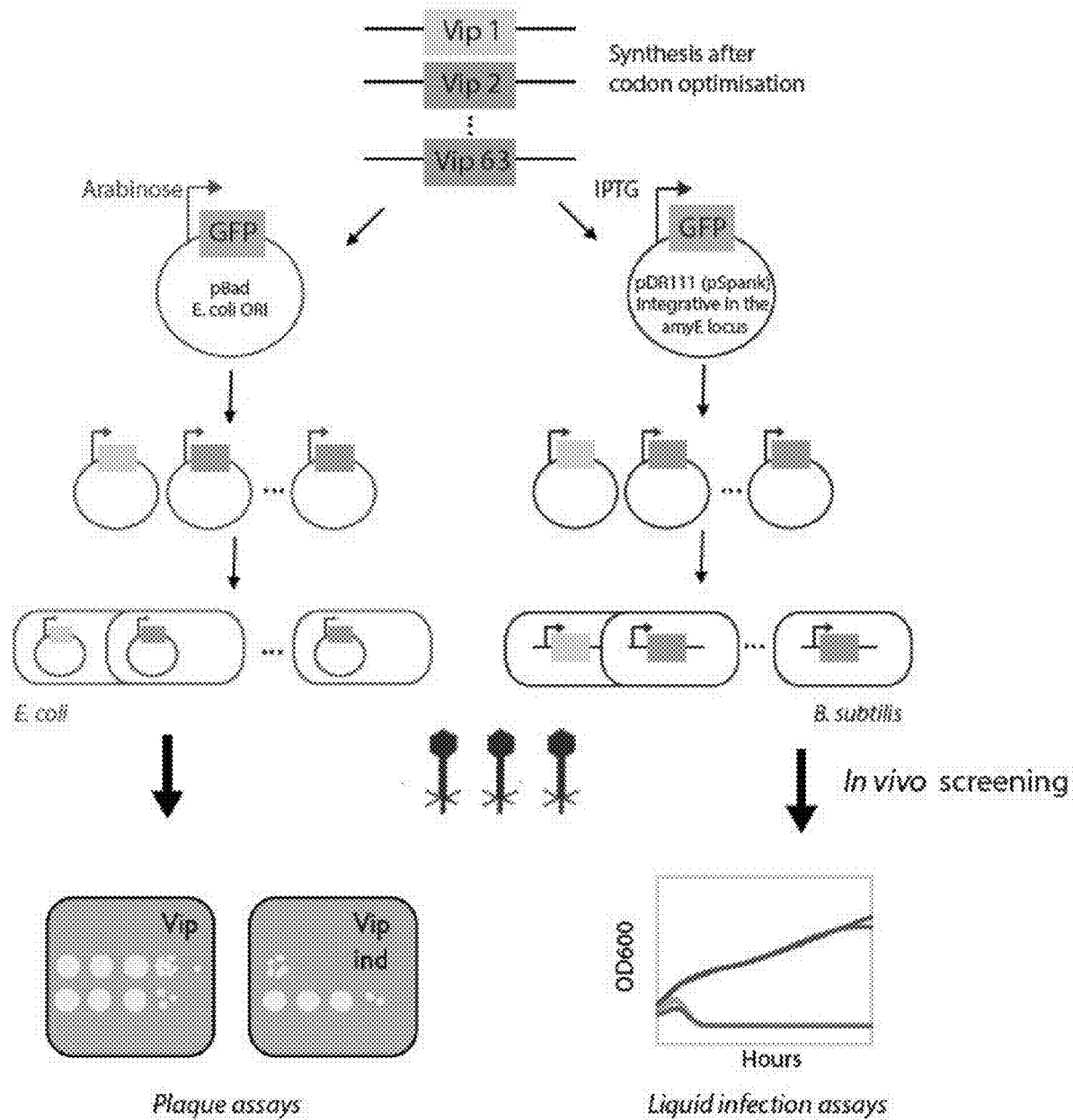
FIG. 4 shows the experimental approach used for functional validation of pVips. pVip gene candidates were synthetized and cloned in two different vectors under inducible promoters. *E. coli* and *B. subtilis* bacteria were transfected with these vectors and then tested for viral resistance against a collection of phages. Anti-viral activity of pVips was assessed in two types of assays: solid plaque assays and liquid infection assays.
Figure 5A:
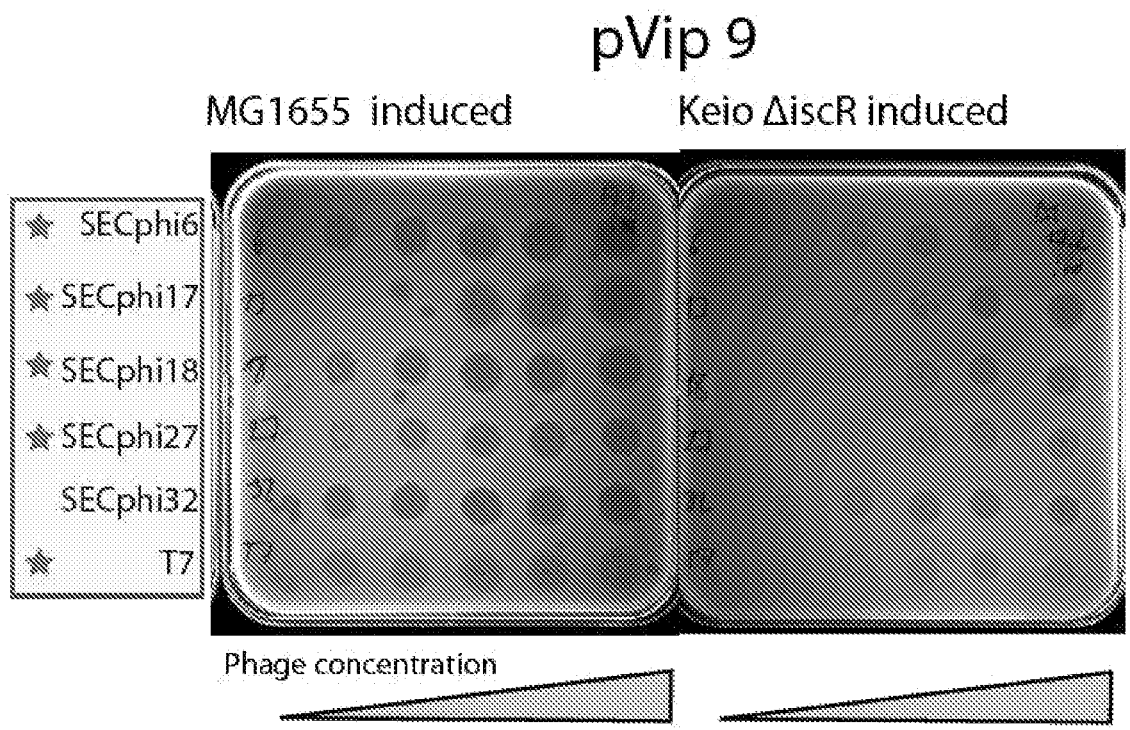
FIGS. 5A-5B show that a strain with a knockout in the iscR gene (Keio ΔiscR) rescues pVips activity in vivo.
Figure 5B:
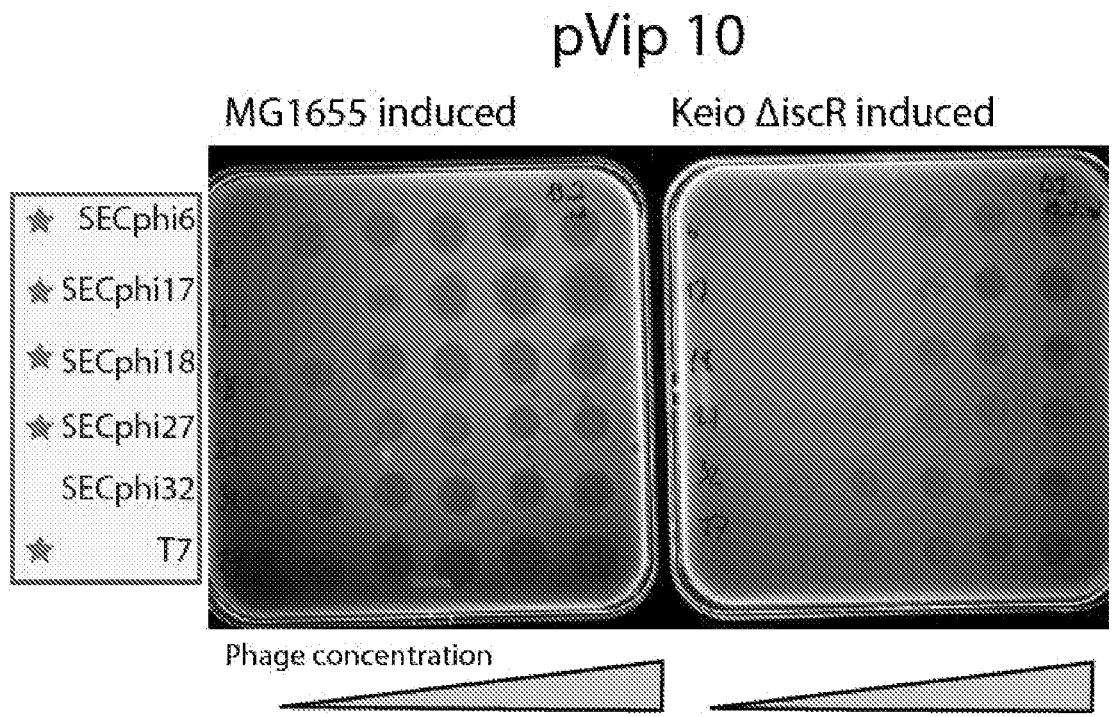

The objective of this study was testing whether prokaryotic homologs of viperins (pVips) provide defense against bacteriophages in vivo. 25 genes that span across the pVip phylogenetic tree were selected to assess activity of diverse representatives of the family. MoaA from *E. coli*, structurally similar to viperins but with a demonstrated function in metabolism and not in antiviral activity, was used as a negative control. The sequences of these genes were codon optimized for expression in lab bacteria (*E. coli*), resulting in the codon-optimized sequences presented in (SEQ ID NOs: 384-408), and cloned in vectors for *E. coli* and *B. subtilis* under the control of inducible promoters (pAra for *E. coli*, pHypraspank for *B. subtilis*) to avoid potential toxicity effects (FIG. 4).

pVips, as well as eukaryotic viperins, are Radical-SAM enzymes that contain an iron sulfur cluster 4Fe-4S. For such enzymes, the 4Fe-4S cluster is built by a complex of proteins and then carried into the apoenzyme making it an active holoenzyme. This metabolic step can require some specific interactions between the proteins that build the iron sulfur cluster and the protein that receive it, in this case the pVip. Heterologous expression of iron-sulfur cluster enzymes such as viperins can thus lead to loss of catalytic activity, if the cell in which the viperin is expressed does not express the iron sulfur clusters to high enough levels.

Some of the tested pVip candidates could be inactive in vivo in *E. coli* or in *B. subtilis* because of this limitation. Several strategies have been employed to circumvent this issue for other iron-sulfur cluster proteins, such as the expression of an exogenous set of genes responsible for iron sulfur cluster formation or the endogenous overexpression of the iron sulfur cluster metabolism genes of *E. coli* through deletion of the endogenous repressor of these genes, iscR, in *E. coli*. In the current study we used the second approach, and pVips were cloned into an *E. coli* strain from the Keio collection deleted for iscR. As a control, *E. coli* Keio ΔiscR were transfected with MoaA.

Figure 6A:
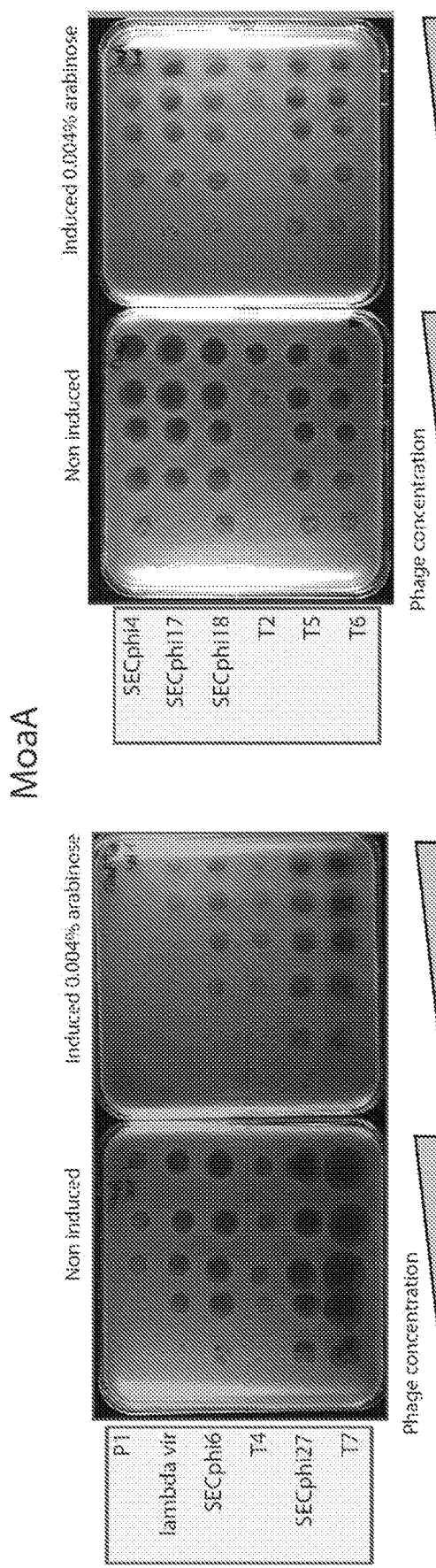
FIGS. 6A-6Z show plaque assays of multiple pVips cloned and expressed in Keio ΔiscR colonies indicating in vivo anti-viral activity of the pVips. Shown are plaque assays in which pVip expression was either non induced or induced by adding 0.004% arabinose, as indicated. Colonies were challenged with the following phages: P1, lambda vir, SECPhi6, T4, SECPhi27, T7, SECPhi4, SECPhi17, SECPhi18, T2, T5, and T6 as indicated. Phages were diluted from $10^{-1}$ to $10^{-6}$ of the original stock. Star indicates phages for which activity of pVip was observed.
Figure 6B:
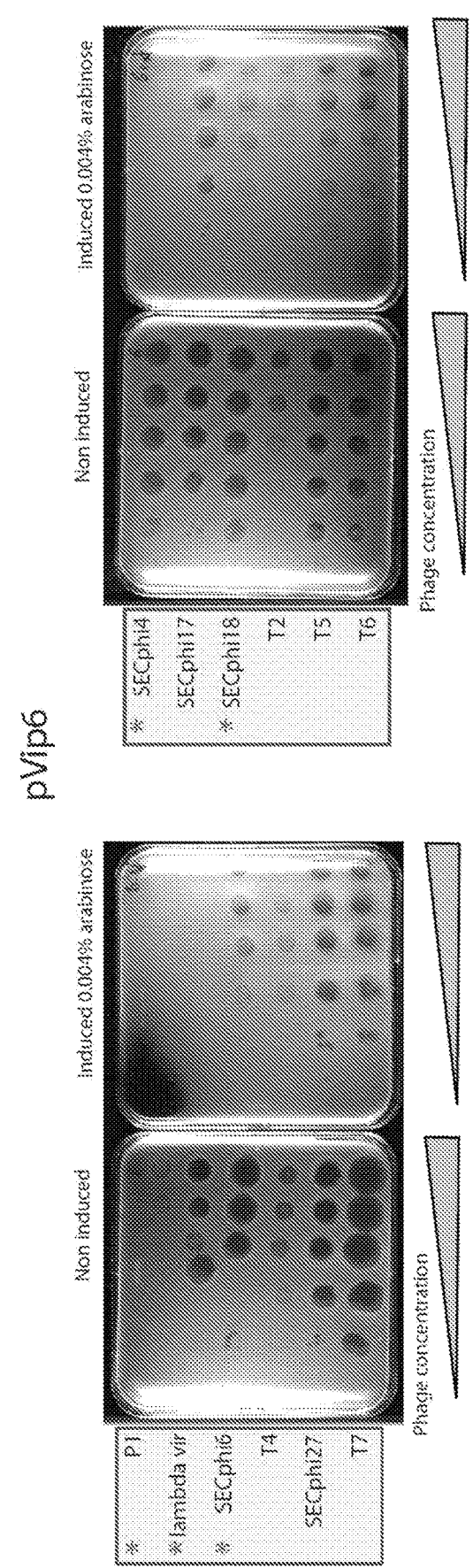
Figure 6E:
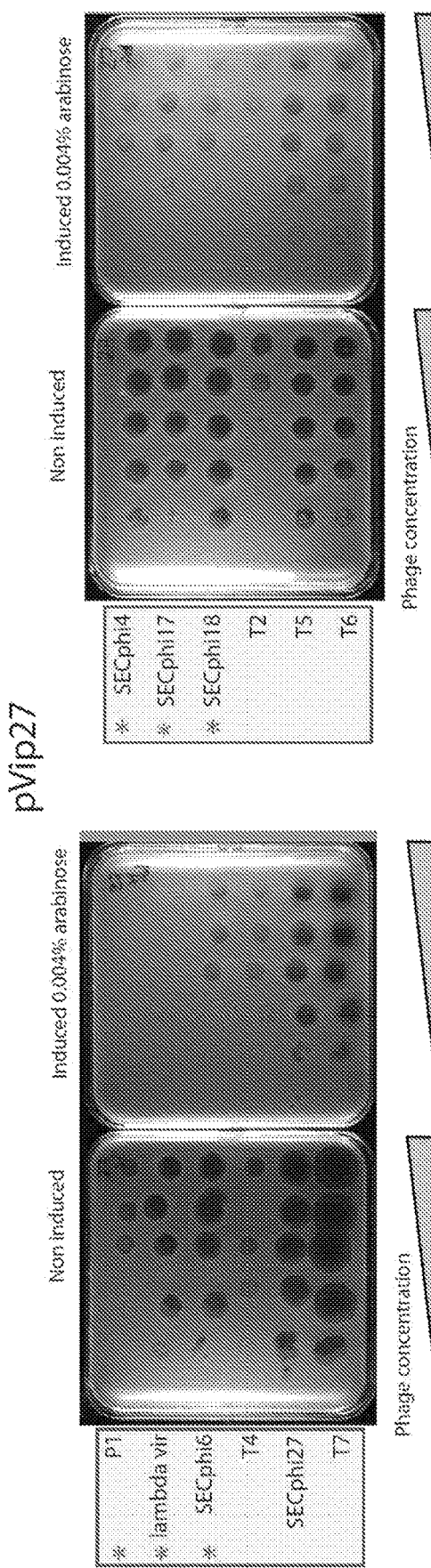
Figure 6F:
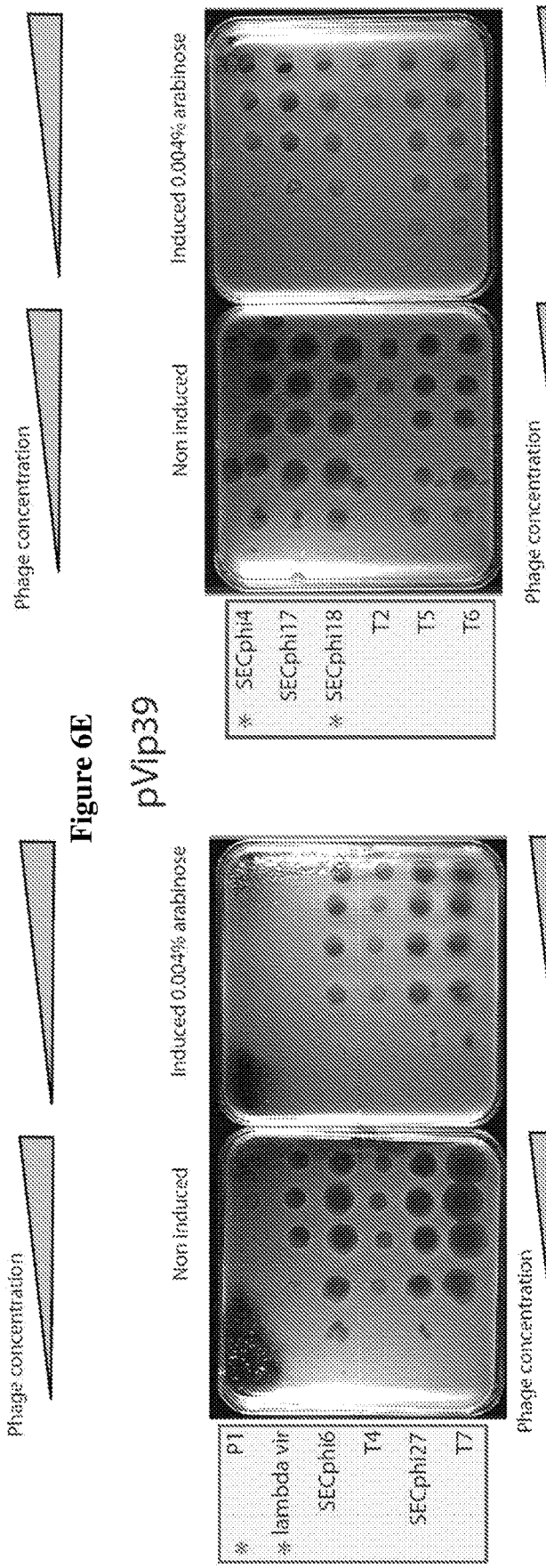
Figure 6G:
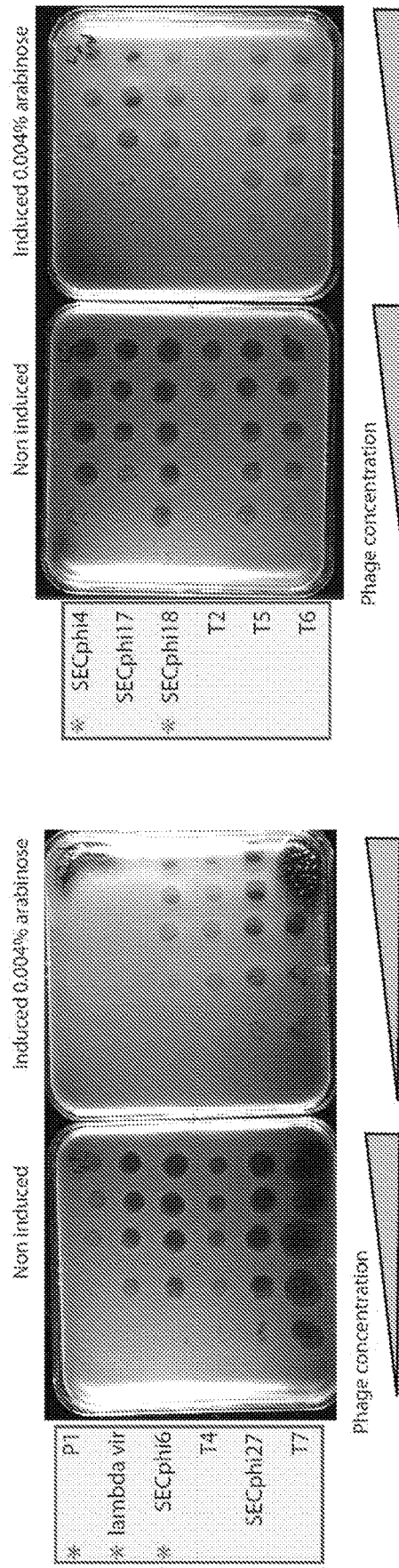
Figure 6H:
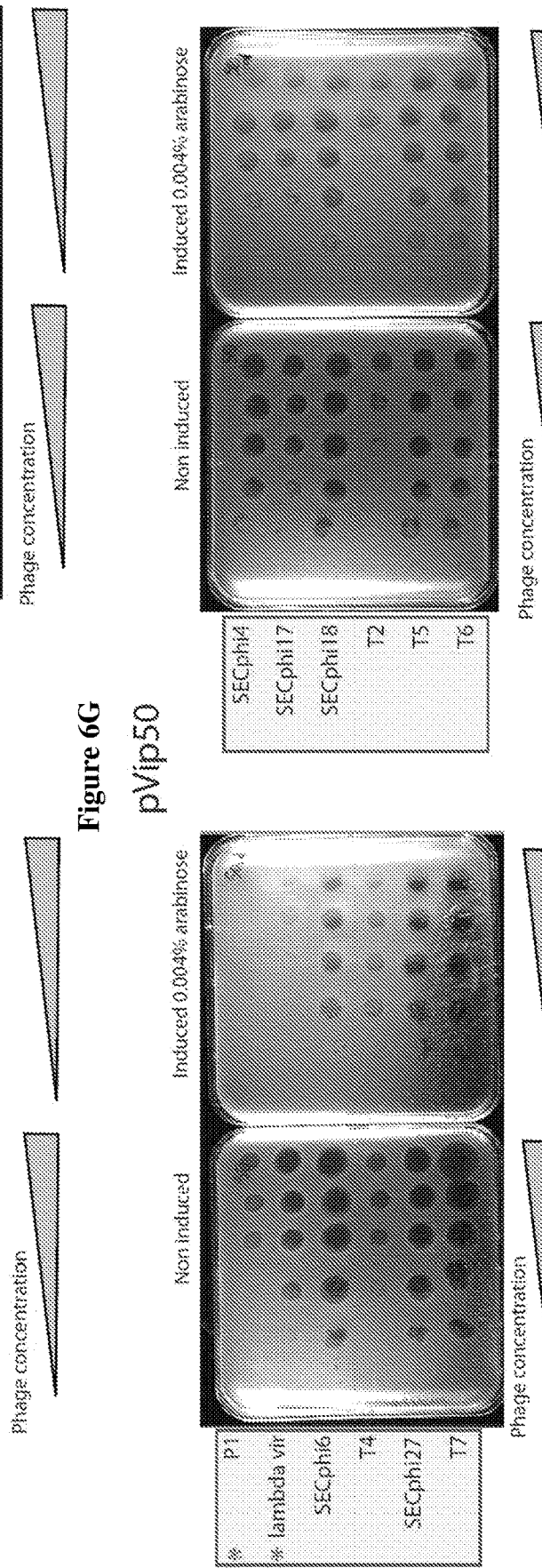
Figure 6K:
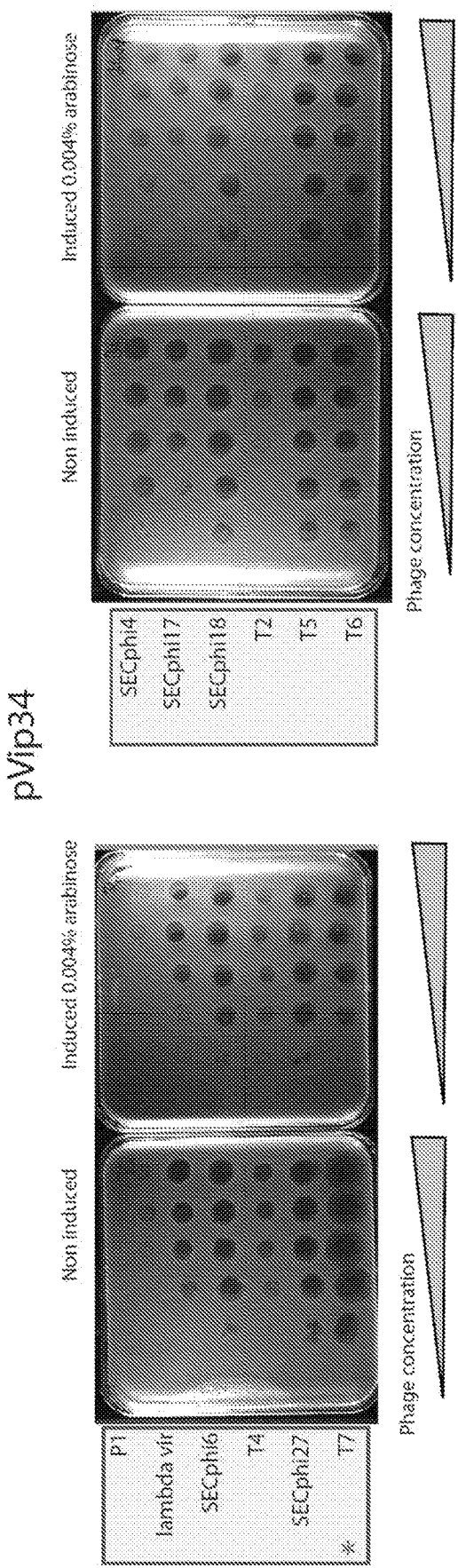
Figure 6L:
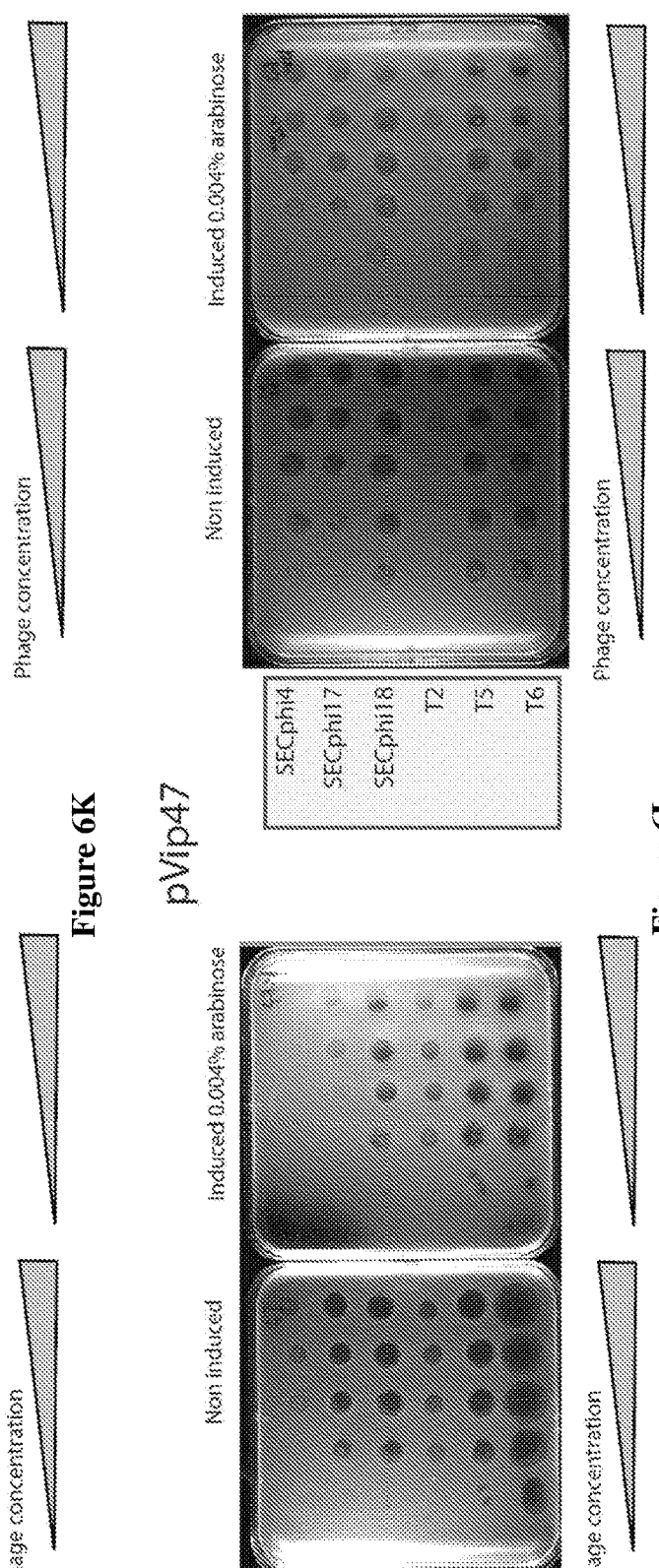
Figure 6O:
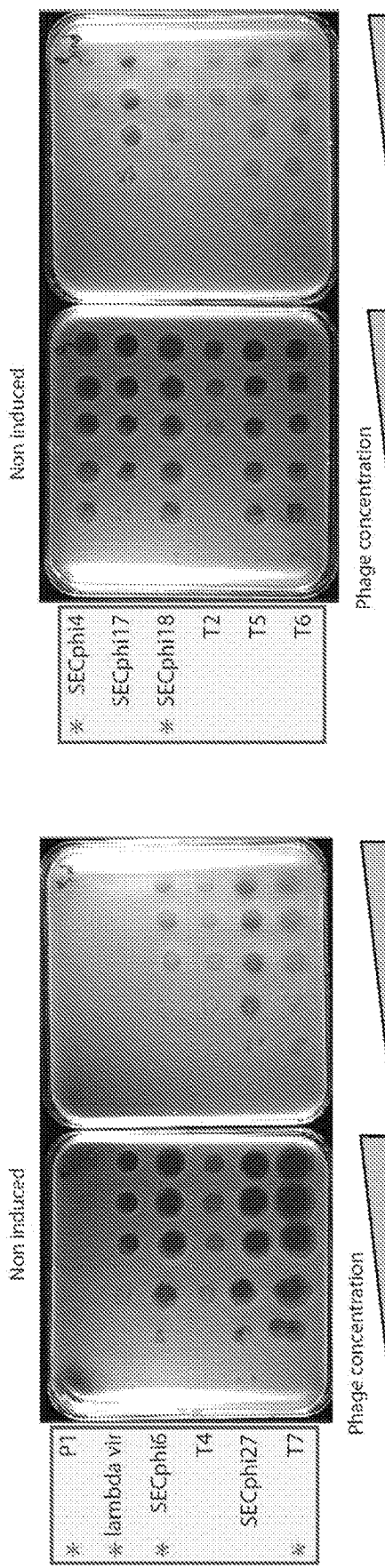
Figure 6P:
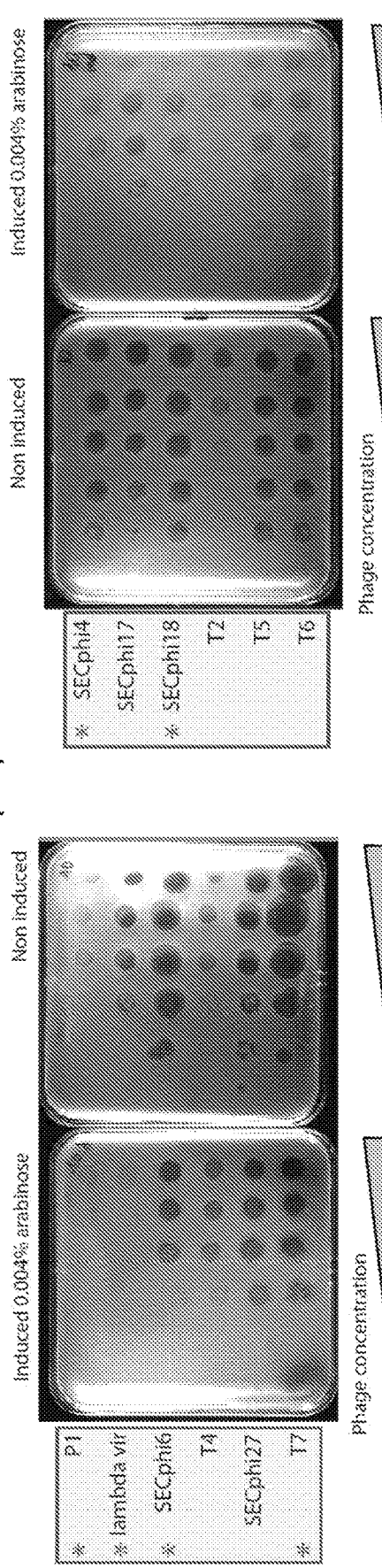
Figure 6Q:
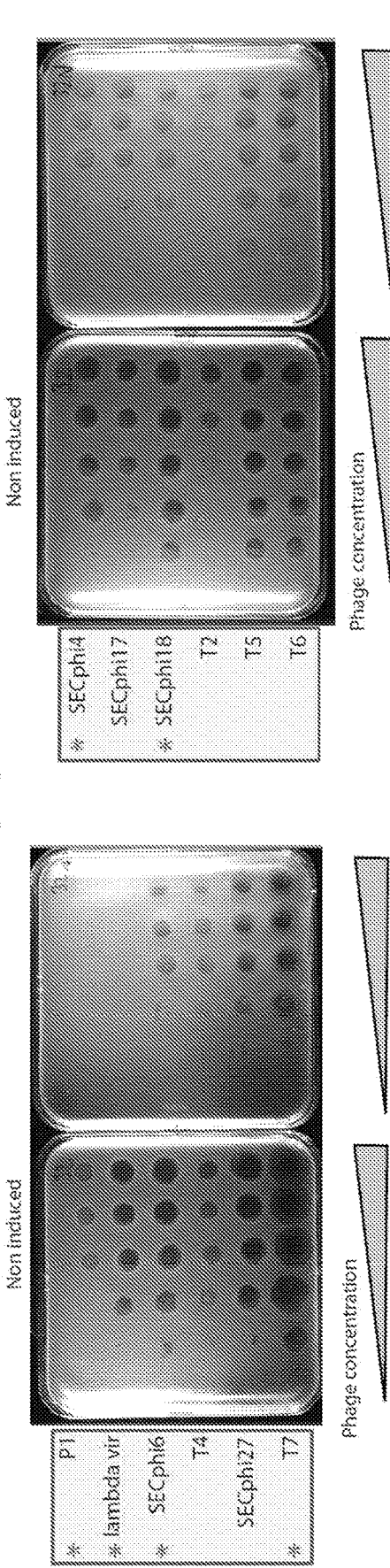
Figure 6R:
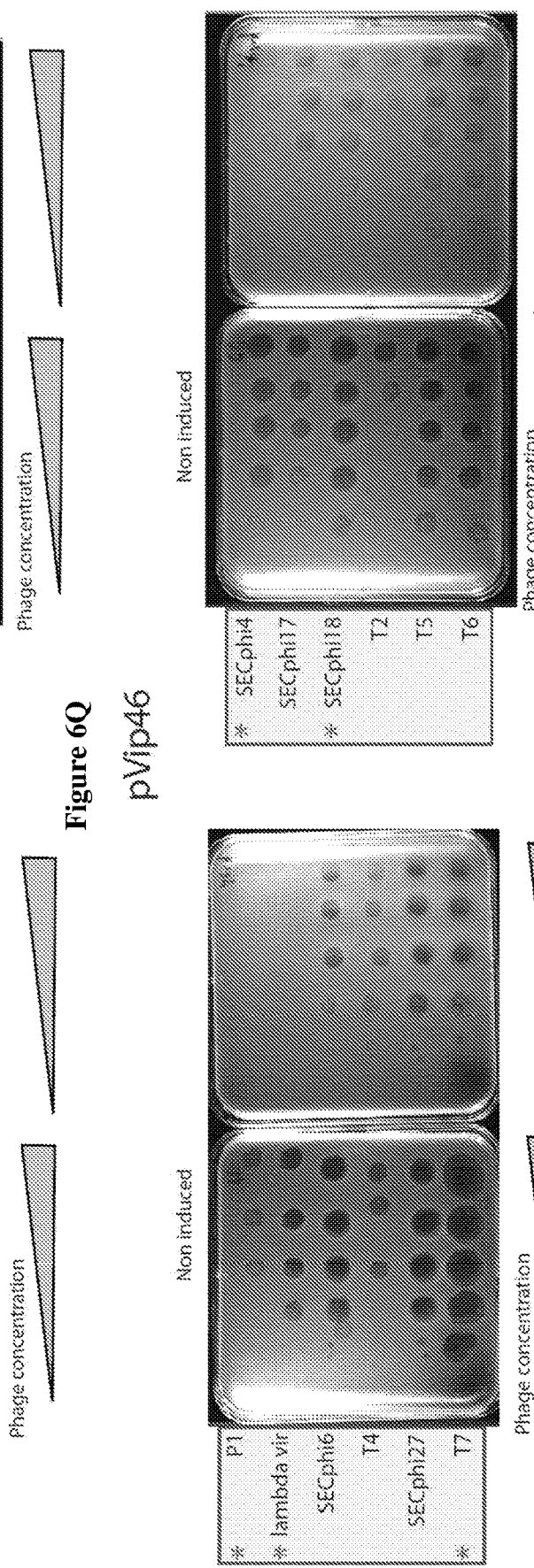
Figure 6U:
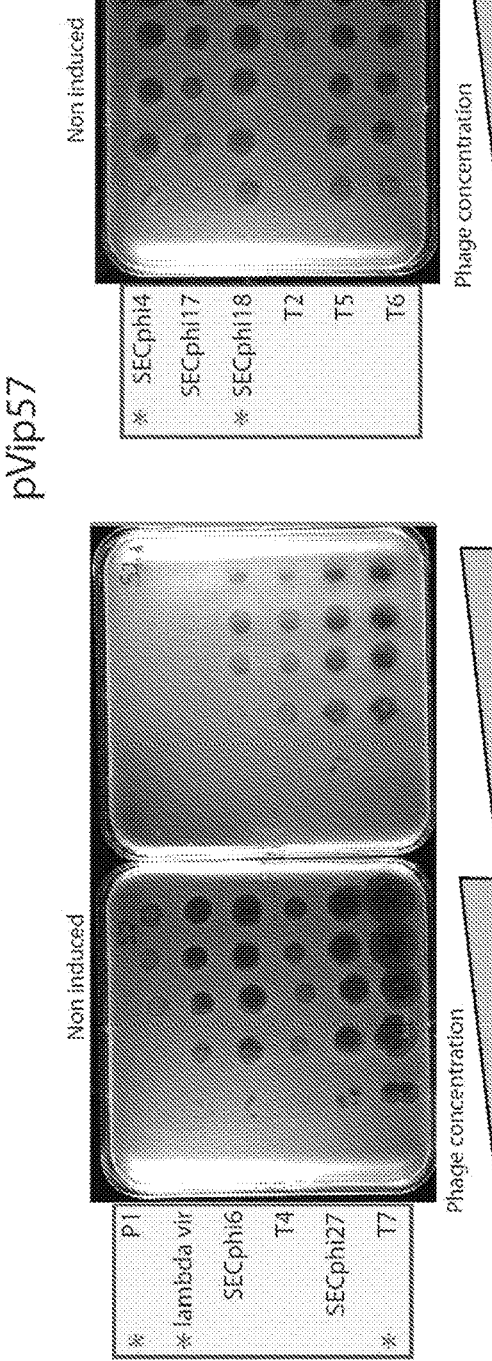
Figure 6V:
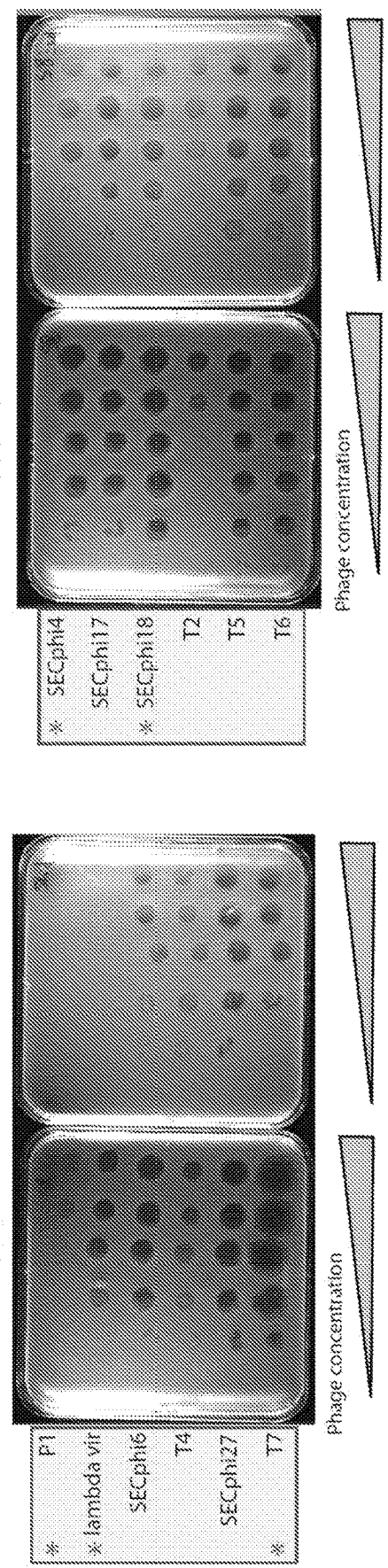
Figure 6W:
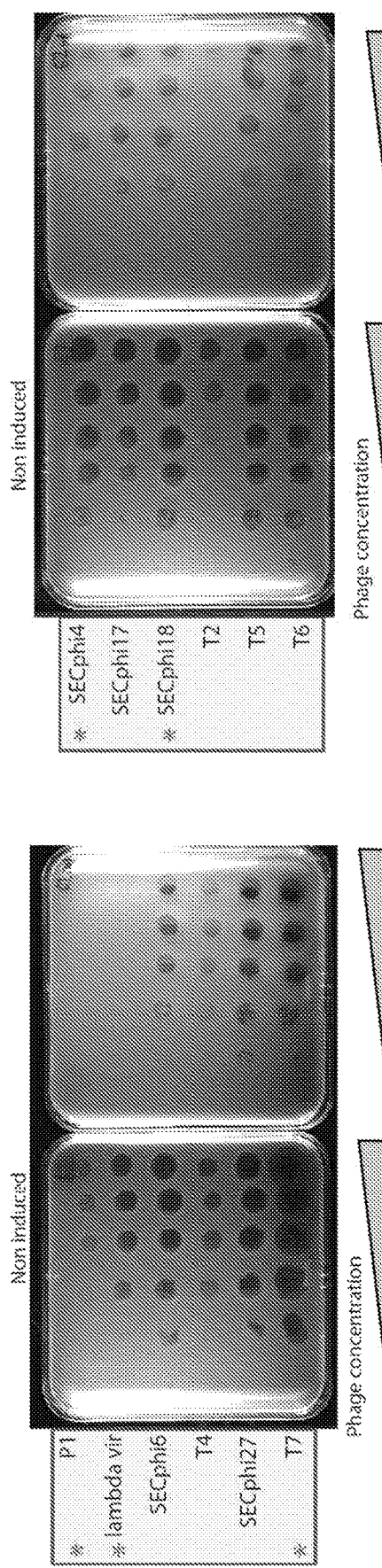
Figure 6X:
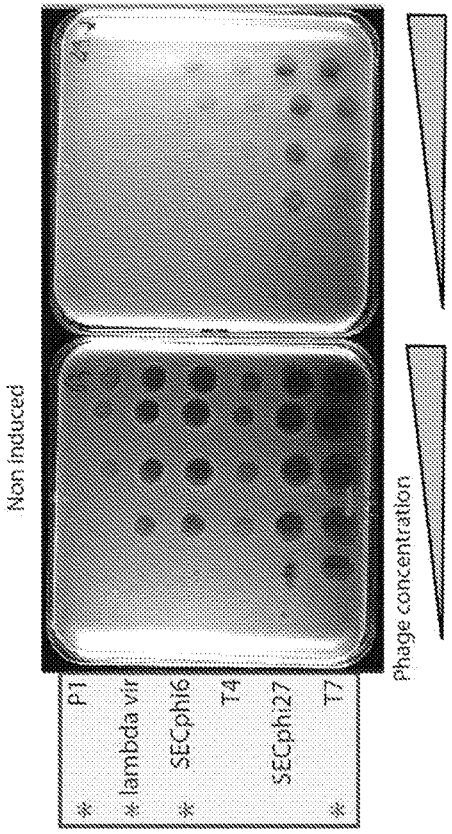
Figure 6Y:
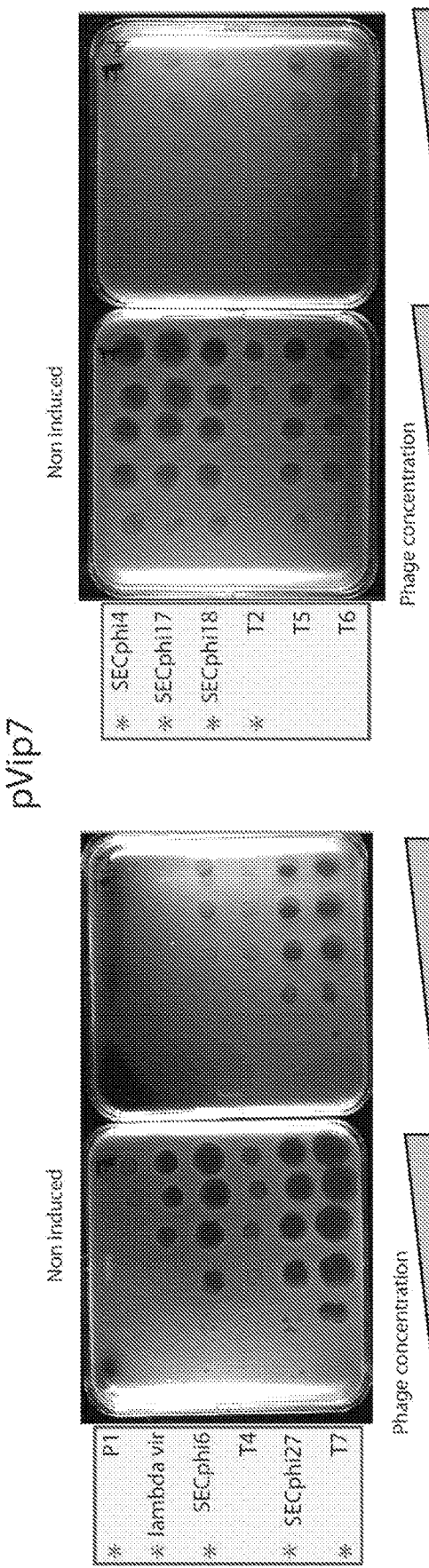
Figure 6Z:
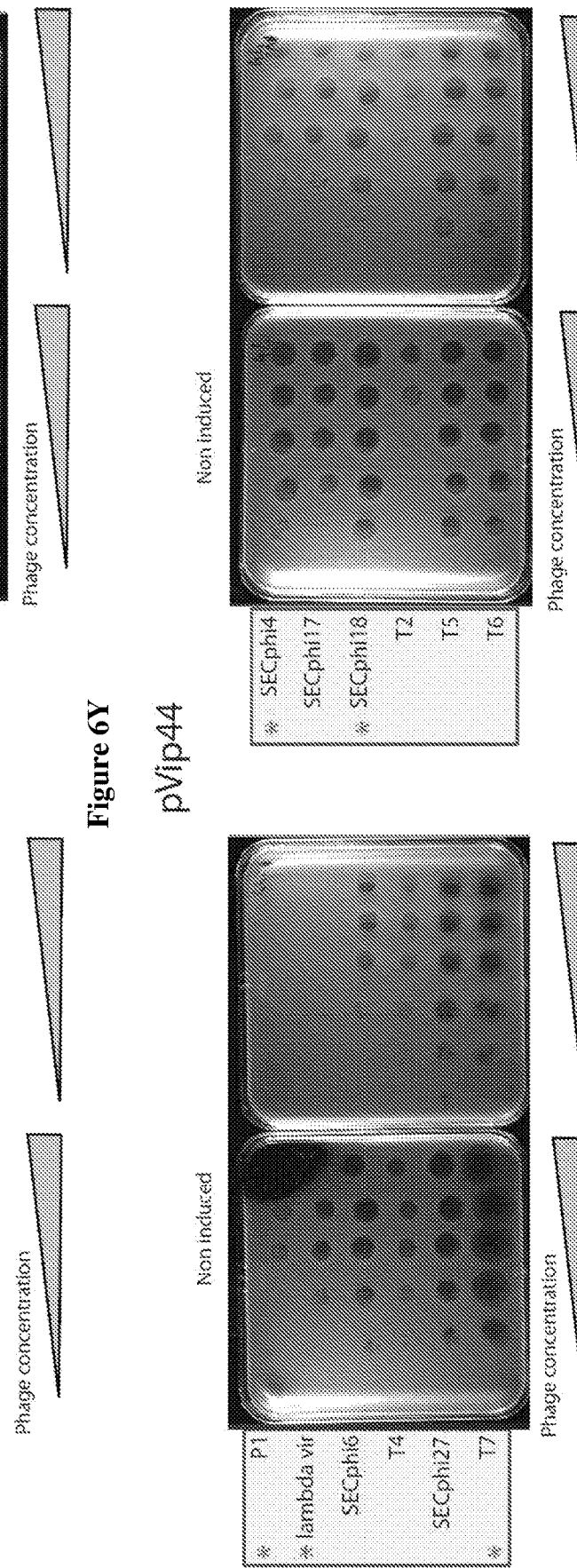

To test if pVips have antiviral activities, their expression (as well as the expression of the MoaA control) was induced with 0.004% arabinose. A reduction in plaque numbers as compared to MoaA control was observed for the 25 pVips including pVip6, pVip7, pVip8, pVip9, pVip10, pVip12, pVip15, pVip19, pVip21, pVip27, pVip32, pVip34, pVip39, pVip42, pVip44, pVip46, pVip47, pVip48, pVip50, pVip56, pVip57, pVip58, pVip60, pVip62, and pVip63 provided defense against phages in the strain Keio ΔiscR (FIGS. 5A and 5B, FIGS. 6A-6Z, Table 2, and Table 8). Phages P1, lambda vir, T7, SecPhi4, SecPhi6, SecPhi17, and SecPhi18 were found susceptible to pVips. At least one viperin from each major clade of the protein family characterized showed activity against phages (FIG. 3A, Table 2 and Table 8). Three main defense phenotypes were observed for the different pVips: strong activity against T7 only (FIGS. 6W-6M), strong activity against P1 and lambda but not T7 (FIGS. 6B-6H) and strong activity against P1, lambda and T7 (FIGS. 6N-6Z). While clades 1, 2 and 6 seem to encode pVips with strong activity against P1 and lambda but not against T7, pVips with strong activity against T7 only are restricted to clade 3, and pVips with strong activity against P1, lambda and T7 are found in clades 3, 4, 5, and 7 (FIG. 3A). Given the homology with the eukaryotic viperins, it was hypothesized that the mechanism of defense involved synthesis of small anti-viral molecules, most probably chain terminators. These different phenotypes against the same phages suggest the existence of several different pVip products. These products could be, for example, nucleotide analogs other than ddhCTP; deoxy versions of ddh nucleotides; or other chain terminator nucleotide analogs.

Table 8 shows candidate pVips that were found to be active in protecting *E. coli* bacteria against phage infection

TABLE 8

| pVips found to protect bacteria against phage infection | | | |
|---|---|---|---|
| pVip_number | IMG gene identifier | Genome name | Clade |
| 6 | 2624749465 | *Selenomonas ruminatium* S137 | 1 |
| 7 | 2739066738 | *Fibrobacter* sp. UWT3 | 5 |
| 8 | 2521798317 | *Psychrobacter lutiphocae* DSM 21542 | 4 |
| 9 | 2574301464 | *Vibrio porteresiae* DSM 19223 | 7 |
| 10 | 2720695169 | *Vibrio vulnificus* ATL 6-1306 | 7 |
| 12 | 2698137626 | *Ruegeria intermedia* DSM 29341 | 6 |
| 15 | 646713396 | *Coraliomargarita akajimensis* DSM 45221 | 3 |
| 19 | 2506475787 | *Methanoplanus limicola* M3, DSM 2279 | 2 |
| 21 | 2515428782 | *Lewinella persica* DSM 23188 | 3 |
| 27 | 2574506394 | *Desulfovibrio senezii* DSM 8436 | 6 |
| 32 | 2609132705 | *Phormidium* sp. OSCR GFM (version 2) | 5 |
| 34 | 2619892213 | *Cryomorphaceae bacterium* EBPR_Bin_135 | 3 |
| 39 | 2634960437 | Burkholderiales-76 (UID4002) | 6 |
| 42 | 2639213731 | *Planktothricoides* sp. SR001 | 2 |
| 44 | 2648875132 | *Chondromyces crocatus* Cm c5 | 3 |
| 46 | 2649993803 | *Photobacterium swingsii* CAIM 1393 | 7 |
| 47 | 2651203508 | *Flammeovirga pacifica* WPAGA1 | 3 |
| 48 | 2651490945 | *Vibrio crassostreae* J5-19 | 7 |
| 50 | 2661858798 | Methanogenic archaeon ISO4-H5 | 2 |
| 56 | 2701115162 | *Fibrobacter* sp. UWH6 | 5 |
| 57 | 2718503187 | *Flavobacterium lacus* CGMCC 1.12504 | 3 |
| 58 | 2721736750 | *Pseudoalteromonas ulvae* TC14 | 7 |
| 60 | 2733913669 | *Lacinutrix* sp. JCM 13824 | 3 |
| 62 | 2743907592 | *Fibrobacteria bacterium* GUT31 IN01_31 | 5 |
| 63 | 2744633848 | *Pseudoalteromonas* sp. XI10 | 7 |

Example 5—pVips Provide Defense in *B. subtilis*

Next it was tested if pVips could provide anti-viral activity in bacteria other than *E. Coli*. We cloned pVip7 from

Figure 7A:
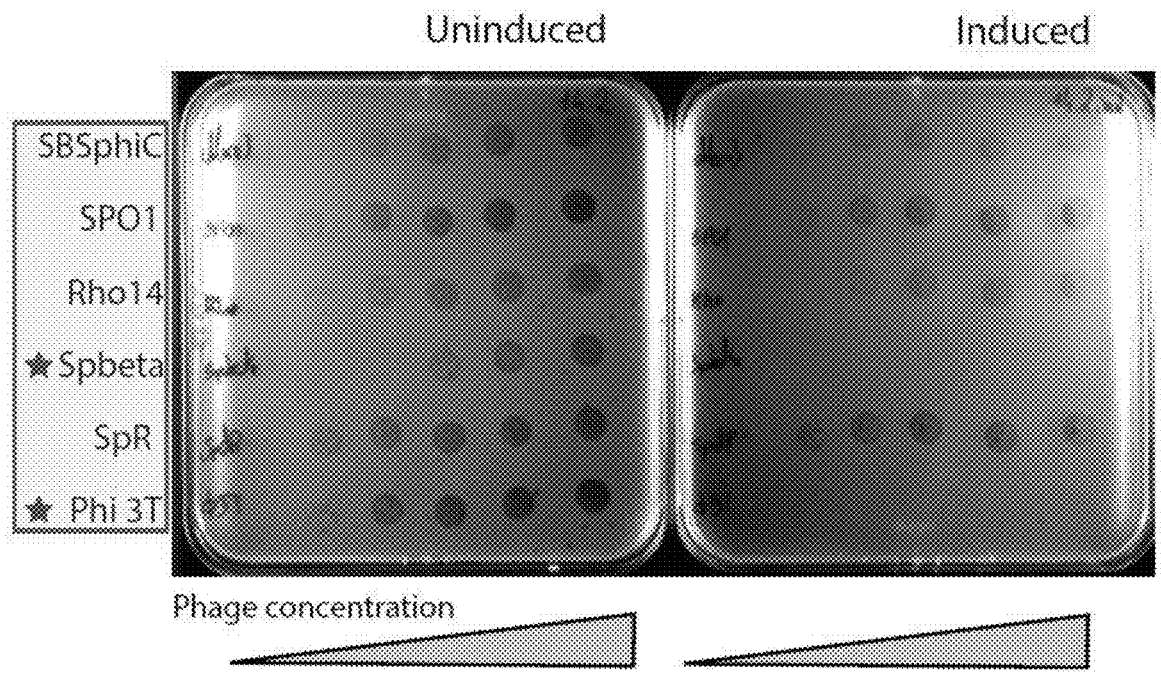
FIGS. 7A-7B show in vivo anti-viral activity of pVip7 in *B. subtilis*.
Figure 7B:
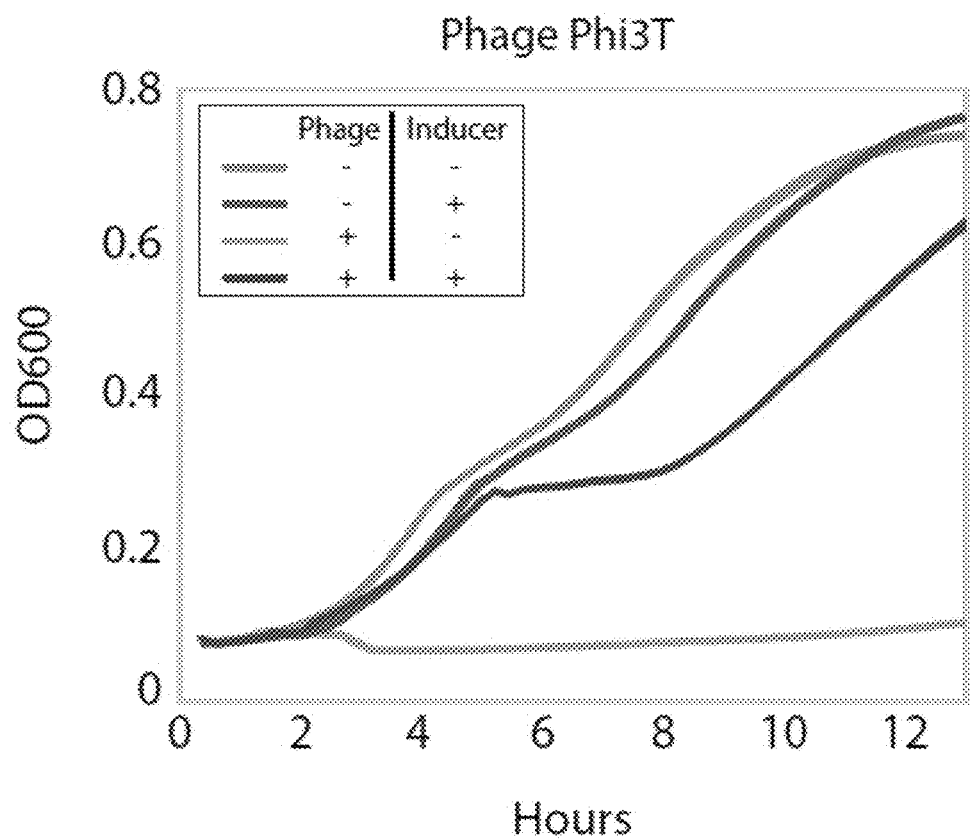

*Fibrobacter* sp. UWT3 in *Bacillus subtilis* BEST7003 and tested it against an array of 12 different phages (detailed in Example 1).

pVip7 showed protection in *B. subtilis* against two phages: phi3T and spbeta (FIG. 7A). They both belong to the spBeta group of phages (Siphovridae). Protection against these two phages was very strong (more than 10,000 fold, which is the limit of detection of the assay used). Protection against phi3T was confirmed with liquid infection assays, where the population in which the pVip expression was induced fully survived the phage infection, while the non-induced collapsed due to phage infection (FIG. 7B). Temperature was found to be another important parameter. While pVip7 was fully active at 25° C. in *B. subtilis*, it did not show a strong defense phenotype at 37° C. in liquid assays.

Example 6—T7 RNA Polymerase is Susceptible to Some of the Products of pVips

Figure 8A:
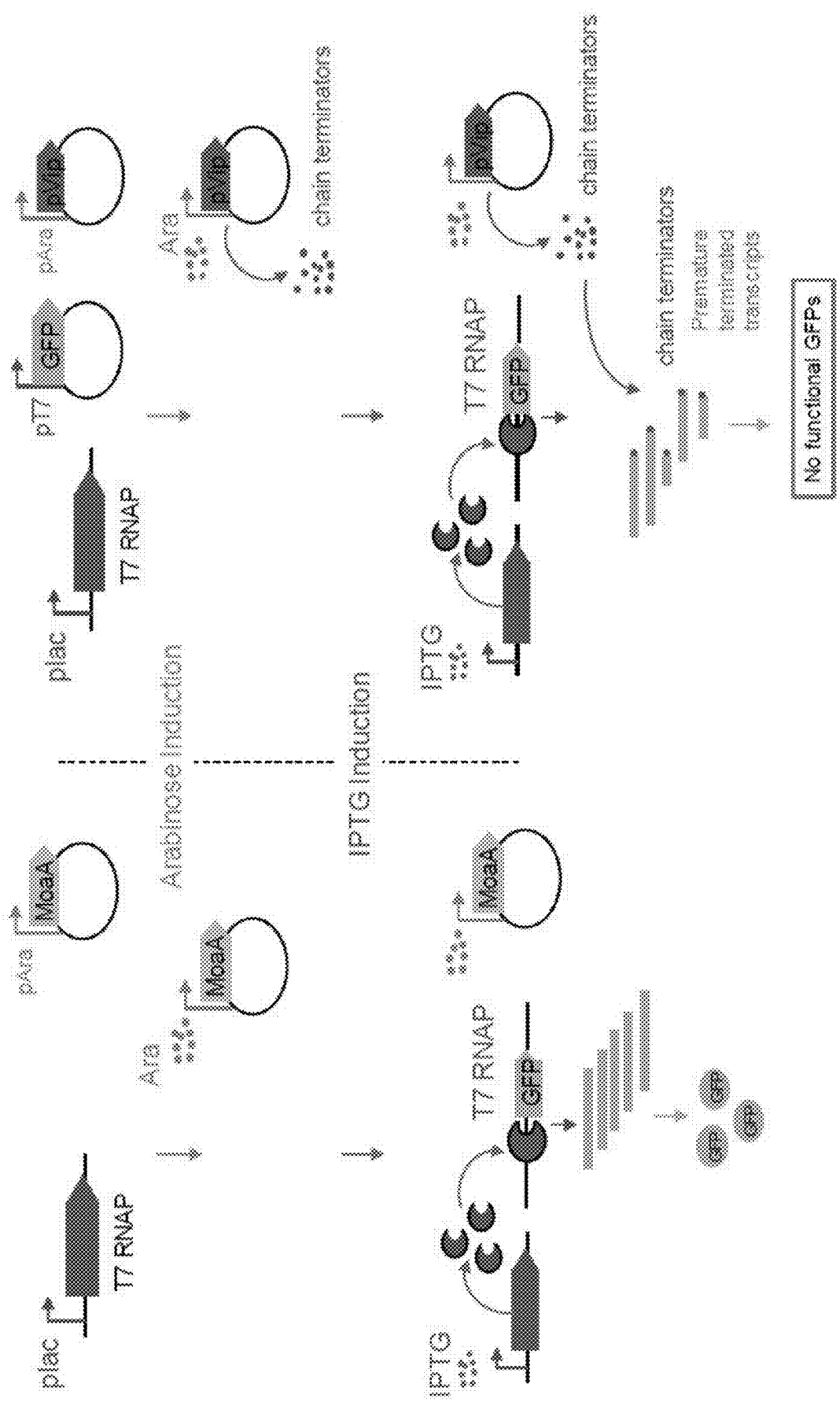
FIGS. 8A-8G shows T7 RNA polymerase (RNAP) susceptibility to pVips products.
Figure 8B:
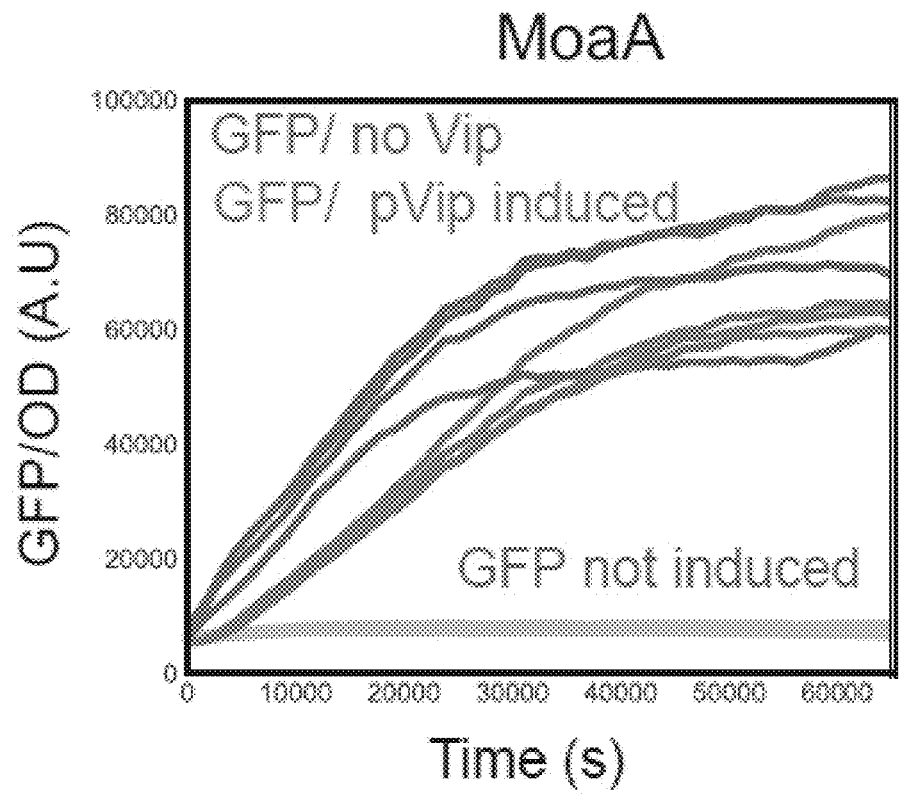
Figure 8C:
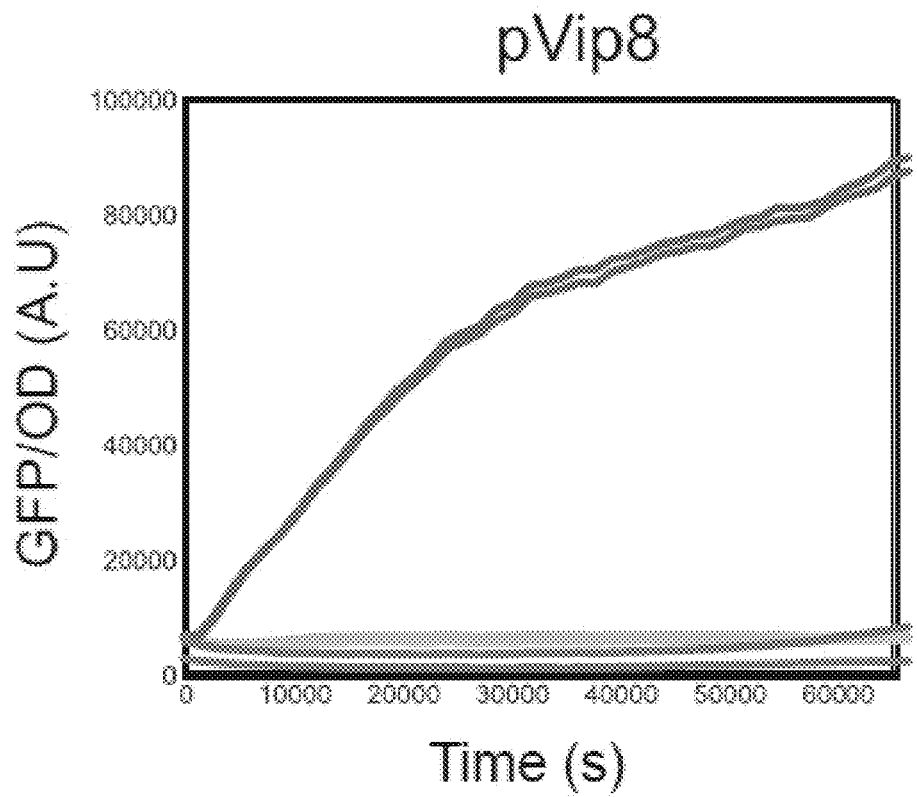
Figure 8D:
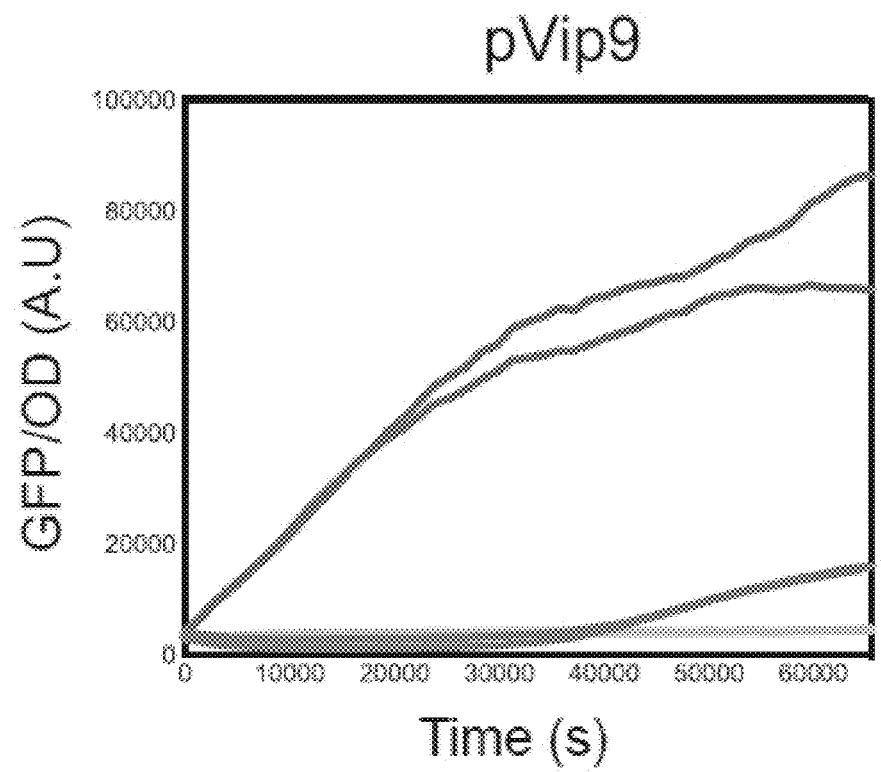
Figure 8E:
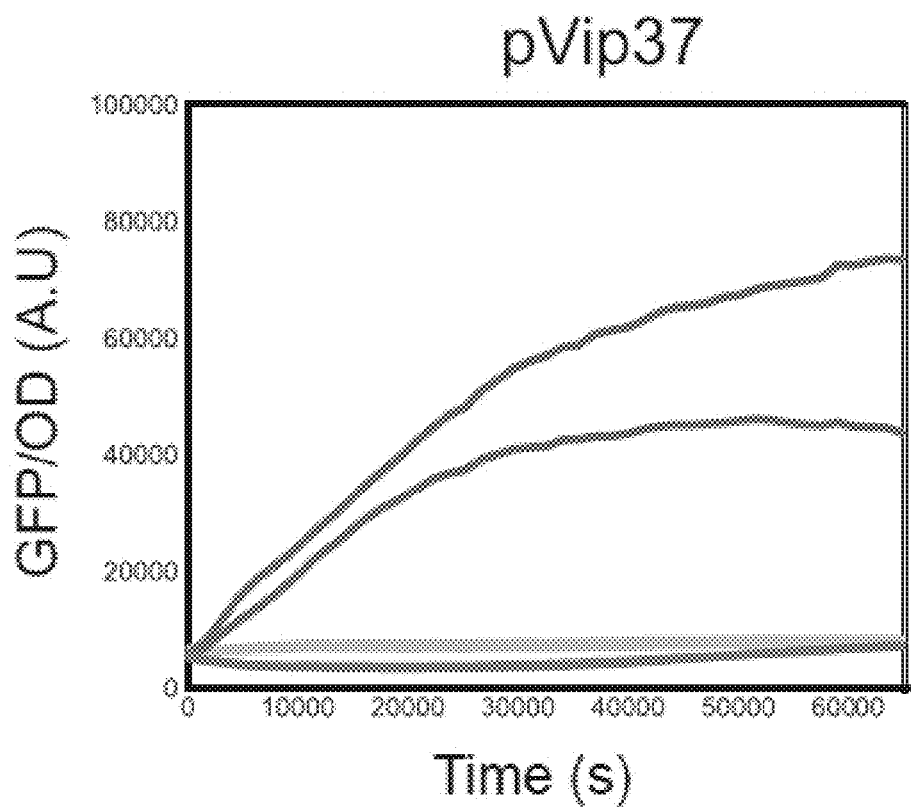
Figure 8F:
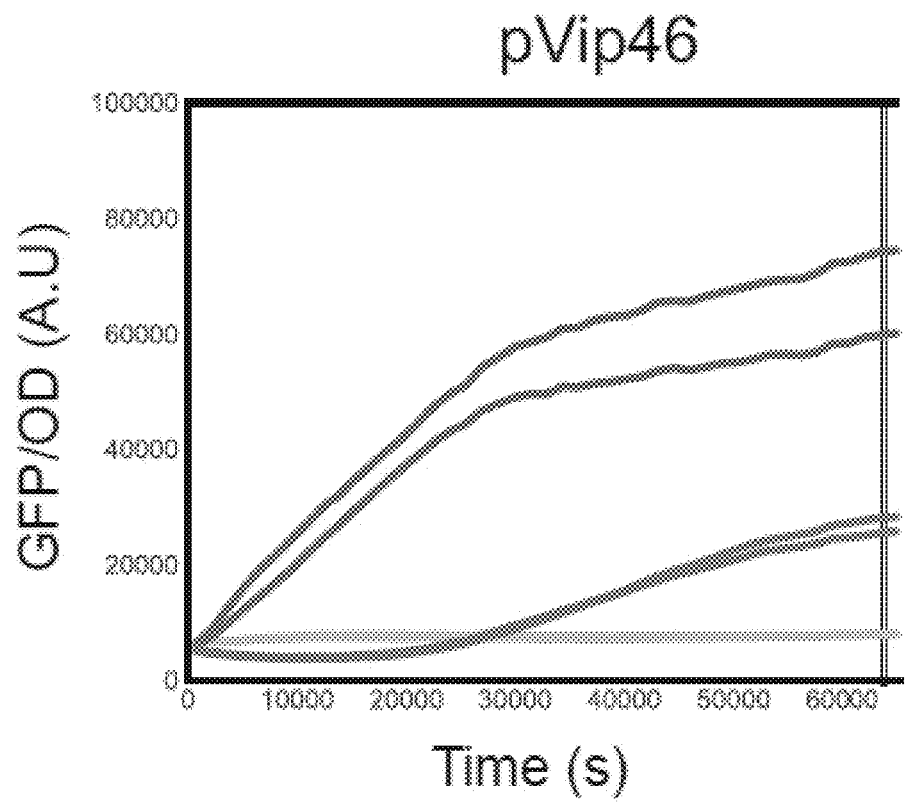
Figure 8G:
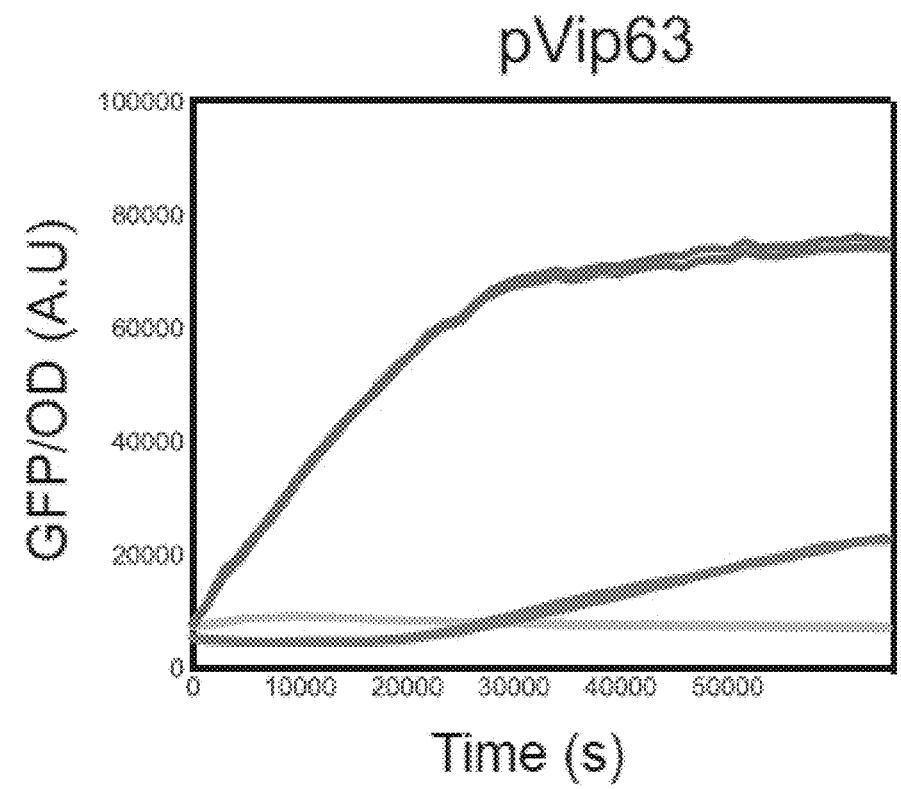

Given that some pVips provide defense against phage T7, it was hypothesized that T7 polymerase-dependent RNA synthesis might be affected by the nucleotide chain terminators produced by pVips. Therefore, it was tested if expression of a reporter gene (GFP) by the T7 polymerase was impacted by different pVips activities To do so, a collection of strains derivatives of BL21-DE3, which encodes a T7 RNA polymerase (RNAP) under the control of a lac promoter, was created. The derivative strains bore the reporter plasmid pAGG encoding a GFP under the control of T7 promoter, and a module with T7 lyzozyme to limit basal expression of T7 RNAP. Further derivative strains bore a pVip candidate under the control of arabinose promoter. In these constructs, the T7 RNA polymerase is induced by the addition of IPTG, thus activating the T7 promoter and inducing GFP transcription. We hypothesized that upon arabinose addition, pVips would be expressed inducing synthesis of polynucleotide chain terminators, which would terminate GFP transcription prematurely (FIG. 8A).

Cells were grown to OD600 0.1 overnight and pVips were induced by addition of arabinose 0.02%. After 45 minutes T7 RNAP expression was induced by addition of IPTG 0.01 mM (FIG. 8A). GFP and OD were monitored with a plate reader (Tecan, Switzerland).

It was observed that induction of pVip8, pVip9, pVip37, pVip46, and pVip63 prevented or substantially inhibited the expression of GFP by T7 polymerase (FIGS. 8B-8G). However, co-expression of MoaA, which is structurally similar to pVip, did not inhibit GFP expression. This suggests that the pVip product inhibits T7-RNAP-dependent expression of GFP by a chain terminator that interrupts the nascent GFP mRNA.

Example 7—Production of New Chain Terminators

The pVips disclosed herein can be used in order to produce chain terminators, including (but not limited to) ddhUTP, ddhATP, ddhGTP, ddhCTP, ddh-deoxy-GTP, and ddh-deoxy-ATP, ddh-deoxy-TTP, and ddh-deoxy-CTP. For this, the pVip protein would first be expressed in a heterologous expression system (e.g., in bacteria such a *E. coli* or *B. subtilis*, or in a eukaryotic expression system). Then, the expressed pVip will be purified, and then supplied with the necessary cofactors (e.g., s-adenosyl methionine) and the substrate (e.g., CTP, TTP etc, depending on the substrate of the specific pVip).

The pVip will produce the chain terminator, which will then be purified from the reaction and used for the proper application. Example 4 shows the importance of iron sulfur cluster metabolism for expression of functional pVips. Therefore, protein expression for pVips should be performed in strains such as ΔiscR or that contain plasmids like pDB1282, that encodes the iscR operon from *Azotobacter vinelandii*, or in another strain that allows expression of iron-sulfur cluster genes. Given the sensitive nature of iron sulfur cluster enzymes to oxygen, protein purification should preferentially be performed in anaerobic conditions.

While nucleotide analogs are actual chain terminators in vivo, nucleoside analogs, which is the version without phosphate groups, are the molecules generally used as drugs. The phosphate groups of the nucleotides may prevent entry to the cell due to its charge. Once nucleoside analogs enter the cells, they can be phosphorylated by endogenous enzymes or enzymes of the phage, and thus generate the cognate nucleotide analogs. Such an approach was used to show the efficiency of ddhC as an anti-viral molecule by Gizzi, A. S. et al. A naturally occurring antiviral ribonucleotide encoded by the human genome. Nature 558, 610-614 (2018). Upon entry to the cell, ddhC is phosphorylated to become ddhCTP and provides anti-viral activity against for example Zika virus. Similarly, cognate nucleoside analogs to the modified nucleotides produced by the pVips may be for example (but not limited to): ddhT, ddh-deoxy-G, ddh-deoxy-A, etc. Chemical strategies can be used to synthetize such types of nucleosides and could be applied to obtain these molecules.

Example 8—pVips and Products Thereof

Examples 1-6 reveal the existence of a new family of prokaryotic anti-viral genes, pVips. A homology-based search in 69425 prokaryotic genomes followed by a detailed and quantitative analysis of gene neighborhoods allowed to discriminate potential anti-viral genes among a wider family of radical-SAM enzymes. The pVips family was further enriched with similar genes extracted from a database of 9769 metagenomes. The analysis of the evolutionary history of pVips and the eukaryotic viperin (a known anti-viral enzyme which produces ddhCTP, a chain terminator) suggests that eukaryotic viperins has evolutionarily originated from pVips and represent only a small fraction of the diversity of the protein family. Furthermore, the analysis of pVip accessory genes (nucleoside kinases or nucleotide kinases) suggests the existence of diverse substrate for the pVips, suggesting a diversity of pVips chain terminator products.

An experimental approach to screen active pVips in vivo was developed. After selection, codon optimization and synthesis of diverse pVips, strains encoding pVips were screened against a diverse collection of phages. It was found that the use of a specific strain of *E. coli*, where iron sulfur cluster auxiliary genes are more highly expressed, greatly improves pVips activity.

Products of the pVip enzymes may include nucleotide analogs or nucleoside analogs. These can include, for example, ddhUTP, ddhGTP, ddhATP, ddhCTP, ddh-deoxy-GTP, ddh-deoxy-ATP, ddh-deoxy-TTP, ddh-deoxy-CTP, as well as modified versions of these modified nucleotides that can be used as new anti-viral or anti-tumor drugs functioning as DNA or RNA chain terminators.

Example 9—pVips Produce Diverse Anti-Viral Molecules

Material and Methods

Cell Lysates Preparation

Overnight cultures of Keio ΔiscR encoding pVips, MoaA or the human viperin were diluted 1:100 in 100 ml LB medium and grown at 37° C. (250 r.p.m.) for 1 hour and 45 minutes. The expression of viperin or MoaA was induced by the addition of arabinose (final concentration 0.2%) and cells were further incubated at 37° C. (250 r.p.m.) for one hour. Cells were then centrifuged at 3,900 g for 10 min at 4° C. and samples kept on ice throughout the cell lysate preparation. Pellets were resuspended in 600 μl PBS buffer containing 100 mM sodium phosphate (pH 7.4). The resuspended pellet was supplemented with 1 μl of hen-lysozyme (Merck) (final hen-lysozyme concentration of 10 μg/ml). The resuspended cells were then mixed with Lysing matrix B (MP) beads and cells were disrupted mechanically using a FastPrep-24 bead-beater device (MP) (2 cycles of 40 s, 6 m s$^{-1}$, at 4° C.). Cell lysates were then centrifuged at 12,000 g for 10 min at 4° C. and the supernatant was loaded onto a 3-kDa filter Amicon Ultra-0.5 centrifugal filter unit (Merck) and centrifuged at 14,000 g for 30 min at 4° C. The resulting flow-through, containing substances smaller than 3 kDa, was used as the lysate sample for evaluating the presence of ddh nucleotides by LC-MS.

Detection of Ddh-Nucleotides

Sample analysis was carried out by MS-Omics (Vedbok, Denmark) as follows. Samples where diluted 1:1 in 10 mM ammonium acetate in 90% acetonitrile. The analysis was carried out using a UHPLC system (Vanquish, Thermo Fisher Scientific, US) coupled with a high-resolution quadrupole-orbitrap mass spectrometer (Q Exactive™ HF Hybrid Quadrupole-Orbitrap, Thermo Fisher Scientific). An electrospray ionization interface was used as ionization source. Analysis was performed in positive ionization mode. The UPLC was performed using a slightly modified version of a previously described protocol. Peak areas were extracted using Compound Discoverer 2.0 (Thermo Scientific).

Quantification of 3'-deoxy-3',4'-didehydro cytidine (ddhC)

The 3'-deoxy-3',4'-didehydro cytidine molecule was synthesized by Jena Bioscience (Jena, Germany) and was used as a standard for ddC quantification in cell lysates using LC-MS. Sample analysis was carried out by MS-Omics (Vedbok, Denmark) as follows. Samples were diluted 1:1 in 10 mM ammonium formate and 0.1% formic acid in ultra-pure water. The analysis was carried out using the LC-MS setup described above. An electrospray ionization interface was used as ionization source performed in positive ionization mode. The UHPLC method is based on Waters Application note 2011, 720004042en (Waters Corporation, Milford, US). Peak areas of 3'-deoxy-3',4'-didehydrocytidine (ddhC) were extracted using Trace Finder™ Version 4.1 (Thermo Fisher Scientific, US) and quantified using an external calibration with the standard.

Results

Figure 10:
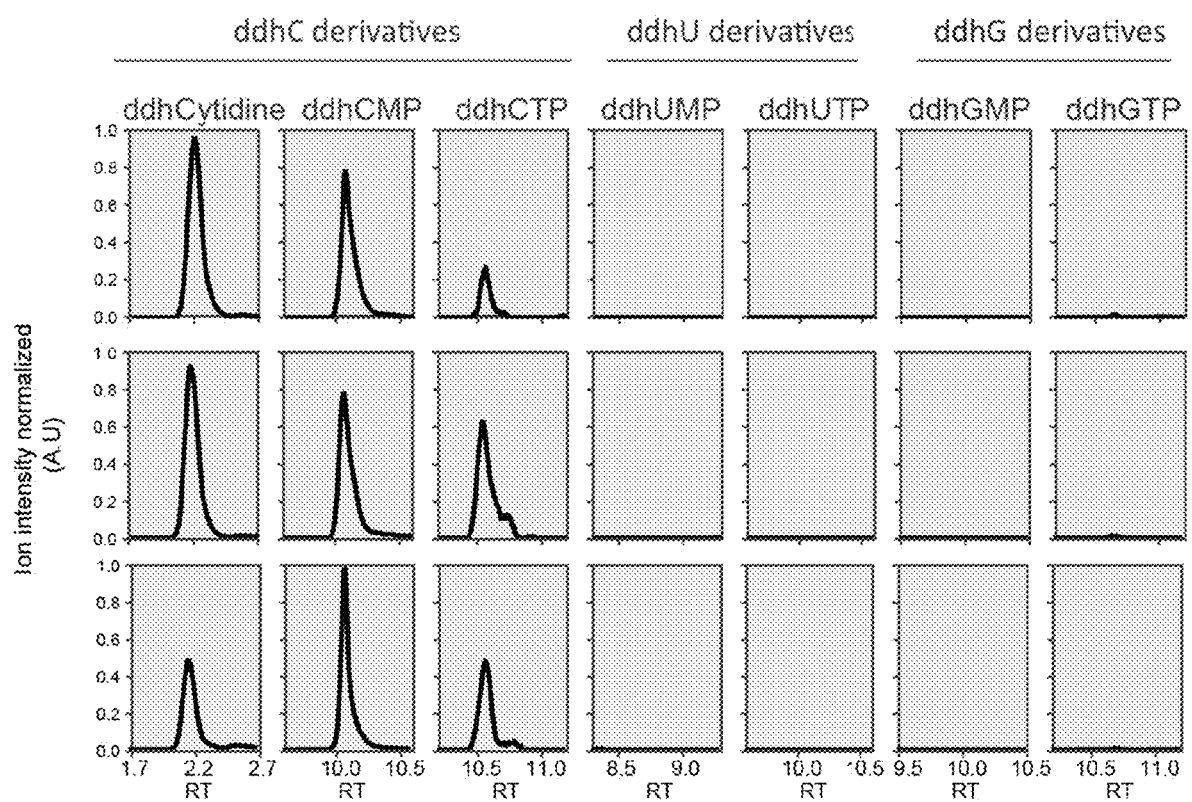
FIG. 10 shows detection of ddhCTP and ddhCTP derivatives in cell lysates from an *E. coli* strain expressing the human viperin. Extracted ion chromatogram for singly charged masses corresponding to ddhC (m/z 226.08223, retention time (RT) of 2.2 minutes), ddhCMP (m/z 306.04856, RT 9.7), ddhCTP (m/z 465.98122, RT 11.1), ddhUMP (m/z 307.03258, RT 8.7), ddhUTP (m/z 466.96524, RT 9.5), ddhGMP (m/z 266.08838, RT 9.8), and ddhGTP (m/z 505.98737, RT 10.6). X-axis depicts RT in minutes. Y axis, normalized ion intensity (arbitrary units). Normalization was performed on all human viperin and MoaA samples, with maximal value set to 1.0. Three biological replicates are presented.
Figure 12:
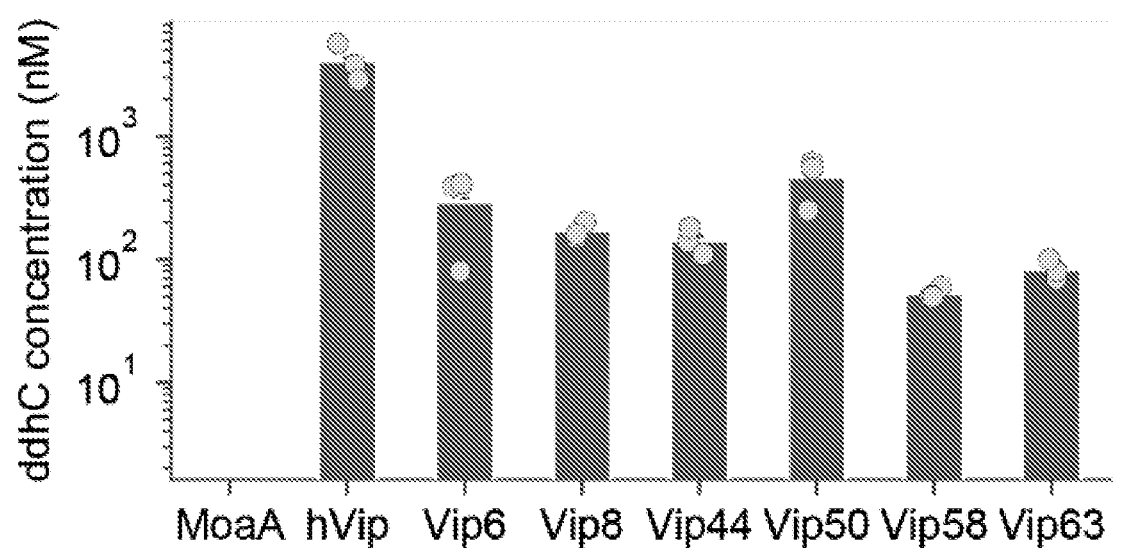

The animal viperin catalyzes the production of ddhCTP. Whether pVips produce ddhCTP and/or other types of modified nucleotides was examined. For this, pVips were expressed in *E. coli* and the fraction of small molecules was extracted from the cell lysates, presuming that the pVip-produced molecule would be present in that fraction. These lysates were analyzed with liquid chromatography followed by mass spectrometry (LC-MS) using an untargeted approach. As a positive control, cell lysates from cells expressing the human viperin protein were similarly analyzed. As expected, a compound conforming with the mass of ddhCTP was readily detected in lysates from cells expressing the human viperin but not in the negative control lysates that were derived from MoaA-expressing cells (FIG. 10). Additional compounds found in the human viperin sample matched the masses of ddh-cytidine (ddhC) and ddh-cytidine monophosphate (CMP), possibly derived from natural decay of ddhCTP as also known to occur for CTP in neutral or acidic pH. Analysis of fragment ions using MS-MS further supported that the identified masses are ddhCTP, ddhCMP and ddhC with additional confirmation attained by subjecting synthesized ddhC standard to MS-MS analysis (FIG. 12). These results confirm that the human viperin actively produces ddhCTP when expressed in *E. coli*, explaining its observed anti-phage activity.

Figure 9A:
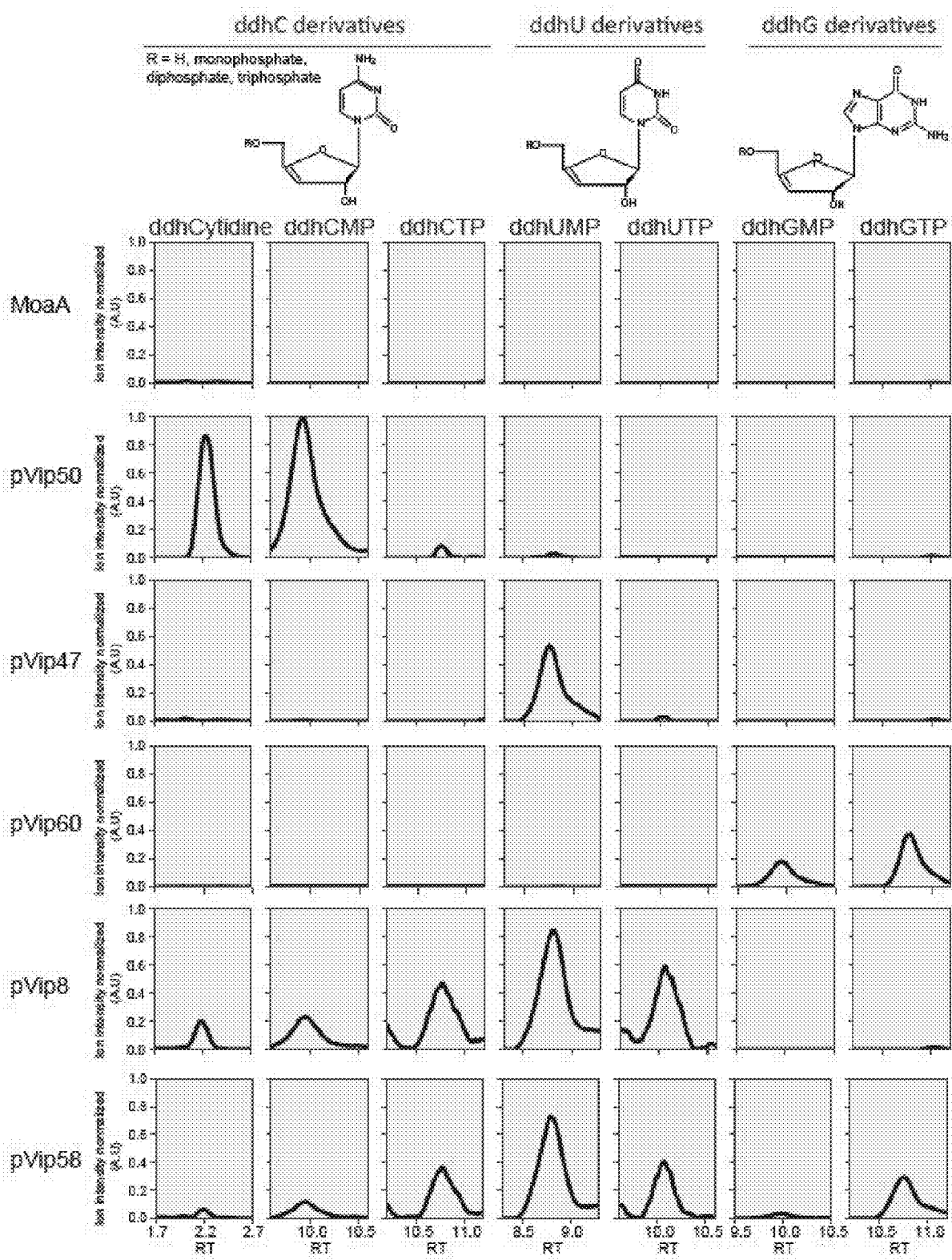
FIGS. 9A-9B show pVips produce a variety of modified ribonucleotides.
Figure 9B:
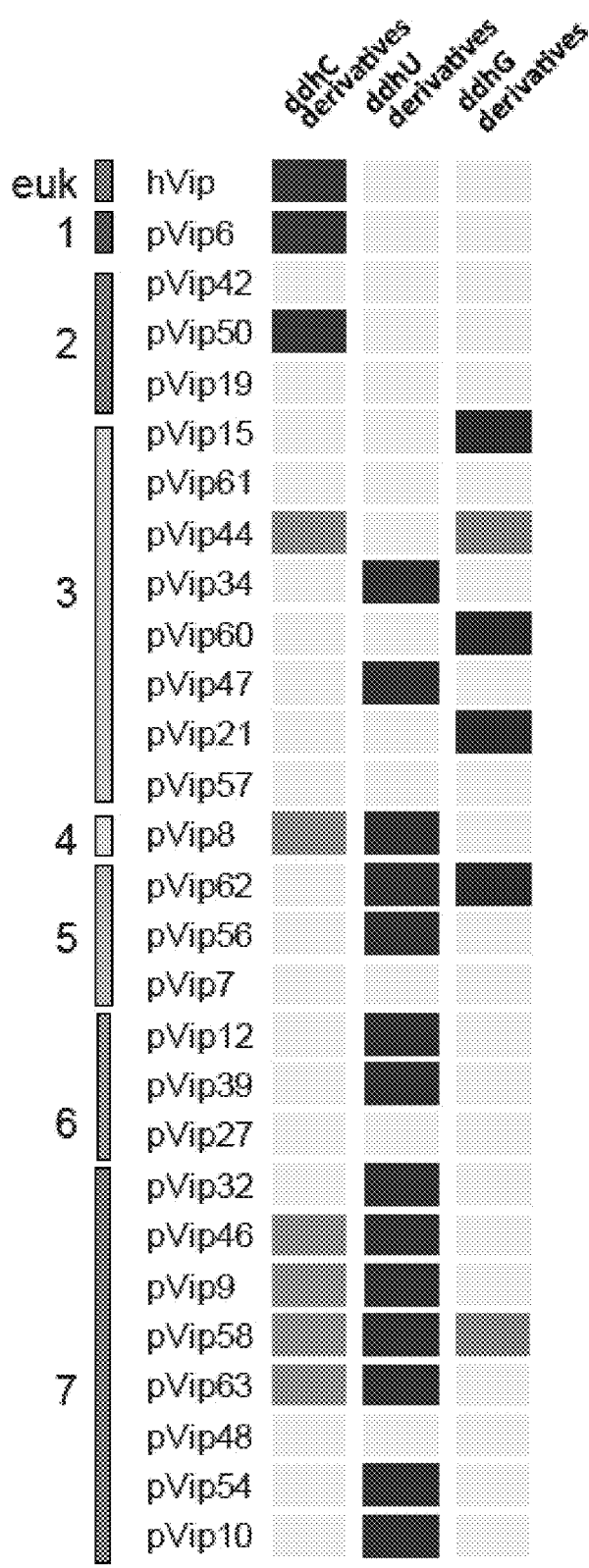
Figure 11:
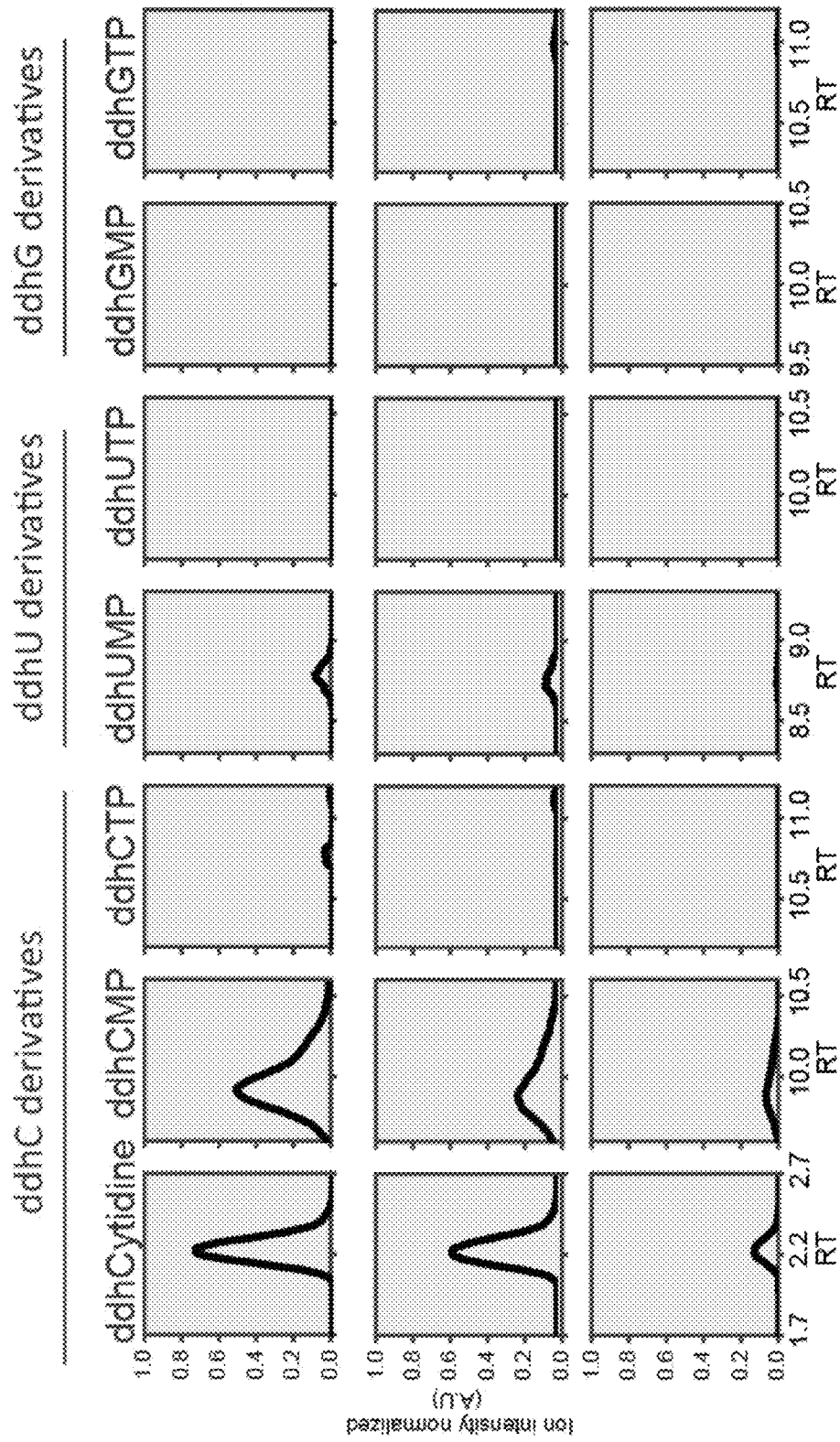
FIG. 11 shows detection of ddh nucleotides in lysates of cells that express pVips. Extracted ion chromatogram for singly charged masses corresponding to ddhC (m/z 226.08223, retention time (RT) of 2.2 minutes), ddhCMP (m/z 306.04856, RT 9.7), ddhCTP (m/z 465.98122, RT 11.1), ddhUMP (m/z 307.03258, RT 8.7), ddhUTP (m/z 466.96524, RT 9.5), ddhGMP (m/z 266.08838, RT 9.8), and ddhGTP (m/z 505.98737, RT 10.6). X-axis depicts RT in minutes. Y axis, normalized ion intensity (arbitrary units). Normalization was performed on all pVips and MoaA samples, with maximal value set to 1.0. Three biological replicates are presented for each pVip.
Figure 11:
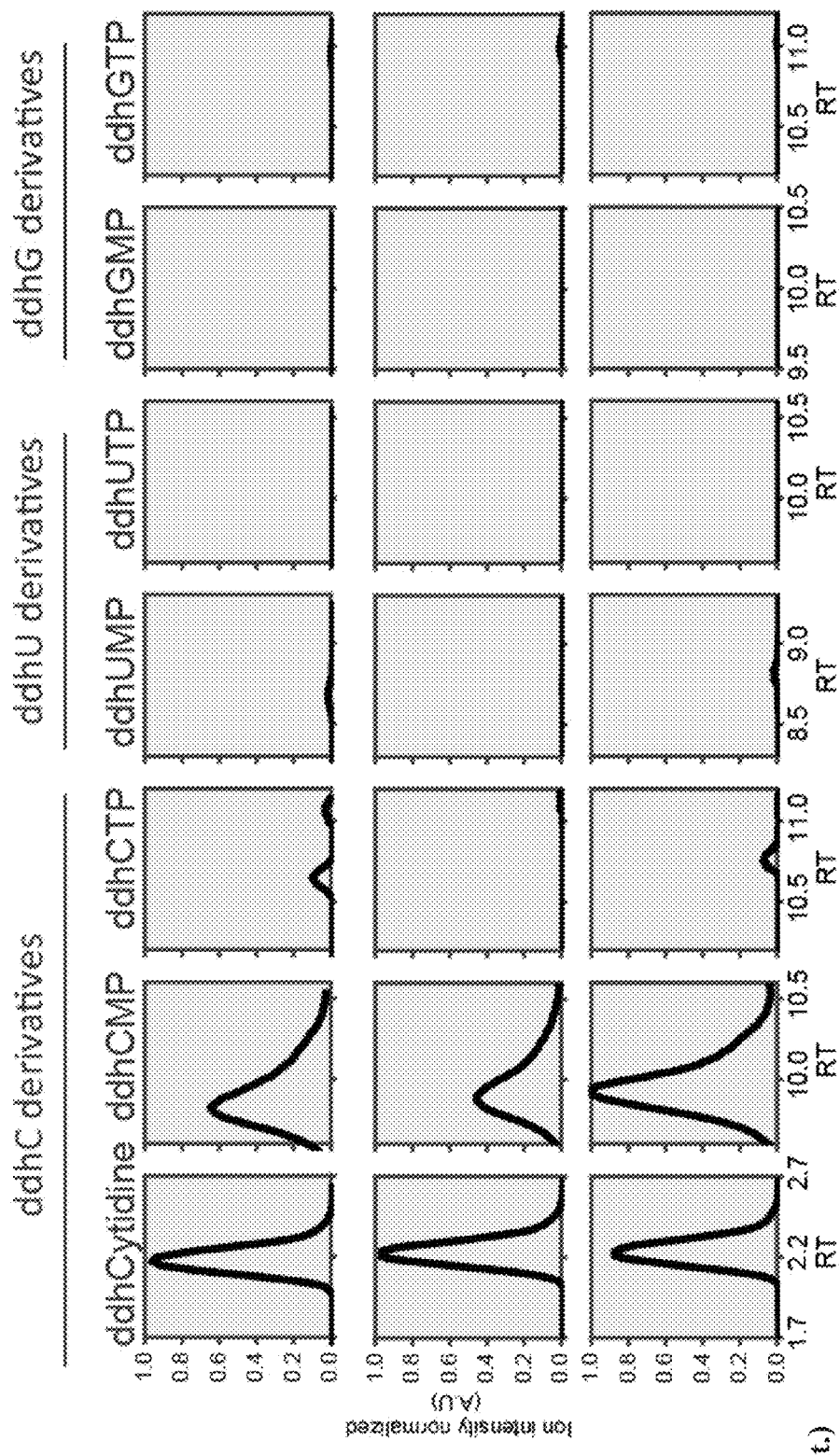
Figure 11:
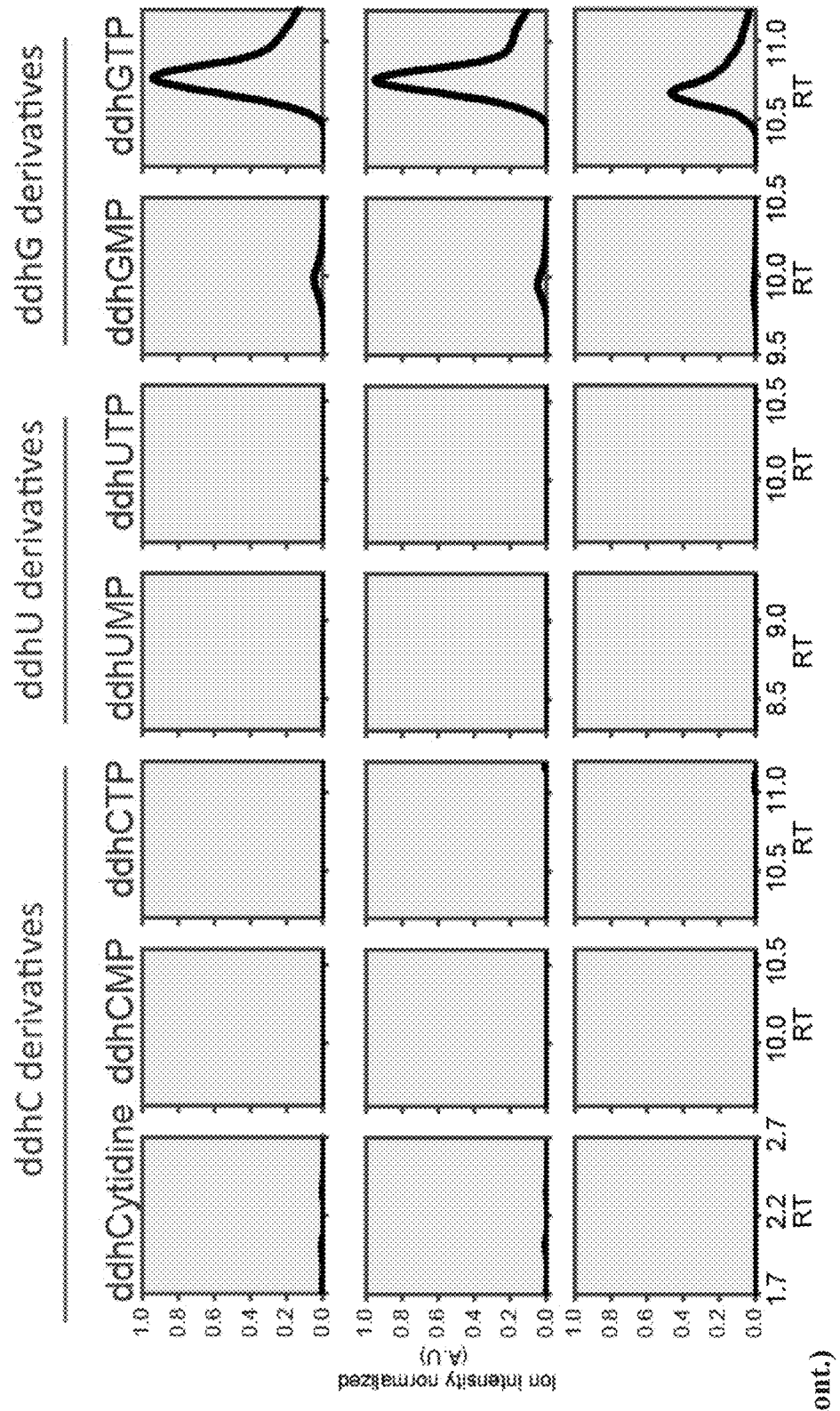
Figure 11:
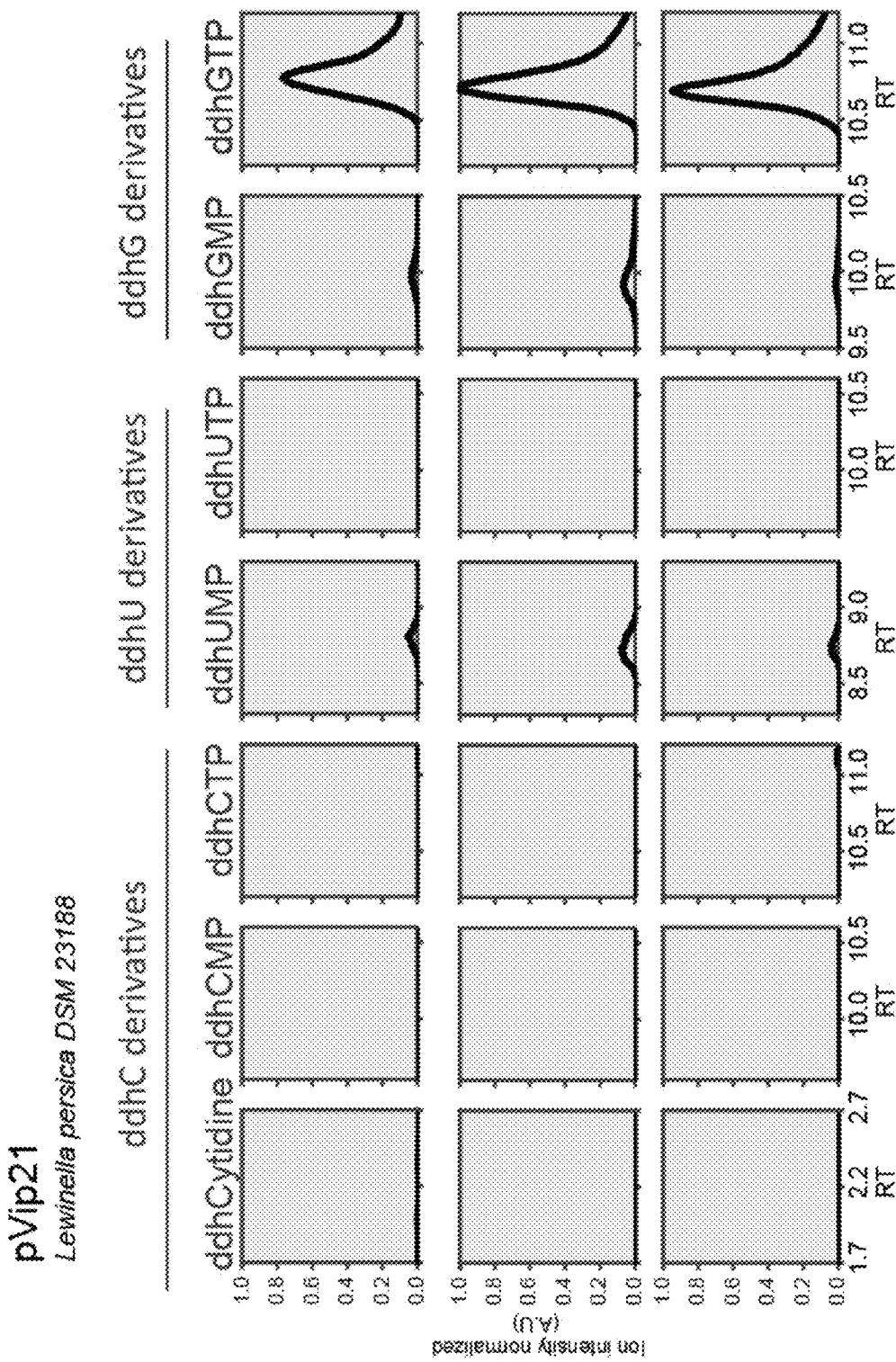
Figure 11:
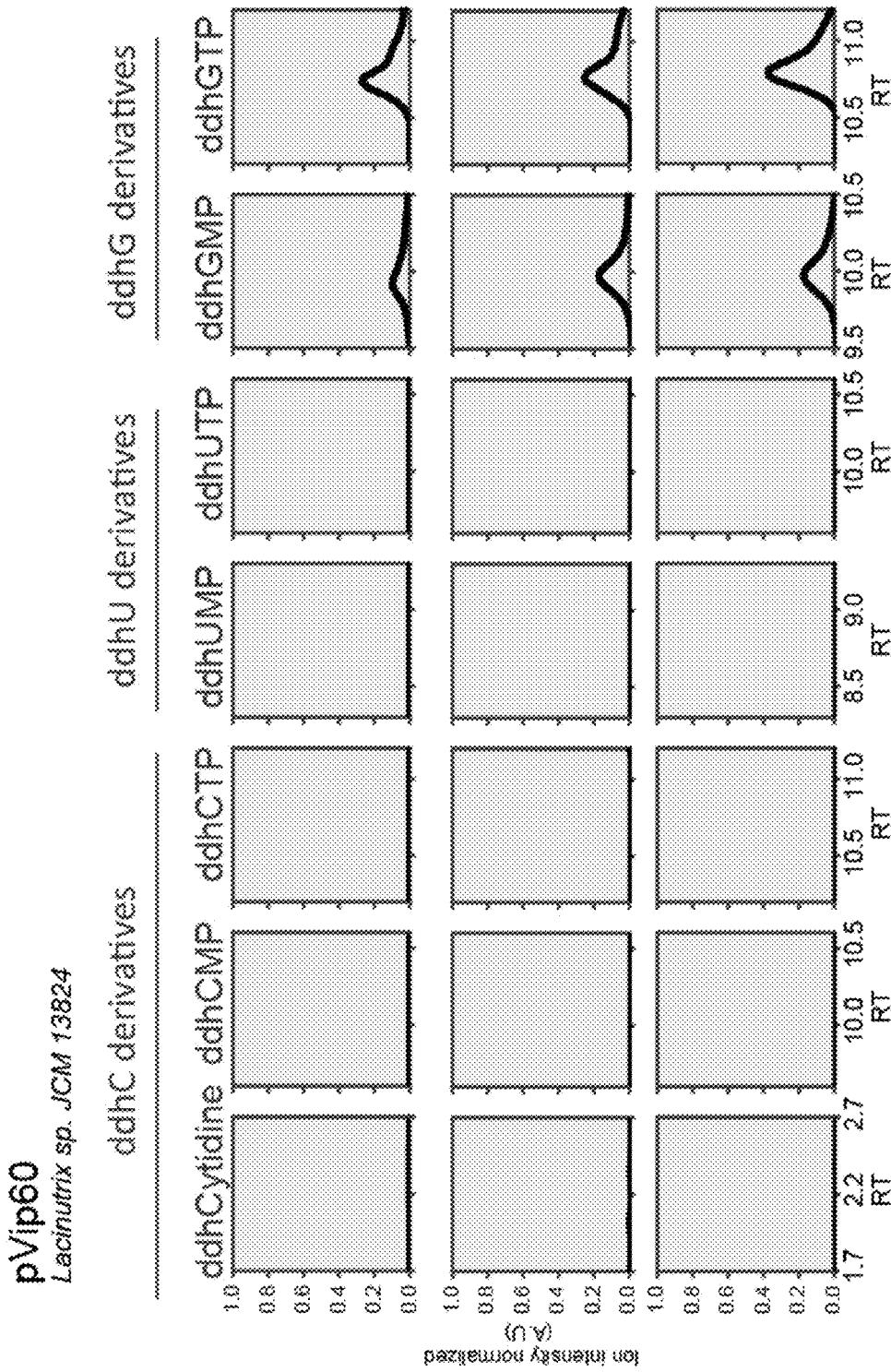
Figure 11:
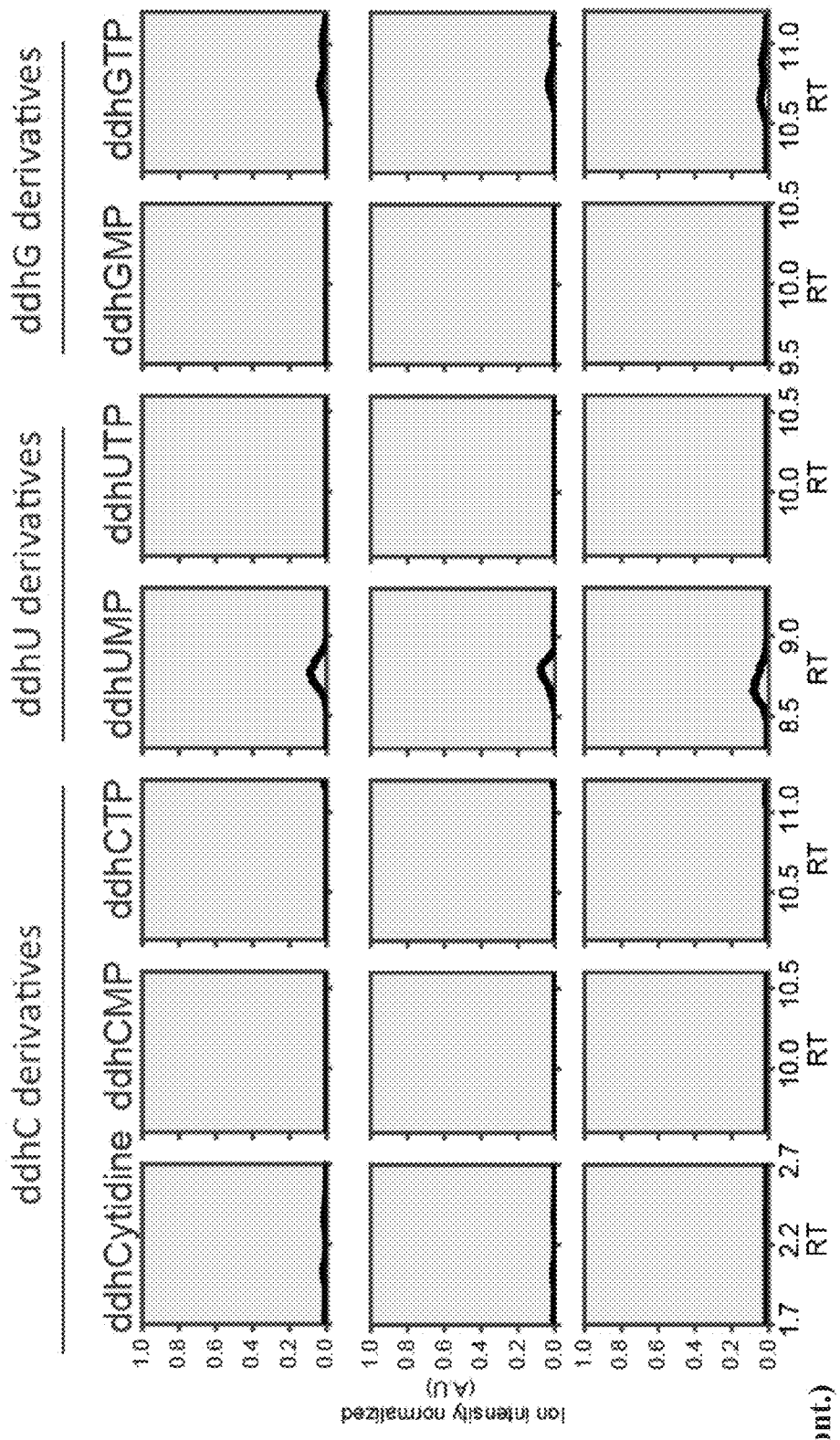
Figure 11:
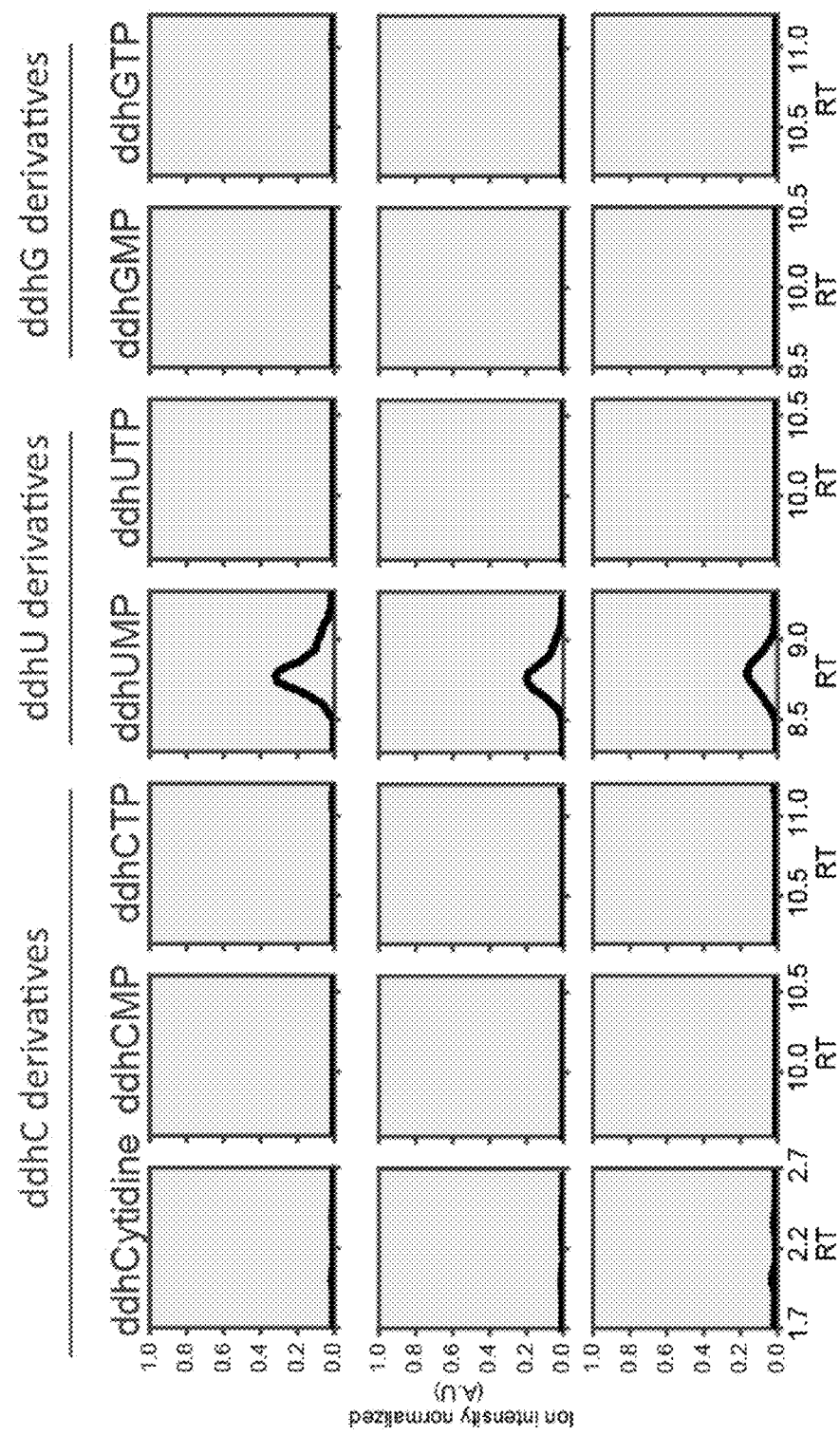
Figure 11:
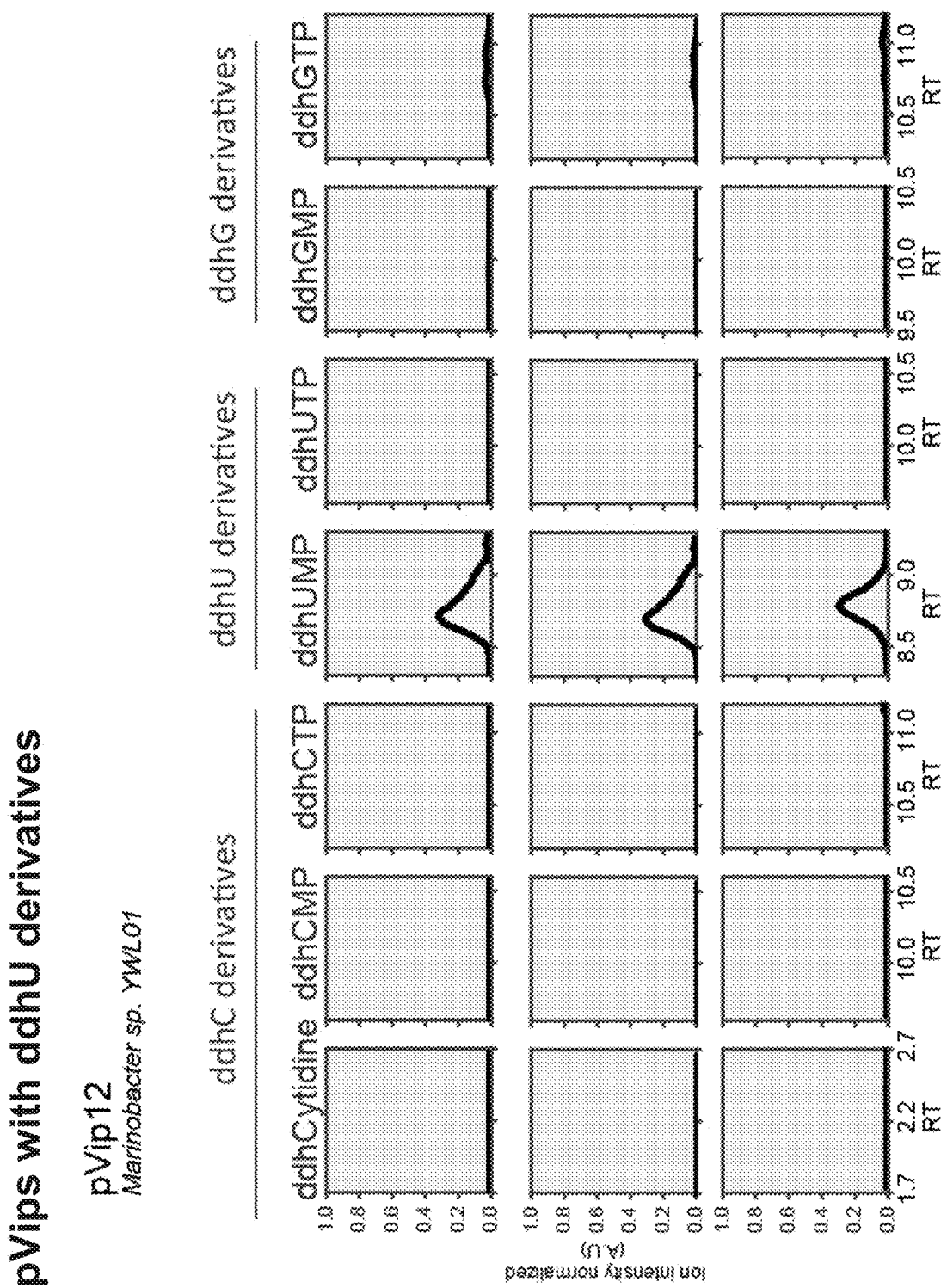
Figure 11:
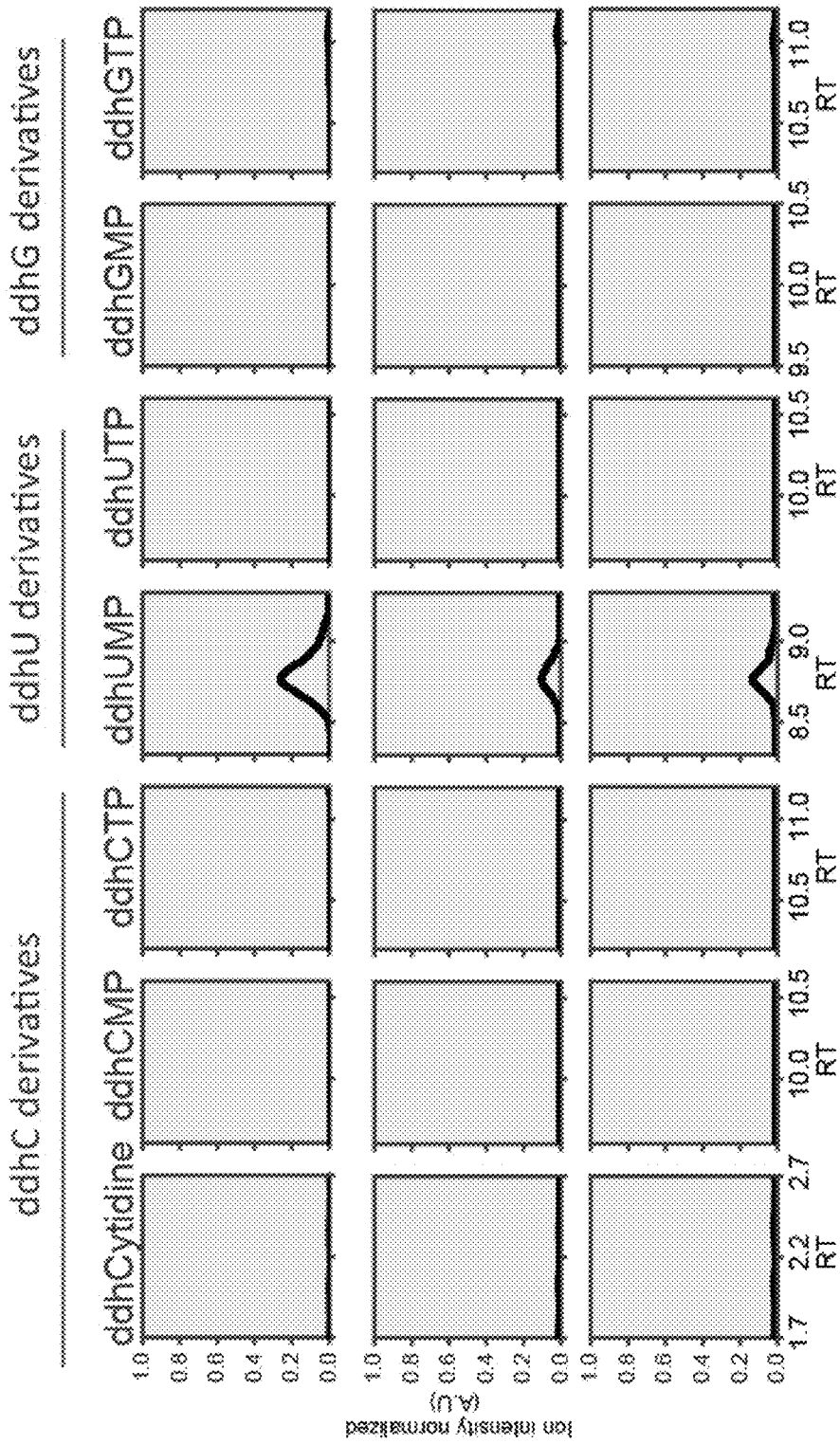
Figure 11:
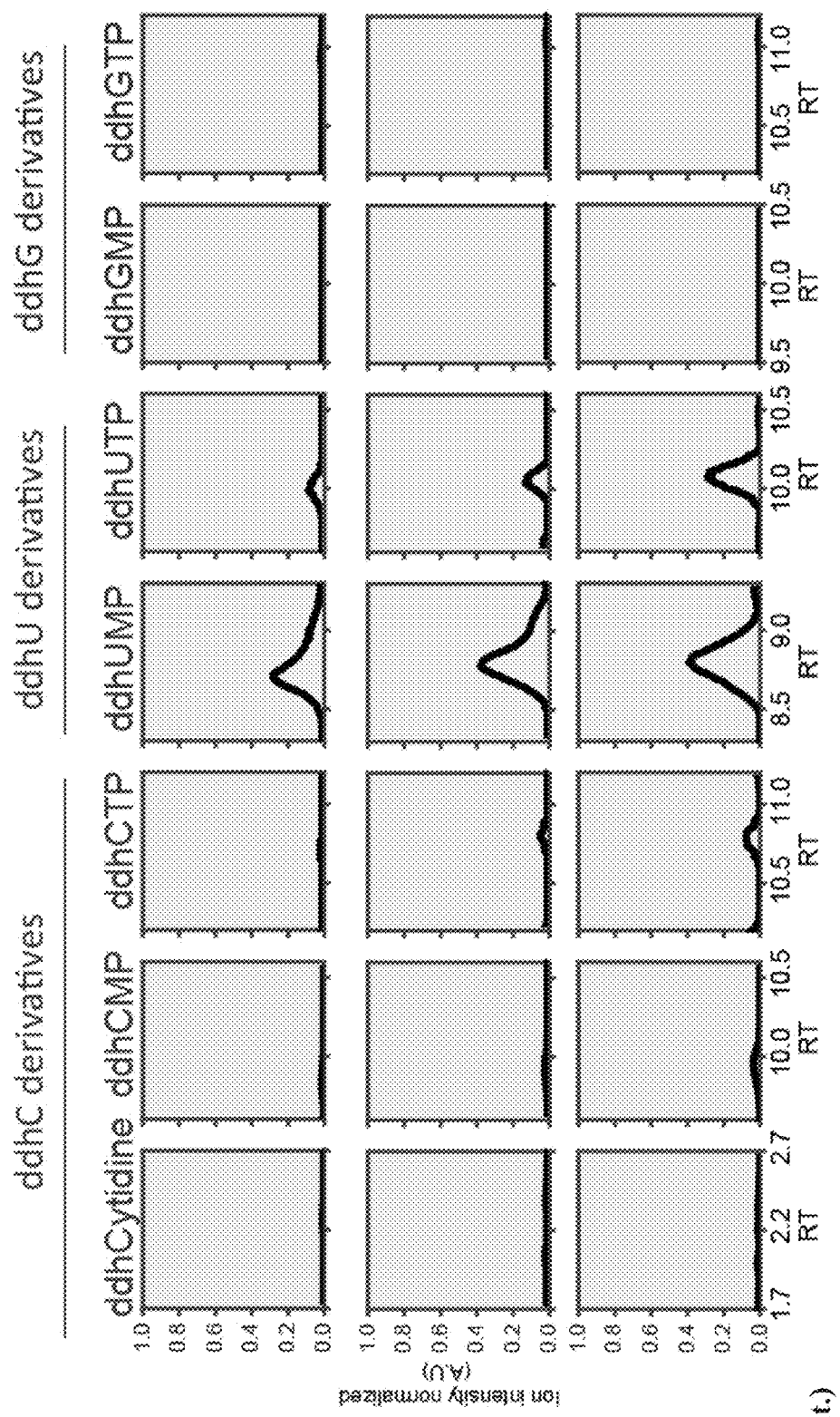
Figure 11:
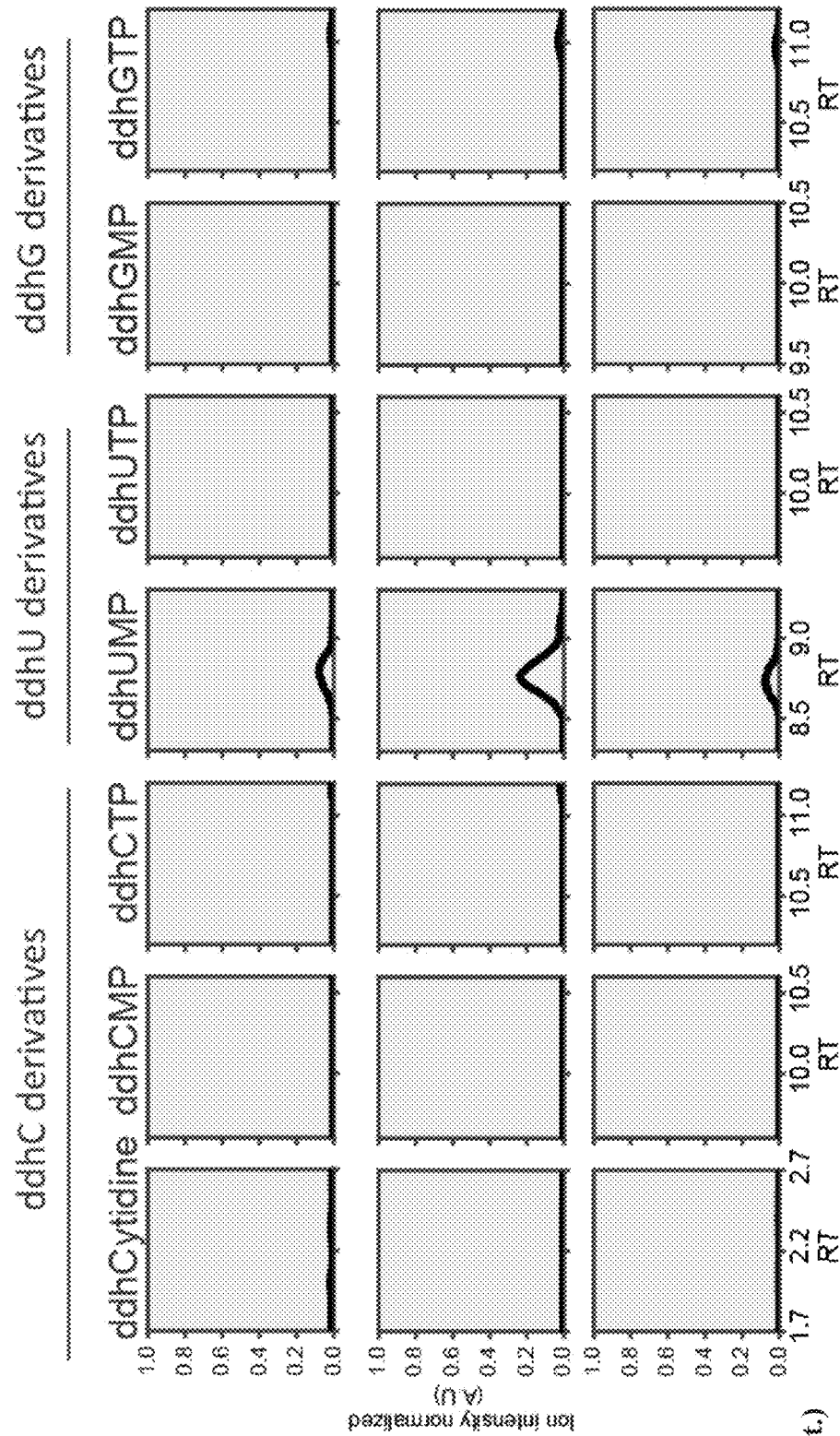
Figure 11:
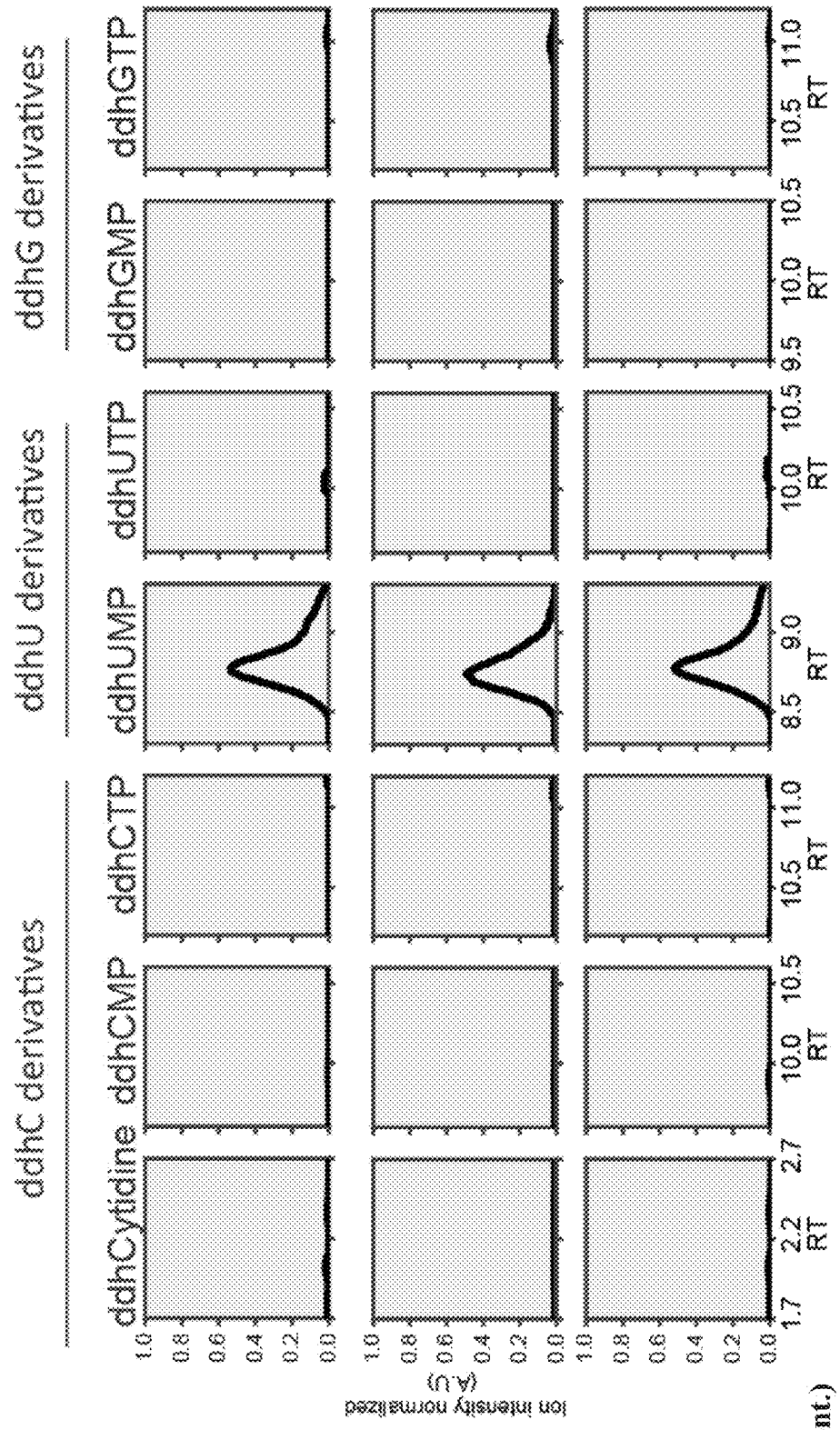
Figure 11:
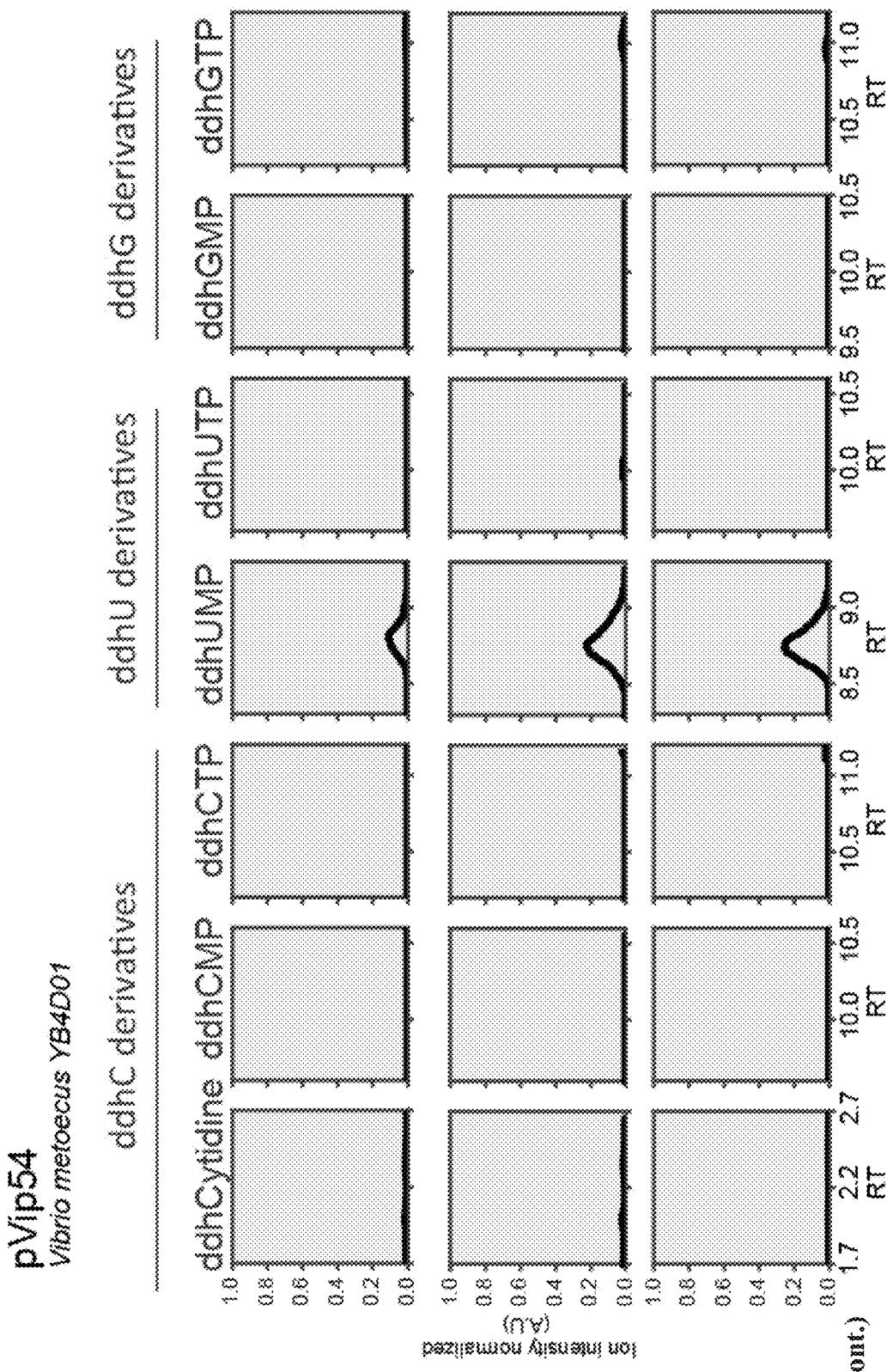
Figure 11:
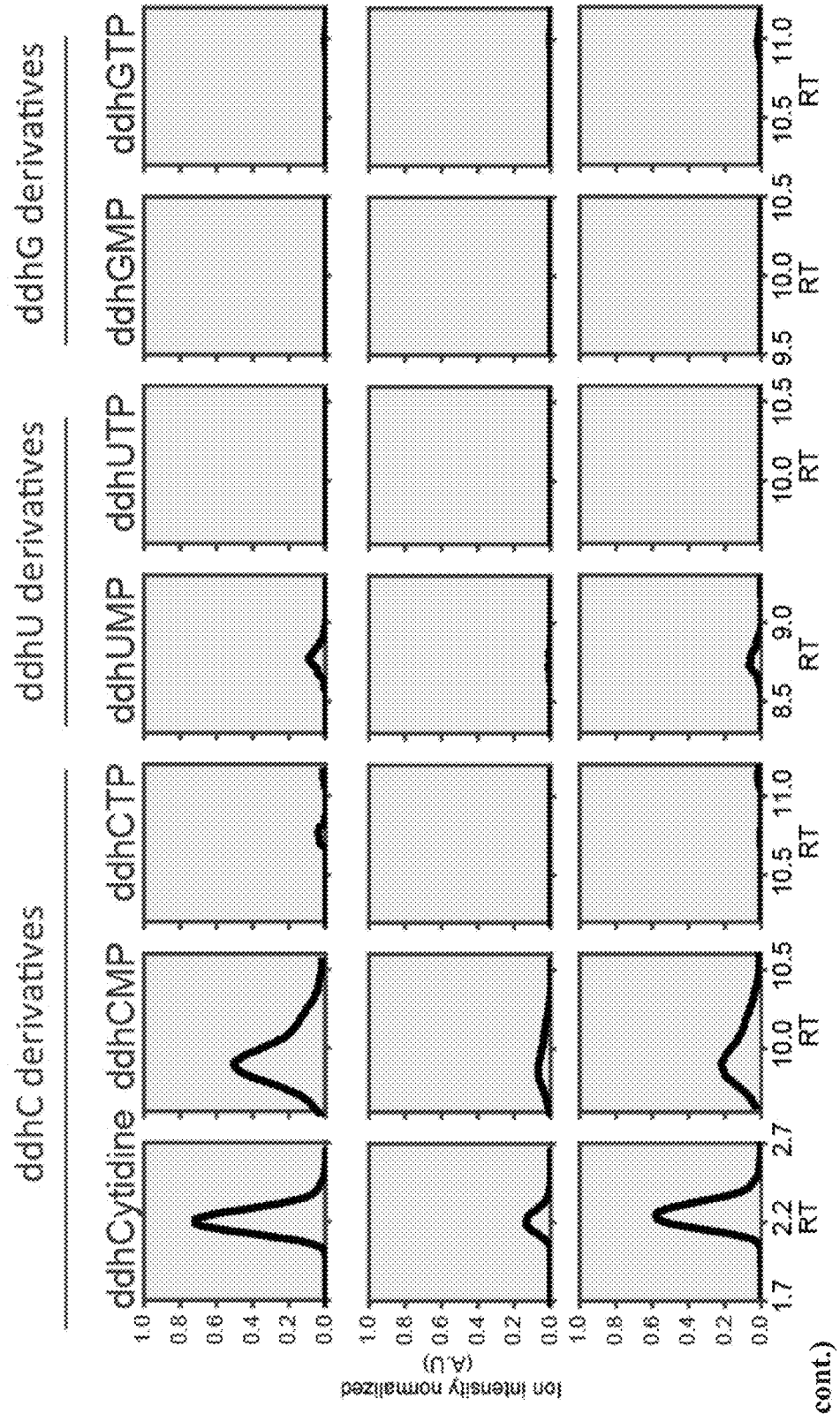
Figure 11:
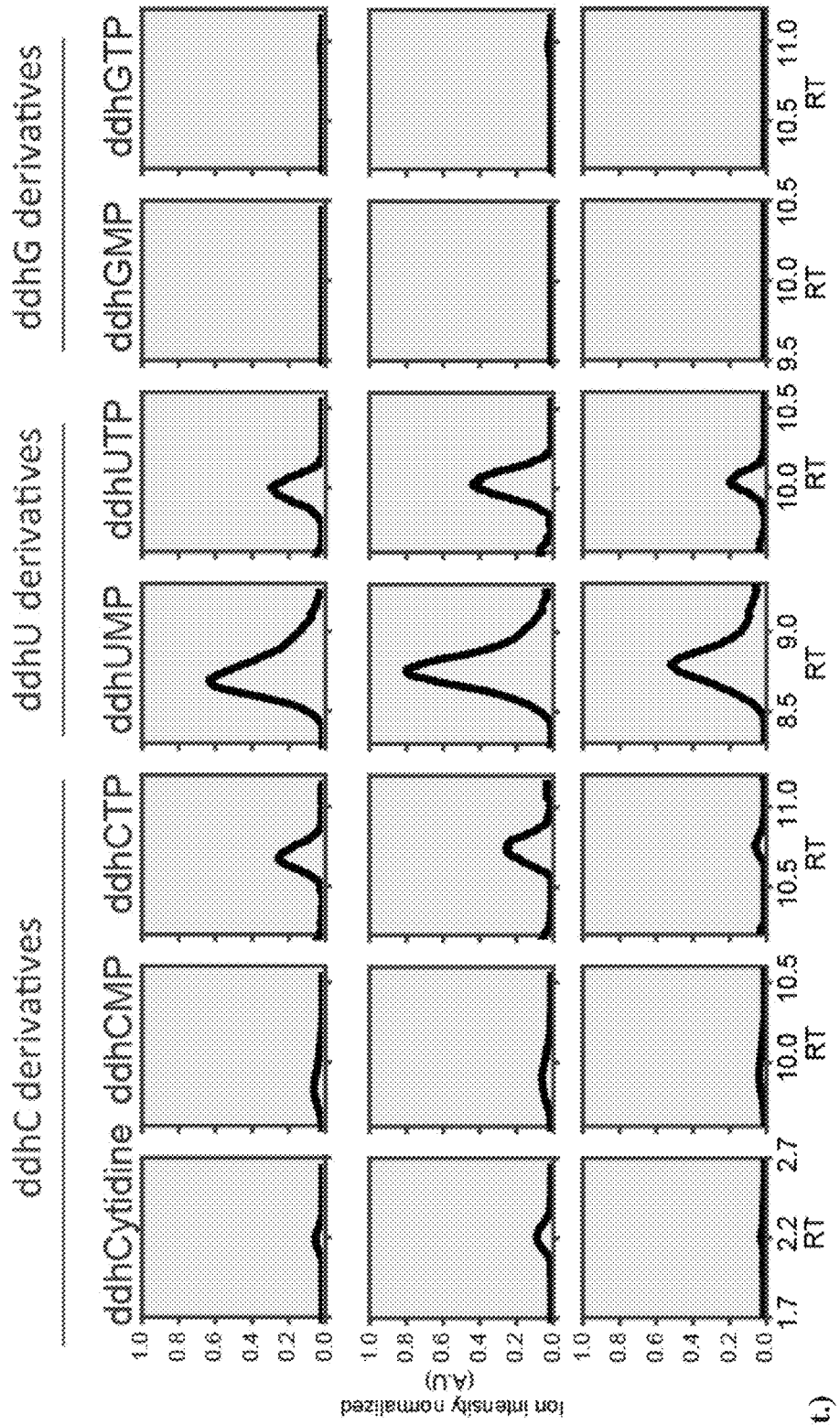
Figure 11:
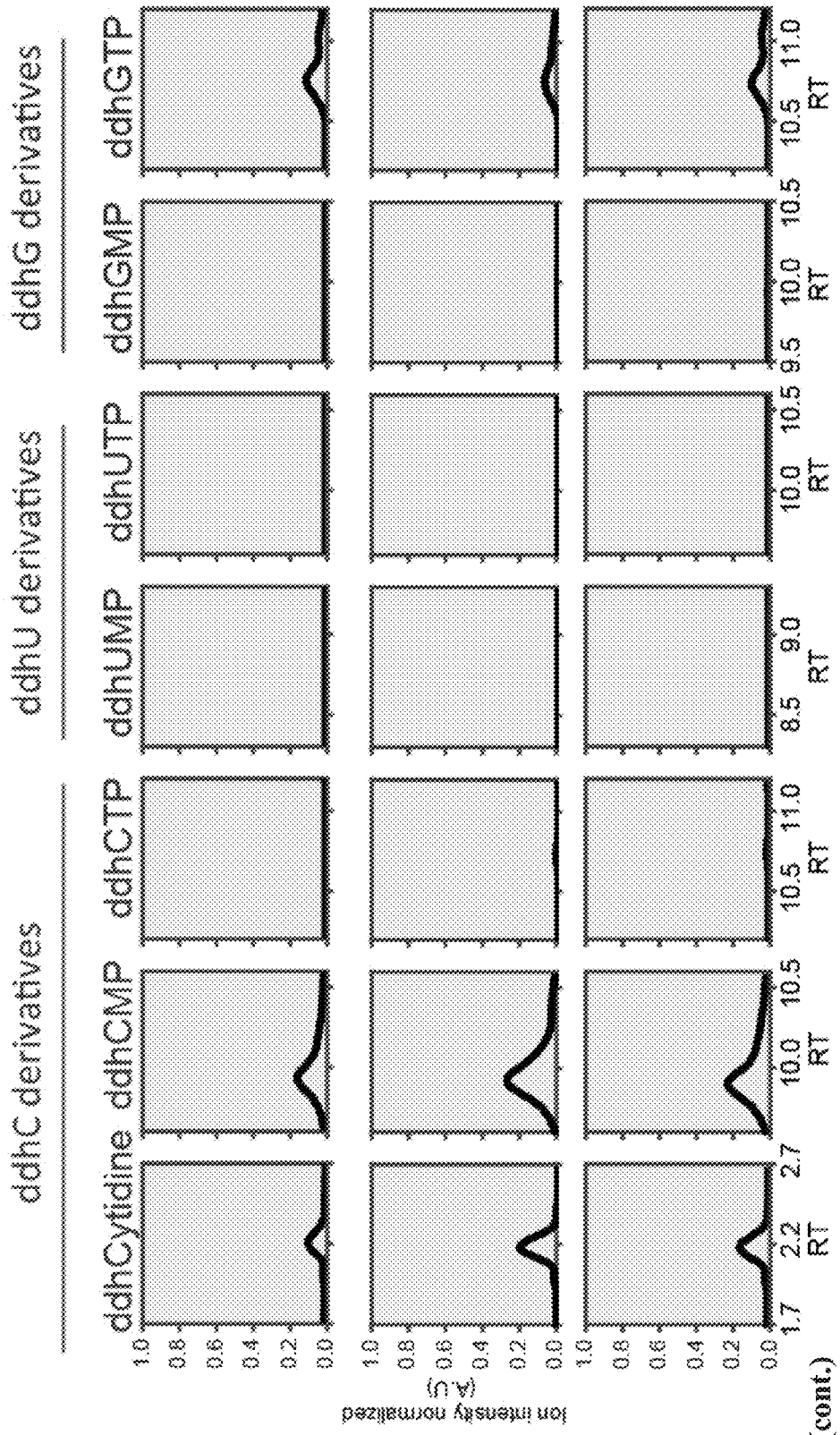
Figure 11:
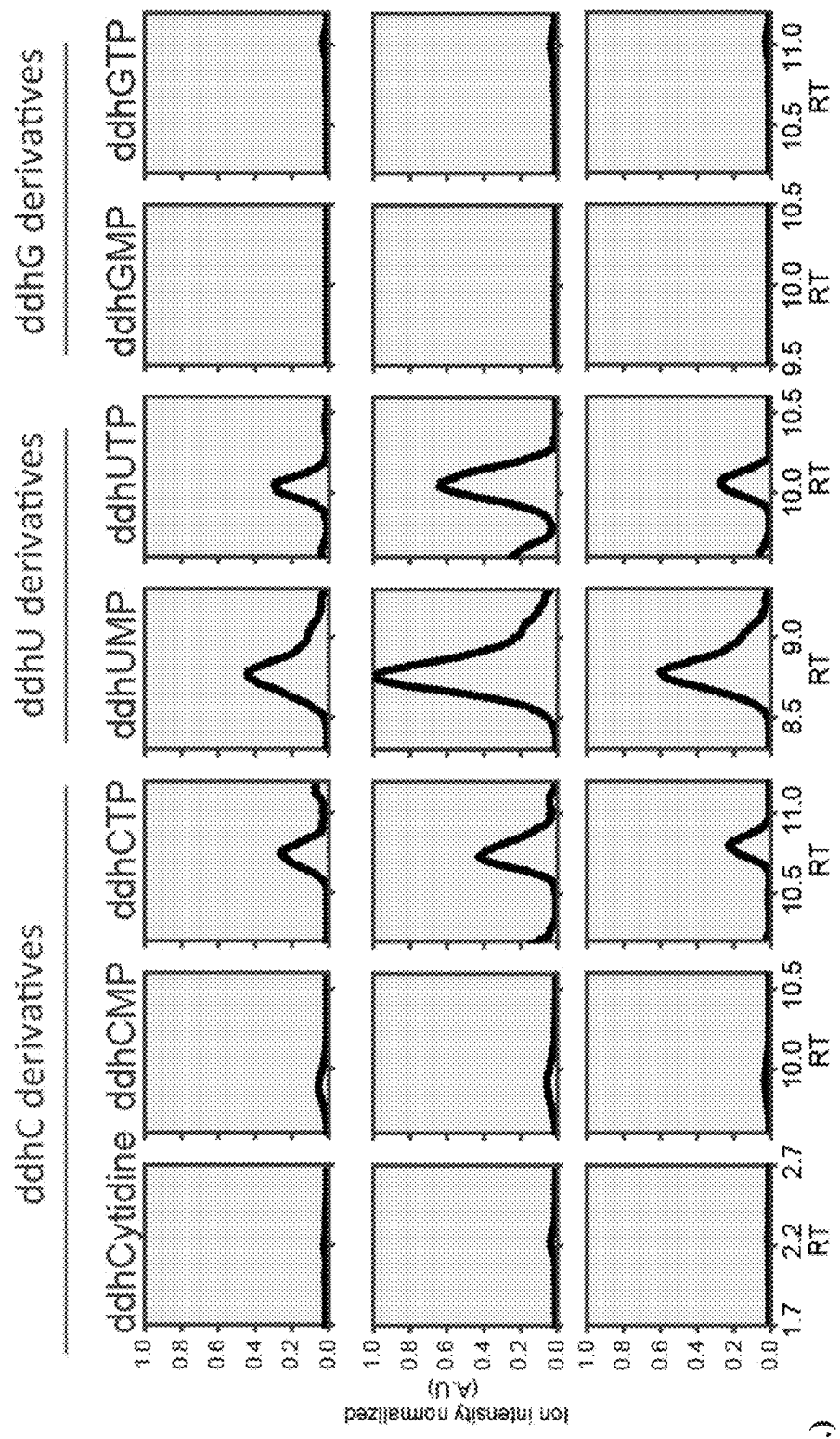
Figure 11:
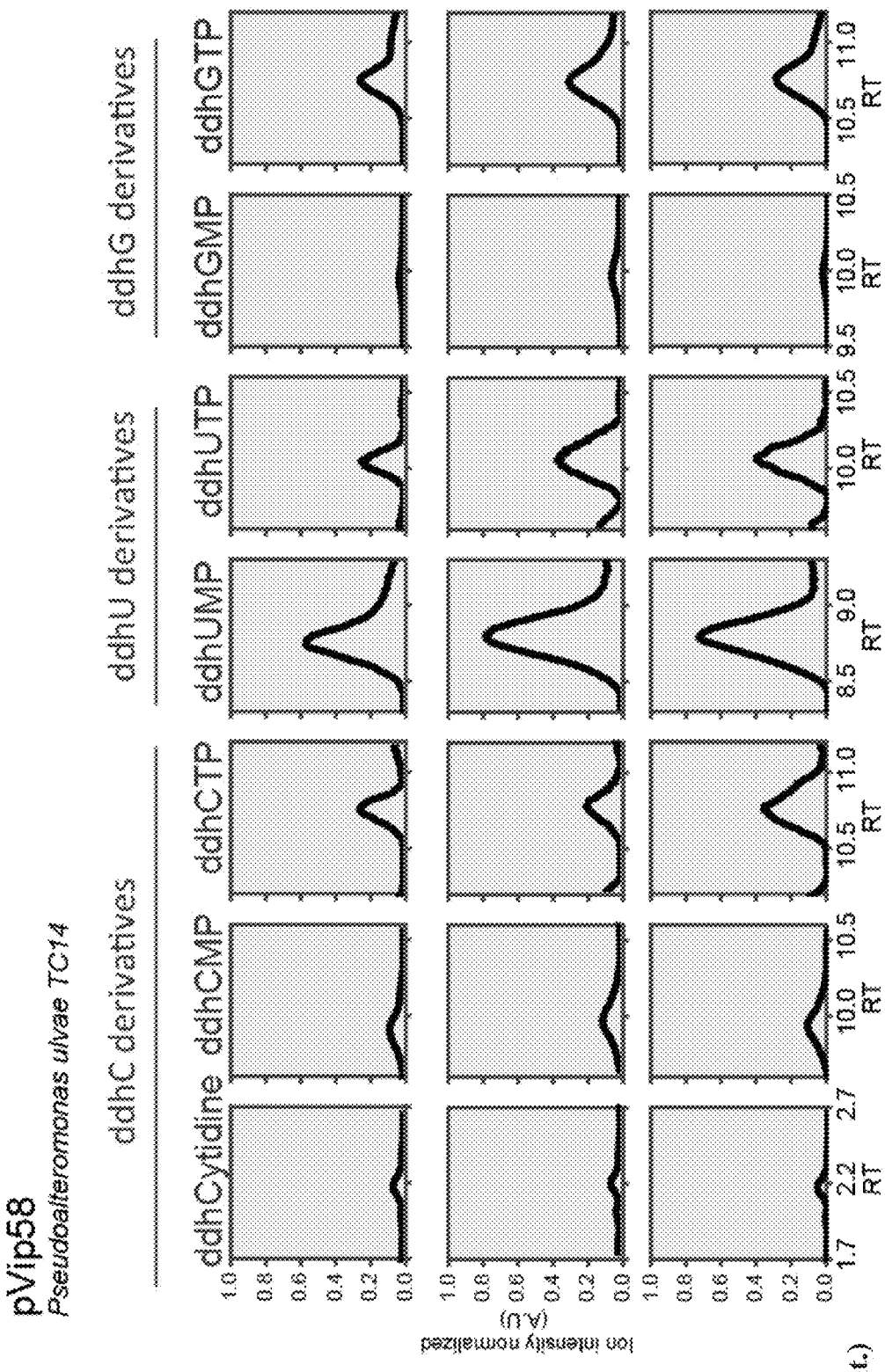
Figure 11:
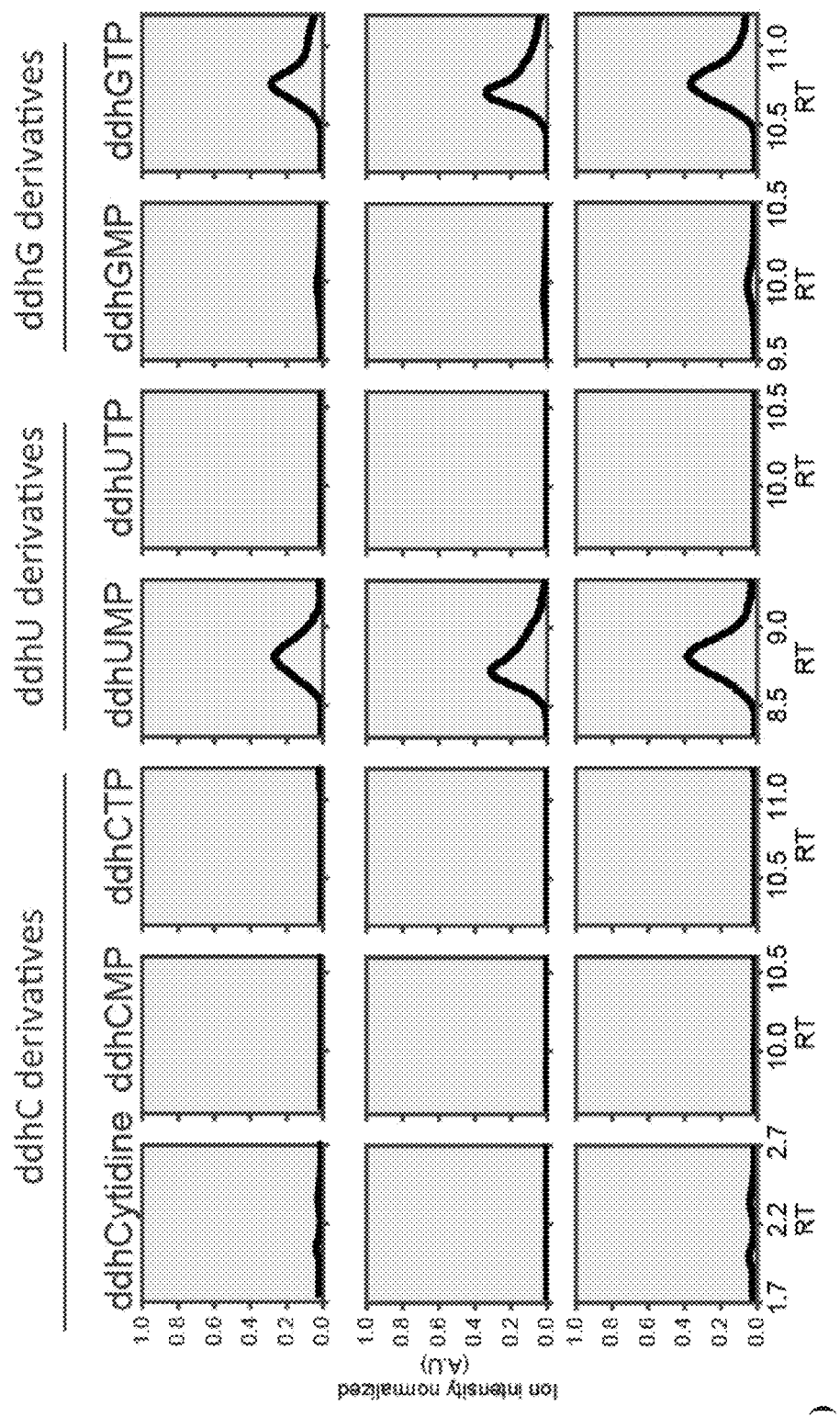
Figure 11:
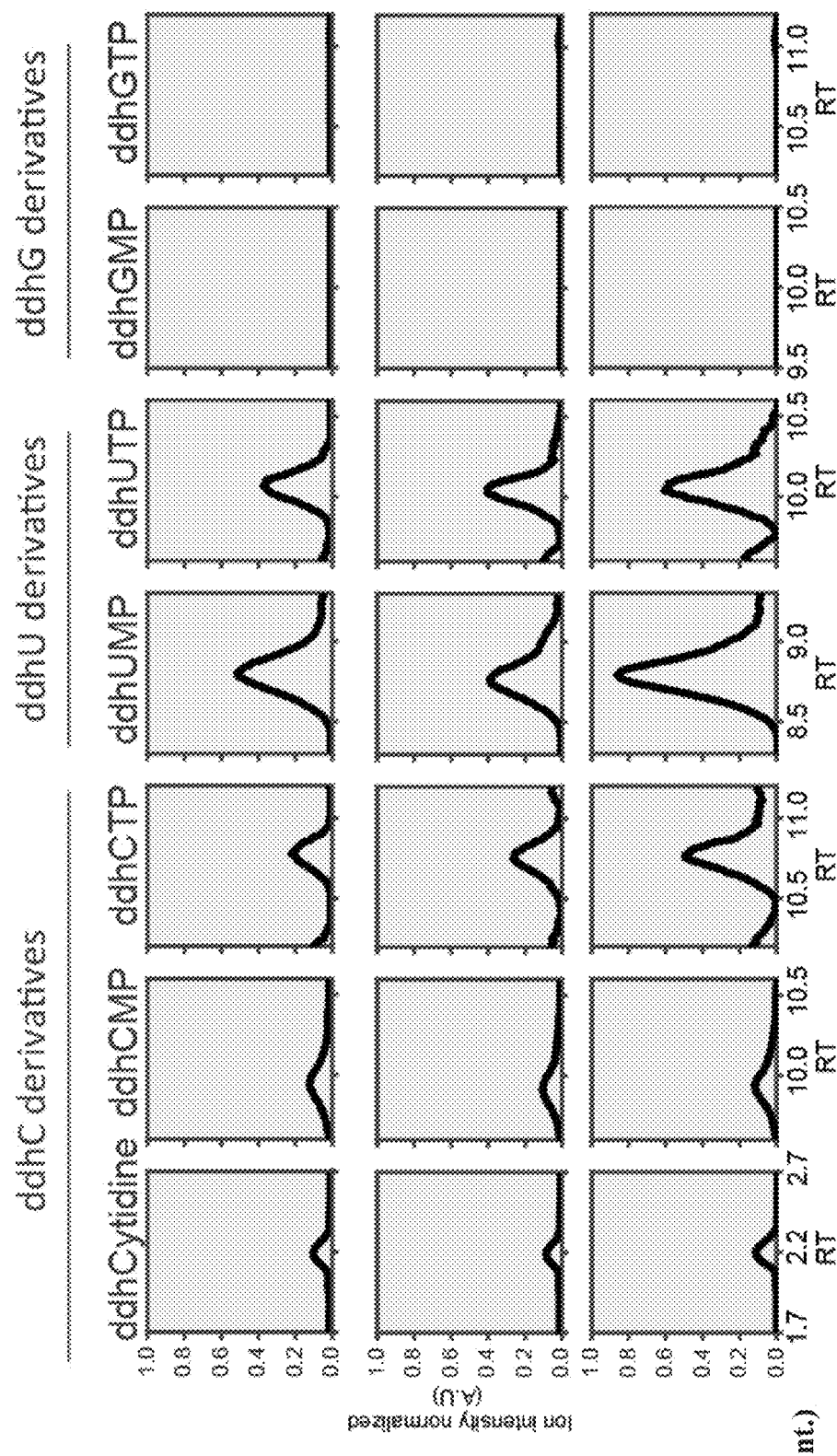
Figure 11:
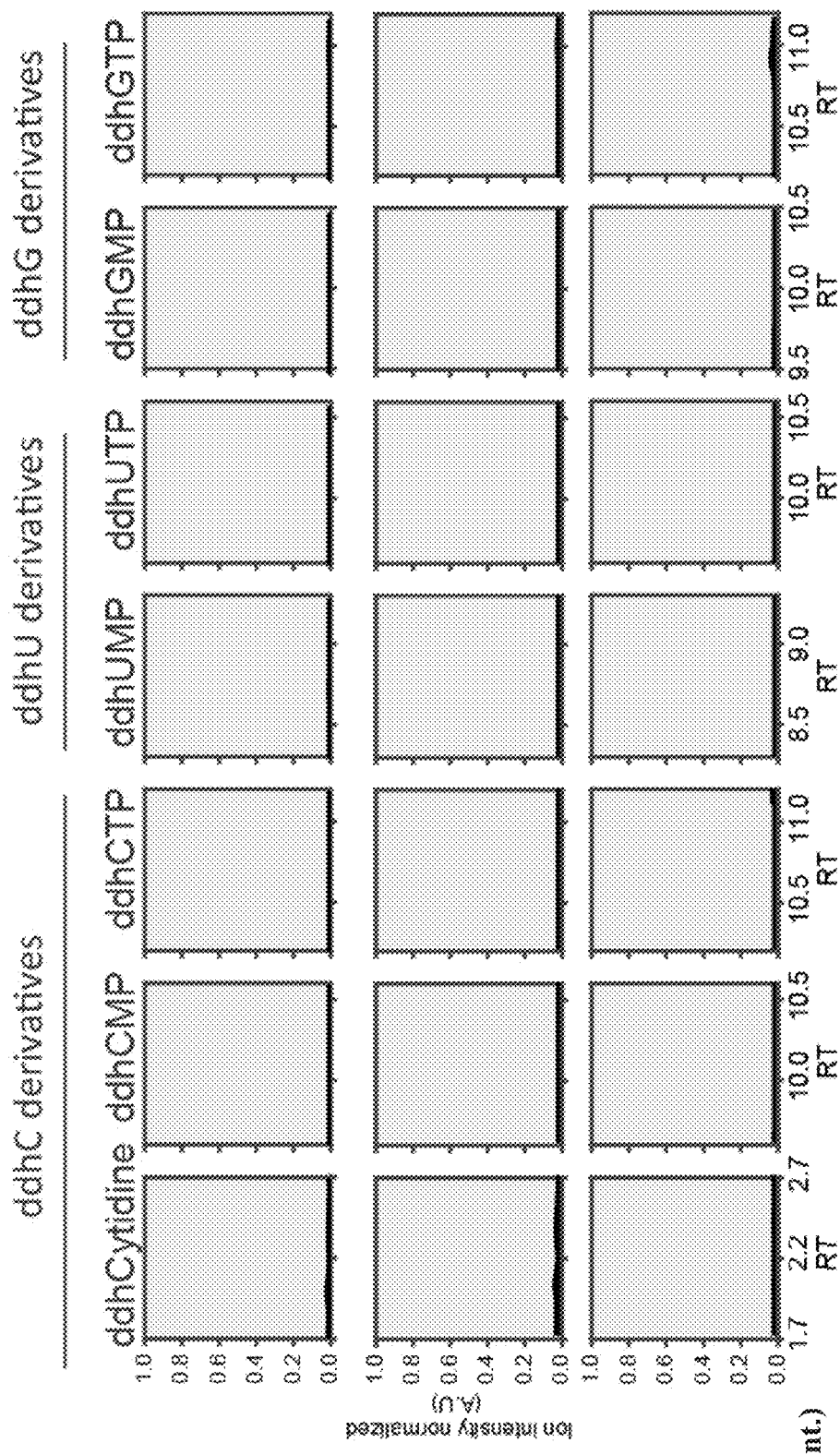
Figure 11:
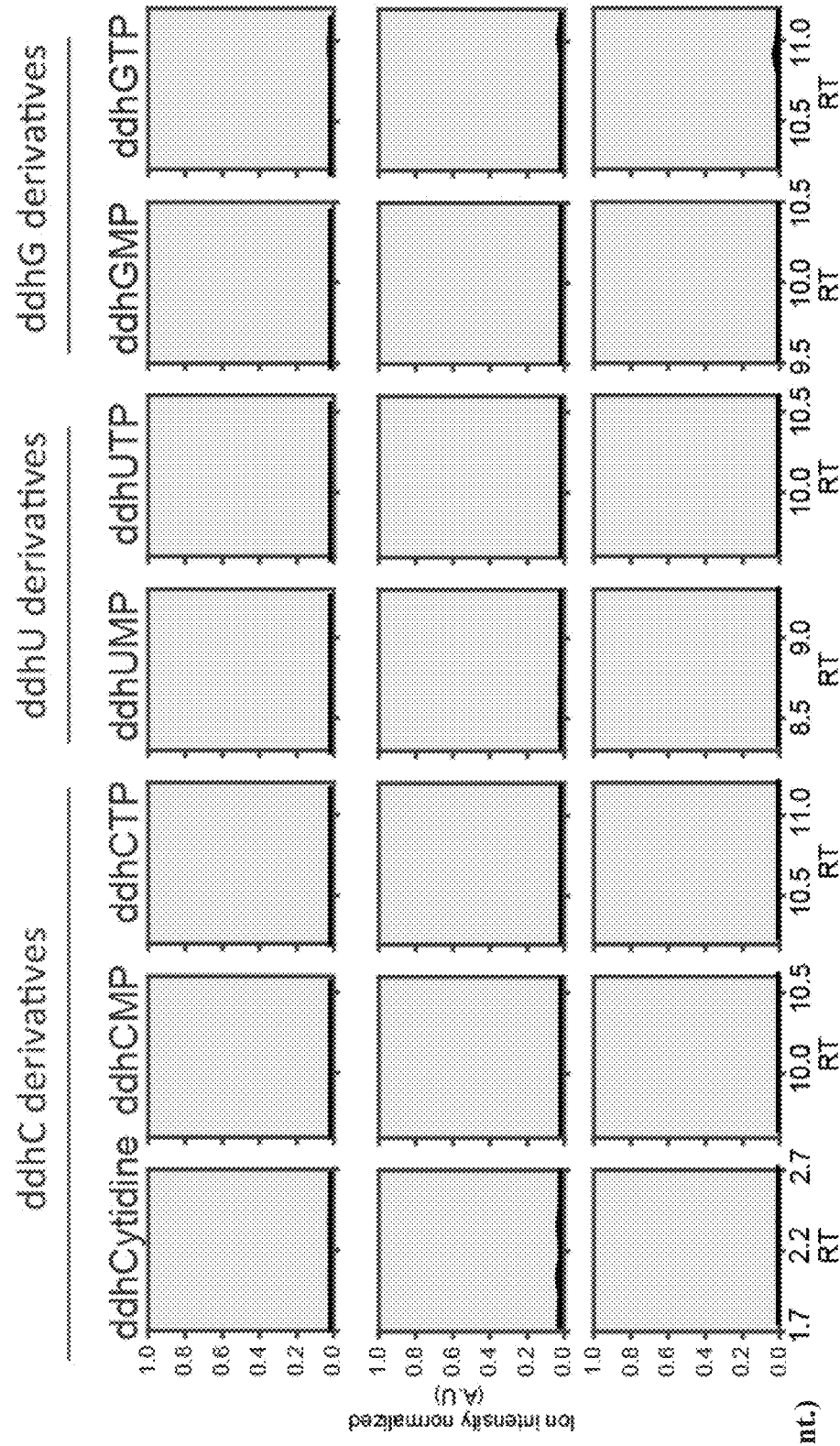
Figure 11:
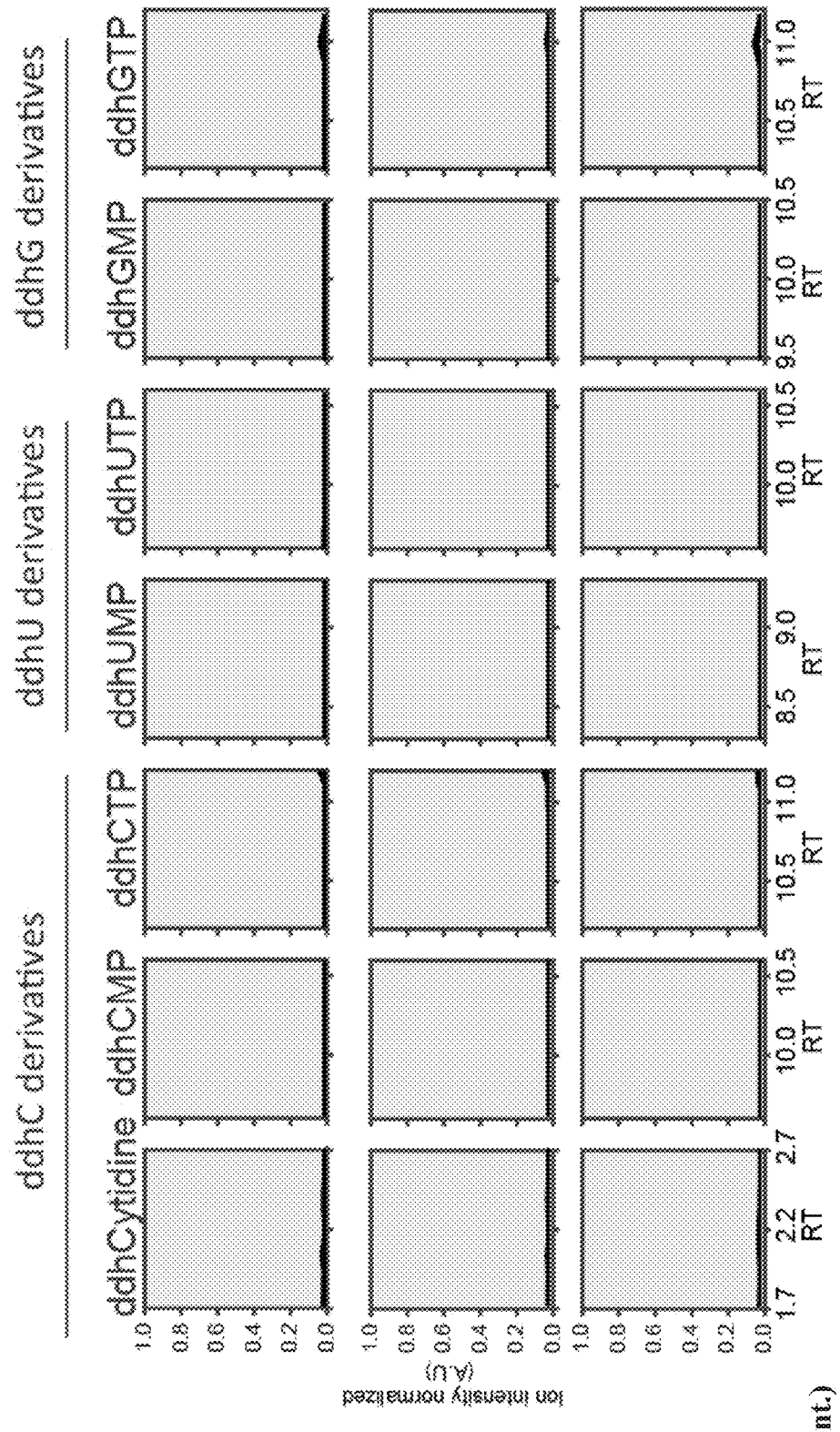
Figure 11:
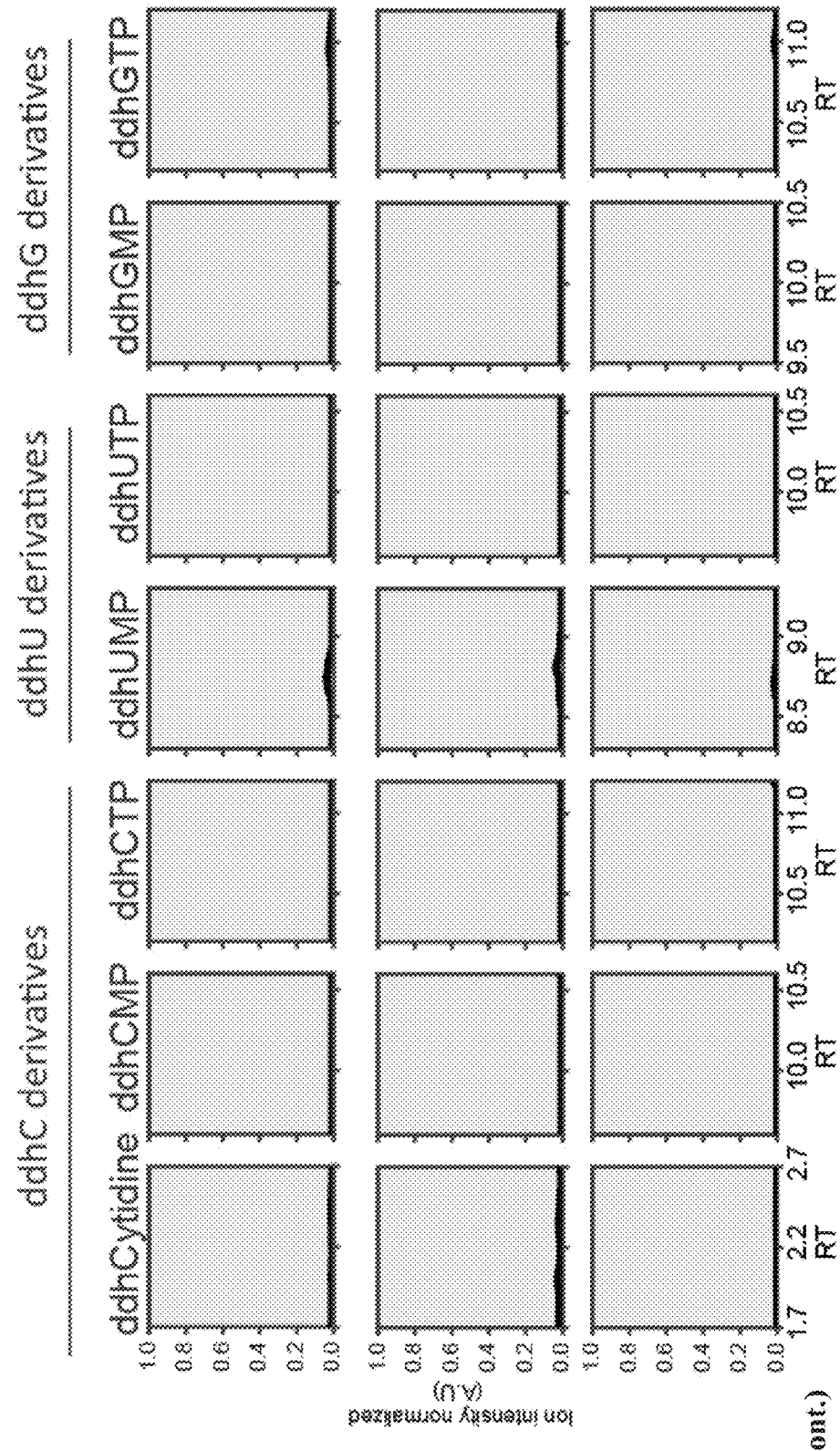
Figure 11:
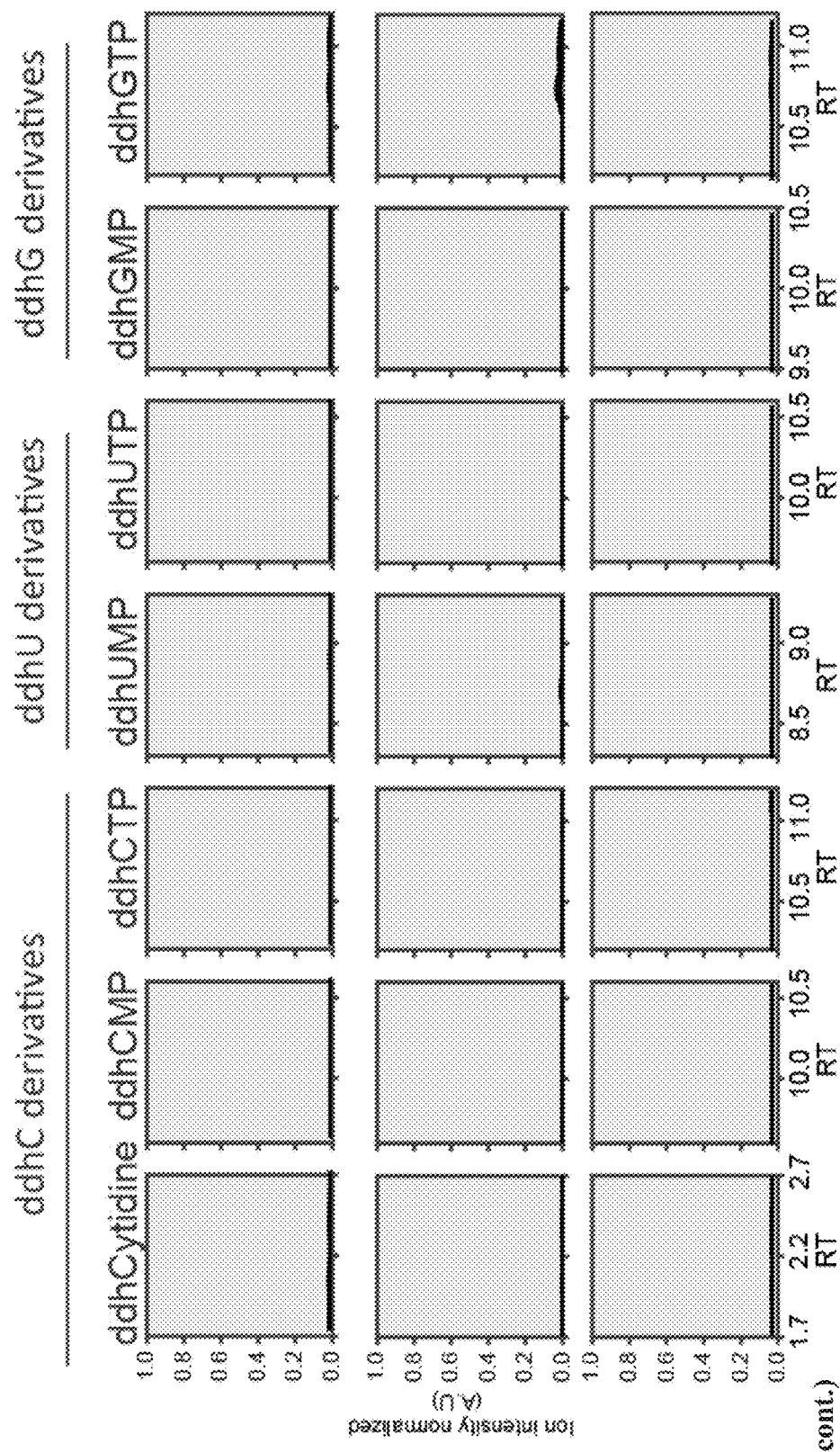
Figure 11:
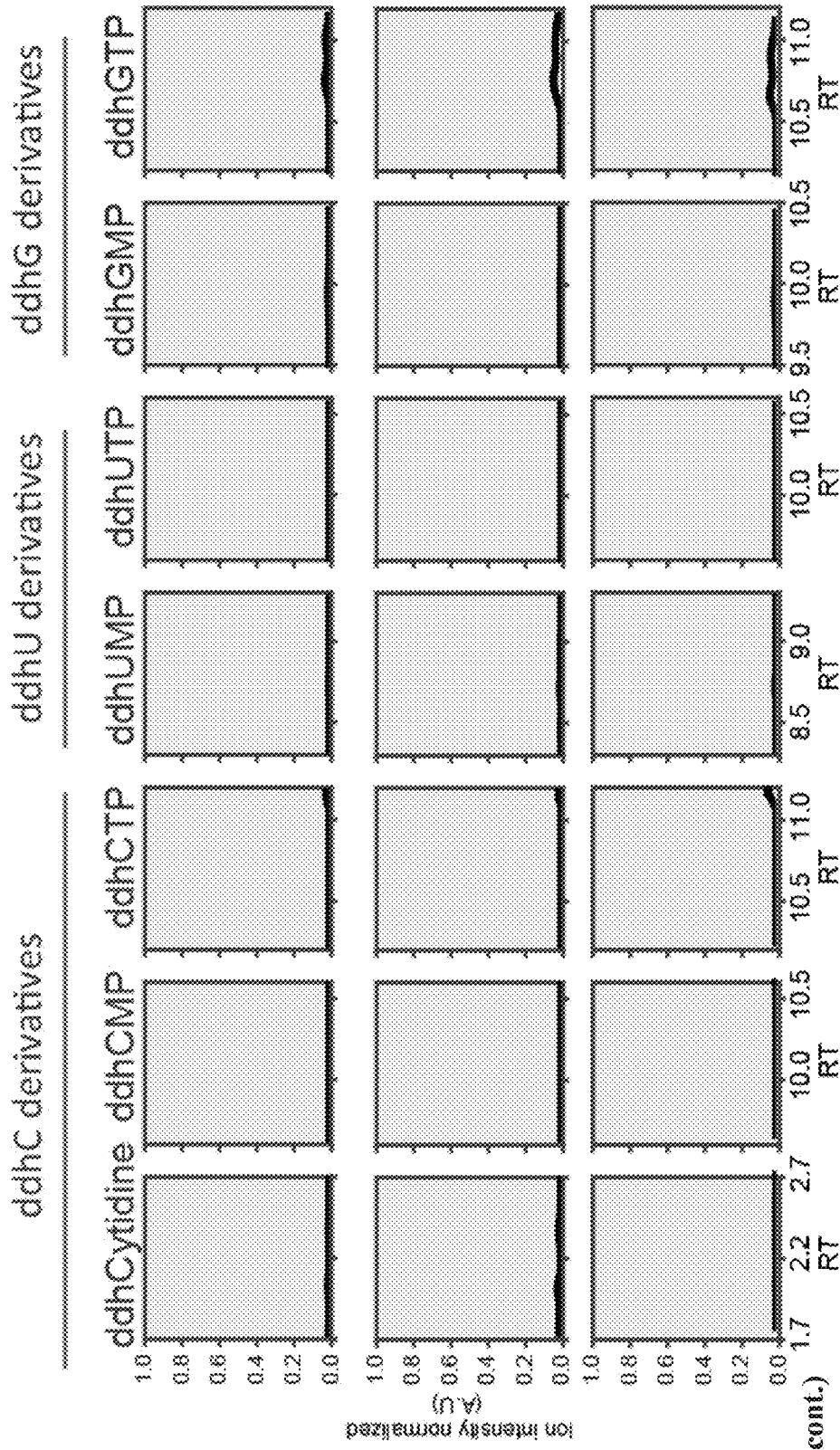

The small molecule fractions from lysates of cells expressing 27 pVips that were found to have an anti-phage activity were then analyzed. Derivatives of ddhCTP were detected by LC-MS in the lysate of pVip50, a protein derived from a methanogenic archaeon that belongs to clade 2 of the pVips tree, verifying that pVips are indeed functional homologs of the human viperin that produce similar antiviral molecules. Moreover, other masses that were markedly enriched in the lysates of cells expressing pVips and absent from the negative control lysate were also examined. For several of the pVips it was found masses that conform with 3'-deoxy-3',4'-didehydro-guanosine-triphosphate (ddhGTP) and 3'-deoxy-3',4'-didehydro-guanosine-diphosphate (ddhGDP), and for other pVips other molecules were found with masses matching 3'-deoxy-3',4'-didehydro-uridine triphosphate (ddhUTP) and 3'-deoxy-3',4'-didehydro-uridine monophosphate (ddhUMP) (FIGS. 9A and 9B, FIG. 11). These results suggest that pVips produce new types of antiviral ribonucleotides that were not observed before in nature.

For most of the pVips, predicted derivatives of a single modified nucleotide were observed in the lysate (either ddhCTP, ddhGTP or ddhUTP). However, seven of the pVips were found to produce derivatives of multiple ddh ribonucleotides. For example, in lysates derived from pVip8-expressing cells, it was found both ddhCTP and ddhUTP, and in lysates from pVip58 cells, ddhCTP, ddhUTP, ddhGTP and their derivatives were detected (FIG. 11). These results suggest that throughout evolution some pVips may have become more promiscuous and can modify more than one ribonucleotide to its ddh antiviral form. Presumably such pVips may have an advantage when encountering phages that can overcome one of these antiviral molecules but not the other two.

For seven of the tested pVips, no ddh nucleotide or its derivatives were detected in the cell lysates, despite a clear antiviral activity conferred by these pVips (FIG. 9A). It is possible that these pVips produce a different antiviral molecule that could not have been detected via the LC-MS protocol, or, alternatively, that these pVips have evolved to confer defense by another mechanism of action that does not involve production of antiviral molecules.

The identity of the molecules produced by the various pVips is largely consistent with their phylogenetic relatedness. pVips from clades 4-7 were predicted to produce ddhUTP, with some of these also producing additional ddh ribonucleotides. In clade 1 and clade 2, which resides together with the eukaryotic viperins on the same superclade, certain pVips were found to produce ddhCTP. Clade 3 includes pVips that were predicted to generate either ddhGTP or ddhUTP (FIG. 9B).

Example 10—Anti-Viral Activities of ddh-Nucleotides

The present example examines the antiviral activities for ddhC (compound AB21650), ddhU (compound AB21649) and ddhG (compound AB21651).

The compounds were tested against a panel of 17 viruses: adenovirus-5 (Ad5), acaribe virus (TCRV), Rift Valley fever virus (RVFV), SARS-CoV, dengue virus-2 (DV-2), Japanese encephalitis virus (JEV), Powassan virus (POWV), West Nile virus (WNV), Yellow fever virus (YFV), Zika virus, Influenza A (H1N1), Influenza A (H5N1), Influenza B, RSV, poliovirus-1 (POV-1), enterovirus-68 (EV-68), and Venezuelan equine encephalitis virus (VEEV). Cell types used were A549 for Ad5; Vero E6 for TCRV; Huh7 for DV-2 and YFV; BHK-21 for POWV; RD for EV-68; MA-104 for RSV; MDCK for influenza viruses; and Vero 76 for all other viruses.

The compounds were solubilized in DMSO to prepare a 400 mM stock solution. The compounds were then serially diluted using eight half-log dilutions in test medium (MEM supplemented with 2% FBS and 50 μg/mL gentamicin) so that the starting (high) test concentration was 2 mM. Each dilution was added to 5 wells of a 96-well plate with 80-100% confluent cells. Three wells of each dilution were infected with virus, and two wells remained uninfected as toxicity controls. Six wells were infected and untreated as virus controls, and six wells were uninfected and untreated as cell controls. The viruses were prepared to achieve the lowest possible multiplicity of infection (MOI) that would yield >80% cytopathic effect (CPE) within 3-7 days. Positive control compounds were tested in parallel for each virus tested. Plates infected with EV-68 were incubated at 33±2° C., 5% $CO_2$; all other plates were incubated at 37±2° C., 5% $CO_2$.

On day 3-7 post-infection, once untreated virus control wells reached maximum CPE, the plates were stained with neutral red dye for approximately 2 hours (±15 minutes). Supernatant dye was removed and the wells were rinsed with PBS, and the incorporated dye was extracted in 50:50 Sorensen citrate buffer/ethanol for >30 minutes and optical density was read on a spectrophotometer at 540 nm. Optical densities were converted to percent of cell controls and normalized to the virus control, then the concentration of test compound required to inhibit CPE by 50% ($EC_{50}$) was calculated by regression analysis. The concentration of compound that would cause 50% cell death in the absence of virus was similarly calculated ($CC_{50}$). The selective index (SI) is the $CC_{50}$ divided by $EC_{50}$.

The results are shown in Table 9. It is found that ddhG exhibits antiviral activity against Influenza A (H1N1) and Influenza A (H5N1); ddhU exhibits antiviral activity against Influenza B and Influenza A (H1N1 and H5N1); ddhC exhibits some activity against enterovirus EV-68.

TABLE 9

In vitro antiviral activity of AB21650 (ddhC), AB21651 (ddhG), and AB21649 (ddhU).

| | | AB21650 | | | AB21651 | | | AB21649 | | | Positive Control | | |
|---|---|---|---|---|---|---|---|---|---|---|---|---|---|
| | Positive Control | $EC_{50}$ | $CC_{50}$ | SI | $EC_{50}$ | $CC_{50}$ | SI | $EC_{50}$ | $CC_{50}$ | SI | $EC_{50}$ | $CC_{50}$ | SI |
| Ad5 | 2-3 Dideoxycytidine | >2 | >2 | 0 | >2 | >2 | 0 | >2 | >2 | 0 | 1.8 | >100 | >56 |
| TCRV | Ribavirin | >2 | >2 | 0 | >2 | >2 | 0 | >1.2 | 1.2 | 0 | 13 | 820 | 63 |
| RVFV | Ribavirin | >2 | >2 | 0 | >2 | >2 | 0 | >1.1 | 1.1 | 0 | 14 | 870 | 62 |
| SARS-CoV | M128533 | >2 | >2 | 0 | >2 | >2 | 0 | >1.5 | 1.5 | 0 | 0.075 | >100 | >1300 |
| DV-2 | Infergen | | | | | | | | | | | | |
| JEV | Infergen | >2 | >2 | 0 | >2 | >2 | 0 | >1.7 | 1.7 | 0 | 0.043 | >10 | >230 |
| POWV | Infergen | | | | | | | | | | | | |
| WNV | Infergen | >2 | >2 | 0 | >2 | >2 | 0 | >1.4 | 1.4 | 0 | 0.12 | >10 | >83 |
| YFV | Infergen | >2 | >2 | 0 | >2 | >2 | 0 | >2 | >2 | 0 | 0.012 | >10 | >830 |
| VEEV | Infergen | >2 | >2 | 0 | >2 | >2 | 0 | >1.1 | 1.1 | 0 | 0.17 | >10 | >59 |
| Zika | NITD008 | >2 | >2 | 0 | >2 | >2 | 0 | >1.5 | 1.5 | 0 | 1.8 | 44 | 24 |
| Influenza A(H1N1) | Ribavirin | >2 | >2 | 0 | 0.44 | >2 | >4.5 | 0.56 | 1.4 | 2.5 | 4.6 | >1000 | >220 |
| Influenza A(H5N1) | Ribavirin | >2 | >2 | 0 | 1.3 | >2 | >1.5 | 0.8 | 1.3 | 1.6 | 1.8 | >1000 | >560 |
| Influenza B | Ribavirin | >2 | >2 | 0 | >2 | >2 | 0 | 0.31 | 1.3 | 4.2 | 1.4 | >1000 | >710 |
| RSV | Ribavirin | >2 | >2 | 0 | >2 | >2 | 0 | >1.9 | 1.9 | 0 | 7.3 | 42 | 5.8 |
| POV-1 | Enviroxime | >2 | >2 | 0 | >2 | >2 | 0 | >1.0 | 1.0 | 0 | 0.0095 | 3.3 | 350 |
| EV-68 | Pirodavir | 0.91 | 1.8 | 2 | >1.1 | 1.1 | 0 | >0.39 | 0.39 | 0 | 0.039 | 4.3 | 110 |
| SARS-CoV-2 | | | | | | | | | | | | | |

Units are in mM for test compounds, ng/mL for Infergen ™, and μg/mL for all other positive control compounds.

$EC_{50}$: 50% effective antiviral concentration $CC_{50}$: 50% cytotoxic concentration of compound without virus added

SI = $CC_{50}/EC_{50}$

TABLE 1

| | pVip genes | | |
|---|---|---|---|
| SEQ ID No | IMG id | pVip # | Metagenome genome IMG ID |
| 3 | 2624749465 | 6 | 2623620517 |
| 4 | 2739066738 | 7 | 2738541339 |
| 5 | 2521798317 | 8 | 2521172648 |
| 6 | 2574301464 | 9 | 2574179732 |
| 7 | 2720695169 | 10 | 2718218250 |
| 8 | 2698137626 | 12 | 2695420938 |
| 9 | 646713396 | 15 | 646564524 |
| 10 | 2506475787 | 19 | 2506381025 |
| 11 | 2515428782 | 21 | 2515154070 |
| 12 | 2574506394 | 27 | 2574179788 |
| 13 | 2609132705 | 32 | 2608642208 |
| 14 | 2619892213 | 34 | 2619618891 |
| 15 | 2634960437 | 39 | 2634166261 |
| 16 | 2639213731 | 42 | 2636416084 |
| 17 | 2648875132 | 44 | 2648501185 |
| 18 | 2649993803 | 46 | 2648501459 |
| 19 | 2651203508 | 47 | 2648501771 |
| 20 | 2651490945 | 48 | 2648501840 |
| 21 | 2661858798 | 50 | 2660238307 |
| 22 | 2701115162 | 56 | 2700988679 |
| 23 | 2718503187 | 57 | 2718217692 |
| 24 | 2721736750 | 58 | 2718218507 |
| 25 | 2733913669 | 60 | 2731957952 |
| 26 | 2743907592 | 62 | 2740892545 |
| 27 | 2744633848 | 63 | 2744054527 |
| 28 | 2695043264 | 1 | 2693429896 |
| 29 | 2684559953 | 2 | 2681813561 |
| 30 | 2507146842 | 3 | 2506783068 |
| 31 | 2632766730 | 11 | 2630968672 |
| 32 | 2744653400 | 13 | 2744054531 |
| 33 | 2654783232 | 14 | 2654587543 |
| 34 | 2504625218 | 17 | 2504557017 |
| 35 | 2506474236 | 18 | 2506381025 |
| 36 | 2509664214 | 20 | 2509601008 |
| 37 | 2518436022 | 22 | 2518285547 |
| 38 | 2522341593 | 23 | 2522125098 |
| 39 | 2524269675 | 24 | 2524023156 |
| 40 | 2525334630 | 25 | 2524614668 |
| 41 | 2557036911 | 26 | 2556921023 |
| 42 | 2574517928 | 28 | 2574179790 |
| 43 | 2582805913 | 29 | 2582580599 |
| 44 | 2582946381 | 30 | 2582580664 |
| 45 | 2596421479 | 31 | 2595698251 |
| 46 | 2618018523 | 33 | 2617270916 |
| 47 | 2631333032 | 36 | 2630968323 |
| 48 | 2632937107 | 37 | 2630968711 |
| 49 | 2633985761 | 38 | 2630968972 |
| 50 | 2635314107 | 40 | 2634166348 |
| 51 | 2637497700 | 41 | 2636415666 |
| 52 | 2641427518 | 43 | 2639762959 |
| 53 | 2649163162 | 45 | 2648501251 |
| 54 | 2651585264 | 49 | 2648501863 |
| 55 | 2665950188 | 51 | 2663763173 |
| 56 | 2674184607 | 52 | 2671180787 |
| 57 | 2684813341 | 53 | 2684622550 |
| 58 | 2693697599 | 54 | 2693429564 |
| 59 | 2694112273 | 55 | 2693429660 |
| 60 | 2728147792 | 59 | 2724679805 |
| 61 | 2741341560 | 61 | 2740891962 |
| 62 | 2741409035 | 64 | 2740891993 |
| 63 | 2504129180 | 65 | 2503982047 |
| 64 | 637160692 | 66 | 637000327 |
| 65 | 637364324 | 67 | 637000336 |
| 66 | 637468954 | 68 | 637000337 |
| 67 | 637586319 | 69 | 637000206 |
| 68 | 637752529 | 70 | 637000204 |
| 69 | 639797708 | 71 | 639633052 |
| 70 | 640805406 | 72 | 640753033 |
| 71 | 640830189 | 73 | 640753049 |
| 72 | 641096015 | 74 | 640963011 |
| 73 | 641147750 | 75 | 640963027 |
| 74 | 641288534 | 76 | 641228507 |
| 75 | 643461066 | 77 | 643348574 |
| 76 | 646369858 | 78 | 646311927 |
| 77 | 646419713 | 79 | 646311963 |

TABLE 1-continued pVip genes

| SEQ ID No | IMG id | pVip # | Metagenome genome IMG ID |
|---|---|---|---|
| 78 | 647622404 | 80 | 647533121 |
| 79 | 649804297 | 81 | 649633054 |
| 80 | 650410387 | 82 | 650377991 |
| 81 | 650419199 | 83 | 650377942 |
| 82 | 650463340 | 84 | 650377984 |
| 83 | 650537321 | 85 | 650377925 |
| 84 | 650742368 | 86 | 650716002 |
| 85 | 650921542 | 87 | 650716044 |
| 86 | 2501733929 | 88 | 2501651210 |
| 87 | 2502233141 | 89 | 2502171154 |
| 88 | 2509552219 | 90 | 2509276055 |
| 89 | 2512440669 | 91 | 2512047059 |
| 90 | 2519473577 | 92 | 2519103099 |
| 91 | 2519473579 | 93 | 2519103099 |
| 92 | 2519484486 | 94 | 2519103103 |
| 93 | 2519815572 | 95 | 2519103180 |
| 94 | 2521802859 | 96 | 2521172649 |
| 95 | 2522303848 | 97 | 2522125086 |
| 96 | 2524107537 | 98 | 2524023060 |
| 97 | 2525610838 | 99 | 2524614740 |
| 98 | 2525930338 | 100 | 2524614816 |
| 99 | 2528325157 | 101 | 2528311002 |
| 100 | 2531202617 | 102 | 2529293096 |
| 101 | 2532381218 | 103 | 2531839141 |
| 102 | 2532646932 | 104 | 2531839206 |
| 103 | 2538932271 | 105 | 2537561856 |
| 104 | 2540642849 | 106 | 2540341105 |
| 105 | 2540668036 | 107 | 2540341115 |
| 106 | 2540825991 | 108 | 2540341170 |
| 107 | 2541039228 | 109 | 2540341248 |
| 108 | 2541315631 | 110 | 2541046975 |
| 109 | 2546450678 | 111 | 2545824694 |
| 110 | 2546738312 | 112 | 2545824767 |
| 111 | 2547718745 | 113 | 2547132187 |
| 112 | 2551476655 | 114 | 2551306039 |
| 113 | 2551491916 | 115 | 2551306042 |
| 114 | 2551562099 | 116 | 2551306058 |
| 115 | 2551596444 | 117 | 2551306067 |
| 116 | 2553401559 | 118 | 2551306520 |
| 117 | 2553886541 | 119 | 2551306646 |
| 118 | 2558097217 | 120 | 2556921621 |
| 119 | 2559286049 | 121 | 2558860239 |
| 120 | 2559416375 | 122 | 2558860277 |
| 121 | 2562001279 | 123 | 2561511079 |
| 122 | 2563081558 | 124 | 2562617115 |
| 123 | 2563230595 | 125 | 2562617155 |
| 124 | 2565569616 | 126 | 2563367142 |
| 125 | 2565702223 | 127 | 2563367170 |
| 126 | 2566542256 | 128 | 2565956643 |
| 127 | 2566736970 | 129 | 2565956698 |
| 128 | 2569938648 | 130 | 2568526421 |
| 129 | 2574423613 | 131 | 2574179766 |
| 130 | 2574578667 | 132 | 2574179802 |
| 131 | 2577747326 | 133 | 2576861245 |
| 132 | 2577787495 | 134 | 2576861258 |
| 133 | 25804401517 | 135 | 2579778656 |
| 134 | 25810324187 | 136 | 2579778800 |
| 135 | 2581542389 | 137 | 2579778918 |
| 136 | 2582293224 | 138 | 2579779100 |
| 137 | 2582959978 | 139 | 2582580668 |
| 138 | 2583671671 | 140 | 2582580861 |
| 139 | 2584203718 | 141 | 2582580995 |
| 140 | 2585240392 | 142 | 2582581301 |
| 141 | 2587265930 | 143 | 2585427937 |
| 142 | 2589217693 | 144 | 2588253911 |
| 143 | 2597063350 | 145 | 2596583606 |
| 144 | 2600497862 | 146 | 2600254970 |
| 145 | 2600833866 | 147 | 2600255071 |
| 146 | 2609594859 | 148 | 2609459643 |
| 147 | 2609930410 | 149 | 2609459764 |
| 148 | 2611345001 | 150 | 2609460080 |
| 149 | 2611749855 | 151 | 2609460164 |
| 150 | 2612132826 | 152 | 2609460245 |
| 151 | 2617465221 | 153 | 2617270765 |
| 152 | 2617538802 | 154 | 2617270789 |

TABLE 1-continued pVip genes

| SEQ ID No | IMG id | pVip # | Metagenome genome IMG ID |
|---|---|---|---|
| 153 | 2619647987 | 155 | 2619618818 |
| 154 | 2619760352 | 156 | 2619618853 |
| 155 | 2620549291 | 157 | 2619619052 |
| 156 | 2621169600 | 158 | 2619619266 |
| 157 | 2623278845 | 159 | 2622736530 |
| 158 | 2632746825 | 160 | 2630968667 |
| 159 | 2642232622 | 161 | 2639763156 |
| 160 | 2644760915 | 162 | 2643221740 |
| 161 | 2645912334 | 163 | 2645727543 |
| 162 | 2647434260 | 164 | 2645727892 |
| 163 | 2649993012 | 165 | 2648501459 |
| 164 | 2651793160 | 166 | 2648501913 |
| 165 | 2652273697 | 167 | 2651869653 |
| 166 | 2654809173 | 168 | 2654587547 |
| 167 | 2658339966 | 169 | 2657245169 |
| 168 | 2667505054 | 170 | 2663763602 |
| 169 | 2667963948 | 171 | 2667527390 |
| 170 | 2668144532 | 172 | 2667527434 |
| 171 | 2668847476 | 173 | 2667527626 |
| 172 | 2672407511 | 174 | 2671180348 |
| 173 | 2674782375 | 175 | 2671180928 |
| 174 | 2677278474 | 176 | 2675903261 |
| 175 | 2682061458 | 177 | 2681812894 |
| 176 | 2684092807 | 178 | 2681813425 |
| 177 | 2688794699 | 179 | 2687453440 |
| 178 | 2693209812 | 180 | 2690316327 |
| 179 | 2694949528 | 181 | 2693429874 |
| 180 | 2700499480 | 182 | 2698536835 |
| 181 | 2701140257 | 183 | 2700988686 |
| 182 | 2701911183 | 184 | 2700989248 |
| 183 | 2705695255 | 185 | 2703719122 |
| 184 | 2706043000 | 186 | 2703719236 |
| 185 | 2712662546 | 187 | 2711768198 |
| 186 | 2714077658 | 188 | 2713896747 |
| 187 | 2719376594 | 189 | 2718217925 |
| 188 | 2719498267 | 190 | 2718217953 |
| 189 | 2719828580 | 191 | 2718218033 |
| 190 | 2722236530 | 192 | 2721755284 |
| 191 | 2727845415 | 193 | 2724679709 |
| 192 | 2728971251 | 194 | 2728369061 |
| 193 | 2729066335 | 195 | 2728369080 |
| 194 | 2730169305 | 196 | 2728369366 |
| 195 | 2731232863 | 197 | 2728369654 |
| 196 | 2735939253 | 198 | 2734482289 |
| 197 | 2740266671 | 199 | 2739367982 |
| 198 | 2741408272 | 200 | 2740891993 |
| 199 | 2742412079 | 201 | 2740892189 |
| 200 | 2742415354 | 202 | 2740892190 |
| 201 | 2743908240 | 203 | 2740892545 |
| 202 | 2751139676 | 204 | 2747843223 |
| 203 | 2752652723 | 205 | 2751185612 |
| 204 | 2753090639 | 206 | 2751185737 |
| 205 | 2753093587 | 207 | 2751185738 |
| 206 | 2753363234 | 208 | 2751185801 |
| 207 | 2753367132 | 209 | 2751185802 |
| 208 | 2753371117 | 210 | 2751185803 |
| 209 | 2753755176 | 211 | 2751185895 |
| 210 | 2758508848 | 212 | 2757320913 |
| 211 | 2758538137 | 213 | 2757320982 |
| 212 | 2758668677 | 214 | 2758568024 |
| 213 | 2766104288 | 215 | 2765235962 |
| 214 | 2770832229 | 216 | 2767802753 |
| 215 | 2558444101 | 217 | 2558309039 |
| 216 | 2620552401 | 218 | 2619619052 |
| 217 | 2620553354 | 219 | 2619619052 |
| 218 | 2671326339 | 220 | 2671180039 |
| 219 | 2722096198 | 221 | 2721755233 |
| 220 | 2725246328 | 222 | 2724679053 |
| 221 | 2049941002 assembled LHMISPF_00252280 | 223 | 2049941002 |
| 222 | 2061766007 assembled_HiSeq_03538890 | 224 | 2061766007 |
| 223 | 2061766007 assembled_HiSeq_08062520 | 225 | 2061766007 |
| 224 | 2061766007 assembled_HiSeq_12004210 | 226 | 2061766007 |
| 225 | 2061766007 assembled_HiSeq_13805260 | 227 | 2061766007 |
| 226 | 2061766007 assembled_HiSeq_17035850 | 228 | 2061766007 |
| 227 | 2061766007 assembled_HiSeq_22354030 | 229 | 2061766007 |

TABLE 1-continued pVip genes

| SEQ ID No | IMG id | pVip # | Metagenome genome IMG ID |
|---|---|---|---|
| 228 | 3300000553 assembled TBL_comb47_HYPODRAFT_1000031312 | 230 | 3300000553 |
| 229 | 3300000558 assembled Draft_1000017819 | 231 | 3300000558 |
| 230 | 3300000558 assembled Draft_1020415419 | 232 | 3300000558 |
| 231 | 3300000568 assembled Draft_1000864417 | 233 | 3300000568 |
| 232 | 3300000970 assembled BBAY66_100003029 | 234 | 3300000970 |
| 233 | 3300001102 assembled BBAY67_1000022226 | 235 | 3300001102 |
| 234 | 3300001200 assembled BBAY65_1000011634 | 236 | 3300001200 |
| 235 | 3300001348 assembled JGI20154J14316_1000097623 | 237 | 3300001348 |
| 236 | 3300001450 assembled JGI24006J15134_1000007033 | 238 | 3300001450 |
| 237 | 3300001450 assembled JGI24006J15134_1000007151 | 239 | 3300001450 |
| 238 | 3300001598 assembled EMG_100002329 | 240 | 3300001598 |
| 239 | 3300001749 assembled JGI24025J20009_1000044120 | 241 | 3300001749 |
| 240 | 3300001750 assembled JGI24023J19991_100005742 | 242 | 3300001750 |
| 241 | 3300001835 assembled shallow_100084433 | 243 | 3300001835 |
| 242 | 3300002119 assembled JGI20170J26628_1000030318 | 244 | 3300002119 |
| 243 | 3300002165 assembled JGI24527J20359_100014812 | 245 | 3300002165 |
| 244 | 3300002180 assembled JGI24724J26744_1000065020 | 246 | 3300002180 |
| 245 | 3300002219 assembled SCADCLC_1000381914 | 247 | 3300002219 |
| 246 | 3300002219 assembled SCADCLC_1000709320 | 248 | 3300002219 |
| 247 | 3300002220 assembled MLSBCLC_100183129 | 249 | 3300002220 |
| 248 | 3300002220 assembled MLSBCLC_1002228019 | 250 | 3300002220 |
| 249 | 3300002462 assembled JGI24702J35022_1000091311 | 251 | 3300002462 |
| 250 | 3300002518 assembled JGI25134J35505_1000001183 | 252 | 3300002518 |
| 251 | 3300002835 assembled B570J40625_1000006467 | 253 | 3300002835 |
| 252 | 3300003765 assembled Ga0056911_100030025 | 254 | 3300003765 |
| 253 | 3300003767 assembled Ga0056908_1000061101 | 255 | 3300003767 |
| 254 | 3300004166 assembled Ga0066427_100005916 | 256 | 3300004166 |
| 255 | 3300004173 assembled Ga0066412_100001438 | 257 | 3300004173 |
| 256 | 3300004173 assembled Ga0066412_100011719 | 258 | 3300004173 |
| 257 | 3300004178 assembled Ga0066410_100009118 | 259 | 3300004178 |
| 258 | 3300004197 assembled Ga0066420_100001947 | 260 | 3300004197 |
| 259 | 3300004197 assembled Ga0066420_100010317 | 261 | 3300004197 |
| 260 | 3300004202 assembled Ga0066418_100009418 | 262 | 3300004202 |
| 261 | 3300004203 assembled Ga0066419_100000529 | 263 | 3300004203 |
| 262 | 3300004203 assembled Ga0066419_100003817 | 264 | 3300004203 |
| 263 | 3300004230 assembled Ga0066452_100000937 | 265 | 3300004230 |
| 264 | 3300004250 assembled Ga0066472_1000237 | 266 | 3300004250 |
| 265 | 3300004253 assembled Ga0066464_100004618 | 267 | 3300004253 |
| 266 | 3300004253 assembled Ga0066464_100006643 | 268 | 3300004253 |
| 267 | 3300004806 assembled Ga0007854_100000246 | 269 | 3300004806 |
| 268 | 3300005080 assembled Ga0069611_1000016445 | 270 | 3300005080 |
| 269 | 3300005124 assembled Ga0070424_1100226 | 271 | 3300005124 |
| 270 | 3300005125 assembled Ga0070411_1062712 | 272 | 3300005125 |
| 271 | 3300005144 assembled Ga0068711_100038117 | 273 | 3300005144 |
| 272 | 3300005286 assembled Ga0065721_1000460410 | 274 | 3300005286 |
| 273 | 3300005326 assembled Ga0074195_10008286 | 275 | 3300005326 |
| 274 | 3300005531 assembled Ga0070738_1000151042 | 276 | 3300005531 |
| 275 | 3300005588 assembled Ga0070728_1000021436 | 277 | 3300005588 |
| 276 | 3300005588 assembled Ga0070728_1000125023 | 278 | 3300005588 |
| 277 | 3300005589 assembled Ga0070729_10000081117 | 279 | 3300005589 |
| 278 | 3300005589 assembled Ga0070729_1000129613 | 280 | 3300005589 |
| 279 | 3300005609 assembled Ga0070724_1000012829 | 281 | 3300005609 |
| 280 | 3300005609 assembled Ga0070724_1000028613 | 282 | 3300005609 |
| 281 | 3300005609 assembled Ga0070724_1000048517 | 283 | 3300005609 |
| 282 | 3300005675 assembled Ga0074424_10021430 | 284 | 3300005675 |
| 283 | 3300005915 assembled Ga0075122_100007968 | 285 | 3300005915 |
| 284 | 3300005920 assembled Ga0070725_1000012429 | 286 | 3300005920 |
| 285 | 3300005920 assembled Ga0070725_1000027223 | 287 | 3300005920 |
| 286 | 3300005920 assembled Ga0070725_100003449 | 288 | 3300005920 |
| 287 | 3300005986 assembled Ga0075152_1000034111 | 289 | 3300005986 |
| 288 | 3300006056 assembled Ga0075163_1000220113 | 290 | 3300006056 |
| 289 | 3300006104 assembled Ga0007882_1000004313 | 291 | 3300006104 |
| 290 | 3300006104 assembled Ga0007882_1000014836 | 292 | 3300006104 |
| 291 | 3300006182 assembled Ga0075033_10000633 | 293 | 3300006182 |
| 292 | 3300006226 assembled Ga0099364_100017018 | 294 | 3300006226 |
| 293 | 3300006243 assembled Ga0099348_1001723 | 295 | 3300006243 |
| 294 | 3300006417 assembled Ga0069787_1004128015 | 296 | 3300006417 |
| 295 | 3300006417 assembled Ga0069787_1005605520 | 297 | 3300006417 |
| 296 | 3300006417 assembled Ga0069787_1005688918 | 298 | 3300006417 |
| 297 | 3300006417 assembled Ga0069787_1021696324 | 299 | 3300006417 |
| 298 | 3300006417 assembled Ga0069787_1113807921 | 300 | 3300006417 |
| 299 | 3300006736 assembled Ga0098033_1000001464 | 301 | 3300006736 |
| 300 | 3300006738 assembled Ga0098035_100006013 | 302 | 3300006738 |
| 301 | 3300006789 assembled Ga0098054_10000219 | 303 | 3300006789 |

TABLE 1-continued

| pVip genes | | | |
|---|---|---|---|
| SEQ ID No | IMG id | pVip # | Metagenome genome IMG ID |
| 302 | 3300006790 assembled Ga0098074_100033128 | 304 | 3300006790 |
| 303 | 3300006810 assembled Ga0070754_1000007993 | 305 | 3300006810 |
| 304 | 3300006879 assembled Ga0079226_100011884 | 306 | 3300006879 |
| 305 | 3300006927 assembled Ga0098034_100013824 | 307 | 3300006927 |
| 306 | 3300006929 assembled Ga0098036_100012625 | 308 | 3300006929 |
| 307 | 3300006987 assembled Ga0098063_100010810 | 309 | 3300006987 |
| 308 | 3300006988 assembled Ga0098064_10002211 | 310 | 3300006988 |
| 309 | 3300007344 assembled Ga0070745_100033022 | 311 | 3300007344 |
| 310 | 3300007346 assembled Ga0070753_100014333 | 312 | 3300007346 |
| 311 | 3300007462 assembled Ga0099934_110520 | 313 | 3300007462 |
| 312 | 3300007485 assembled Ga0099929_1008119 | 314 | 3300007485 |
| 313 | 3300007516 assembled Ga0105050_1000139429 | 315 | 3300007516 |
| 314 | 3300007640 assembled Ga0070751_1000004111 | 316 | 3300007640 |
| 315 | 3300007961 assembled Ga0079305_100003992 | 317 | 3300007961 |
| 316 | 3300007963 assembled Ga0110931_100009625 | 318 | 3300007963 |
| 317 | 3300008050 assembled Ga0098052_10001839 | 319 | 3300008050 |
| 318 | 3300008050 assembled Ga0098052_100026416 | 320 | 3300008050 |
| 319 | 3300008224 assembled Ga0105350_100000945 | 321 | 3300008224 |
| 320 | 3300009093 assembled Ga0105240_100005042 | 322 | 3300009093 |
| 321 | 3300009169 assembled Ga0105097_1000009945 | 323 | 3300009169 |
| 322 | 3300009175 assembled Ga0073936_1000120334 | 324 | 3300009175 |
| 323 | 3300009415 assembled Ga0115029_100184931 | 325 | 3300009415 |
| 324 | 3300009419 assembled Ga0114982_10001831 | 326 | 3300009419 |
| 325 | 3300009488 assembled Ga0114925_1000023517 | 327 | 3300009488 |
| 326 | 3300009488 assembled Ga0114925_100003506 | 328 | 3300009488 |
| 327 | 3300009508 assembled Ga0115567_1000068222 | 329 | 3300009508 |
| 328 | 3300009512 assembled Ga0115003_100022198 | 330 | 3300009512 |
| 329 | 3300009546 assembled Ga0099799_100233 | 331 | 3300009546 |
| 330 | 3300009669 assembled Ga0116148_10010742 | 332 | 3300009669 |
| 331 | 3300009779 assembled Ga0116152_100003906 | 333 | 3300009779 |
| 332 | 3300009788 assembled Ga0114923_1000042134 | 334 | 3300009788 |
| 333 | 3300009838 assembled Ga0116153_100010806 | 335 | 3300009838 |
| 334 | 3300010028 assembled Ga0134115_1006245 | 336 | 3300010028 |
| 335 | 3300010160 assembled Ga0114967_100001146 | 337 | 3300010160 |
| 336 | 3300010162 assembled Ga0131853_1000011621 | 338 | 3300010162 |
| 337 | 3300010162 assembled Ga0131853_1000234120 | 339 | 3300010162 |
| 338 | 3300010162 assembled Ga0131853_1000511220 | 340 | 3300010162 |
| 339 | 3300010270 assembled Ga0129306_100025163 | 341 | 3300010270 |
| 340 | 3300010313 assembled Ga0116211_100026028 | 342 | 3300010313 |
| 341 | 3300010373 assembled Ga0134128_1000050820 | 343 | 3300010373 |
| 342 | 3300010379 assembled Ga0136449_1000153745 | 344 | 3300010379 |
| 343 | 3300010396 assembled Ga0134126_1000011835 | 345 | 3300010396 |
| 344 | 3300010430 assembled Ga0118733_10000149451 | 346 | 3300010430 |
| 345 | 3300010430 assembled Ga0118733_10000158731 | 347 | 3300010430 |
| 346 | 3300010430 assembled Ga0118733_10000628422 | 348 | 3300010430 |
| 347 | 3300012103 assembled Ga0136578_1000209 | 349 | 3300012103 |
| 348 | 3300012533 assembled Ga0138256_1000042615 | 350 | 3300012533 |
| 349 | 3300012950 assembled Ga0163108_1000095519 | 351 | 3300012950 |
| 350 | 3300012979 assembled Ga0123348_1000024225 | 352 | 3300012979 |
| 351 | 3300012983 assembled Ga0123349_1000049625 | 353 | 3300012983 |
| 352 | 3300013088 assembled Ga0163200_1000002129 | 354 | 3300013088 |
| 353 | 3300013092 assembled Ga0163199_1000006211 | 355 | 3300013092 |
| 354 | 3300013131 assembled Ga0172373_100005744 | 356 | 3300013131 |
| 355 | 3300014491 assembled Ga0182014_100007864 | 357 | 3300014491 |
| 356 | 3300014499 assembled Ga0182012_100003757 | 358 | 3300014499 |
| 357 | 3300017795 assembled Ga0189288_1022816 | 359 | 3300017795 |
| 358 | 3300017798 assembled Ga0189289_1026116 | 360 | 3300017798 |
| 359 | 3300017805 assembled Ga0189287_100018226 | 361 | 3300017805 |
| 360 | 3300017990 assembled Ga0180436_1000345026 | 362 | 3300017990 |
| 361 | 3300018018 assembled Ga0187886_100041240 | 363 | 3300018018 |
| 362 | 3300018018 assembled Ga0187886_100069122 | 364 | 3300018018 |
| 363 | 3300018033 assembled Ga0187867_1000087624 | 365 | 3300018033 |
| 364 | 3300018038 assembled Ga0187855_1000057816 | 366 | 3300018038 |
| 365 | 3300018042 assembled Ga0187871_100009711 | 367 | 3300018042 |
| 366 | 3300018080 assembled Ga0180433_1001105911 | 368 | 3300018080 |
| 367 | 3300018428 assembled Ga0181568_1000115027 | 369 | 3300018428 |
| 368 | 3300018475 assembled Ga0187907_1000663212 | 370 | 3300018475 |
| 369 | 3300018475 assembled Ga0187907_100078053 | 371 | 3300018475 |
| 370 | 3300018475 assembled Ga0187907_1000859111 | 372 | 3300018475 |
| 371 | 3300018493 assembled Ga0187909_1000543313 | 373 | 3300018493 |
| 372 | 3300018494 assembled Ga0187911_1000586113 | 374 | 3300018494 |
| 373 | 3300018494 assembled Ga0187911_1001224520 | 375 | 3300018494 |
| 374 | 3300018495 assembled Ga0187908_1000576413 | 376 | 3300018495 |
| 375 | 3300018495 assembled Ga0187908_1000603814 | 377 | 3300018495 |
| 376 | 3300018495 assembled Ga0187908_100073603 | 378 | 3300018495 |

TABLE 1-continued pVip genes

| SEQ ID No | IMG id | pVip # | Metagenome genome IMG ID |
|---|---|---|---|
| 377 | 3300018878 assembled Ga0187910_1000693112 | 379 | 3300018878 |
| 378 | 3300018878 assembled Ga0187910_1000711113 | 380 | 3300018878 |
| 379 | 3300018878 assembled Ga0187910_100083003 | 381 | 3300018878 |
| 380 | 3300018878 assembled Ga0187910_1000906015 | 382 | 3300018878 |
| 381 | 3300019373 assembled Ga0187895_100043618 | 383 | 3300019373 |
| 382 | 3300019457 assembled Ga0193932_1007821 | 384 | 3300019457 |
| 383 | 3300019750 assembled Ga0194000_100000539 | 385 | 3300019750 |

TABLE 2 pVip-encoding Polynucleotides

| SEQ ID No | pVip number |
|---|---|
| 384 | 6 |
| 385 | 7 |
| 386 | 8 |
| 387 | 9 |
| 388 | 10 |
| 389 | 12 |
| 390 | 15 |
| 391 | 19 |
| 392 | 21 |
| 393 | 27 |
| 394 | 32 |
| 395 | 34 |
| 396 | 39 |
| 397 | 42 |
| 398 | 44 |
| 399 | 46 |
| 400 | 47 |
| 401 | 48 |
| 402 | 50 |
| 403 | 56 |
| 404 | 57 |
| 405 | 58 |
| 406 | 60 |
| 407 | 62 |
| 408 | 63 |

TABLE 3 pVip Proteins

| SEQ ID No | IMG id | pVip # | Clade | Metagenome genome IMG ID | Genome Metagenome Name | Kinase |
|---|---|---|---|---|---|---|
| 409 | 2624749465 | 6 | 1 | 2623620517 | Selenomonas ruminatium S137 | No |
| 410 | 2739066738 | 7 | 5 | 2738541339 | Fibrobacter sp. UWT3 | No |
| 411 | 2521798317 | 8 | 4 | 2521172648 | Psychrobacter lutiphocae DSM 21542 | No |
| 412 | 2574301464 | 9 | 7 | 2574179732 | Vibrio porteresiae DSM 19223 | Yes |
| 413 | 2720695169 | 10 | 7 | 2718218250 | Vibrio vulnificus ATL 6-1306 | Yes |
| 414 | 2698137626 | 12 | 6 | 2695420938 | Ruegeria intermedia DSM 29341 | No |
| 415 | 646713396 | 15 | 3 | 646564524 | Coralionargarita akajimensis DSM 45221 | No |
| 416 | 2506475787 | 19 | 2 | 2506381025 | Methanoplanus limicola M3, DSM 2279 | No |
| 417 | 2515428782 | 21 | 3 | 2515154070 | Lewinella persica DSM 23188 | No |
| 418 | 2574506394 | 27 | 6 | 2574179788 | Desulfovibrio senezii DSM 8436 | No |
| 419 | 2609132705 | 32 | 5 | 2608642208 | Phormidium sp. OSCR GFM (version 2) | Yes |
| 420 | 2619892213 | 34 | 3 | 2619618891 | Cryomorphaceae bacterium EBPR_Bin_135 | No |
| 421 | 2634960437 | 39 | 6 | 2634166261 | Burkholderiales-76 (UID4002) | No |
| 422 | 2639213731 | 42 | 2 | 2636416084 | Plankothricoides sp. SR001 | Yes |
| 423 | 2648875132 | 44 | 3 | 2648501185 | Chondromyces crocatus Cm c5 | No |
| 424 | 2649993803 | 46 | 7 | 2648501459 | Photobacterium swingsii CAIM 1393 | Yes |
| 425 | 2651203508 | 47 | 3 | 2648501771 | Flammeovirga pacifica WPAGA1 | No |
| 426 | 2651490945 | 48 | 7 | 2648501840 | Vibrio crassostreae J5-19 | No |
| 427 | 2661858798 | 50 | 2 | 2660238307 | Methanogenic archaeon ISO4-H5 | No |
| 428 | 2701115162 | 56 | 5 | 2700988679 | Fibrobacter sp. UWH6 | No |
| 429 | 2718503187 | 57 | 3 | 2718217692 | Flavobacterium lacus CGMCC 1.12504 | No |
| 430 | 2721736750 | 58 | 7 | 2718218507 | Pseudoalteromonas ulvae TC14 | No |
| 431 | 2733913669 | 60 | 3 | 2731957952 | Lacinutrix sp. JCM 13824 | No |
| 432 | 2743907592 | 62 | 5 | 2740892545 | Fibrobacteria bacterium GUT31 IN01_31 | No |
| 433 | 2744633848 | 63 | 6 | 2744054527 | Pseudoalteromonas sp. XI10 | Yes |
| 434 | 2695043264 | 1 | 3 | 2693429896 | Lutibacter oricola DSM 24956 | No |
| 435 | 2684459953 | 2 | 3 | 2681813561 | Chryseobacterium gambrini DSM 18014 | Yes |
| 436 | 2507146842 | 3 | 2 | 2506783068 | Methanofollis liminatans GKZPZ, DSM 4140 | No |
| 437 | 2632766730 | 11 | 7 | 2630968672 | Shewanella baltica OS678 | No |
| 438 | 2744654531 | 13 | 6 | 2744054531 | Marinobacter sp. YWL01 | No |
| 439 | 2654783232 | 14 | 6 | 2654587543 | Pseudomonas nitroreducens B | No |
| 440 | 2504625218 | 17 | 7 | 2504557017 | Marinomonas sp GOBB3-320 | No |
| 441 | 2506474236 | 18 | 2 | 2506381025 | Methanoplanus limicola M3, DSM 2279 | No |
| 442 | 2509664214 | 20 | 2 | 2509601008 | Methanomethylovorans hollandica DSM 15978 | No |
| 443 | 2518436022 | 22 | 3 | 2518285547 | Pelobacter carbinolicus Bd1, GraBd1 | No |
| 444 | 2522341593 | 23 | 5 | 2522125098 | Tolumonas lignilytica BRL6-1 | No |
| 445 | 2524269675 | 24 | 4 | 2524023156 | Conchiformibius kuhniae DSM 17694 | No |
| 446 | 2525334630 | 25 | 2 | 2524614668 | Methanocorpusculum bavaricum DSM 4179 | No |
| 447 | 2557036911 | 26 | 7 | 2556921023 | Pseudoalteromonas sp. H105 PacBio methylation | No |
| 448 | 2574517928 | 28 | 7 | 2574179790 | Endozoicomonas numazuensis DSM 25634 | No |
| 449 | 2582805913 | 29 | 3 | 2582580599 | Composite genome from Lake Mendota Epilimnion pan-assembly MEint.metabat.6813 | No |
| 450 | 2582946381 | 30 | 3 | 2582580664 | Composite genome from Trout Bog Hypolimnion pan-assembly TBhypo.metabat.2746 | No |
| 451 | 2596421479 | 31 | 3 | 2595698251 | Kibdelosporangium aridum DSM 43828 | No |
| 452 | 2618018523 | 33 | 6 | 2617270916 | Marinobacter zhejiangensis CGMCC 1.7061 | No |

TABLE 3-continued pVip Proteins

| SEQ ID No | IMG id | pVip # | Clade | Metagenome genome IMG ID | Genome Metagenome Name | Kinase |
|---|---|---|---|---|---|---|
| 453 | 2631333032 | 36 | 7 | 2630968323 | *Nitrincola* sp. A-D6 | No |
| 454 | 2632937107 | 37 | 7 | 2630968711 | *Shewanella* sp. cp20 | No |
| 455 | 2633985761 | 38 | 2 | 2630968972 | Methanococcoides methylutens DSM 2657 | Yes |
| 456 | 2635314107 | 40 | 3 | 2634166348 | Actinomadura echinospora DSM 43163 | No |
| 457 | 2637497700 | 41 | 7 | 2636415666 | Photobacterium leiognathi mandapamensis KNH6 | No |
| 458 | 2641427518 | 43 | 6 | 2639762959 | Actinobacteria bacterium OK074 | No |
| 459 | 2649163162 | 45 | 7 | 2648501251 | Moritella viscosa 06/09/139 | Yes |
| 460 | 2651588264 | 49 | 6 | 2648501863 | Aeromonas caviae CECT 4221 | No |
| 461 | 2665950188 | 51 | 6 | 2663763173 | Legionella santicrucis SC-63-C7 | No |
| 462 | 2674184607 | 52 | 6 | 2671180787 | Pseudomonas stutzeri C2 | No |
| 463 | 2684813341 | 53 | 6 | 2684622550 | Aquabacterium parvum B6 | No |
| 464 | 2693697599 | 54 | 7 | 2693429564 | Vibrio metoecus YB4D01 | No |
| 465 | 2694112273 | 55 | 4 | 2693429660 | Helicobacter bilis Missouri | No |
| 466 | 2728147792 | 59 | 6 | 2724679805 | Shimia sagamensis DSM 29734 | No |
| 467 | 2741341560 | 61 | 3 | 2740891962 | Marine group II.A Euryarchaeota archaeon SCGC AG-487_M08 (contamination screened) | No |
| 468 | 2741409035 | 64 | 2 | 2740891993 | Candidatus Heimdallarchaeota archaeon LC_3 | No |
| 469 | 2504129180 | 65 | 2 | 2503982047 | Anabaena cylindrica PCC7 122 | Yes |
| 470 | 637160692 | 66 | 1 | 637000327 | Treponema denticola ATCC 35405 | No |
| 471 | 637364324 | 67 | 7 | 637000336 | Vibrio vulnificus CMCP6 | Yes |
| 472 | 637468954 | 68 | 7 | 637000337 | Vibrio vulnificus YJ016 | Yes |
| 473 | 637586319 | 69 | 7 | 637000206 | Photobacterium profundum SS9 | Yes |
| 474 | 637752529 | 70 | 3 | 637000204 | Pelobacter carbinolicus Bd1, GraBd1 | No |
| 475 | 639797708 | 71 | 7 | 639633052 | Psychromonas ingrahamii 37 | No |
| 476 | 640805406 | 72 | 7 | 640753033 | *Marinomonas* sp. MWYL1 | No |
| 477 | 640830189 | 73 | 7 | 640753049 | Shewanella baltica OS185 | No |
| 478 | 641096015 | 74 | 4 | 640963011 | *Beggiatoa* sp. PS | No |
| 479 | 641147750 | 75 | 6 | 640963027 | Marinobacter algicola DG893 | No |
| 480 | 641288534 | 76 | 7 | 641228507 | Shewanella baltica OS195 | No |
| 481 | 643461066 | 77 | 7 | 643348574 | Shewanella baltica OS223 | No |
| 482 | 644369858 | 78 | 5 | 646311927 | Fibrobacter succinogenes S85 | No |
| 483 | 644619713 | 79 | 3 | 646311963 | Thermomonospora curvata DSM 43183 | No |
| 484 | 647622404 | 80 | 4 | 647533121 | *Campylobacterales* sp. GD 1 | No |
| 485 | 649804297 | 81 | 4 | 649633054 | Helicobacter felis CS1, ATCC 49179 | No |
| 486 | 650410387 | 82 | 6 | 650377991 | Marinobacter adhaerens HP15 | No |
| 487 | 650419199 | 83 | 5 | 650377942 | Fibrobacter succinogenes S85 | No |
| 488 | 650463340 | 84 | 7 | 650377984 | Vibrio furnissii 2510/74, NCTC 11218 | No |
| 489 | 650537321 | 85 | 1 | 650377925 | Coprococcus catus GD/7 | No |
| 490 | 650716002 | 86 | 6 | 650716002 | Acidiphilium multivorum AIU301 | No |
| 491 | 650921542 | 87 | 3 | 650716044 | *Lacinutrix* sp. 5H-3-7-4 | No |
| 492 | 2501733929 | 88 | 7 | 2501651210 | Photobacterium profundum 3TCK | Yes |
| 493 | 2502233141 | 89 | 2 | 2502171154 | Thermoplasmatales archaeon BRNA1 | No |
| 494 | 2509552219 | 90 | 1 | 2509276055 | Treponema saccharophilum PB, DSM 2985 | No |
| 495 | 2512440669 | 91 | 4 | 2512047059 | Haemophilus haemolyticus M21621 | No |
| 496 | 2519473577 | 92 | 2 | 2519103099 | Methanolobus psychrophilus R15 | No |
| 497 | 2519473579 | 93 | 2 | 2519103099 | Methanolobus psychrophilus R15 | No |
| 498 | 2519484486 | 94 | 1 | 2519103103 | Brachyspira pilosicoli B2904 | No |
| 499 | 2519815572 | 95 | 6 | 2519103180 | Curvibacter lanceolatus ATCC 14669 | No |

TABLE 3-continued pVip Proteins

| SEQ ID No | IMG id | pVip # | Clade | Metagenome genome IMG ID | Genome Metagenome Name | Kinase |
|---|---|---|---|---|---|---|
| 500 | 2521802859 | 96 | 6 | 2521172649 | Rheinheimera perlucida DSM 18276 | No |
| 501 | 2522303848 | 97 | 1 | 2522125086 | Succinimonas amylolytica DSM 2873 | No |
| 502 | 2524107537 | 98 | 7 | 2524023060 | Ferrimonas kyonanensis DSM 18153 | No |
| 503 | 2525610838 | 99 | 6 | 2524614740 | Pseudomonas stutzeri MF28 | No |
| 504 | 2525930338 | 100 | 5 | 2524614816 | Halodesulfovibrio aestuarii DSM 10141 | No |
| 505 | 2528325157 | 101 | 6 | 2528311002 | Comamonas testosteroni ZNC0007 | No |
| 506 | 2531202617 | 102 | 4 | 2529293096 | Sulfurimonas gotlandica GD1 | No |
| 507 | 2532381218 | 103 | 1 | 2531839141 | Kingella kingae PYKK081 | No |
| 508 | 2532646932 | 104 | 6 | 2531839206 | Thauera sp. 63 | No |
| 509 | 2538932271 | 105 | 1 | 2537561856 | Brachyspira hampsonii 30446 | No |
| 510 | 2540642849 | 106 | 2 | 2540341105 | Methanoculleus bourgensis MS2 | No |
| 511 | 2540668036 | 107 | 2 | 2540341115 | Candidatus Methanomethylophilus alvus Mx1201 | No |
| 512 | 2540825991 | 108 | 3 | 2540341170 | Pseudodesulfovibrio piezophilus C1TLV30 | No |
| 513 | 2541039228 | 109 | 1 | 2540341248 | Ruminococcus flavefaciens AE3010 | No |
| 514 | 2541315631 | 110 | 1 | 2541046975 | Treponema medium ATCC 700293 | No |
| 515 | 2546450678 | 111 | 6 | 2545824694 | Marinobacter santoriniensis NKSG1 | Yes |
| 516 | 2546738312 | 112 | 7 | 2545824767 | Bacteriovorax sp. DB6_IX | No |
| 517 | 2547718745 | 113 | 4 | 2547132187 | Acinetobacter sp. MDS7A | No |
| 518 | 2551476655 | 114 | 7 | 2551306039 | Vibrio harveyi ZJ0603 | No |
| 519 | 2551491916 | 115 | 7 | 2551306042 | Vibrio genomosp. F10 ZF-129 | No |
| 520 | 2551562099 | 116 | 7 | 2551306058 | Vibrio splendidus 12E03 | No |
| 521 | 2551596444 | 117 | 7 | 2551306067 | Vibrio rumoiensis 1S-45 | No |
| 522 | 2553401559 | 118 | 7 | 2551306520 | Aliivibrio logei ATCC 35077 | No |
| 523 | 2553886541 | 119 | 7 | 2551306646 | Vibrio harveyi AOD131 | No |
| 524 | 2558097217 | 120 | 4 | 2556921621 | Acinetobacter towneri DSM 14962 | No |
| 525 | 2559286049 | 121 | 1 | 2558860239 | Spiroplasma culicicola AES-1 | No |
| 526 | 2559416375 | 122 | 1 | 2558860277 | Treponema primitia ZAS-1 | No |
| 527 | 2562001279 | 123 | 7 | 2561511079 | Selenomonas sp. FC4001 | No |
| 528 | 2563081558 | 124 | 3 | 2562617115 | Myxococcus hansupus DSM 436 | No |
| 529 | 2563230595 | 125 | 4 | 2562617155 | Helicobacter bilis ATCC 43879 | No |
| 530 | 2565569616 | 126 | 7 | 2563367142 | Vibrio halioticoli NBRC 102217 | No |
| 531 | 2565702223 | 127 | 4 | 2563367170 | Helicobacter bilis WiWa | No |
| 532 | 2566542256 | 128 | 4 | 2565956643 | Acinetobacter parvus NIPH 1103 | No |
| 533 | 2566736970 | 129 | 4 | 2565956698 | Acinetobacter towneri DSM 14962 | No |
| 534 | 2569938648 | 130 | 7 | 2568526421 | Vibrio parahaemolyticus TUMSAT_H10_S6 | Yes |
| 535 | 2574423613 | 131 | 3 | 2574179766 | Thiomonas sp. FB-Cd, DSM 25617 | No |
| 536 | 2574578667 | 132 | 5 | 2574179802 | Sulfitobacter mediterraneus KCTC 32188 | No |
| 537 | 2577744326 | 133 | 7 | 2576861245 | Pseudoalteromonas haloplanktis VIP4-0444 | Yes |
| 538 | 2577718495 | 134 | 7 | 2576861258 | Pseudoalteromonas haloplanktis TB25 | No |
| 539 | 2580440517 | 135 | 7 | 2579778656 | Pseudoalteromonas haloplanktis AC163 | No |
| 540 | 2581032418 | 136 | 7 | 2579778800 | Vibrio metoecus PPCK-2014 | Yes |
| 541 | 2581542389 | 137 | 7 | 2579778918 | Vibrio harveyi E385 | No |
| 542 | 2582293224 | 138 | 7 | 2579779100 | Vibrio parahaemolyticus VIP4-0430 | Yes |
| 543 | 2582959978 | 139 | 3 | 2582580668 | Composite genome from Trout Bog Hypolimnion pan-assembly TBhypo.metabat.3004 | No |
| 544 | 2583671671 | 140 | 7 | 2582580861 | Pseudoalteromonas sp. TAE56 | No |
| 545 | 2584203718 | 141 | 7 | 2582580995 | Vibrio parahaemolyticus TUMSAT_DE2_S2 | Yes |
| 546 | 2585240392 | 142 | 6 | 2582581301 | Janthinobacterium sp. RA13 | No |

TABLE 3-continued

| | | | | pVip Proteins | | |
|---|---|---|---|---|---|---|
| SEQ ID No | IMG id | pVip # | Clade | Metagenome genome IMG ID | Genome Metagenome Name | Kinase |
| 547 | 2587265930 | 143 | 7 | 2585427937 | *Pseudoalteromonas* sp. 520P1 | No |
| 548 | 2589217693 | 144 | 3 | 2588253911 | *Chondromyces apiculatus* DSM 436 | No |
| 549 | 2597063350 | 145 | 5 | 2596583606 | *Fibrobacter succinogenes elongatus* HM2 | No |
| 550 | 2600497862 | 146 | 6 | 2600254970 | *Pseudomonas* sp. 1-7 | No |
| 551 | 2600833866 | 147 | 7 | 2600255071 | *Vibrio ezurae* NBRC 102218 | No |
| 552 | 2609594859 | 148 | 6 | 2609459643 | *Janthinobacterium* sp. OK676 | No |
| 553 | 2609930410 | 149 | 6 | 2609459764 | *Marinobacter* sp. ES.048 | No |
| 554 | 2611345001 | 150 | 3 | 2609460080 | *Hyalangium minutum* DSM 14724 | No |
| 555 | 2611749855 | 151 | 6 | 2609460164 | *Acidithiobacillus thiooxidans* Licanantay | No |
| 556 | 2612132826 | 152 | 6 | 2609460245 | *Delftia tsuruhatensis* 391 | No |
| 557 | 2617465221 | 153 | 6 | 2617270765 | *Marinobacter mobilis* CGMCC 1.7059 | No |
| 558 | 2617538802 | 154 | 3 | 2617270789 | *Flavobacterium omnivorum* CGMCC 1.2747 | No |
| 559 | 2619647987 | 155 | 7 | 2619618818 | *Pseudidiomarina donghaiensis* CGMCC 1.7284 | Yes |
| 560 | 2619760352 | 156 | 6 | 2619618853 | *Betaproteobacteria* sp. genome_bin_13 | No |
| 561 | 2620549291 | 157 | 3 | 2619619052 | Unclassified Chloroflexi bacterium bin152 | Yes |
| 562 | 2621169600 | 158 | 7 | 2619619266 | *Photobacterium phosphoreum* ANT220 | No |
| 563 | 2623278845 | 159 | 6 | 2622736530 | *Roseovarius lutimaris* DSM 28463 | No |
| 564 | 2632746825 | 160 | 3 | 2630968667 | *Nonlabens ulvanivorans* JCM 19297 | No |
| 565 | 2642232622 | 161 | 6 | 2639763156 | *Aeromonas sobria* CECT 4245 | No |
| 566 | 2644760915 | 162 | 3 | 2643221740 | *Chryseobacterium* sp. Leaf201 | Yes |
| 567 | 2645912334 | 163 | 7 | 2645727543 | *Aeromonas tecta* CECT 7082 | No |
| 568 | 2647434260 | 164 | 6 | 2645727892 | *Comamonas testosteroni* KF712 | No |
| 569 | 2649993012 | 165 | 7 | 2648501459 | *Photobacterium swingsii* CAIM 1393 | No |
| 570 | 2651793160 | 166 | 6 | 2648501913 | *Pseudomonas nitroreducens* DPB | No |
| 571 | 2652273697 | 167 | 6 | 2651869653 | *Rubrivivax* sp. AAP121 | No |
| 572 | 2654809173 | 168 | 6 | 2654487547 | *Achromobacter spanius* CGMCC9173 | No |
| 573 | 2658359168 | 169 | 2 | 2657245169 | *Methanoculleus* sp. EBM-46 | No |
| 574 | 2667505054 | 170 | 6 | 2663763602 | *Pseudomonas hussainii* JCM 19513 | No |
| 575 | 2667963948 | 171 | 3 | 2667527390 | *Fabibacter pacificus* CGMCC 1.12402 | Yes |
| 576 | 2668144532 | 172 | 6 | 2667527434 | *Pseudomonas oryzae* KCTC 32247 | Yes |
| 577 | 2668847476 | 173 | 7 | 2667527626 | *Vibrio parahaemolyticus* S164 | Yes |
| 578 | 2672407511 | 174 | 7 | 2671180348 | *Vibrio tritonius* AM2 | Yes |
| 579 | 2674782375 | 175 | 7 | 2671180928 | *Vibrio parahaemolyticus* CFSAN007447 | Yes |
| 580 | 2677278474 | 176 | 2 | 2675903261 | *Anabaena* sp. 4-3 | No |
| 581 | 2682065255 | 177 | 6 | 2681812894 | *Sphaerotilus natans* ATCC 13338 | No |
| 582 | 2684092807 | 178 | 2 | 2681813425 | *Methanoculleus* sp. MAB1 | No |
| 583 | 2688794699 | 179 | 6 | 2687453440 | *Aeromonas veronii* TH0426 | No |
| 584 | 2693209812 | 180 | 7 | 2690316327 | *Vibrio parahaemolyticus* S165 | Yes |
| 585 | 2694949528 | 181 | 3 | 2693429874 | *Olleya namhaensis* DSM 28881 | No |
| 586 | 2700499480 | 182 | sp | 2698536835 | Microgenomates bacterium JGI CrystG Apr02-3-G15 (contamination screened) | No |
| 587 | 2701140257 | 183 | 5 | 2700988686 | *Fibrobacter* sp. UWH9 | No |
| 588 | 2701911183 | 184 | 7 | 2700989248 | *Vibrio parahaemolyticus* CFSAN007448 | Yes |
| 589 | 2705695255 | 185 | 5 | 2703719122 | unclassified Deltaproteobacteria bin 1 | No |
| 590 | 2706043000 | 186 | 5 | 2703719236 | *Fibrobacter* sp. UWB7 | No |
| 591 | 2712662546 | 187 | 6 | 2711768198 | *Arsukibacterium ikkense* GCM72 | No |
| 592 | 2714077658 | 188 | 7 | 2713896747 | *Vibrio alginolyticus* V2 | No |
| 593 | 2719376594 | 189 | 7 | 2718217925 | *Alteromonas* sp. Mex14 | No |
| 594 | 2719498267 | 190 | 6 | 2718217953 | *Marinobacter salinus* Hb8 | No |

TABLE 3-continued pVip Proteins

| SEQ ID No | IMG id | pVip # | Clade | Metagenome genome IMG ID | Genome Metagenome Name | Kinase |
|---|---|---|---|---|---|---|
| 595 | 2719828580 | 191 | 3 | 2718218033 | Lutibacter sp. LPB0138 | No |
| 596 | 2722236530 | 192 | 6 | 2721755284 | Gammaproteobacteria bacterium GWF2_41_13 | No |
| 597 | 2727845415 | 193 | 3 | 2724679709 | Saccharicrinis carchari DSM 27040 | No |
| 598 | 2728971251 | 194 | 7 | 2728369061 | Aliivibrio wodanis CL7 | No |
| 599 | 2729066335 | 195 | 6 | 2728369080 | Dechloromonas denitrificans ATCC BAA-841 | No |
| 600 | 2730169305 | 196 | 3 | 2728369366 | Tenacibaculum sp. LPB0136 | No |
| 601 | 2731232863 | 197 | 7 | 2728369654 | Vibrio sp. JCM 19061 | Yes |
| 602 | 2735939253 | 198 | 5 | 2734482289 | Sulfitobacter mediterraneus DSM 12244 | No |
| 603 | 2740266671 | 199 | 5 | 2739367982 | Oceanospirillales bacterium JGI 01_G13_750m (contamination screened) | No |
| 604 | 2741408272 | 200 | 2 | 2740891993 | Candidatus Heimdallarchaeota archaeon LC_3 | No |
| 605 | 2742412079 | 201 | 6 | 2740892189 | Marinobacter sp. EN3 | No |
| 606 | 2742415354 | 202 | 4 | 2740892190 | Acinetobacter sp. COS3 | No |
| 607 | 2743908240 | 203 | 5 | 2740892545 | Fibrobacteria bacterium GUT31 IN01_31 | Yes |
| 608 | 2751139676 | 204 | 6 | 2747843223 | Janthinobacterium sp. 64 | No |
| 609 | 2752652723 | 205 | 2 | 2751185612 | Bacteroidales bacterium Bact_07 | No |
| 610 | 2753090639 | 206 | 7 | 2751185737 | Salinivibrio sp. DV | No |
| 611 | 2753093587 | 207 | 7 | 2751185738 | Salinivibrio sp. BNH | No |
| 612 | 2753363234 | 208 | 7 | 2751185801 | Aliivibrio sp. 1S128 | Yes |
| 613 | 2753367132 | 209 | 7 | 2751185802 | Aliivibrio sp. 1S165 | No |
| 614 | 2753371117 | 210 | 7 | 2751185803 | Aliivibrio sp. 1S175 | No |
| 615 | 2753755176 | 211 | 4 | 2751185895 | Haemophilus quentini MP1 | No |
| 616 | 2758508848 | 212 | 6 | 2757320913 | Diaphorobacter polyhydroxybutyrativorans SL-205 | No |
| 617 | 2758538137 | 213 | 3 | 2757320982 | Winogradskyella sp. PC-19 | No |
| 618 | 2758668677 | 214 | 2 | 2758568024 | Thermococcus siculi RG-20 | No |
| 619 | 2766104288 | 215 | 4 | 2765235962 | Neisseria sp. 10023 | No |
| 620 | 2770832229 | 216 | 3 | 2767802753 | Cystobacter ferrugineus Cbfe23 | No |
| 621 | 2558444101 | 217 | sp | 2558309039 | Megasphaera elsdenii T81 | Yes |
| 622 | 2620552401 | 218 | 3 | 2619619052 | Unclassified Chloroflexi bacterium bin152 | No |
| 623 | 2620555354 | 219 | 3 | 2619619052 | Unclassified Chloroflexi bacterium bin152 | No |
| 624 | 2671326339 | 220 | sp | 2671180039 | Streptomyces rubidus CGMCC 4.2026 | No |
| 625 | 2722096198 | 221 | sp | 2721755233 | Nitrospirae bacterium GWD2_57_9 | No |
| 626 | 2725246328 | 222 | 7 | 2724679053 | Photobacterium kishitanii 201212X | No |
| 627 | 2049941002_assembled_LHMISPF_00252280 | 223 | 3 | 2049941002 | Sinkhole freshwater microbial communities from Lake Huron, US, Sample 419 (*) (MER-FS) (assembled) | Yes |
| 628 | 2061766007_assembled_HiSeq_03538890 | 224 | 2 | 2061766007 | Bovine rumen microbial communities fromthe University of Illinois at Urbana-Champaign, USA, that are switchgrass associated - Sample 470 (*) (MER-FS) (assembled) | No |
| 629 | 2061766007_assembled_HiSeq_08062520 | 225 | 5 | 2061766007 | Bovine rumen microbial communities fromthe University of Illinois at Urbana-Champaign, USA, that are switchgrass associated - Sample 470 (*) (MER-FS) (assembled) | No |
| 630 | 2061766007_assembled_HiSeq_12004210 | 226 | 2 | 2061766007 | Bovine rumen microbial communities fromthe University of Illinois at Urbana-Champaign, USA, that are switchgrass associated - Sample 470 (*) (MER-FS) (assembled) | No |
| 631 | 2061766007_assembled_HiSeq_13805260 | 227 | 1 | 2061766007 | Bovine rumen microbial communities fromthe University of Illinois at Urbana-Champaign, USA, that are switchgrass associated - Sample 470 (*) (MER-FS) | Yes |

TABLE 3-continued

| | | | | Metagenome | | |
|---|---|---|---|---|---|---|
| | | | | | pVip Proteins | |
| SEQ ID No | IMG id | pVip # | Clade | genome IMG ID | Genome Metagenome Name | Kinase |
| 632 | 2061766007 assembled_HiSeq_17035850 | 228 | 5 | 2061766007 | Bovine rumen microbial communities fromthe University of Illinois at Urbana-Champaign, USA, that are switchgrass associated - Sample 470 (*) (MER-FS) (assembled) | |
| 633 | 2061766007 assembled_HiSeq_22354030 | 229 | 1 | 2061766007 | Bovine rumen microbial communities fromthe University of Illinois at Urbana-Champaign, USA, that are switchgrass associated - Sample 470 (*) (MER-FS) (assembled) | |
| 634 | 3300000553 assembled TBL_comb47_HYPODRAFT_1000031312 | 230 | 1 | 3300000553 | Trout Bog Lake May 28, 2007 Hypolimnion (Trout Bog Lake Combined Assembly 47 Hypolimnion Samples, August 2012 Assem) (*) (MER-FS) (assembled) | |
| 635 | 3300000558 assembled Draft_1000017819 | 231 | 6 | 3300000558 | Wastewater microbial communities from Syncrude, Ft. McMurray, Alberta - West In Pit SyncrudeMLSB2011 (*) (MER-FS) (assembled) | |
| 636 | 3300000558 assembled Draft_1020415419 | 232 | 2 | 3300000558 | Wastewater microbial communities from Syncrude, Ft. McMurray, Alberta - West In Pit SyncrudeMLSB2011 (*) (MER-FS) (assembled) | |
| 637 | 3300000568 assembled Draft_1000864417 | 233 | 2 | 3300000568 | Tailings pond microbial communities from Northern Alberta -Short chain hydrocarbon degrading methanogenic enrichment culture SCADC: (*) (MER-FS) (assembled) | |
| 638 | 3300000970 assembled BBAY66_100003029 | 234 | 3 | 3300000970 | Macroalgal surface ecosystem from Botany Bay, Sydney, Australia - BBAY66 (*) (MER-FS) (assembled) | |
| 639 | 3300001102 assembled BBAY67_1000022226 | 235 | 3 | 3300001102 | Macroalgal surface ecosystem from Botany Bay, Sydney, Australia - BBAY67 (*) (MER-FS) (assembled) | |
| 640 | 3300001200 assembled BBAY65_1000011634 | 236 | 3 | 3300001200 | Macroalgal surface ecosystem from Botany Bay, Sydney, Australia - BBAY65 (*) (MER-FS) (assembled) | |
| 641 | 3300001348 assembled JGI20154J14316_1000097623 | 237 | 2 | 3300001348 | Pelagic Microbial community sample from North Sea - COGITO 998_met_04 (*) (MER-FS) (assembled) | |
| 642 | 3300001450 assembled JGI24006J15134_1000007033 | 238 | 6 | 3300001450 | Marine viral communities from the Pacific Ocean - LP-53 (*) (MER-FS) (assembled) | |
| 643 | 3300001450 assembled JGI24006J15134_1000007151 | 239 | 6 | 3300001450 | Marine viral communities from the Pacific Ocean - LP-53 (*) (MER-FS) (assembled) | |
| 644 | 3300001598 assembled EMG_100002329 | 240 | sp | 3300001598 | Elephant fecal microbiome from Asian Elephant in Hamburg Zoo, Germany (*) (MER-FS) (assembled) | |
| 645 | 3300001749 assembled JGI24025J20009_1000044120 | 241 | 7 | 3300001749 | Oil polluted marine microbial communities from Coal Oil Point, Santa Barbara, California, USA - Sample 3 (*) (MER-FS) (assembled) | |
| 646 | 3300001750 assembled JGI24023J19991_100005742 | 242 | 3 | 3300001750 | Oil polluted marine microbial communities from Coal Oil Point, Santa Barbara, California, USA - Sample 1 (*) (MER-FS) (assembled) | |
| 647 | 3300001835 assembled shallow_10000084433 | 243 | 7 | 3300001835 | Hydrothermal vent plume microbial communities from the Mid Cayman Rise - Shallow Sites - gte4kb (*) (MER-FS) (assembled) | |
| 648 | 3300002119 assembled JGI20170J26628_1000030318 | 244 | 1 | 3300002119 | Nasutitermes corniger P3 segment microbial communities from Max Planck Institute, Germany - Nc150P3 (*) (MER-FS) (assembled) | |
| 649 | 3300002165 assembled JGI24527J20359_100014812 | 245 | 7 | 3300002165 | Marine viral communities from the Subarctic Pacific Ocean - LP-52 (*) (MER-FS) (assembled) | |
| 650 | 3300002180 assembled JGI24724J26744_1000065020 | 246 | 3 | 3300002180 | Oil polluted marine microbial communities from Coal Oil Point, Santa Barbara, California, USA - Sample 7 (*) (MER-FS) (assembled) | |
| 651 | 3300002219 assembled SCADCLC_1000381914 | 247 | 6 | 3300002219 | Tailings pond microbial communities from Northern Alberta -Short chain hydrocarbon degrading methanogenic enrichment culture SCADC: (*) (MER-FS) (assembled) | |
| 652 | 3300002219 assembled SCADCLC_1000709320 | 248 | 2 | 3300002219 | Tailings pond microbial communities from Northern Alberta -Short chain hydrocarbon degrading methanogenic enrichment culture SCADC: (*) (MER-FS) (assembled) | |

TABLE 3-continued pVip Proteins

| SEQ ID No | IMG id | pVip # | Clade | Metagenome genome IMG ID | Genome Metagenome Name | Kinase |
|---|---|---|---|---|---|---|
| 653 | 3300002220_assembled_MLSBC1C_100183129 | 249 | 6 | 3300002220 | Wastewater microbial communities from Syncrude, Ft. McMurray, Alberta - West In Pit SyncrudeMLSB2011 (*) (MER-FS) (assembled) | |
| 654 | 3300002220_assembled_MLSBC1C_1002228019 | 250 | 2 | 3300002220 | Wastewater microbial communities from Syncrude, Ft. McMurray, Alberta - West In Pit SyncrudeMLSB2011 (*) (MER-FS) (assembled) | |
| 655 | 3300002462_assembled_JGI24702135022_1000091311 | 251 | 2 | 3300002462 | Termite gut P4 segment microbial communities from Max Planck Institute, Germany - Th196 (*) (MER-FS) (assembled) | |
| 656 | 3300002518_assembled_JGI25134135505_1000001183 | 252 | 6 | 3300002518 | Marine viral communities from the Pacific Ocean - ETNP_6_100 (*) (MER-FS) (assembled) | |
| 657 | 3300002835_assembled_B570140625_1000006467 | 253 | 3 | 3300002835 | Freshwater microbial communities from Lake Mendota, WI - (Lake Mendota Combined Ray assembly, ASSEMBLY_DATE = 2014 Jun. 5) (*) (MER-FS) (assembled) | |
| 658 | 3300003765_assembled_Ga0056911_100030025 | 254 | 3 | 3300003765 | Wastewater treatment Type I Accumulibacter community from EBPR Bioreactor in Madison, WI, USA - Reactor 2_May 13, 2013_DNA (*) (MER-FS) (assembled) | |
| 659 | 3300003767_assembled_Ga0056908_1000061101 | 255 | 3 | 3300003767 | Wastewater treatment Type I Accumulibacter community from EBPR Bioreactor in Madison, WI, USA - Reactor I_Oct. 4, 2010_DNA (*) (MER-FS) (assembled) | |
| 660 | 3300004166_assembled_Ga0066427_100005916 | 256 | 3 | 3300004166 | Freshwater sediment methanotrophic microbial communities from Lake Washington under simulated oxygen tension - Sediment Metagenome 39_LOW7 (*) (MER-FS) (assembled) | |
| 661 | 3300004173_assembled_Ga0066412_100001438 | 257 | 3 | 3300004173 | Freshwater sediment methanotrophic microbial communities from Lake Washington under simulated oxygen tension - Sediment Metagenome 16_LOW5 (*) (MER-FS) (assembled) | |
| 662 | 3300004173_assembled_Ga0066412_100011719 | 258 | 3 | 3300004173 | Freshwater sediment methanotrophic microbial communities from Lake Washington under simulated oxygen tension - Sediment Metagenome 16_LOW5 (*) (MER-FS) (assembled) | |
| 663 | 3300004178_assembled_Ga0066410_100009118 | 259 | 3 | 3300004178 | Freshwater sediment methanotrophic microbial communities from Lake Washington under simulated oxygen tension - Sediment Metagenome 14_LOW5 (*) (MER-FS) (assembled) | |
| 664 | 3300004197_assembled_Ga0066420_100001947 | 260 | 3 | 3300004197 | Freshwater sediment methanotrophic microbial communities from Lake Washington under simulated oxygen tension - Sediment Metagenome 28_LOW6 (*) (MER-FS) (assembled) | |
| 665 | 3300004197_assembled_Ga0066420_100010317 | 261 | 3 | 3300004197 | Freshwater sediment methanotrophic microbial communities from Lake Washington under simulated oxygen tension - Sediment Metagenome 28_LOW6 (*) (MER-FS) (assembled) | |
| 666 | 3300004202_assembled_Ga0066418_100009418 | 262 | 3 | 3300004202 | Freshwater sediment methanotrophic microbial communities from Lake Washington under simulated oxygen tension - Sediment Metagenome 26_LOW6 (*) (MER-FS) (assembled) | |
| 667 | 3300004203_assembled_Ga0066419_100000529 | 263 | 3 | 3300004203 | Freshwater sediment methanotrophic microbial communities from Lake Washington under simulated oxygen tension - Sediment Metagenome 27_LOW6 (*) (MER-FS) (assembled) | |
| 668 | 3300004203_assembled_Ga0066419_100003817 | 264 | 3 | 3300004203 | Freshwater sediment methanotrophic microbial communities from Lake Washington under simulated oxygen tension - Sediment Metagenome 27_LOW6 (*) (MER-FS) (assembled) | |
| 669 | 3300004230_assembled_Ga0066452_100000937 | 265 | 6 | 3300004230 | Freshwater sediment methanotrophic microbial communities from Lake Washington under simulated oxygen tension - Sediment Metagenome 76_LOW10 (*) (MER-FS) (assembled) | |
| 670 | 3300004250_assembled_Ga0066472_1000237 | 266 | 6 | 3300004250 | Freshwater sediment methanotrophic microbial communities from Lake Washington under simulated oxygen tension - Sediment Metagenome 106_HOW12 (*) (MER-FS) (assembled) | |

TABLE 3-continued

| SEQ ID No | IMG id | Metagenome genome IMG ID | Clade | pVip # | Genome Metagenome Name | Kinase |
|---|---|---|---|---|---|---|
| 671 | 3300004253 assembled Ga0066464_100004618 | 3300004253 | 6 | 267 | Freshwater sediment methanotrophic microbial communities from Lake Washington under simulated oxygen tension - Sediment Metagenome 94_HOW11 (*) (MER-FS) (assembled) | |
| 672 | 3300004253 assembled Ga0066464_100006643 | 3300004253 | 6 | 268 | Freshwater sediment methanotrophic microbial communities from Lake Washington under simulated oxygen tension - Sediment Metagenome 94_HOW11 (*) (MER-FS) (assembled) | |
| 673 | 3300004806 assembled Ga0007854_100000246 | 3300004806 | 3 | 269 | Freshwater microbial communities from Crystal Bog, Wisconsin, USA - CBH12 Aug. 2008 (*) (MER-FS) (assembled) | |
| 674 | 3300005080 assembled Ga0069611_1000016445 | 3300005080 | 3 | 270 | Combined Assembly of Gp0111534, Gp0111535, Gp0111536, Gp0111537, Gp0111539, Gp0111540, Gp0111541, Gp0111542, Gp0111543 (*) (MER-FS) (assembled) | |
| 675 | 3300005124 assembled Ga0070424_1100226 | 3300005124 | 3 | 271 | Active sludge cell enrichment microbial communities from Klosterneuburg, Austria - Nitrospira DOME DR08B08 (*) (MER-FS) (assembled) | |
| 676 | 3300005125 assembled Ga0070411_1062712 | 3300005125 | 3 | 272 | Active sludge cell enrichment microbial communities from Klosterneuburg, Austria - Nitrosomonas DOME CR02B12 (*) (MER-FS) (assembled) | |
| 677 | 3300005144 assembled Ga0068711_100038117 | 3300005144 | 2 | 273 | Enrichment culture microbial communities from Arthur Kill intertidal strait, New Jersey, USA, that are MTBE-degrading - MTBE-AKM (Arthur Kill Methanogenic) MetaG (*) (MER-FS) (assembled) | |
| 678 | 3300005286 assembled Ga0065721_1000460410 | 3300005286 | 6 | 274 | Mesophilic microbial community from rice straw/compost enrichment Sample: eDNA_1 (*) (MER-FS) (assembled) | |
| 679 | 3300005326 assembled Ga0074195_10008286 | 3300005326 | 2 | 275 | Bioremediated contaminated groundwater from EPA Superfund site, New Mexico - Sample HSF6-23 (*) (MER-FS) (assembled) | |
| 680 | 3300005531 assembled Ga0070738_1000151042 | 3300005531 | 3 | 276 | Surface soil microbial communities from Centralia Pennsylvania, which are recovering from an underground coalmine fire - Coalmine Soil_Cen12_06102014_R2 (*) (MER-FS) (assembled) | |
| 681 | 3300005588 assembled Ga0070728_1000021436 | 3300005588 | 3 | 277 | Marine sediment microbial communities from the Atlantic coast under amendment with organic carbon and nitrate - tdDd47.1 (*) (MER-FS) (assembled) | |
| 682 | 3300005588 assembled Ga0070728_1000125023 | 3300005588 | 3 | 278 | Marine sediment microbial communities from the Atlantic coast under amendment with organic carbon and nitrate - tdDd47.1 (*) (MER-FS) (assembled) | |
| 683 | 3300005589 assembled Ga0070729_1000081117 | 3300005589 | 3 | 279 | Marine sediment microbial communities from the Atlantic coast under amendment with organic carbon and nitrate - tdDd47.2 (*) (MER-FS) (assembled) | |
| 684 | 3300005589 assembled Ga0070729_1000129613 | 3300005589 | 3 | 280 | Marine sediment microbial communities from the Atlantic coast under amendment with organic carbon and nitrate - tdDd47.2 (*) (MER-FS) (assembled) | |
| 685 | 3300005609 assembled Ga0070724_1000012829 | 3300005609 | 7 | 281 | Marine sediment microbial communities from the Atlantic coast under amendment with organic carbon and nitrate - tdDd00.1 (*) (MER-FS) (assembled) | |
| 686 | 3300005609 assembled Ga0070724_1000028613 | 3300005609 | 3 | 282 | Marine sediment microbial communities from the Atlantic coast under amendment with organic carbon and nitrate - tdDd00.1 (*) (MER-FS) (assembled) | |
| 687 | 3300005609 assembled Ga0070724_1000048517 | 3300005609 | 3 | 283 | Marine sediment microbial communities from the Atlantic coast under amendment with organic carbon and nitrate - tdDd00.1 (*) (MER-FS) (assembled) | |
| 688 | 3300005675 assembled Ga0074424_10021430 | 3300005675 | 3 | 284 | Enhanced biological phosphorus removal bioreactor viral communities from the University of Queensland, Australia - SBR4-V90806 Phage Sequencing (*) (MER-FS) (assembled) | |
| 689 | 3300005915 assembled Ga0075122_100007968 | 3300005915 | 2 | 285 | Saline lake microbial communities from Ace Lake, Antarctica - Antarctic Ace Lake Metagenome 02UKB (*) (MER-FS) (assembled) | |
| 690 | 3300005920 assembled Ga0070725_1000012429 | 3300005920 | 7 | 286 | Marine sediment microbial communities from the Atlantic coast under amendment with organic carbon and nitrate - tdDd00.2 (*) (MER-FS) (assembled) | |
| 691 | 3300005920 assembled Ga0070725_1000027223 | 3300005920 | 3 | 287 | Marine sediment microbial communities from the Atlantic coast under amendment with organic carbon and nitrate - tdDd00.2 (*) (MER-FS) (assembled) | |

TABLE 3-continued pVip Proteins

| SEQ ID No | pVip # | Clade | IMG id | Metagenome genome IMG ID | Genome Metagenome Name | Kinase |
|---|---|---|---|---|---|---|
| 692 | 288 | 3 | 3300005920_assembled Ga0070725_10003449 | 3300005920 | Marine sediment microbial communities from the Atlantic coast under amendment with organic carbon and nitrate - tdDd00.2 (*) (MER-FS) (assembled) | |
| 693 | 289 | 3 | 3300005986_assembled Ga0075152_1000034111 | 3300005986 | Wastewater effluent complex algal communities from Wisconsin, to seasonally profile nutrient transformation and Carbon sequestration - JI Jun. 11, 2014 C2 DNA (*) (MER-FS) (assembled) | |
| 694 | 290 | 3 | 3300006056_assembled Ga0075163_1000220113 | 3300006056 | Wastewater effluent complex algal communities from Wisconsin, to seasonally profile nutrient transformation and Carbon sequestration - JI Oct. 23, 2014 1A DNA (*) (MER-FS) (assembled) | |
| 695 | 291 | 3 | 3300006104_assembled Ga0007882_10004313 | 3300006104 | Freshwater microbial communities from Crystal Bog, Wisconsin, USA - CBH12 Aug. 2009.1 (*) (MER-FS) (assembled) | |
| 696 | 292 | 3 | 3300006104_assembled Ga0007882_1000014836 | 3300006104 | Freshwater microbial communities from Crystal Bog, Wisconsin, USA - CBH12 Aug. 2009.1 (*) (MER-FS) (assembled) | |
| 697 | 293 | 6 | 3300006182_assembled Ga0075033_10000633 | 3300006182 | Synthetic microbial communities from Ohio, USA - SynthPrep_5_END_DS10_MetaG (*) (MER-FS) (assembled) | |
| 698 | 294 | 3 | 3300006226_assembled Ga0099364_10017018 | 3300006226 | Termite gut P3 segment microbial communities from Max Planck Institute, Germany - Th196 (*) (MER-FS) (assembled) | |
| 699 | 295 | 4 | 3300006243_assembled Ga0099348_1001723 | 3300006243 | Human buccal mucosa microbial communities from NIH, USA - visit 2, subject 37042S937 (*) (MER-FS) (assembled) | |
| 700 | 296 | 3 | 3300006417_assembled Ga0069787_1004128015 | 3300006417 | Combined Assembly of Gp0110018, Gp0110022, Gp0110020 (*) (MER-FS) (assembled) | |
| 701 | 297 | 3 | 3300006417_assembled Ga0069787_1005605520 | 3300006417 | Combined Assembly of Gp0110018, Gp0110022, Gp0110020 (*) (MER-FS) (assembled) | |
| 702 | 298 | 6 | 3300006417_assembled Ga0069787_1005688918 | 3300006417 | Combined Assembly of Gp0110018, Gp0110022, Gp0110020 (*) (MER-FS) (assembled) | |
| 703 | 299 | 3 | 3300006417_assembled Ga0069787_1021696324 | 3300006417 | Combined Assembly of Gp0110018, Gp0110022, Gp0110020 (*) (MER-FS) (assembled) | |
| 704 | 300 | 3 | 3300006417_assembled Ga0069787_1113807921 | 3300006417 | Combined Assembly of Gp0110018, Gp0110022, Gp0110020 (*) (MER-FS) (assembled) | |
| 705 | 301 | 6 | 3300006736_assembled Ga0098033_1000001464 | 3300006736 | Marine viral communities from the Subarctic Pacific Ocean - 1_ETSP_OMZ_AT15124 metaG (*) (MER-FS) (assembled) | |
| 706 | 302 | 6 | 3300006738_assembled Ga0098034_10001464 | 3300006738 | Marine viral communities from the Subarctic Pacific Ocean - 3_ETSP_OMZ_AT15126 metaG (*) (MER-FS) (assembled) | |
| 707 | 303 | 6 | 3300006789_assembled Ga0098035_100006013 | 3300006789 | Marine viral communities from the Subarctic Pacific Ocean - 16_ETSP_OMZ_AT15313 metaG (*) (MER-FS) (assembled) | |
| 708 | 304 | 6 | 3300006790_assembled Ga0098054_10000219 | 3300006790 | Marine viral communities from the Gulf of Mexico - 32_GoM_OMZ_CsCl_metaG (*) (MER-FS) (assembled) | |
| 709 | 305 | 3 | 3300006810_assembled Ga0098074_10033128 | 3300006810 | Aqueous microbial communities from the Delaware River and Bay under freshwater to marine salinity gradient to study organic matter cycling in a time-series - Viral MetaG DEL_Sep_01 (*) (MER-FS) (assembled) | |
| 710 | 306 | 3 | 3300006879_assembled Ga0079226_100011884 | 3300006879 | Agricultural soil microbial communities from Georgia to study Nitrogen management - Poultry litter 2014 (*) (MER-FS) (assembled) | |
| 711 | 307 | 6 | 3300006927_assembled Ga0098034_100013824 | 3300006927 | Marine viral communities from the Subarctic Pacific Ocean - 2_ETSP_OMZ_AT15125 metaG (*) (MER-FS) (assembled) | |
| 712 | 308 | 6 | 3300006929_assembled Ga0098036_100012625 | 3300006929 | Marine viral communities from the Subarctic Pacific Ocean - 4_ETSP_OMZ_AT15127 metaG (*) (MER-FS) (assembled) | |
| 713 | 309 | 6 | 3300006987_assembled Ga0098063_100010810 | 3300006987 | Marine viral communities from the Gulf of Mexico - 24_WHOI_OMZ metaG (*) (MER-FS) (assembled) | |

TABLE 3-continued

| SEQ ID No | IMG id | Metagenome genome IMG ID | pVip # | Clade | Genome Metagenome Name | Kinase |
|---|---|---|---|---|---|---|
| 714 | 3300006988_assembled_Ga0098064_10002211 | 3300006988 | 310 | 6 | Marine viral communities from the Gulf of Mexico - 24B_WHOI_OMZ_CsCl metaG (*) (MER-FS) (assembled) | |
| 715 | 3300007344_assembled_Ga0070745_100033022 | 3300007344 | 311 | 7 | Aqueous microbial communities from the Delaware River and Bay under freshwater to marine salinity gradient to study organic matter cycling in a time-series - Viral MetaG DEL_Mar_4 (*) (MER-FS) (assembled) | |
| 716 | 3300007346_assembled_Ga0070753_100014333 | 3300007346 | 312 | 7 | Aqueous microbial communities from the Delaware River and Bay under freshwater to marine salinity gradient to study organic matter cycling in a time-series - Viral MetaG DEL_Aug_31 (*) (MER-FS) (assembled) | |
| 717 | 3300007462_assembled_Ga0099934_110520 | 3300007462 | 313 | 3 | Active sludge microbial communities from Klosterneuburg, Austria - Klosterneuburg WWTP active sludge D35_HANv2 (*) (MER-FS) (assembled) | |
| 718 | 3300007485_assembled_Ga0099929_1008119 | 3300007485 | 314 | 3 | Active sludge microbial communities from Klosterneuburg, Austria - Klosterneuburg WWTP active sludge D02_HANv2 (*) (MER-FS) (assembled) | |
| 719 | 3300007516_assembled_Ga0105050_1000139429 | 3300007516 | 315 | 3 | Freshwater microbial communities from Lake Fryxell liftoff mats and glacier meltwater in Antarctica - FRY-01 (*) (MER-FS) (assembled) | |
| 720 | 3300007640_assembled_Ga0070751_1000004111 | 3300007640 | 316 | 7 | Aqueous microbial communities from the Delaware River and Bay under freshwater to marine salinity gradient to study organic matter cycling in a time-series - Viral MetaG DEL_Aug_28 (*) (MER-FS) (assembled) | |
| 721 | 3300007961_assembled_Ga0079305_100003992 | 3300007961 | 317 | 2 | Deep subsurface shale carbon reservoir microbial communities from Ohio, USA - LMS_cellobiose_enrichment (*) (MER-FS) (assembled) | |
| 722 | 3300007963_assembled_Ga0110931_100009625 | 3300007963 | 318 | 6 | Marine viral communities from the Subarctic Pacific Ocean - 4_ETSP_OMZ_AT15127 metaG (version 2) (*) (MER-FS) (assembled) | |
| 723 | 3300008050_assembled_Ga0098052_10001839 | 3300008050 | 319 | 6 | Marine viral communities from the Subarctic Pacific Ocean - 15_ETSP_OMZ_AT15312 metaG (*) (MER-FS) (assembled) | |
| 724 | 3300008050_assembled_Ga0098052_100026416 | 3300008050 | 320 | 3 | Marine viral communities from the Subarctic Pacific Ocean - 15_ETSP_OMZ_AT15312 metaG (*) (MER-FS) (assembled) | |
| 725 | 3300008224_assembled_Ga0105350_100000945 | 3300008224 | 321 | 3 | Methane-oxidizing microbial communities from mesocosms in the Hudson Canyon - EN1E Hudson Canyon (*) (MER-FS) (assembled) | |
| 726 | 3300009093_assembled_Ga0105240_10000504 2 | 3300009093 | 322 | 3 | Corn rhizosphere microbial communities from Kellogg Biological Station, Michigan, USA - KBS C5-4 metaG (*) (MER-FS) (assembled) | |
| 727 | 3300009169_assembled_Ga0105097_1000009945 | 3300009169 | 323 | 3 | Freshwater sediment microbial communities from Prairie Pothole Lake near Jamestown, North Dakota, USA - PPLs Lake P7 Core (1) Depth 10-12 cm May 2015 (*) (MER-FS) (assembled) | |
| 728 | 3300009175_assembled_Ga0073936_1000120334 | 3300009175 | 324 | 3 | Freshwater lake bacterial and archeal communities from Alinen Mustajarvi, Finland, to study Microbial Dark Matter (Phase II) - Alinen Mustajarvi 5m metaG (*) (MER-FS) (assembled) | |
| 729 | 3300009415_assembled_Ga0115029_100184931 | 3300009415 | 325 | 3 | Marine algal microbial communities from Sidmouth, United Kingdom - Sidmouth_Asex1 metaG (*) (MER-FS) (assembled) | |
| 730 | 3300009419_assembled_Ga0114982_10001831 | 3300009419 | 326 | 3 | Subsurface microbial communities from deep shales in Ohio, USA - Utica-3 well 1 S input2 FT (*) (MER-FS) (assembled) | |
| 731 | 3300009488_assembled_Ga0114925_1000023517 | 3300009488 | 327 | 2 | Deep subsurface microbial communities from Indian Ocean to uncover new lineages of life (NeLLi) - Sumatra_00607 metaG (*) (MER-FS) (assembled) | |
| 732 | 3300009488_assembled_Ga0114925_100003506 | 3300009488 | 328 | 2 | Deep subsurface microbial communities from Indian Ocean to uncover new lineages of life (NeLLi) - Sumatra_00607 metaG (*) (MER-FS) (assembled) | |
| 733 | 3300009508_assembled_Ga0115567_1000068222 | 3300009508 | 329 | 7 | Pelagic marine microbial communities from North Sea - COGITO_mtgs_120412 (*) (MER-FS) (assembled) | |

TABLE 3-continued pVip Proteins

| SEQ ID No | IMG id | pVip # | Clade | Metagenome genome IMG ID | Genome Metagenome Name | Kinase |
|---|---|---|---|---|---|---|
| 734 | 3300009512_assembled Ga0115003_100022198 | 330 | 3 | 3300009512 | Marine microbial communities from western Arctic Ocean - ArcticOcean_MG_CB11_88 (*) (MER-FS) (assembled) | |
| 735 | 3300009546_assembled Ga0099799_100233 | 331 | 3 | 3300009546 | Marine eukaryotic communities from CALCOFI LINE 67, Pacific Ocean - CN11_C50_N6_SortLC_1 (*) (MER-FS) (assembled) | |
| 736 | 3300009669_assembled Ga0116148_10010742 | 332 | 3 | 3300009669 | Active sludge microbial communities of municipal wastewater-treating anaerobic digesters from USA - AD_UKC055_MetaG (*) (MER-FS) (assembled) | |
| 737 | 3300009779_assembled Ga0116152_100003906 | 333 | 3 | 3300009779 | Active sludge microbial communities of municipal wastewater-treating anaerobic digesters from Hong Kong - AD_UKC119_MetaG (*) (MER-FS) (assembled) | |
| 738 | 3300009788_assembled Ga0114923_10000278 | 334 | 2 | 3300009788 | Deep subsurface microbial communities from Indian Ocean to uncover new lineages of life (NeLLi) - Sumatra_00157 metaG (*) (MER-FS) (assembled) | |
| 739 | 3300009838_assembled Ga0116153_100010806 | 335 | 6 | 3300009838 | Active sludge microbial communities of municipal wastewater-treating anaerobic digesters from USA - AD_UKC028_MetaG (*) (MER-FS) (assembled) | |
| 740 | 3300010028_assembled Ga0134115_1006245 | 336 | 3 | 3300010028 | Active sludge microbial communities from wastewater treatment plant in Klosterneuburg, Austria - C35_LANv3 (*) (MER-FS) (assembled) | |
| 741 | 3300010160_assembled Ga0114967_100001146 | 337 | 3 | 3300010160 | Freshwater microbial communities from Lake Montjoie, Canada to study carbon cycling - M_130628_MF_MetaG (*) (MER-FS) (assembled) | |
| 742 | 3300010162_assembled Ga0131853_100011621 | 338 | 3 | 3300010162 | Termite gut microbial communities from Petit-Saut, French Guiana - Lab288P1 metaG (version 2) (*) (MER-FS) (assembled) | |
| 743 | 3300010162_assembled Ga0131853_100234120 | 339 | 3 | 3300010162 | Termite gut microbial communities from Petit-Saut, French Guiana - Lab288P1 metaG (version 2) (*) (MER-FS) (assembled) | |
| 744 | 3300010162_assembled Ga0131853_100511220 | 340 | 3 | 3300010162 | Termite gut microbial communities from Petit-Saut, French Guiana - Lab288P1 metaG (version 2) (*) (MER-FS) (assembled) | |
| 745 | 3300010270_assembled Ga0129306_100025163 | 341 | 1 | 3300010270 | Capybara group fecal microbial communities from Wisconsin, USA - P827 metagenome (*) (MER-FS) (assembled) | |
| 746 | 3300010313_assembled Ga0116211_100026028 | 342 | 6 | 3300010313 | Hot spring microbial communities from South Africa to study Microbial Dark Matter (Phase II) - Sagole hot spring metaG (*) (MER-FS) (assembled) | |
| 747 | 3300010373_assembled Ga0134128_1000050820 | 343 | 3 | 3300010373 | Terrestrial soil microbial communities with excess Nitrogen fertilizer from Kellogg Biological Station, Michigan, USA - KB3-175-4 (*) (MER-FS) (assembled) | |
| 748 | 3300010379_assembled Ga0136449_1000153745 | 344 | 2 | 3300010379 | Sb_50d combined assembly (*) (MER-FS) (assembled) | |
| 749 | 3300010396_assembled Ga0134126_1000011835 | 345 | 3 | 3300010396 | Terrestrial soil microbial communities with excess Nitrogen fertilizer from Kellogg Biological Station, Michigan, USA - KB3-175-2 (*) (MER-FS) (assembled) | |
| 750 | 3300010430_assembled Ga0118733_1000149451 | 346 | 3 | 3300010430 | Marine sediment microbial communities from Gulf of Thailand under amendment with organic carbon and nitrate - JGI co-assembly of 8 samples (*) (MER-FS) (assembled) | |
| 751 | 3300010430_assembled Ga0118733_1000158731 | 347 | 6 | 3300010430 | Marine sediment microbial communities from Gulf of Thailand under amendment with organic carbon and nitrate - JGI co-assembly of 8 samples (*) (MER-FS) (assembled) | |
| 752 | 3300010430_assembled Ga0118733_1000628422 | 348 | 3 | 3300010430 | Marine sediment microbial communities from Gulf of Thailand under amendment with organic carbon and nitrate - JGI co-assembly of 8 samples (*) (MER-FS) (assembled) | |
| 753 | 3300012103_assembled Ga0136578_1000209 | 349 | 6 | 3300012103 | Saline lake microbial communities from Deep lake, Antarctica - Metagenome #190 (*) (MER-FS) (assembled) | |
| 754 | 3300012533_assembled Ga0138256_1000042615 | 350 | 6 | 3300012533 | Active sludge microbial communities from wastewater in Klosterneuburg, Austria - KNB2014incub_MG (*) (MER-FS) (assembled) | |

TABLE 3-continued

| | | | | pVip Proteins | | |
|---|---|---|---|---|---|---|
| SEQ ID No | IMG id | pVip # | Clade | Metagenome genome IMG ID | Genome Metagenome Name | Kinase |
| 755 | 3300012950_assembled Ga0163108_1000095519 | 351 | 3 | 3300012950 | Marine microbial communities from the Central Pacific Ocean - Fk160115 155m metaG (*) (MER-FS) (assembled) | |
| 756 | 3300012979_assembled Ga0123348_1000024225 | 352 | 5 | 3300012979 | Fecal eukaryotic communites from dung pellets of Tule Elk in California, USA - Elk Dung B1 Day 1 Metagenome (*) (MER-FS) (assembled) | |
| 757 | 3300012983_assembled Ga0123349_1000049625 | 353 | 5 | 3300012983 | Fecal eukaryotic communites from dung pellets of Tule Elk in California, USA - Elk Dung C2 Day 2 Metagenome (*) (MER-FS) (assembled) | |
| 758 | 3300013088_assembled Ga0163200_1000002129 | 354 | 6 | 3300013088 | Freshwater microbial communities from Powell Lake, British Columbia, Canada to study Microbial Dark Matter (Phase II) - PL_2010_200m (*) (MER-FS) (assembled) | |
| 759 | 3300013092_assembled Ga0163199_1000006211 | 355 | 6 | 3300013092 | Freshwater microbial communities from Powell Lake, British Columbia, Canada to study Microbial Dark Matter (Phase II) - PL_2010_150m (*) (MER-FS) (assembled) | |
| 760 | 3300013131_assembled Ga0172373_100005744 | 356 | 3 | 3300013131 | Freshwater microbial communities from Kabuno Bay, South-Kivu, Congo? kab_Sep. 20 2012_10m (*) (MER-FS) (assembled) | |
| 761 | 3300014491_assembled Ga0182014_100007864 | 357 | 2 | 3300014491 | Permafrost microbial communities from Stordalen Mire, Sweden - 612S2D metaG (*) (MER-FS) (assembled) | |
| 762 | 3300014499_assembled Ga0182012_100003757 | 358 | 3 | 3300014499 | Permafrost microbial communities from Stordalen Mire, Sweden - 612S2S metaG (*) (MER-FS) (assembled) | |
| 763 | 3300017795_assembled Ga0189288_1022816 | 359 | 6 | 3300017795 | Marine microbial communities from the Costa Rica Dome - UW105 mini metaG (*) (MER-FS) (assembled) | |
| 764 | 3300017798_assembled Ga0189289_1026116 | 360 | 6 | 3300017798 | Marine microbial communities from the Costa Rica Dome - UW106 mini metaG (*) (MER-FS) (assembled) | |
| 765 | 3300017805_assembled Ga0189287_100018226 | 361 | 6 | 3300017805 | Marine microbial communities from the Costa Rica Dome - UW86 mini metaG (*) (MER-FS) (assembled) | |
| 766 | 3300017990_assembled Ga0180436_1000345026 | 362 | 3 | 3300017990 | Hypersaline lake sediment archaeal communities from the Salton Sea, California, USA - SS_3_S_2 metaG (*) (MER-FS) (assembled) | |
| 767 | 3300018018_assembled Ga0187886_100041240 | 363 | 2 | 3300018018 | Peatland microbial communities from SPRUCE experiment site at the Marcell Experimental Forest, Minnesota, USA - June 2016WEW_20_150 (*) (MER-FS) (assembled) | |
| 768 | 3300018018_assembled Ga0187886_100069122 | 364 | 2 | 3300018018 | Peatland microbial communities from SPRUCE experiment site at the Marcell Experimental Forest, Minnesota, USA - June 2016WEW_20_150 (*) (MER-FS) (assembled) | |
| 769 | 3300018033_assembled Ga0187867_1000087624 | 365 | 3 | 3300018033 | Peatland microbial communities from SPRUCE experiment site at the Marcell Experimental Forest, Minnesota, USA - June 2016WEW_13_10 (*) (MER-FS) (assembled) | |
| 770 | 3300018038_assembled Ga0187855_1000057816 | 366 | 3 | 3300018038 | Peatland microbial communities from SPRUCE experiment site at the Marcell Experimental Forest, Minnesota, USA - June 2016WEW_8_10 (*) (MER-FS) (assembled) | |
| 771 | 3300018042_assembled Ga0187871_100009711 | 367 | 3 | 3300018042 | Peatland microbial communities from SPRUCE experiment site at the Marcell Experimental Forest, Minnesota, USA - June 2016WEW_16_10 (*) (MER-FS) (assembled) | |
| 772 | 3300018080_assembled Ga0180433_1001105911 | 368 | 3 | 3300018080 | Hypersaline lake sediment archaeal communities from the Salton Sea, California, USA - SS_1_D_1 metaG (*) (MER-FS) (assembled) | |
| 773 | 3300018428_assembled Ga0181568_1000115027 | 369 | 3 | 3300018428 | Coastal salt marsh microbial communities from the Groves Creek Marsh, Skidaway Island, Georgia - 101404AT metaG (megahit assembly) (*) (MER-FS) (assembled) | |
| 774 | 3300018475_assembled Ga0187907_1000663212 | 370 | 1 | 3300018475 | Goat fecal pellet fungal communities from Santa Barbara, California, USA? pellet 1 (*) (MER-FS) (assembled) | |
| 775 | 3300018475_assembled Ga0187907_100078053 | 371 | 1 | 3300018475 | Goat fecal pellet fungal communities from Santa Barbara, California, USA? pellet 1 (*) (MER-FS) (assembled) | |

TABLE 3-continued pVip Proteins

| SEQ ID No | IMG id | pVip # | Clade | Metagenome genome IMG ID | Genome Metagenome Name | Kinase |
|---|---|---|---|---|---|---|
| 776 | 3300018475_assembled Ga0187907_1000859111 | 372 | 1 | 3300018475 | Goat fecal pellet fungal communities from Santa Barbara, California, USA? pellet 1 (*) (MER-FS) (assembled) | |
| 777 | 3300018493_assembled Ga0187909_1000543313 | 373 | 1 | 3300018493 | Goat fecal pellet fungal communities from Santa Barbara, California, USA? pellet 3 (*) (MER-FS) (assembled) | |
| 778 | 3300018494_assembled Ga0187911_1000586113 | 374 | 1 | 3300018494 | Goat fecal pellet fungal communities from Santa Barbara, California, USA? diluted pellet 2 (*) (MER-FS) (assembled) | |
| 779 | 3300018494_assembled Ga0187911_1001224520 | 375 | 1 | 3300018494 | Goat fecal pellet fungal communities from Santa Barbara, California, USA? diluted pellet 2 (*) (MER-FS) (assembled) | |
| 780 | 3300018495_assembled Ga0187908_1000576413 | 376 | 1 | 3300018495 | Goat fecal pellet fungal communities from Santa Barbara, California, USA? pellet 2 (*) (MER-FS) (assembled) | |
| 781 | 3300018495_assembled Ga0187908_1000603814 | 377 | 1 | 3300018495 | Goat fecal pellet fungal communities from Santa Barbara, California, USA? pellet 2 (*) (MER-FS) (assembled) | |
| 782 | 3300018495_assembled Ga0187908_100073603 | 378 | 1 | 3300018495 | Goat fecal pellet fungal communities from Santa Barbara, California, USA? diluted pellet 2 (*) (MER-FS) (assembled) | |
| 783 | 3300018878_assembled Ga0187910_1000693112 | 379 | 1 | 3300018878 | Goat fecal pellet fungal communities from Santa Barbara, California, USA? diluted pellet 1 (*) (MER-FS) (assembled) | |
| 784 | 3300018878_assembled Ga0187910_1000711113 | 380 | 1 | 3300018878 | Goat fecal pellet fungal communities from Santa Barbara, California, USA? diluted pellet 1 (*) (MER-FS) (assembled) | |
| 785 | 3300018878_assembled Ga0187910_100083003 | 381 | 1 | 3300018878 | Goat fecal pellet fungal communities from Santa Barbara, California, USA? diluted pellet 1 (*) (MER-FS) (assembled) | |
| 786 | 3300018878_assembled Ga0187910_1000906015 | 382 | sp | 3300018878 | Goat fecal pellet fungal communities from Santa Barbara, California, USA? diluted pellet 1 (*) (MER-FS) (assembled) | |
| 787 | 3300019373_assembled Ga0187895_100043618 | 383 | 1 | 3300019373 | Goat fecal pellet enrichment culture fungal communities from Isla Vista, California, USA - Alfalfa, Gen0, Rep 3 (*) (MER-FS) (assembled) | |
| 788 | 3300019457_assembled Ga0193932_1007821 | 384 | sp | 3300019457 | Sorted cell/s from Southern Trench hydrothermal vent microbial mat, Guaymas Basin, Mexico? 6X_4868_18_01 (*) (MER-FS) (assembled) | |
| 789 | 3300019750_assembled Ga0194000_100000539 | 385 | 1 | 3300019750 | Sediment microbial communities from the Broadkill River, Lewes, Delaware, United States? FLT_6-7_MG (*) (MER-FS) (assembled) | |

SEQUENCE LISTING

The patent contains a lengthy sequence listing. A copy of the sequence listing is available in electronic form from the USPTO web site (https://seqdata.uspto.gov/?pageRequest=docDetail&DocID=US12419902B2). An electronic copy of the sequence listing will also be available from the USPTO upon request and payment of the fee set forth in 37 CFR 1.19(b)(3).

What is claimed is:

1. A method of treating a disease in a subject in need, said method comprising administering a nucleoside analog that is derived from a nucleotide analog produced by a prokaryotic homolog of viperin (pVip), wherein said nucleoside analog comprises the nucleotide analog produced by the pVip without the phosphate residues, wherein said pVip has the amino acid sequence of SEQ ID NOs: 409-789, or wherein said pVip is encoded by a pVip gene comprising the sequence of one of SEQ ID Nos: 3-408—with—SEQ ID NOs: 411, 417, 421, 425, 431, 432, 433, 438, 439 and 440; wherein said administration treats the disease.

2. The method of claim 1, wherein said disease comprises a virus-induced disease, a cancer or a tumor, an autoimmune disease, an immune disorder, or a combination thereof.

3. The method of claim 1, wherein said nucleotide analog or nucleoside analog comprises ddhUTP, ddhGTP, ddhATP, ddhGDP, ddhUDP, ddhUMP, ddh-deoxy-GTP, ddh-deoxy-ATP, ddh-deoxy-TTP, ddhG, ddhA, ddhU, ddh-deoxy-G, ddh-deoxy-A, ddh-deoxy-T, or any combination thereof.

4. The method of claim 3, where said nucleotide analog or nucleoside analog or combination thereof, further comprises ddhCTP, ddhCDP, ddhCMP, ddh-deoxy-CTP, ddhC, ddh-deoxy-C, or a combination thereof.

* * * * *